(12) United States Patent
Mittl et al.

(10) Patent No.: US 7,052,851 B2
(45) Date of Patent: May 30, 2006

(54) CRYSTAL STRUCTURE OF CYSTEINE PROTEASE

(75) Inventors: Peer Mittl, Maulburg (DE); Stefania Di Marco, Rieti (IT); Markus Grütter, Hochwald (CH)

(73) Assignee: Novartis International AG, Basel (CH)

( * ) Notice: Subject to any disclaimer, the term of this patent is extended or adjusted under 35 U.S.C. 154(b) by 424 days.

(21) Appl. No.: 10/100,655

(22) Filed: Mar. 18, 2002

(65) Prior Publication Data

US 2003/0138840 A1 Jul. 24, 2003

Related U.S. Application Data

(63) Continuation of application No. 09/242,286, filed on May 17, 1999, now abandoned, which is a continuation of application No. 08/689,583, filed on Aug. 12, 1996, now abandoned.

(51) Int. Cl.
*G01N 33/53* (2006.01)

(52) U.S. Cl. ............... 435/7.1; 435/226; 530/333; 530/350

(58) Field of Classification Search .......... 435/7.1, 435/226; 530/333, 350
See application file for complete search history.

(56) References Cited

U.S. PATENT DOCUMENTS 5,834,228 A * 11/1998 Becker et al. ............ 435/23

FOREIGN PATENT DOCUMENTS

| WO | 95/35367 | 12/1995 |
|---|---|---|
| WO | 97/31018 | 8/1997 |

OTHER PUBLICATIONS

Wang et al., J. Biol. Chem. vol. 270, No. 30 pp. 18044-18050 (Jul. 1995).*
Nicholson, D.W., Nature 376, 37-43 (1995).
Casciola-Rosen, L.A. et al., J. Biol. Chem. 269, 30757-30760 (1994).
Bernstein, F.C. et al., J. Mol. Biol. 112: 535-542 (1977).
Fernandes-Alnemci, T. et al., J. Biol. Chem. 269, 30761-30764 (1994).
Travis, J., Science 262, 1374 (1993).
Meng, E.C. et al., J. Comp. Chem. 13, 505-524 (1992).
Thornberry et al., Nature 356—768-774 (1992).
Jones, T.A. et al., EMBO Journal 5, 819-822 (1986).
Ponder, J.W. et al., J. Mol. Biol. 193, 775-791 (1987).
Brunger, A.T. et al., Science 235—458-460 (1987).
Navazo, J., Acta Cryst. D50, 157-163 (1994).
Jones, T., et al., Acta Cryst. A47, 110-119 (1991).
Litwack, et al., (Jeffereson University) U.S. Appl. No. 446,927, filed Jun. 18, 1995.
Wilson, K., et al., Nature 370, 270-274 (1994).
Rotonda, J., et al., Nature Structural Biology 3, 619-625 (1996).
Nicholson, D.W., Nature Biotechnology 14, 297-301 (1996).
Sali, A., Current Opinion in Biotechnology 6, 437-451 (1995).
Casciola-Rosen et al., J. Exp. Med., vol. 183—1957-1964, May 1996.
International Search Report, Feb. 3, 1998.
Mittle et al., The Journal of Biological Chemistry, vol. 272, No. 10, 6539-6547, 1997.
Walker et al., Cell, vol. 78—343-352, Jul. 29, 1994 (No translation).
Protein Crystallography; T. L. Blundell and L. N. Johnson; 1976 Academic Press; p. 94, Table 411.

* cited by examiner

*Primary Examiner*—Bennett Celsa
(74) *Attorney, Agent, or Firm*—Novartis

(57) ABSTRACT

The present invention relates to the death protease CPP32 in crystallized form and a method for the preparation thereof. The invention further provides a three-dimensional model of CPP32 and improved means for the design of CPP32 modulators.

2 Claims, No Drawings

SEQUENCE LISTING

<160> NUMBER OF SEQ ID NOS: 5

<210> SEQ ID NO 1
<211> LENGTH: 4
<212> TYPE: PRT
<213> ORGANISM: Homo sapiens

<400> SEQUENCE: 1

Asp Glu Val Asp
1

<210> SEQ ID NO 2
<211> LENGTH: 4
<212> TYPE: PRT
<213> ORGANISM: Homo sapiens

<400> SEQUENCE: 2

Asp Val Ala Asp
1

<210> SEQ ID NO 3
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: x in position 1 is acetyl ASP; X in position 4
      is ASP fluoromethyl ketone
<220> FEATURE:
<221> NAME/KEY: MISC_FEATURE
<222> LOCATION: (1)..(4)
<223> OTHER INFORMATION: Xaa in position 1 is acetyl ASP; Xaa in

```
            position 4 is ASP fluoromethyl ketone

<400> SEQUENCE: 3

Xaa Val Ala Xaa
1

<210> SEQ ID NO 4
<211> LENGTH: 4
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: at positions 2 and 3, can be any amino acid

<400> SEQUENCE: 4

Tyr Xaa Xaa Asp
1

<210> SEQ ID NO 5
<211> LENGTH: 4
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: at positions 2 and 3, can be any amino acid

<400> SEQUENCE: 5

Asp Xaa Xaa Asp
1
```

CRYSTAL STRUCTURE OF CYSTEINE PROTEASE

This is a continuation of Ser. No. 09/242,286, May 17, 1999, now abandoned, which is a continuation of Ser. No. 08/689,583, Aug. 12, 1996, now abandoned.

The present invention relates to the death protease CPP32 in crystallized form and a method for the preparation thereof. The invention further provides a three-dimensional model of CPP32 and improved means for the design of CPP32 modulators.

Excessive, premature or insufficient apoptosis is a prominent morphological feature of several human diseases including neurological, cardiovascular and proliferative diseases. Members of the ICE/CED-3 like cysteine protease family have been identified as biochemical players associated with this process of physiological or programmed cell death. Interleukin-1β concerting enzyme (ICE) is a mammalian cysteine protease that activates pro-interleukin-1β. CED-3 which was initially identified as the product of a gene that is necessary for programmed cell death in the nematode *C. elegans*, is highly related to interleukin-1β converting enzyme. Molecular cloning has identified several human homologues of ICE and CED-3 including $ICE_{rel}$-II, $ICE_{rel}$-III, ICH-I, CPP32, Mch2 and Mch3. Members of the ICE/CED-3 protease family cluster into two structurally distinguished subfamilies: those related to ICE ($ICE_{rel}$-II, $ICE_{rel}$-III) and those related to CED-3 (ICH-I, CPP32, Mch2 and Mch3) (Nicholson, D. W., Nature 376, 37–43 (1995)).

CPP32, also referred to as apopain or Yama, is a 32 kDa cysteine protease composed of two different subunits of molecular mass 17 kDa and 12 kDa, hereinbelow referred to as P17 and P12, respectively. CPP32, which is synthezised as an inactive pro-enzyme, is e.g. responsible for cleavage of key homeostatic and repair enzymes at the onset of apoptosis. Known substrates of CPP32 include the U1 small nuclear ribonucleoprotein, which is necessary for mRNA splicing (Casciola-Rosen, L. A. et al., J. Biol. Chem. 269, 30757–30760 (1994)), the 460 kDa catalytic subunit of the DNA-dependent protein kinase and poly(ADP-ribose) polymerase (PARP). CPP32-dependent cleavage occurs at the ($P_4$)Asp-Glu-Val-Asp ($P_1$) site (SEQ ID NO:1), in PARP, for example, resulting in the separation of the N-terminal DNA-binding domain (Zn-finger) from the C-terminal catalytic domain. It has been shown that inhibition of CPP32-mediated proteolytic breakdown of PARP which occurs concomitantly with the onset of apoptosis attenuates apoptosis (Nicholson, D. W. et al., Nature 376, 37–43 (1995)). Additional potential substrates for CPP32 include structural proteins and lupus autoantigens. Modulation of CPP32 activity may be an appropriate point for therapeutic intervention, e.g. intervention of pathological conditions wherein inappropriate apoptosis is prominent. Knowledge of the three-dimensional structure of CPP32 is a prerequisite for the rational design of molecules that are capable of specifically and selectively interacting with CPP32.

It is an object of the present invention to provide information on the three-dimensional structure of CPP32, thereby enabling e.g. rational design of small molecules that specifically inhibit CPP32, or CPP32 mutants with altered catalytic activity.

SUMMARY OF THE INVENTION

More specifically, the present invention relates to CPP32 in crystallized form and a method of preparing CPP32 crystals.

In other aspects, the invention relates to a structural model of CPP32, and a computer readable medium having stored thereon a model of CPP32.

Furthermore, the present invention provides a method for designing a chemical entity capable of interacting with CPP32.

BRIEF DESCRIPTION OF THE TABLE

Table 1 lists the atomic structure coordinates for CPP32 in Brookhaven format (Bernstein F. C. et al. (1977), The Protein Data Bank: A computer-based archival file for macromolecular structures, J. Mol. Biol. 112:535–542) as derived by X-ray diffraction from a crystal of CPP32 associated with an irreversible tetrapeptide inhibitor. The following data are given (column numbering from left to right): column 1: atom number; column 2: atom type; column 3: residue type; column 4: residue number; column 5: x-coordinate; column 6: y-coordinate; column 7: z-coordinate; column 8: temperature factor; column 9: occupancy; column 10: segment identification string; column 11: CPP32 subunit (U1, U2), inh=inhibitor, wat=water.

DETAILED DESCRIPTION OF THE INVENTION

The present invention provides a CPP32 polypeptide in crystallized form. In particular, the present invention provides a CPP32-inhibitor complex in crystallized form. The nucleotide and amino acid sequences of human CPP32 are known, and set forth e.g. in FIG. 4b of Nicholson et al., Nature 376, page 41 (1995), which is incorporated herein by reference. The active site cysteine is at position 163. Referring to the numbering in the before-mentioned figure, the following amino acid residues are believed to contribute to the active site: 58–66, 120–124, 128, 161–168, 201–214 and 247–256.

The present invention relates to crystals comprising CPP32, and optionally, a low molecular weigth compound associated with CPP32 (CPP32 co-complex). Preferred are crystals of a monoclinic space group, especially the space group $P2_1$. For example, the crystals of natural human CPP32 can be grown in the presence of an irreversible tetrapeptide inhibitor from solutions containing polyethyleneglycol.

As used herein, a CPP32 inhibitor is a chemical entity or signal which inhibits CPP32 biological activity, particularly CPP32 cysteine protease activity. Peptide aldehydes, nitriles and ketones are potent irreversible inhibitors of CPP32, while compounds which form thiomethyl ketone adducts with the active site cysteine are potent irreversible inhibitors. Preferably, the inhibitor is an irreversible inhibitor, e.g. a short peptide derivative, particularly a tetrapeptide derivative comprising a fluoromethylketo group at the C-terminal amino acid residue and a suitable protection group, e.g. an acetyl group, at the N-terminal end. In context with CPP32 inhibitor, the terms "peptide" or "peptide derivative" are intended to embrace a "peptidomimetic" or "peptide analogue" which is modelled to resemble the three-dimensional structure of the above-identified cleavage site targetted by CPP32.

In a preferred embodiment, the invention relates to a crystal comprising CPP32 and an irreversible inhibitor of CPP32 protease activity, particularly an appropriately derivatized tetrapeptide having the amino acid sequence Asp-Val-Ala-Asp (SEQ ID NO:2). As used herein, CPP32 is intended to include wild-type CPP32, particularly human wild-type CPP32, CPP32 isoforms, CPP32 mutants and CPP32 fusion proteins, e.g. histidine-tagged CPP32.

The term "mutant" refers to a polypeptide, whose amino acid sequence differs from the wild-type sequence given in Nicholson et al. (supra) by deletion, insertion or preferably replacement of one or more selected amino acids. For example, a CPP32 mutant may be designed to be crystallizable in the absence of an inhibitor. An example of such CPP32 mutant is a CPP32 polypeptide, wherein the cysteine at position 163 is replaced with alanine.

Particularly preferred is a crystal comprising the CPP32 (p17p12)$_2$-tetramer, several histidine residues, e.g. from about four to about ten histidine residues, particularly six, fused to CPP32 at its C-terminal end, and the peptidic inhibitor.

Most preferred is a crystal comprising CPP32 belonging to the monoclinic space group P2$_1$ with unit cell dimensions of a=50.9 Å, b=69.1 Å, c=93.8 Å, $\alpha$=90°, $\beta$=101.2° and $\gamma$=90° with one (p17p12)$_2$-tetramer and two inhibitor molecules in the asymmetric unit. The inhibitor is the tetrapeptide derivative Ac-Asp-Val-Ala-Asp-fluoromethyl ketone (SEQ ID NO:3), which is capable of irreversibly inhibiting the enzymatic activity of CPP32. The data are obtained by X-ray diffraction of a CPP32 crystal, wherein the CPP32 inhibitor is complexed with CPP32. Depending on the particular conditions used for crystallization, the above parameters characterizing the unit cell may vary within a limited range, e.g. a, b, c may each vary by up to 5 Å, and $\beta$ may vary by up to 5 degrees. The crystals are stable for at least one month, if kept under suitable conditions, e.g. if kept at 4° C. in a buffer consisting of 28% (w/v) PEG 8000, 100 mM sodium cacodylate, 200 mM magnesium acetate, pH 6.4.

In another aspect, the present invention relates to a method of crystallizing CPP32 comprising submitting CPP32 or a CPP32-inhibitor complex to a suitable crystallization process employing the vapour diffusion technique.

In particular, preparation of crystals comprising CPP32 comprises the steps of (a) preparation of purified CPP32, (b) if required, suitably stabilizing CPP32, e.g. by reacting CPP32 with a suitable low molecular weight compound to form a complex comprising CPP32 and said compound, and (c) crystallizing CPP32 or said complex from a solution using a suitable precipitating agent and the vapour diffusion technique.

Purified CPP32 comprises the p17 and p12 subunits in a molar ratio of 1:1, and, preferably, is a dimer of the formula (p17p12)$_2$. The purified protein is obtainable according to conventional methods. Thus CPP32, or the individual subunits, may be prepared by isolation from natural sources, e.g. cultured human cells (see e.g. Nicholson, D. et al., Nature 376, 37–43 (1995), or preferably by recombinant (heterologous) expression. Expression of recombinant CPP32 is achievable in eukaryotic or prokaryotic systems. For example, recombinant human CPP32 may be expressed in insect cells, such as Sf9 cells, using a suitable recombinant baculovirus system (Fernandes-Alnemri, T. et al., J. Biol. Chem. 269, 30761–30764 (1994), or bacteria, such as *E. coli*. Preferably, CPP32 is expressed in *E. coli* in a soluble form. The enzyme may be expressed as a fusion protein, e.g. a glutathione-S-transferase (GST) or histidine-tagged fusion protein. If desired, the fusion partner is removed before crystallization. The heterotogously produced CPP32 to be used for crystallization is biologically active, e.g. it is capable of inducing apoptosis. Such ability may be determined by morphological, biochemical or viability analysis well-known in the art.

Methods for the preparation of CPP32 mutants are commonly known in the art. For example, CPP32 mutants may be prepared by expression of CPP32 DNA previously modified in its coding region by oligo-nucleotide dierected mutagenesis.

Conventional methods are suitable for isolation of CPP32 from the natural source, the recombinant host cell, or the culture broth, as well as subsequent protein purification. For example, purification methods include commonly known chromatographic procedures including affinity chromatography, particularly metal chelating affinity chromatography, such as $Ni^{2+}$ chromatography.

As defined herein, purified CPP32 is more than 95% homogeneous. Protein homogeneity is determinable according to analytical methods well-known in the art, e.g. sequence analysis, electrophoresis, spectroscopic or chromatographic techniques. The purified protein is enzymatically active. Appropriate assays for determining CPP32 protease activity towards a suitable substrate, e.g. a natural substrate, such as PARP, or a synthetic substrate which is cleavable by CPP32, is known in the art. Advantagously, a peptide, such as aminomethylcoumarin, is used as synthetic substrate.

Prior to crystallization, CPP32 may be reacted with a low molecular weight compound, which is capable of suitably stabilizing CPP32 in case of need, e.g. by binding to the CPP32 active site, advantageously without substantially affecting CPP32 conformation. Preferred is a compound inhibiting CPP32 enzymatic activity. Protease inhibition is determinable employing assays known in the art. Suitable inhibitors include irreversible cysteine protease inhibitors, e.g. low molecular weight compounds, such as peptidic compounds comprising, or derivable from, the CPP32-specific substrate cleavage site with the amino acid sequence Asp-Glu-Val-Asp (SEQ ID NO:1). The amino acid residues of a CPP32 substrate are designated $P_1$, $P_2$, etc., for those extending toward the N-terminus from the scissile bond of the substrate. The residues are designated $P_1'$, $P_2'$ for those extending toward the C-terminus from the scissile bond of the substrate. Accordingly, the amino acids in the above-identified sequence are referred to as (substrate) $P_4$ to $P_1$ amino acids (starting from the N-terminal Asp, thus Glu being $P_3$, and Val being $P_2$). The portions of a CPP32 inhibitor which correspond to the P or P' residues of the substrate are analogously labeled.

Advantageously, the CPP32 inhibitor is a suitably derivatized tetrapeptide. An irreversible cysteine protease inhibitor is characterized by a group capable of reacting with the thiol group of CPP32 cysteine, resulting in abolishment of the proteolytic cleavage of a CPP32 substrate, such as PARP. Usually, this group will be located at the $P_1$ amino acid, e.g. derivatizing the $\gamma$-carboxy group of the $P_1$ aspartatic acid.

Peptides derived from the CPP32 cleavage site must contain an aspartic acid (Asp) residue at the substrate $P_4$ position, and preferably also contain an Asp residue at the $P_1$ postion. Preferably, the $P_4$ and $P_1$ residues are modified. For example, the N-terminal amino group of the $P_4$ aspartatic acid residue may be modified with a suitable amino-protecting group. Suitable protecting groups are generally known and routinely employed by those skilled in the art, and include e.g. an acyl group, particularly an acetyl group. Particularly preferred as CPP32 inhibitor is a derivatized tetrapeptide having the amino acid sequence Asp-Val-Ala-Asp (SEQ ID NO:2), which peptide is capable of irreversibly inhibiting CPP32. Preferred derivatizations are an acetyl group at the $P_5$ position, i.e. at the N-terminal amino group of the $P_4$ aspartatic acid, and a fluoromethylketo group at the $\gamma$-carboxy group of $P_1$.

In the crystallization process a crystallization buffer is prepared, e.g. by mixing a CPP32 solution with a "reservoir buffer", preferably in a 1:1 ratio, with a lower concentration of the precipitating agent necessary for crystal formation. For crystal formation, the concentration of the precipitating agent has to be increased, e.g. by addition of precipitating agent, for example by titration, or by allowing the concentration of precipitating agent to balance by diffusion between the crystallization buffer and a reservoir buffer. Under suitable conditions such diffusion of precipitating agent occurs along the gradient of precipitating agent, e.g. from the reservoir buffer having a higher concentration of precipitating agent into the crystallization buffer having a lower concentration of precipitating agent. Diffusion may be achieved e.g. by vapour diffusion techniques allowing diffusion in the common gas phase. Known techniques are e.g. vapour diffusion methods, such as the "hanging drop" or the "sitting drop" method. In the vapour diffusion method a drop of crystallization buffer containing the protein is hanging above or sitting beside a much larger pool of reservoir buffer. Alternatively, the balancing of the precipitating agent can be achieved through a semipermeable membrane that separates the crystallization buffer from the reservoir buffer and prevents dilution of the protein into the reservoir buffer.

In the crystallization buffer CPP32 preferably has a concentration of up to 30 mg/ml, preferably from about 2 mg/ml to about 4 mg/ml.

Formation of CPP32 crystals can be achieved under various conditions which are essentially determined by the following parameters: pH, presence of salts and additives, precipitating agent, protein concentration and temperature. The pH may range from about 4.0 to 9.0. The concentration and type of buffer is rather unimportant, and therefore variable, e.g. in dependence with the desired pH. Suitable buffer systems include phosphate, acetate, citrate, Tris, MES and HEPES buffers. Useful salts and additives include e.g. chlorides, sulfates and further salts specified in Example 1. The buffer contains a precipitating agent selected from the group consisting of a water miscible organic solvent, preferably polyethylene glycol having a molecular weight of between 100 and 20000, preferentially between 4000 and 10000, or a suitable salt, such as a sulfates, particularly ammonium sulfate, a chloride, a citrate or a tartrate. Crystallization is successful e.g. under the conditions identified in Example 3.

A CPP32 crystal of the invention may be chemically modified, e.g. by heavy atom derivatization. Briefly, such derivatization is achievable by soaking a CPP crystal in a solution containing heavy metal atom salts, or a organometallic compounds, e.g. lead chloride, gold thiomalate, thimerosal or uranyl acetate, which is capable of diffusing through the crystal and binding to the surface of the protein. The location(s) of the bound heavy metal atom(s) can be determined by X-ray diffraction analysis of the soaked crystal, which information may be used e.g. to construct a three-dimensional model of CPP32.

A three-dimensional CPP32 model is obtainable, for example, from a heavy atom derivative of a CPP32 crystal. Also, a model of CPP32 or a CPP32 homologue, such as CED-3; ICH-I, Mch2 and Mch3, can be built or refined from all or part of the CPP32 structural data provided herein, e.g. using the X-ray diffraction data and/or the data provided in Table 1, particularly the structure coordinates. Preferably building of such model involves homology modelling and/or molecular replacement. In more detail, homology modeling of CPP32 or a CPP32 homologue comprises the steps of (a) aligning the sequence of CPP32 or a CPP32 homologue with the CPP32 sequence and incorporating this sequence into the CPP32 model (b) subjecting a preliminary CPP32 model to energy minimization resulting in an energy minimized model, (c) remodeling the regions of said energy minimized model where stereochemistry restraints are violated (d) obtaining a final homology model.

The preliminary homology model can be created by a combination of sequence alignment with any of the ICE-like proteases the sequence of which is known, secondary structure prediction and screening of structural libraries. For example, the sequences of CPP32 and ICE can be aligned using a suitable software program.

Computational software may also be used to predict the secondary structure of CPP32. The CPP32 sequence may be incorporated into the ICE structure. Structural incoherences, e.g. structural fragments around insertions/deletions can be modeled by screening a structural library for peptides of the desired length and with a suitable conformation. For prediction of the side chain conformation, a side chain rotamer library may be employed.

The final homology model is used to solve the crystal structure of CPP32 by molecular replacement using suitable computer software. The homology model is positioned according to the results of molecular replacement, and subjected to further refinement comprising molecular dynamics calculations and modelling of the inhibitor used for crystallization into the electron density.

Data of a completely refined model of a complex comprising human wild-type CPP32 and inhibitor are provided in Table 1. The completely refined model has a final R-factor of 20.1% ($R_{free}$=31.8%) for all data between 8.0 and 2.6 Å resolution. The model consists of 3746 protein atoms, 60 atoms from the inhibitor and 208 water molecules The root mean square deviations from standard bond-lengths and bond-angles are 0.01 Å and 1.71°, respectively. Based on this CPP32 model, it is concluded that the interface is formed by residues 232 to 268 from strand f, helix H5, C-terminal end of $\alpha$-chain and N-terminal end of $\beta$-chain. There is a 17×5×11 Å cavity between (p17p12) subunits, filled with water molecules. The interface is formed by all the atoms belonging to the first (p17, p12) heterodimer (U1 in Table 1) within a radius of 4 Å around any atom of the second (p17, p12) heterodimer (U2 in Table 1). CPP32 and ICE possess similar three-dimensional structures. They are tetramers with a central 12-stranded $\beta$-sheet that is ligated by 10 $\alpha$-helices on both sides. The hydrogen bond network of ICE and CPP32 is different. ICE has a smaller cavity (9*5*11 Å). Significant differences, and these differences are crucial for the design of inhibitors, are observed in the loops that are flanking the active site pocket and in the subunit orientation. The most significant differences include the following:

CPP32 is a (p17p12)$_2$-tetramer consisting of 12 $\beta$-strands and 10 $\alpha$-helices.

In CPP32 the two (p17p12)-dimers are rotated 13° around an axis that lies roughly in the plane of the central $\beta$-sheet and intersects the two-fold axis that relates the two subunits. The rotation axis is tilted ≈30° against the $\beta$-sheet strands.

In CPP32 the N-terminal $\alpha$-helix of ICE (residues 138–148) is missing.

Three loops that are flanking the active-site possess different conformations. More specifically, the loops that are different comprise CPP32 residues:

| | Residues in CPP32 | No. of residues deleted (−)/inserted (+) compared to ICE |
|---|---|---|
| Loop 1. | 56–61 | +3 |
| Loop 2. | 131–133 | −7 |
| Loop 3. | 242–260 | +10 |

Due to the high number of inserted/deleted residues the conformations of these loops cannot be predicted based on the structure of ICE. Especially the long insertion in loop 3. interacts with the bound inhibitor and confers selectivity. Therefore, the data in Table 1 relating to loop 3 are of particular importance.

Compared to the ICE amino acid sequence, a number of changes occur in the CPP32 active site. Knowledge of the three-dimensional arrangement of the modifications can be utilized for the design of new CPP32-selective inhibitors:

| Modifications in p17-subunit of CPP32 and p20 subunit of ICE | | Modifications in p12-subunit of CPP32 and p10 subunit of ICE | |
|---|---|---|---|
| CPP32 | ICE | CPP32 | ICE |
| Met 61 | Ile 176 | Tyr 204 | Val 338 |
| Thr 62 | Pro 177 | Asn 208 | His 342 |
| Ser 65 | Thr 180 | Ser 209 | Pro 343 |
| Glu 123 | Ile 239 | Lys 210 | Thr 344 |
| Glu 124 | Arg 240 | Asp 211 | Met 345 |
| Gly 125 | Glu 241 | Trp 214 | Val 348 |
| Ile 126 | Gly 242 | | |
| Phe 128 | Ser 244 | | |
| Thr 166 | Asp 288 | | |

The recognized cleavage sites for ICE and CPP32 are at the C-terminal ends of YxxD (SEQ ID NO:4) and DxxD (SEQ ID NO:5), respectively. The selectivity of CPP32 for a small acidic residue can be addressed to several modifications (see Table above) and insertions/deletions.

The polar interactions between CPP32 and the tetrapeptide CPP32 inhibitor AcAspValAlaAsp-fluoromethylketone (SEQ ID NO:3) are shown below.

| Binding site | Atom in CPP32 | Atom in the inhibitor | Distance between the atoms [Å] |
|---|---|---|---|
| $P_1$ | Asp993-OD1 | Arg64-NE | 2.7 |
| | " | Arg207-NH1 | 2.6 |
| | Asp993-OD2 | Arg64-NH2 | 2.8 |
| | " | Gln161-NE2 | 2.7 |
| | Asp993-O | Gly122-N | 3.3 |
| | Asp993-N | Ser205-O | 2.8 |
| $P_2$ | — | — | |
| $P_3$ | Val991-N | Arg207-O | 2.5 |
| | Val991-O | Arg207-N | 2.9 |
| $P_4$ | Asp990-N | Phe250-O | 3.4 |
| | Asp990-OD2 | Trp214-NE1 | 3.4 |
| | Asp990-OD1 | Phe250-N | 2.8 |

-continued

| Binding site | Atom in CPP32 | Atom in the inhibitor | Distance between the atoms [Å] |
|---|---|---|---|
| $P_5$ | Ace989-O | Ser209-N | 2.7 |
| | " | Ser209-OG | 2.8 |

The recognition characteristics of the inhibitor may be summarized as follows:
1. $P_1$–$P_5$ form an antiparallel β-sheet with CPP32 residues 205–209.
2. The small acidic side chain of $P_1$ is recognized by Arg 64, Arg 207 and Gln 161 of CPP32.
3. The small acidic side chain of $P_2$ must fit into the cavity formed by residues Tyr 204, Trp 206, Phe 256.
4. For $P_3$, there is no obvious preference.
5. The small polar side-chain of $P_4$ is recognized by Asn208 and Trp 214.

The CPP32 structural information provided herein is useful for the design of molecules which are capable of selectively interacting with CPP32 and thereby specifically modulating the biological activity of said target protein. Furthermore, this information can be used to design and prepare CPP32 mutants, e.g. CPP32 mutants with altered catalytic activity, model the three-dimensional structure and solve the crystal structure of proteins, such as CPP32 homologues. CPP32 mutants or CPP32 co-complexes, involving e.g. molecular replacement. In particular, the present invention provides a computer controlled method for designing a chemical entity capable of interacting with CPP32, said method comprising (a) providing a model of the crystal structure of CPP32 (b) analyzing said model to design the chemical entity which interacts with CPP32; and determining the effect of said entity on CPP32. Preferred is a method for designing a CPP32 inhibitor. The present invention also relates to the chemical entity identified by such method.

Compounds inhibiting CPP32 activity are potentially useful for the treatment of diseases which follow from excessive or insufficient apoptosis. Some peptide-based inhibitors of CPP32 protease activity are known in the art. However, due to their peptidic nature, such inhibitors are typically characterized by undesirable pharmacologic properties including e.g. poor stability, rapid metabolism and poor oral absorption. The present invention enables the use of molecular design techniques, particularly the rational drug design approach, to prepare new or improved chemical entities and compounds, including CPP32 inhibitors, capable of irreversibly or, preferably reversibly, modulating CPP32 protease activity. Improved entities or compounds means that these entities or compounds are superior to the "original" or parent compound they are derived from with regard to a property relevant to therapeutic use including suitability for in vivo administration, e.g. cellular uptake, solubility, stability against (enzymatic) degradation, binding affinity or specificity, and the like.

For example, on the basis on the information provided herein it is possible to specially design CPP32 inhibitors which covalently, or preferably non-covalently, bind to CPP32. Such inhibitors may act in a competitive or uncompetitive manner, bind at or close to the active site of CPP32, or act allosterically.

In the design of CPP32 modulators the following aspects should be considered: (a) is the candidate compound capable of physically and structurally associating with CPP32, and/or (b) is the compound capable of assuming a conformation allowing it to associate with CPP32.

Advantageously, computer modelling techniques are used in the process of assessing these abilities for the modulator as a whole, or a fragment thereof—in order to minimize efforts in the synthesis or testing of insuccessful candidate compounds. Specialized computer software is well-known in the art.

Another design approach is to probe a CPP32 crystal with a variety of different chemical entities to determine optimal sites for interaction beween candidate CPP32 inhibitors and the target enzyme (see e.g. Travis, J., Science 262, 1374 (1993)).

Yet another possibility which opens from the present invention is to screen computationally small molecule data bases for chemical entities or compounds that are capable of binding, in whole or in part, to CPP32. The quality of fit to the binding site may be judged e.g. by shape complementarity or by estimated interaction energy (see e.g. Meng, E. C. et al., J. Comp. Chem. 13, 505–524 (1992)).

CPP32 may also crystallize in a form different from the one disclosed herein. The structural information provided herein is also useful for solving the structure of other crystal forms. Furthermore, it may serve to solve the structure of a CPP32 mutant, a CPP32 co-complex or a sufficiently homolgous protein, particularly an ICE-like protease of the CED-3 subclass. One method that may be employed for this purpose is molecular replacement.

The present invention also enables mutants of CPP32 and the solving of their crystal structure. Based on the structure of CPP32 the effects of site-specific mutations can be predicted. More specifically, the structural information provided herein permits the identification of desirable sites for amino acid modification, particularly amino acid mutation resulting in substitutional, insertional or deletional variants. Such variants may be designed to have special properties, particularly properties distinct from wild-type CPP32, such as altered catalytic activity. Substitutions, deletions and insertions may be combined to arrive at a desired variant. Such variants can be prepared by methods well-known in the art, e.g. starting from wild-type CPP32, or by de novo synthesis.

In another aspect, the invention provides a computer readable medium having stored theron a model of the CPP32 crystal structure. In a preferred embodiment, said model is built from all or part of the X-ray diffraction data shown in the data collection of Example 3 and/or all or part of the data shown in Table 1. In said Table, the data relating to CPP32 loop 1 (amino acid residues 56–61, loop 2 (amino acid residues 131–133) or loop 3 (amino acid residues 242–260) are particularly useful, e.g. for rational drug design.

The present invention provides the structure coordinates of human CPP32. The term "structure coordinates" refers to mathematical coordinates derived from the mathematical equations related to the pattern obtained on diffraction of a monochromatic beam of X-rays by the atoms (scattering centers) of a crystal comprising CPP32 and a particular tetrapeptide derivative. The diffraction data are used to calculate an electron density map of the repeating unit of the crystal. The electron density maps are used to establish the positions of the individual atoms within the unit cell of the crystal.

The following Examples serve to illustrate the present invention, but should not be construed as a limitation thereof. The invention particularly relates to the specific embodiments described in these Examples.

EXAMPLE 1

Expression of Soluble CPP32

The cloned full length CPP32 gene (Fernandes-Alnemri et al., J. Biol. Chem. 269, 30761–30764 (1994)) is inserted into the Bamh1/Xho I sites of the pET21b plasmid (Novagen, Madison, Wis.) which fuses a $(His)_6$ tag to the CPP32 C-terminus. E. coli BL21 (DE3) cells containing this plasmid are grown to $A_{600nm}=1.9$ at 37° C. in 3 l induction medium (20 g/l tryptone, 10 g/l yeast extract, 5 g/l NaCl, 0.5×M9 salts, 0.4% glucose, 1 mM $MgCl_2$, 0.1 mM $CaCl_2$, 0.1 mg/ml ampicillin, pH 7.4). IPTG, 1 mM, is added and the culture is shaken at 25° C. for 3 h. Cells are pelleted and resuspended in 100 ml cold binding buffer (20 mM Tris-HCl, 5 mM imidazole, 500 mM NaCl, pH 8.0) containing 0.1 mg/ml lysozyme and 0.1% Triton X-100. After incubation on ice for 40 min, the cells are flash frozen and stored at −80° C. Soluble, active recombinant CPP32 is produced in E.coli using a T7 expression system. The enzymatic activity present in the induced cell lysate indicates that 46 mg active CPP32 is produced from the 3 l culture.

EXAMPLE 2

Purification and Characterization of Recombinant Human CPP32 Protein with a C-terminal 6His Tag Recombinant human CPP32 expressed in a soluble form in E. coli (E. coli BL21) is purified to homogeneity by $Ni^{2+}$ chromatography using an imidazole gradient (60 mM-1 M). After elution (300–500 mM imidazole), the protein is treated with 50 mM DTT, 50 mM HEPES, pH 8.0, on ice. After 10 min, a slight excess (1.6×) of the irreversible CPP32 inhibitor Ac-Asp-Val-Ala-Asp-fluoromethylketone (SEQ ID NO:3) ($C_{19}H_{29}FN_4O_9$, Mw 476.5) is added until the enzyme is 99.9% inhibited. Next, the sample is concentrated by ultrafiltration (10 kDa molecular weight cut-off) and buffer exchanged into 25 mM HEPES, 2 mM DTT, 1 mM EDTA, 50 mM KCl, 0.02% sodium azide, pH 7.5. The purified CPP32 protein is more than 95% homogeneous, as determined by SDS-PAGE (10–20% gradient gel), reverse phase high performance liquid chromatography (RP-HPLC), MALDI-TOF mass spectrometry, N-terminal sequence and amino acid analysis. A 1:1 molar ratio between the p17 and the p12 subunits is found. The purified CPP32 protein which is a $(p17p12)_2$ tetramer in solution, as analyzed by dynamic light scattering, compares to the published CPP32 amino acid sequence (Fernandes-Alnemri, T., Litwack, G. & Alnemri, E. S. (1994). J. Biol. Chem. 269, 30761–30764, FIG. 1, p.30762) as follows:

|  | CPP32 amino acid residue nos. | | |
| --- | --- | --- | --- |
| PRO-Peptide | 1 | 28 | removed |
| β-CHAIN | 29 | 175 | CPP32 P17 SUBUNIT, |
| α-CHAIN | 176 | 277 | CPP32 P12 SUBUNIT, |
| | + Leu + Glu + 6 His | | |
| Active Site | 121 | 121 | BY SIMILARITY with ICE |
| Active Site | 163 | 163 | BY SIMILARITY with ICE |

EXAMPLE 3

Crystallization

A large set of experiments, all at 4° C., is performed varying precipitant, pH, ionic strength and additives, concentration of protein, drop size and crystallization technique. The following parameters are investigated:
  precipitants, including polyethylene glycol (PEG) 400, 1000, 4000, 6000, 8000, 10000, 20000; polyethylene glycol monomethyl ether (PEG MME) 550, 2000, 5000; sodium chloride, ethylene glycol, dioxane, isopropanol, sodium citrate, sodium acetate, sodium formate, lithium sulfate, glycerol, ammonium sulfate, ammonium phosphate, Na/K phosphate, polyethyleneimine, tert-butanol, Jeffamine M-600, imidazole, ethanol, 2-methyl-2,4-pentanediol (MPD), 1,6 hexandiol, 2-propanol, magnesium sulfate and magnesium formate;
  pH range 4.0 to 9.0;
  a salts and additives, including calcium chloride, sodium citrate, magnesium chloride, ammonium acetate, ammonium sulfate, potassium phosphate, magnesium acetate, zinc acetate, calcium acetate, cetyl-trimethyl ammonium bromide, cobalt chloride, cadmium chloride, K/Na tartrate, ferric chloride, manganese chloride, Na/K phosphate, cesium chloride, zinc sulfate, cadmium sulfate, calcium chloride, nickel chloride and ammonium phosphate;
  protein concentration from 8 mg/ml to 2 mg/ml;
  Successful crystallization conditions are as described below:
  The "hanging drop" method (McPherson, (1982) Preparation and Analysis of Protein Crystals, John Wiley and Sons, Inc., New York) is used to crystallize CPP32 protein inhibited with the peptidic inhibitor Ac-Asp-Val-Ala-Asp-fluoromethylketone (SEQ ID NO:3) ($C_{19}H_{29}FN_4O_9$, Mw 476.5). 2–4 µl of solution containing the CPP32 inhibitor complex with a protein concentration of 5.3 mg/ml are mixed with 2–4 µl reservoir buffer on a siliconized cover slip. The reservoir buffer consists of 5% (w/v) PEG 8000, 50 mM magnesium acetate, 90 mM sodium cacodylate, 80 mM sodium sulfate (pH 6.3–6.5). The cover slip is inverted and placed over the reservoir vessel that is filled with 600 µl reservoir buffer. Reservoir vessel and cover slip are sealed with pure vaseline. After approximately 1 week at 4° C. crystals are discovered under the light microscope (size 300×200×50 µm³). The crystals are stable for at least 1 month at 4° in a buffer consisting of 28% (w/v) PEG 8000, 100 mM sodium cacodylate, 200 mM magnesium acetate, pH 6.4.
  Crystals are also obtained in the following conditions:
  10–8% PEG 6000, 0–5% MPD and 0–0.2 M sodium sulfate in 0.1 M HEPES, pH 7.5;
  15–5% PEG 8000 and 200–50 mM magnesium acetate in 0.1 M sodium cacodylate, pH 6.5;
  10–5% PEG 8000 and 8–6% ethylene glycol in 0.1 M HEPES, pH 7.5;
  10–7% PEG 4000 and 0–10% isopropanol in 0.1 M HEPES, pH 7.5;
  25–15% PEG 4000 and 0–0.2 M lithium sulfate monohydrate in 0.1 M TRIS-HCl, pH 8.5;
  5% isopropanol and 2 M ammonium sulfate, pH 5.8;
  10% dioxane, 1.6 M ammonium sulfate, 0.1 M MES, pH 6.5;
  1.6 M ammonium sulfate, 0.1 M NaCl, 0.1 M HEPES, pH 7.5;
  2 M ammonium sulfate and 0.2 M K/Na tartrate in 0.1 M sodium citrate, pH 5.6;
  10% PEG 1000 and 10% PEG 8000;
  5% PEG 6000 in 0.1 M MES, pH 6.0;
  5% PEG 6000 in 0.1 M HEPES, pH 7.0;
  20% PEG 6000 and 1 M LiCl in 0.1 M MES, pH 6.0;
  20% PEG 6000 and 1 M LiCl in 0.1 M HEPES, pH 7.0

Data collection: The crystals belong to the monoclinic space-group $P2_1$ with unit-cell dimensions of a=50.9 Å, b=69.1 Å, c=93.8 Å, α=90°, β=101.2° and γ=90° with one (p17p12)$_2$-tetramer in the asymmetric unit (Vm=2.65 Å³Da⁻¹). Data are collected at the European Synchrotron Radiation Facility (Grenoble/France) to a maximum resolution of 2.6 Å. The data-set is 94.4% complete and has a $R_{merge}$=8.1% for all data between 15.0 and 2.6 Å resolution.

EXAMPLE 4

Homology Modeling

In order to facilitate molecular replacement a homology model of CPP32 is created by a combination of sequence alignment, secondary structure prediction and screening of structural libraries. The sequences of CPP32 (Fernandes-Alnemri, T., Litwack, G. & Alnemri, E. S. (1994). J. Biol. Chem. 269, 30761–30764) and ICE (Thornberry et al. (1992). Nature 356, 768–774) are aligned using the Wisconsin Program Package (Wisconsin Program Package Program Manual for the Wisconsin Package, Version 8, September 1994, Genetics Computer Group, 575 Science Drive, Madison, Wis., USA 53711 The same software is used to predict the secondary structure of CPP32.

Because the predicted secondary structure of CPP32 resembles the observed secondary structure of ICE (Nicholson, D. W. et al., 1994) the CPP32 sequence is incorporated into the ICE structure. Structural fragments around insertions/deletions are modeled by screening a structural library for peptides of the desired length and with a suitable conformation (Jones, T. A. & Thirup, S. (1986). EMBO J. 5, 819–822). The conformation of side chains is retained, if possible. Otherwise a side chain rotamer library is used for prediction of the side chain conformation (Ponder, J. W. & Richards, F. M. (1987). J. Mol. Biol. 193, 775–791). A preliminary CPP32 model, consisting of amino acid residues 45–165 and 188–277, is subjected to 1000 cycles of energy minimization using the program XPLOR (Brünger, A. T., Kuriyan, J. & Karplus, M. (1987). Science 235, 458–460). The stereochemistry of the energy minimized model is checked and regions where the restraints are violated are remodeled. After a few cycles the model is in agreement with the stereochemical restraints.

EXAMPLE 5

Structure Solution

The model obtained in Example 3 is used to solve the crystal structure of CPP32 by molecular replacement with the program AMORE (Nazava, J. (1994). Acta Cryst. D50, 157–163). The cross-rotation function is calculated for the resolution range 8.0–3.0 Å (Patterson radius 0.–25. Å) yieldig two significant peaks for the rotations α=76.1°, β=149.6°, γ=56.3° (5.8 σ above mean) and α=323.1°, β=52.6°, γ=186.8° (5.5 σ above mean). The translation function for the first (p17p12)-subunit is calculated in the resolution range 8.0–3.0 Å. The correlation maximum of this function is found at a=0.4306, b=0.0000, c=0.3672=29.8%, $R_F$=53.5%). The translation function for the second subunit is calculated in the same resolution range, holding the first subunit fixed. The second translation function gives a correlation maximum at a=0.1734, b=0.2189, c=0.1169 (corr=35.8%, $R_F$=52.1%). The orientation of the (p17p12)$_2$-tetramer is further improved by rigid-body refinement (resolution 8.0–3.0 Å, program AMORE). The best orientation has a correlation coefficient of corr=34.7% and $R_F$=51.1% (1. subunit: α=80.9°, β=150.1°, γ=60.2°, a=0.4280, b=−0.0005, c=0.3632; 2. subunit: α=323.2°, β=51.5°, γ=187.3°, a=0.1754, b=0.2171, c=0.1184). The correctly positioned homology-model is further refined by molecular dynamics calculations (program XPLOR) and manual manipulations at a graphical terminal (program O, Jones, et al. (1991). Acta Cryst. A47, 110–119). During the refinement the inhibitor that is used for crystallization is modeled into the electron density in the active-site.

The completely refined model has a final R-factor of 20.1% ($R_{free}$=31.8%) for all data between 8.0 and 2.6 Å resolution. The model consists of 3746 protein atoms, 60 atoms from the inhibitor and 208 water molecules (Table 1). The root mean square deviations from standard bond-lengths and bond-angles are 0.01 Å and 1.71°, respectively.

TABLE 1

Structure coordinates of CPP32

| | | | | | | | | | |
|---|---|---|---|---|---|---|---|---|---|
| ATOM | 1 | CB | ASN | 35 | −7.358 | −2.761 | 22.187 | 1.00 | 76.37 U1 |
| ATOM | 2 | CG | ASN | 35 | −7.866 | −4.142 | 22.585 | 1.00 | 76.37 U1 |
| ATOM | 3 | OD1 | ASN | 35 | −7.202 | −5.152 | 22.323 | 1.00 | 76.37 U1 |
| ATOM | 4 | ND2 | ASN | 35 | −9.035 | −4.196 | 23.214 | 1.00 | 76.37 U1 |
| ATOM | 7 | C | ASN | 35 | −5.059 | −2.723 | 23.277 | 1.00 | 59.06 U1 |
| ATOM | 8 | O | ASN | 35 | −4.435 | −1.723 | 23.605 | 1.00 | 59.06 U1 |
| ATOM | 11 | N | ASN | 35 | −5.454 | −3.884 | 21.067 | 1.00 | 59.06 U1 |
| ATOM | 13 | CA | ASN | 35 | −5.842 | −2.741 | 21.944 | 1.00 | 59.06 U1 |
| ATOM | 14 | N | SER | 36 | −5.031 | −3.842 | 23.998 | 1.00 | 40.21 U1 |
| ATOM | 16 | CA | SER | 36 | −4.338 | −3.921 | 25.280 | 1.00 | 40.21 U1 |
| ATOM | 17 | CB | SER | 36 | −5.354 | −3.927 | 26.426 | 1.00 | 24.04 U1 |
| ATOM | 18 | OG | SER | 36 | −5.787 | −2.629 | 26.793 | 1.00 | 24.04 U1 |
| ATOM | 20 | C | SER | 36 | −3.559 | −5.220 | 25.374 | 1.00 | 40.21 U1 |
| ATOM | 21 | O | SER | 36 | −4.040 | −6.269 | 24.910 | 1.00 | 40.21 U1 |
| ATOM | 22 | N | TYR | 37 | −2.371 | −5.176 | 25.979 | 1.00 | 29.90 U1 |
| ATOM | 24 | CA | TYR | 37 | −1.593 | −6.404 | 26.161 | 1.00 | 29.90 U1 |
| ATOM | 25 | CB | TYR | 37 | −0.196 | −6.094 | 26.666 | 1.00 | 2.00 U1 |
| ATOM | 26 | CG | TYR | 37 | 0.699 | −5.562 | 25.626 | 1.00 | 2.00 U1 |
| ATOM | 27 | CD1 | TYR | 37 | 1.208 | −4.283 | 25.717 | 1.00 | 2.00 U1 |
| ATOM | 28 | CE1 | TYR | 37 | 2.094 | −3.798 | 24.750 | 1.00 | 2.00 U1 |
| ATOM | 29 | CD2 | TYR | 37 | 1.074 | −6.356 | 24.555 | 1.00 | 2.00 U1 |
| ATOM | 30 | CE2 | TYR | 37 | 1.954 | −5.886 | 23.586 | 1.00 | 2.00 U1 |
| ATOM | 31 | CZ | TYR | 37 | 2.464 | −4.608 | 23.694 | 1.00 | 2.00 U1 |
| ATOM | 32 | OH | TYR | 37 | 3.358 | −4.161 | 22.741 | 1.00 | 2.00 U1 |
| ATOM | 34 | C | TYR | 37 | −2.306 | −7.289 | 27.196 | 1.00 | 29.90 U1 |
| ATOM | 35 | O | TYR | 37 | −2.927 | −6.797 | 28.139 | 1.00 | 29.90 U1 |
| ATOM | 36 | N | LYS | 38 | −2.197 | −8.594 | 27.008 | 1.00 | 34.22 U1 |
| ATOM | 38 | CA | LYS | 38 | −2.808 | −9.594 | 27.890 | 1.00 | 34.22 U1 |
| ATOM | 39 | CB | LYS | 38 | −2.792 | −10.960 | 27.176 | 1.00 | 53.78 U1 |
| ATOM | 40 | CG | LYS | 38 | −3.373 | −12.137 | 27.947 | 1.00 | 53.78 U1 |
| ATOM | 41 | CD | LYS | 38 | −3.126 | −13.439 | 27.179 | 1.00 | 53.78 U1 |
| ATOM | 42 | CE | LYS | 38 | −3.388 | −14.698 | 28.026 | 1.00 | 53.78 U1 |
| ATOM | 43 | NZ | LYS | 38 | −4.845 | −15.021 | 28.157 | 1.00 | 53.78 U1 |
| ATOM | 47 | C | LYS | 38 | −2.004 | −9.659 | 29.177 | 1.00 | 34.22 U1 |
| ATOM | 48 | O | LYS | 38 | −0.961 | −10.293 | 29.230 | 1.00 | 34.22 U1 |
| ATOM | 49 | N | MET | 39 | −2.463 | −8.959 | 30.198 | 1.00 | 41.49 U1 |
| ATOM | 51 | CA | MET | 39 | −1.768 | −8.958 | 31.475 | 1.00 | 41.49 U1 |
| ATOM | 52 | CB | MET | 39 | −1.842 | −7.561 | 32.113 | 1.00 | 38.46 U1 |
| ATOM | 53 | CG | MET | 39 | −1.182 | −6.475 | 31.294 | 1.00 | 38.46 U1 |
| ATOM | 54 | SD | MET | 39 | 0.475 | −6.949 | 30.764 | 1.00 | 38.46 U1 |
| ATOM | 55 | CE | MET | 39 | 1.468 | −6.069 | 31.882 | 1.00 | 38.46 U1 |
| ATOM | 56 | C | MET | 39 | −2.337 | −10.016 | 32.437 | 1.00 | 41.49 U1 |
| ATOM | 57 | O | MET | 39 | −2.196 | −9.901 | 33.654 | 1.00 | 41.49 U1 |
| ATOM | 58 | N | ASP | 40 | −2.973 | −11.057 | 31.906 | 1.00 | 46.18 U1 |
| ATOM | 60 | CA | ASP | 40 | −3.529 | −12.062 | 32.789 | 1.00 | 46.18 U1 |
| ATOM | 61 | CB | ASP | 40 | −5.049 | −12.171 | 32.676 | 1.00 | 68.83 U1 |
| ATOM | 62 | CG | ASP | 40 | −5.518 | −12.469 | 31.272 | 1.00 | 68.83 U1 |
| ATOM | 63 | OD1 | ASP | 40 | −5.083 | −13.480 | 30.681 | 1.00 | 68.83 U1 |
| ATOM | 64 | OD2 | ASP | 40 | −6.345 | −11.682 | 30.759 | 1.00 | 68.83 U1 |
| ATOM | 65 | C | ASP | 40 | −2.893 | −13.405 | 32.654 | 1.00 | 46.18 U1 |
| ATOM | 66 | O | ASP | 40 | −3.589 | −14.424 | 32.659 | 1.00 | 46.18 U1 |
| ATOM | 67 | N | TYR | 41 | −1.579 | −13.421 | 32.441 | 1.00 | 38.48 U1 |
| ATOM | 69 | CA | TYR | 41 | −0.889 | −14.705 | 32.407 | 1.00 | 38.48 U1 |
| ATOM | 70 | CB | TYR | 41 | 0.449 | −14.581 | 31.731 | 1.00 | 36.82 U1 |
| ATOM | 71 | CG | TYR | 41 | 0.345 | −14.596 | 30.252 | 1.00 | 36.82 U1 |
| ATOM | 72 | CD1 | TYR | 41 | 0.020 | −13.440 | 29.555 | 1.00 | 36.82 U1 |
| ATOM | 73 | CE1 | TYR | 41 | −0.013 | −13.432 | 28.179 | 1.00 | 36.82 U1 |
| ATOM | 74 | CD2 | TYR | 41 | 0.621 | −15.756 | 29.537 | 1.00 | 36.82 U1 |
| ATOM | 75 | CE2 | TYR | 41 | 0.586 | −15.758 | 28.155 | 1.00 | 36.82 U1 |
| ATOM | 76 | CZ | TYR | 41 | 0.276 | −14.591 | 27.486 | 1.00 | 36.82 U1 |
| ATOM | 77 | OH | TYR | 41 | 0.299 | −14.569 | 26.117 | 1.00 | 36.82 U1 |

TABLE 1-continued

Structure coordinates of CPP32

| | | | | | | | | | | |
|---|---|---|---|---|---|---|---|---|---|---|
| ATOM | 79 | C | TYR | 41 | −0.675 | −15.102 | 33.867 | 1.00 | 38.48 | U1 |
| ATOM | 80 | O | TYR | 41 | −0.973 | −14.320 | 34.783 | 1.00 | 38.48 | U1 |
| ATOM | 81 | N | PRO | 42 | −0.202 | −16.328 | 34.121 | 1.00 | 44.89 | U1 |
| ATOM | 82 | CD | PRO | 42 | −0.090 | −17.519 | 33.257 | 1.00 | 31.52 | U1 |
| ATOM | 83 | CA | PRO | 42 | 0.000 | −16.691 | 35.522 | 1.00 | 44.89 | U1 |
| ATOM | 84 | CB | PRO | 42 | 0.660 | −18.056 | 35.410 | 1.00 | 31.52 | U1 |
| ATOM | 85 | CG | PRO | 42 | −0.082 | −18.645 | 34.262 | 1.00 | 31.52 | U1 |
| ATOM | 86 | C | PRO | 42 | 0.841 | −15.691 | 36.322 | 1.00 | 44.89 | U1 |
| ATOM | 87 | O | PRO | 42 | 0.438 | −15.296 | 37.409 | 1.00 | 44.89 | U1 |
| ATOM | 88 | N | GLU | 43 | 1.942 | −15.206 | 35.751 | 1.00 | 47.47 | U1 |
| ATOM | 90 | CA | GLU | 43 | 2.820 | −14.267 | 36.462 | 1.00 | 47.47 | U1 |
| ATOM | 91 | CB | GLU | 43 | 4.174 | −14.941 | 36.680 | 1.00 | 57.00 | U1 |
| ATOM | 92 | CG | GLU | 43 | 4.046 | −16.291 | 37.371 | 1.00 | 57.00 | U1 |
| ATOM | 93 | CD | GLU | 43 | 5.046 | −17.324 | 36.868 | 1.00 | 57.00 | U1 |
| ATOM | 94 | OE1 | GLU | 43 | 6.237 | −16.978 | 36.720 | 1.00 | 57.00 | U1 |
| ATOM | 95 | OE2 | GLU | 43 | 4.640 | −18.488 | 36.628 | 1.00 | 57.00 | U1 |
| ATOM | 96 | C | GLU | 43 | 2.997 | −12.938 | 35.713 | 1.00 | 47.47 | U1 |
| ATOM | 97 | O | GLU | 43 | 2.899 | −12.910 | 34.479 | 1.00 | 47.47 | U1 |
| ATOM | 98 | N | MET | 44 | 3.241 | −11.839 | 36.433 | 1.00 | 31.93 | U1 |
| ATOM | 100 | CA | MET | 44 | 3.424 | −10.562 | 35.761 | 1.00 | 31.93 | U1 |
| ATOM | 101 | CB | MET | 44 | 3.422 | −9.387 | 36.727 | 1.00 | 29.65 | U1 |
| ATOM | 102 | CG | MET | 44 | 2.038 | −8.886 | 37.099 | 1.00 | 29.65 | U1 |
| ATOM | 103 | SD | MET | 44 | 1.083 | −8.180 | 35.726 | 1.00 | 29.65 | U1 |
| ATOM | 104 | CE | MET | 44 | 1.304 | −6.408 | 35.990 | 1.00 | 29.65 | U1 |
| ATOM | 105 | C | MET | 44 | 4.716 | −10.575 | 34.994 | 1.00 | 31.93 | U1 |
| ATOM | 106 | O | MET | 44 | 4.794 | −10.005 | 33.906 | 1.00 | 31.93 | U1 |
| ATOM | 107 | N | GLY | 45 | 5.733 | −11.225 | 35.547 | 1.00 | 23.58 | U1 |
| ATOM | 109 | CA | GLY | 45 | 7.013 | −11.298 | 34.869 | 1.00 | 23.58 | U1 |
| ATOM | 110 | C | GLY | 45 | 8.184 | −10.805 | 35.689 | 1.00 | 23.58 | U1 |
| ATOM | 111 | O | GLY | 45 | 8.000 | −10.133 | 36.701 | 1.00 | 23.58 | U1 |
| ATOM | 112 | N | LEU | 46 | 9.390 | −11.104 | 35.213 | 1.00 | 23.95 | U1 |
| ATOM | 114 | CA | LEU | 46 | 10.629 | −10.747 | 35.895 | 1.00 | 23.95 | U1 |
| ATOM | 115 | CB | LEU | 46 | 11.788 | −11.507 | 35.266 | 1.00 | 30.00 | U1 |
| ATOM | 116 | CG | LEU | 46 | 12.594 | −12.402 | 36.172 | 1.00 | 30.00 | U1 |
| ATOM | 117 | CD1 | LEU | 46 | 11.684 | −13.412 | 36.802 | 1.00 | 30.00 | U1 |
| ATOM | 118 | CD2 | LEU | 46 | 13.614 | −13.094 | 35.337 | 1.00 | 30.00 | U1 |
| ATOM | 119 | C | LEU | 46 | 10.957 | −9.287 | 35.801 | 1.00 | 23.95 | U1 |
| ATOM | 120 | O | LEU | 46 | 10.668 | −8.659 | 34.795 | 1.00 | 23.95 | U1 |
| ATOM | 121 | N | CYS | 47 | 11.665 | −8.783 | 36.802 | 1.00 | 30.31 | U1 |
| ATOM | 123 | CA | CYS | 47 | 12.096 | −7.394 | 36.832 | 1.00 | 30.31 | U1 |
| ATOM | 124 | CB | CYS | 47 | 11.220 | −6.579 | 37.774 | 1.00 | 27.65 | U1 |
| ATOM | 125 | SG | CYS | 47 | 11.867 | −4.918 | 38.130 | 1.00 | 27.65 | U1 |
| ATOM | 126 | C | CYS | 47 | 13.521 | −7.424 | 37.359 | 1.00 | 30.31 | U1 |
| ATOM | 127 | O | CYS | 47 | 13.721 | −7.653 | 38.540 | 1.00 | 30.31 | U1 |
| ATOM | 128 | N | ILE | 48 | 14.507 | −7.272 | 36.484 | 1.00 | 24.47 | U1 |
| ATOM | 130 | CA | ILE | 48 | 15.901 | −7.304 | 36.888 | 1.00 | 24.47 | U1 |
| ATOM | 131 | CB | ILE | 48 | 16.784 | −7.911 | 35.797 | 1.00 | 22.52 | U1 |
| ATOM | 132 | CG2 | ILE | 48 | 18.217 | −8.018 | 36.277 | 1.00 | 22.52 | U1 |
| ATOM | 133 | CG1 | ILE | 48 | 16.279 | −9.291 | 35.414 | 1.00 | 22.52 | U1 |
| ATOM | 134 | CD1 | ILE | 48 | 16.485 | −10.318 | 36.470 | 1.00 | 22.52 | U1 |
| ATOM | 135 | C | ILE | 48 | 16.362 | −5.890 | 37.084 | 1.00 | 24.47 | U1 |
| ATOM | 136 | O | ILE | 48 | 16.174 | −5.078 | 36.203 | 1.00 | 24.47 | U1 |
| ATOM | 137 | N | ILE | 49 | 16.925 | −5.580 | 38.243 | 1.00 | 30.96 | U1 |
| ATOM | 139 | CA | ILE | 49 | 17.459 | −4.252 | 38.520 | 1.00 | 30.96 | U1 |
| ATOM | 140 | CB | ILE | 49 | 16.908 | −3.653 | 39.850 | 1.00 | 14.81 | U1 |
| ATOM | 141 | CG2 | ILE | 49 | 17.689 | −2.409 | 40.229 | 1.00 | 14.81 | U1 |
| ATOM | 142 | CG1 | ILE | 49 | 15.434 | −3.268 | 39.701 | 1.00 | 14.81 | U1 |
| ATOM | 143 | CD1 | ILE | 49 | 14.658 | −3.247 | 40.992 | 1.00 | 14.81 | U1 |
| ATOM | 144 | C | ILE | 49 | 18.977 | −4.424 | 38.636 | 1.00 | 30.96 | U1 |
| ATOM | 145 | O | ILE | 49 | 19.453 | −5.231 | 39.443 | 1.00 | 30.96 | U1 |
| ATOM | 146 | N | ILE | 50 | 19.733 | −3.719 | 37.803 | 1.00 | 26.44 | U1 |
| ATOM | 148 | CA | ILE | 50 | 21.182 | −3.799 | 37.832 | 1.00 | 26.44 | U1 |
| ATOM | 149 | CB | ILE | 50 | 21.745 | −3.985 | 36.404 | 1.00 | 28.96 | U1 |
| ATOM | 150 | CG2 | ILE | 50 | 23.244 | −3.716 | 36.384 | 1.00 | 28.96 | U1 |
| ATOM | 151 | CG1 | ILE | 50 | 21.448 | −5.406 | 35.910 | 1.00 | 28.96 | U1 |
| ATOM | 152 | CD1 | ILE | 50 | 21.833 | −5.659 | 34.450 | 1.00 | 28.96 | U1 |
| ATOM | 153 | C | ILE | 50 | 21.673 | −2.506 | 38.447 | 1.00 | 26.44 | U1 |
| ATOM | 154 | O | ILE | 50 | 21.703 | −1.476 | 37.786 | 1.00 | 26.44 | U1 |
| ATOM | 155 | N | ASN | 51 | 22.035 | −2.550 | 39.718 | 1.00 | 30.97 | U1 |
| ATOM | 157 | CA | ASN | 51 | 22.473 | −1.355 | 40.443 | 1.00 | 30.97 | U1 |
| ATOM | 158 | CB | ASN | 51 | 21.800 | −1.391 | 41.807 | 1.00 | 23.04 | U1 |
| ATOM | 159 | CG | ASN | 51 | 22.306 | −0.341 | 42.747 | 1.00 | 23.04 | U1 |
| ATOM | 160 | OD1 | ASN | 51 | 22.672 | −0.656 | 43.864 | 1.00 | 23.04 | U1 |
| ATOM | 161 | ND2 | ASN | 51 | 22.297 | 0.909 | 42.330 | 1.00 | 23.04 | U1 |
| ATOM | 164 | C | ASN | 51 | 24.005 | −1.302 | 40.565 | 1.00 | 30.97 | U1 |
| ATOM | 165 | O | ASN | 51 | 24.607 | −2.059 | 41.347 | 1.00 | 30.97 | U1 |
| ATOM | 166 | N | ASN | 52 | 24.640 | −0.425 | 39.785 | 1.00 | 29.51 | U1 |

TABLE 1-continued

Structure coordinates of CPP32

| | | | | | | | | | | |
|---|---|---|---|---|---|---|---|---|---|---|
| ATOM | 168 | CA | ASN | 52 | 26.100 | −0.316 | 39.777 | 1.00 | 29.51 | U1 |
| ATOM | 169 | CB | ASN | 52 | 26.636 | −0.176 | 38.331 | 1.00 | 27.81 | U1 |
| ATOM | 170 | CG | ASN | 52 | 26.920 | −1.528 | 37.639 | 1.00 | 27.81 | U1 |
| ATOM | 171 | OD1 | ASN | 52 | 26.808 | −2.608 | 38.233 | 1.00 | 27.81 | U1 |
| ATOM | 172 | ND2 | ASN | 52 | 27.309 | −1.457 | 36.370 | 1.00 | 27.81 | U1 |
| ATOM | 175 | C | ASN | 52 | 26.511 | 0.905 | 40.568 | 1.00 | 29.51 | U1 |
| ATOM | 176 | O | ASN | 52 | 26.258 | 2.017 | 40.133 | 1.00 | 29.51 | U1 |
| ATOM | 177 | N | LYS | 53 | 27.157 | 0.709 | 41.712 | 1.00 | 21.62 | U1 |
| ATOM | 179 | CA | LYS | 53 | 27.595 | 1.826 | 42.548 | 1.00 | 21.62 | U1 |
| ATOM | 180 | CB | LYS | 53 | 27.104 | 1.600 | 43.972 | 1.00 | 38.48 | U1 |
| ATOM | 181 | CG | LYS | 53 | 27.346 | 2.780 | 44.864 | 1.00 | 38.48 | U1 |
| ATOM | 182 | CD | LYS | 53 | 27.010 | 2.466 | 46.298 | 1.00 | 38.48 | U1 |
| ATOM | 183 | CE | LYS | 53 | 27.278 | 3.667 | 47.189 | 1.00 | 38.48 | U1 |
| ATOM | 184 | NZ | LYS | 53 | 26.869 | 3.384 | 48.602 | 1.00 | 38.48 | U1 |
| ATOM | 188 | C | LYS | 53 | 29.112 | 2.169 | 42.568 | 1.00 | 21.62 | U1 |
| ATOM | 189 | O | LYS | 53 | 29.485 | 3.347 | 42.652 | 1.00 | 21.62 | U1 |
| ATOM | 190 | N | ASN | 54 | 29.973 | 1.150 | 42.482 | 1.00 | 35.19 | U1 |
| ATOM | 192 | CA | ASN | 54 | 31.426 | 1.341 | 42.536 | 1.00 | 35.19 | U1 |
| ATOM | 193 | CB | ASN | 54 | 32.010 | 0.586 | 43.712 | 1.00 | 34.47 | U1 |
| ATOM | 194 | CG | ASN | 54 | 31.295 | 0.874 | 44.994 | 1.00 | 34.47 | U1 |
| ATOM | 195 | OD1 | ASN | 54 | 31.325 | 2.002 | 45.499 | 1.00 | 34.47 | U1 |
| ATOM | 196 | ND2 | ASN | 54 | 30.621 | −0.146 | 45.531 | 1.00 | 34.47 | U1 |
| ATOM | 199 | C | ASN | 54 | 32.142 | 0.848 | 41.295 | 1.00 | 35.19 | U1 |
| ATOM | 200 | O | ASN | 54 | 31.928 | −0.288 | 40.854 | 1.00 | 35.19 | U1 |
| ATOM | 201 | N | PHE | 55 | 33.120 | 1.646 | 40.865 | 1.00 | 50.99 | U1 |
| ATOM | 203 | CA | PHE | 55 | 33.898 | 1.406 | 39.661 | 1.00 | 50.99 | U1 |
| ATOM | 204 | CB | PHE | 55 | 33.593 | 2.544 | 38.676 | 1.00 | 29.49 | U1 |
| ATOM | 205 | CG | PHE | 55 | 32.150 | 2.606 | 38.278 | 1.00 | 29.49 | U1 |
| ATOM | 206 | CD1 | PHE | 55 | 31.707 | 1.968 | 37.132 | 1.00 | 29.49 | U1 |
| ATOM | 207 | CD2 | PHE | 55 | 31.221 | 3.213 | 39.098 | 1.00 | 29.49 | U1 |
| ATOM | 208 | CE1 | PHE | 55 | 30.374 | 1.926 | 36.819 | 1.00 | 29.49 | U1 |
| ATOM | 209 | CE2 | PHE | 55 | 29.876 | 3.181 | 38.801 | 1.00 | 29.49 | U1 |
| ATOM | 210 | CZ | PHE | 55 | 29.449 | 2.535 | 37.663 | 1.00 | 29.49 | U1 |
| ATOM | 211 | C | PHE | 55 | 35.417 | 1.283 | 39.894 | 1.00 | 50.99 | U1 |
| ATOM | 212 | O | PHE | 55 | 35.999 | 1.965 | 40.777 | 1.00 | 50.99 | U1 |
| ATOM | 213 | N | HIS | 56 | 36.046 | 0.403 | 39.103 | 1.00 | 54.48 | U1 |
| ATOM | 215 | CA | HIS | 56 | 37.492 | 0.162 | 39.160 | 1.00 | 54.48 | U1 |
| ATOM | 216 | CB | HIS | 56 | 37.906 | −0.839 | 38.064 | 1.00 | 66.12 | U1 |
| ATOM | 217 | CG | HIS | 56 | 39.227 | −1.512 | 38.309 | 1.00 | 66.12 | U1 |
| ATOM | 218 | CD2 | HIS | 56 | 39.523 | −2.752 | 38.774 | 1.00 | 66.12 | U1 |
| ATOM | 219 | ND1 | HIS | 56 | 40.438 | −0.900 | 38.065 | 1.00 | 66.12 | U1 |
| ATOM | 221 | CE1 | HIS | 56 | 41.420 | −1.729 | 38.367 | 1.00 | 66.12 | U1 |
| ATOM | 222 | NE2 | HIS | 56 | 40.892 | −2.859 | 38.802 | 1.00 | 66.12 | U1 |
| ATOM | 224 | C | HIS | 56 | 38.146 | 1.516 | 38.901 | 1.00 | 54.48 | U1 |
| ATOM | 225 | O | HIS | 56 | 37.715 | 2.223 | 37.980 | 1.00 | 54.48 | U1 |
| ATOM | 226 | N | LYS | 57 | 39.169 | 1.858 | 39.697 | 1.00 | 54.66 | U1 |
| ATOM | 228 | CA | LYS | 57 | 39.879 | 3.147 | 39.596 | 1.00 | 54.66 | U1 |
| ATOM | 229 | CB | LYS | 57 | 41.104 | 3.181 | 40.516 | 1.00 | 88.20 | U1 |
| ATOM | 230 | CG | LYS | 57 | 41.016 | 4.215 | 41.626 | 1.00 | 88.20 | U1 |
| ATOM | 231 | CD | LYS | 57 | 39.817 | 3.920 | 42.521 | 1.00 | 88.20 | U1 |
| ATOM | 232 | CE | LYS | 57 | 39.649 | 4.931 | 43.648 | 1.00 | 88.20 | U1 |
| ATOM | 233 | NZ | LYS | 57 | 38.444 | 4.621 | 44.481 | 1.00 | 88.20 | U1 |
| ATOM | 237 | C | LYS | 57 | 40.311 | 3.499 | 38.187 | 1.00 | 54.66 | U1 |
| ATOM | 238 | O | LYS | 57 | 40.418 | 4.674 | 37.834 | 1.00 | 54.66 | U1 |
| ATOM | 239 | N | SER | 58 | 40.566 | 2.467 | 37.394 | 1.00 | 57.27 | U1 |
| ATOM | 241 | CA | SER | 58 | 40.980 | 2.629 | 36.012 | 1.00 | 57.27 | U1 |
| ATOM | 242 | CB | SER | 58 | 41.283 | 1.268 | 35.430 | 1.00 | 41.27 | U1 |
| ATOM | 243 | OG | SER | 58 | 40.407 | 0.320 | 36.007 | 1.00 | 41.27 | U1 |
| ATOM | 245 | C | SER | 58 | 39.920 | 3.317 | 35.159 | 1.00 | 57.27 | U1 |
| ATOM | 246 | O | SER | 58 | 40.269 | 4.030 | 34.216 | 1.00 | 57.27 | U1 |
| ATOM | 247 | N | THR | 59 | 38.635 | 3.078 | 35.453 | 1.00 | 45.61 | U1 |
| ATOM | 249 | CA | THR | 59 | 37.556 | 3.704 | 34.686 | 1.00 | 45.61 | U1 |
| ATOM | 250 | CB | THR | 59 | 36.170 | 3.098 | 34.966 | 1.00 | 43.38 | U1 |
| ATOM | 251 | OG1 | THR | 59 | 35.735 | 3.485 | 36.276 | 1.00 | 43.38 | U1 |
| ATOM | 253 | CG2 | THR | 59 | 36.198 | 1.588 | 34.849 | 1.00 | 43.38 | U1 |
| ATOM | 254 | C | THR | 59 | 37.461 | 5.163 | 35.041 | 1.00 | 45.61 | U1 |
| ATOM | 255 | O | THR | 59 | 36.876 | 5.940 | 34.293 | 1.00 | 45.61 | U1 |
| ATOM | 256 | N | GLY | 60 | 37.984 | 5.511 | 36.215 | 1.00 | 49.51 | U1 |
| ATOM | 258 | CA | GLY | 60 | 37.974 | 6.894 | 36.686 | 1.00 | 49.51 | U1 |
| ATOM | 259 | C | GLY | 60 | 36.581 | 7.410 | 36.988 | 1.00 | 49.51 | U1 |
| ATOM | 260 | O | GLY | 60 | 36.322 | 8.620 | 36.952 | 1.00 | 49.51 | U1 |
| ATOM | 261 | N | MET | 61 | 35.686 | 6.471 | 37.290 | 1.00 | 57.65 | U1 |
| ATOM | 263 | CA | MET | 61 | 34.293 | 6.774 | 37.584 | 1.00 | 57.65 | U1 |
| ATOM | 264 | CB | MET | 61 | 33.396 | 5.689 | 36.973 | 1.00 | 53.88 | U1 |
| ATOM | 265 | CG | MET | 61 | 33.438 | 5.625 | 35.448 | 1.00 | 53.88 | U1 |
| ATOM | 266 | SD | MET | 61 | 33.005 | 7.213 | 34.674 | 1.00 | 53.88 | U1 |
| ATOM | 267 | CE | MET | 61 | 31.655 | 6.727 | 33.636 | 1.00 | 53.88 | U1 |

TABLE 1-continued

Structure coordinates of CPP32

| | | | | | | | | | | |
|---|---|---|---|---|---|---|---|---|---|---|
| ATOM | 268 | C | MET | 61 | 34.031 | 6.908 | 39.083 | 1.00 | 57.65 | U1 |
| ATOM | 269 | O | MET | 61 | 34.237 | 5.968 | 39.849 | 1.00 | 57.65 | U1 |
| ATOM | 270 | N | THR | 62 | 33.584 | 8.085 | 39.498 | 1.00 | 39.55 | U1 |
| ATOM | 272 | CA | THR | 62 | 33.287 | 8.347 | 40.899 | 1.00 | 39.55 | U1 |
| ATOM | 273 | CB | THR | 62 | 32.913 | 9.815 | 41.063 | 1.00 | 39.35 | U1 |
| ATOM | 274 | OG1 | THR | 62 | 31.997 | 10.174 | 40.022 | 1.00 | 39.35 | U1 |
| ATOM | 276 | CG2 | THR | 62 | 34.144 | 10.692 | 40.929 | 1.00 | 39.35 | U1 |
| ATOM | 277 | C | THR | 62 | 32.101 | 7.476 | 41.317 | 1.00 | 39.55 | U1 |
| ATOM | 278 | O | THR | 62 | 31.123 | 7.402 | 40.569 | 1.00 | 39.55 | U1 |
| ATOM | 279 | N | SER | 63 | 32.177 | 6.826 | 42.484 | 1.00 | 31.79 | U1 |
| ATOM | 281 | CA | SER | 63 | 31.087 | 5.963 | 42.956 | 1.00 | 31.79 | U1 |
| ATOM | 282 | CB | SER | 63 | 31.380 | 5.393 | 44.353 | 1.00 | 43.73 | U1 |
| ATOM | 283 | OG | SER | 63 | 30.699 | 6.093 | 45.385 | 1.00 | 43.73 | U1 |
| ATOM | 285 | C | SER | 63 | 29.785 | 6.735 | 42.967 | 1.00 | 31.79 | U1 |
| ATOM | 286 | O | SER | 63 | 29.795 | 7.966 | 43.131 | 1.00 | 31.79 | U1 |
| ATOM | 287 | N | ARG | 64 | 28.660 | 6.039 | 42.832 | 1.00 | 35.16 | U1 |
| ATOM | 289 | CA | ARG | 64 | 27.390 | 6.750 | 42.775 | 1.00 | 35.16 | U1 |
| ATOM | 290 | CB | ARG | 64 | 26.668 | 6.480 | 41.453 | 1.00 | 20.08 | U1 |
| ATOM | 291 | CG | ARG | 64 | 26.948 | 5.132 | 40.786 | 1.00 | 20.08 | U1 |
| ATOM | 292 | CD | ARG | 64 | 26.631 | 5.192 | 39.286 | 1.00 | 20.08 | U1 |
| ATOM | 293 | NE | ARG | 64 | 25.431 | 5.973 | 38.990 | 1.00 | 20.08 | U1 |
| ATOM | 295 | CZ | ARG | 64 | 24.193 | 5.558 | 39.231 | 1.00 | 20.08 | U1 |
| ATOM | 296 | NH1 | ARG | 64 | 23.996 | 4.352 | 39.758 | 1.00 | 20.08 | U1 |
| ATOM | 299 | NH2 | ARG | 64 | 23.160 | 6.382 | 39.028 | 1.00 | 20.08 | U1 |
| ATOM | 302 | C | ARG | 64 | 26.441 | 6.722 | 43.959 | 1.00 | 35.16 | U1 |
| ATOM | 303 | O | ARG | 64 | 25.455 | 5.974 | 44.013 | 1.00 | 35.16 | U1 |
| ATOM | 304 | N | SER | 65 | 26.703 | 7.648 | 44.865 | 1.00 | 30.73 | U1 |
| ATOM | 306 | CA | SER | 65 | 25.938 | 7.797 | 46.080 | 1.00 | 30.73 | U1 |
| ATOM | 307 | CB | SER | 65 | 26.493 | 8.981 | 46.870 | 1.00 | 42.95 | U1 |
| ATOM | 308 | OG | SER | 65 | 27.914 | 9.026 | 46.770 | 1.00 | 42.95 | U1 |
| ATOM | 310 | C | SER | 65 | 24.473 | 8.038 | 45.760 | 1.00 | 30.73 | U1 |
| ATOM | 311 | O | SER | 65 | 24.158 | 8.719 | 44.787 | 1.00 | 30.73 | U1 |
| ATOM | 312 | N | GLY | 66 | 23.590 | 7.449 | 46.562 | 1.00 | 33.69 | U1 |
| ATOM | 314 | CA | GLY | 66 | 22.168 | 7.638 | 46.368 | 1.00 | 33.69 | U1 |
| ATOM | 315 | C | GLY | 66 | 21.497 | 6.539 | 45.579 | 1.00 | 33.69 | U1 |
| ATOM | 316 | O | GLY | 66 | 20.298 | 6.291 | 45.746 | 1.00 | 33.69 | U1 |
| ATOM | 317 | N | THR | 67 | 22.268 | 5.836 | 44.758 | 1.00 | 34.34 | U1 |
| ATOM | 319 | CA | THR | 67 | 21.717 | 4.774 | 43.940 | 1.00 | 34.34 | U1 |
| ATOM | 320 | CB | THR | 67 | 22.780 | 4.219 | 42.996 | 1.00 | 26.00 | U1 |
| ATOM | 321 | OG1 | THR | 67 | 22.174 | 3.280 | 42.105 | 1.00 | 26.00 | U1 |
| ATOM | 323 | CG2 | THR | 67 | 23.896 | 3.516 | 43.769 | 1.00 | 26.00 | U1 |
| ATOM | 324 | C | THR | 67 | 21.049 | 3.624 | 44.695 | 1.00 | 34.34 | U1 |
| ATOM | 325 | O | THR | 67 | 20.158 | 2.958 | 44.145 | 1.00 | 34.34 | U1 |
| ATOM | 326 | N | ASP | 68 | 21.451 | 3.384 | 45.943 | 1.00 | 20.54 | U1 |
| ATOM | 328 | CA | ASP | 68 | 20.866 | 2.280 | 46.719 | 1.00 | 20.54 | U1 |
| ATOM | 329 | CB | ASP | 68 | 21.656 | 2.009 | 47.991 | 1.00 | 39.17 | U1 |
| ATOM | 330 | CG | ASP | 68 | 23.087 | 1.568 | 47.713 | 1.00 | 39.17 | U1 |
| ATOM | 331 | OD1 | ASP | 68 | 23.297 | 0.452 | 47.153 | 1.00 | 39.17 | U1 |
| ATOM | 332 | OD2 | ASP | 68 | 23.998 | 2.345 | 48.090 | 1.00 | 39.17 | U1 |
| ATOM | 333 | C | ASP | 68 | 19.435 | 2.564 | 47.073 | 1.00 | 20.54 | U1 |
| ATOM | 334 | O | ASP | 68 | 18.640 | 1.651 | 47.273 | 1.00 | 20.54 | U1 |
| ATOM | 335 | N | VAL | 69 | 19.125 | 3.848 | 47.174 | 1.00 | 20.99 | U1 |
| ATOM | 337 | CA | VAL | 69 | 17.780 | 4.304 | 47.469 | 1.00 | 20.99 | U1 |
| ATOM | 338 | CB | VAL | 69 | 17.734 | 5.813 | 47.672 | 1.00 | 28.82 | U1 |
| ATOM | 339 | CG1 | VAL | 69 | 16.319 | 6.240 | 48.027 | 1.00 | 28.82 | U1 |
| ATOM | 340 | CG2 | VAL | 69 | 18.707 | 6.221 | 48.750 | 1.00 | 28.82 | U1 |
| ATOM | 341 | C | VAL | 69 | 16.940 | 4.003 | 46.236 | 1.00 | 20.99 | U1 |
| ATOM | 342 | O | VAL | 69 | 15.835 | 3.488 | 46.333 | 1.00 | 20.99 | U1 |
| ATOM | 343 | N | ASP | 70 | 17.477 | 4.318 | 45.064 | 1.00 | 19.92 | U1 |
| ATOM | 345 | CA | ASP | 70 | 16.736 | 4.053 | 43.848 | 1.00 | 19.92 | U1 |
| ATOM | 346 | CB | ASP | 70 | 17.541 | 4.435 | 42.627 | 1.00 | 19.40 | U1 |
| ATOM | 347 | CG | ASP | 70 | 17.728 | 5.921 | 42.492 | 1.00 | 19.40 | U1 |
| ATOM | 348 | OD1 | ASP | 70 | 16.984 | 6.716 | 43.099 | 1.00 | 19.40 | U1 |
| ATOM | 349 | OD2 | ASP | 70 | 18.641 | 6.296 | 41.748 | 1.00 | 19.40 | U1 |
| ATOM | 350 | C | ASP | 70 | 16.407 | 2.577 | 43.832 | 1.00 | 19.92 | U1 |
| ATOM | 351 | O | ASP | 70 | 15.233 | 2.209 | 43.941 | 1.00 | 19.92 | U1 |
| ATOM | 352 | N | ALA | 71 | 17.441 | 1.737 | 43.843 | 1.00 | 22.32 | U1 |
| ATOM | 354 | CA | ALA | 71 | 17.237 | 0.281 | 43.826 | 1.00 | 22.32 | U1 |
| ATOM | 355 | CB | ALA | 71 | 18.559 | −0.469 | 43.944 | 1.00 | 21.41 | U1 |
| ATOM | 356 | C | ALA | 71 | 16.295 | −0.237 | 44.866 | 1.00 | 22.32 | U1 |
| ATOM | 357 | O | ALA | 71 | 15.684 | −1.274 | 44.650 | 1.00 | 22.32 | U1 |
| ATOM | 358 | N | ALA | 72 | 16.253 | 0.408 | 46.031 | 1.00 | 21.23 | U1 |
| ATOM | 360 | CA | ALA | 72 | 15.357 | −0.021 | 47.105 | 1.00 | 21.23 | U1 |
| ATOM | 361 | CB | ALA | 72 | 15.779 | 0.597 | 48.406 | 1.00 | 19.35 | U1 |
| ATOM | 362 | C | ALA | 72 | 13.915 | 0.380 | 46.765 | 1.00 | 21.23 | U1 |
| ATOM | 363 | O | ALA | 72 | 12.970 | −0.389 | 46.979 | 1.00 | 21.23 | U1 |
| ATOM | 364 | N | ASN | 73 | 13.767 | 1.566 | 46.171 | 1.00 | 26.61 | U1 |

TABLE 1-continued

Structure coordinates of CPP32

| | | | | | | | | | |
|---|---|---|---|---|---|---|---|---|---|
| ATOM | 366 | CA | ASN | 73 | 12.476 | 2.110 | 45.762 | 1.00 | 26.61 U1 |
| ATOM | 367 | CB | ASN | 73 | 12.644 | 3.533 | 45.272 | 1.00 | 34.23 U1 |
| ATOM | 368 | CG | ASN | 73 | 11.376 | 4.345 | 45.399 | 1.00 | 34.23 U1 |
| ATOM | 369 | OD1 | ASN | 73 | 11.394 | 5.576 | 45.235 | 1.00 | 34.23 U1 |
| ATOM | 370 | ND2 | ASN | 73 | 10.267 | 3.675 | 45.732 | 1.00 | 34.23 U1 |
| ATOM | 373 | C | ASN | 73 | 11.913 | 1.269 | 44.627 | 1.00 | 26.61 U1 |
| ATOM | 374 | O | ASN | 73 | 10.755 | 0.884 | 44.653 | 1.00 | 26.61 U1 |
| ATOM | 375 | N | LEU | 74 | 12.742 | 0.933 | 43.652 | 1.00 | 21.52 U1 |
| ATOM | 377 | CA | LEU | 74 | 12.287 | 0.152 | 42.531 | 1.00 | 21.52 U1 |
| ATOM | 378 | CB | LEU | 74 | 13.408 | −0.004 | 41.515 | 1.00 | 25.37 U1 |
| ATOM | 379 | CG | LEU | 74 | 13.663 | 1.290 | 40.745 | 1.00 | 25.37 U1 |
| ATOM | 380 | CD1 | LEU | 74 | 15.033 | 1.250 | 40.066 | 1.00 | 25.37 U1 |
| ATOM | 381 | CD2 | LEU | 74 | 12.519 | 1.505 | 39.750 | 1.00 | 25.37 U1 |
| ATOM | 382 | C | LEU | 74 | 11.784 | −1.214 | 42.954 | 1.00 | 21.52 U1 |
| ATOM | 383 | O | LEU | 74 | 10.772 | −1.710 | 42.412 | 1.00 | 21.52 U1 |
| ATOM | 384 | N | ARG | 75 | 12.486 | −1.825 | 43.909 | 1.00 | 22.29 U1 |
| ATOM | 386 | CA | ARG | 75 | 12.146 | −3.154 | 44.403 | 1.00 | 22.29 U1 |
| ATOM | 387 | CB | ARG | 75 | 13.243 | −3.657 | 45.316 | 1.00 | 35.29 U1 |
| ATOM | 388 | CG | ARG | 75 | 13.014 | −5.055 | 45.812 | 1.00 | 35.29 U1 |
| ATOM | 389 | CD | ARG | 75 | 14.185 | −5.524 | 46.658 | 1.00 | 35.29 U1 |
| ATOM | 390 | NE | ARG | 75 | 13.824 | −6.712 | 47.430 | 1.00 | 35.29 U1 |
| ATOM | 392 | CZ | ARG | 75 | 14.180 | −7.946 | 47.103 | 1.00 | 35.29 U1 |
| ATOM | 393 | NH1 | ARG | 75 | 14.924 | −8.169 | 46.031 | 1.00 | 35.29 U1 |
| ATOM | 396 | NH2 | ARG | 75 | 13.705 | −8.962 | 47.797 | 1.00 | 35.29 U1 |
| ATOM | 399 | C | ARG | 75 | 10.807 | −3.200 | 45.114 | 1.00 | 22.29 U1 |
| ATOM | 400 | O | ARG | 75 | 10.046 | −4.157 | 44.958 | 1.00 | 22.29 U1 |
| ATOM | 401 | N | GLU | 76 | 10.490 | −2.160 | 45.875 | 1.00 | 21.36 U1 |
| ATOM | 403 | CA | GLU | 76 | 9.209 | −2.143 | 46.572 | 1.00 | 21.36 U1 |
| ATOM | 404 | CB | GLU | 76 | 9.177 | −1.113 | 47.698 | 1.00 | 35.73 U1 |
| ATOM | 405 | CG | GLU | 76 | 7.813 | −0.937 | 48.383 | 1.00 | 35.73 U1 |
| ATOM | 406 | CD | GLU | 76 | 7.356 | −2.109 | 49.276 | 1.00 | 35.73 U1 |
| ATOM | 407 | OE1 | GLU | 76 | 8.006 | −3.181 | 49.320 | 1.00 | 35.73 U1 |
| ATOM | 408 | OE2 | GLU | 76 | 6.304 | −1.939 | 49.945 | 1.00 | 35.73 U1 |
| ATOM | 409 | C | GLU | 76 | 8.136 | −1.842 | 45.573 | 1.00 | 21.36 U1 |
| ATOM | 410 | O | GLU | 76 | 7.071 | −2.462 | 45.615 | 1.00 | 21.36 U1 |
| ATOM | 411 | N | THR | 77 | 8.430 | −0.938 | 44.637 | 1.00 | 19.95 U1 |
| ATOM | 413 | CA | THR | 77 | 7.464 | −0.563 | 43.617 | 1.00 | 19.95 U1 |
| ATOM | 414 | CB | THR | 77 | 7.968 | 0.551 | 42.719 | 1.00 | 26.70 U1 |
| ATOM | 415 | OG1 | THR | 77 | 8.403 | 1.659 | 43.506 | 1.00 | 26.70 U1 |
| ATOM | 417 | CG2 | THR | 77 | 6.855 | 1.040 | 41.862 | 1.00 | 26.70 U1 |
| ATOM | 418 | C | THR | 77 | 7.070 | −1.744 | 42.747 | 1.00 | 19.95 U1 |
| ATOM | 419 | O | THR | 77 | 5.896 | −2.054 | 42.638 | 1.00 | 19.95 U1 |
| ATOM | 420 | N | PHE | 78 | 8.036 | −2.443 | 42.167 | 1.00 | 29.30 U1 |
| ATOM | 422 | CA | PHE | 78 | 7.682 | −3.566 | 41.316 | 1.00 | 29.30 U1 |
| ATOM | 423 | CB | PHE | 78 | 8.770 | −3.886 | 40.283 | 1.00 | 24.24 U1 |
| ATOM | 424 | CG | PHE | 78 | 8.848 | −2.889 | 39.153 | 1.00 | 24.24 U1 |
| ATOM | 425 | CD1 | PHE | 78 | 9.675 | −1.786 | 39.236 | 1.00 | 24.24 U1 |
| ATOM | 426 | CD2 | PHE | 78 | 8.068 | −3.033 | 38.031 | 1.00 | 24.24 U1 |
| ATOM | 427 | CE1 | PHE | 78 | 9.717 | −0.825 | 38.210 | 1.00 | 24.24 U1 |
| ATOM | 428 | CE2 | PHE | 78 | 8.111 | −2.083 | 37.013 | 1.00 | 24.24 U1 |
| ATOM | 429 | CZ | PHE | 78 | 8.934 | −0.979 | 37.106 | 1.00 | 24.24 U1 |
| ATOM | 430 | C | PHE | 78 | 7.299 | −4.793 | 42.093 | 1.00 | 29.30 U1 |
| ATOM | 431 | O | PHE | 78 | 7.025 | −5.842 | 41.505 | 1.00 | 29.30 U1 |
| ATOM | 432 | N | ARG | 79 | 7.317 | −4.705 | 43.416 | 1.00 | 34.58 U1 |
| ATOM | 434 | CA | ARG | 79 | 6.911 | −5.852 | 44.224 | 1.00 | 34.58 U1 |
| ATOM | 435 | CB | ARG | 79 | 7.598 | −5.850 | 45.577 | 1.00 | 34.10 U1 |
| ATOM | 436 | CG | ARG | 79 | 7.226 | −7.053 | 46.406 | 1.00 | 34.10 U1 |
| ATOM | 437 | CD | ARG | 79 | 7.850 | −6.966 | 47.761 | 1.00 | 34.10 U1 |
| ATOM | 438 | NE | ARG | 79 | 7.270 | −5.890 | 48.533 | 1.00 | 34.10 U1 |
| ATOM | 440 | CZ | ARG | 79 | 6.099 | −5.979 | 49.148 | 1.00 | 34.10 U1 |
| ATOM | 441 | NH1 | ARG | 79 | 5.385 | −7.108 | 49.094 | 1.00 | 34.10 U1 |
| ATOM | 444 | NH2 | ARG | 79 | 5.620 | −4.914 | 49.771 | 1.00 | 34.10 U1 |
| ATOM | 447 | C | ARG | 79 | 5.412 | −5.700 | 44.403 | 1.00 | 34.58 U1 |
| ATOM | 448 | O | ARG | 79 | 4.646 | −6.649 | 44.270 | 1.00 | 34.58 U1 |
| ATOM | 449 | N | ASN | 80 | 4.988 | −4.481 | 44.692 | 1.00 | 39.67 U1 |
| ATOM | 451 | CA | ASN | 80 | 3.573 | −4.220 | 44.820 | 1.00 | 39.67 U1 |
| ATOM | 452 | CB | ASN | 80 | 3.321 | −2.808 | 45.323 | 1.00 | 56.00 U1 |
| ATOM | 453 | CG | ASN | 80 | 3.609 | −2.669 | 46.792 | 1.00 | 56.00 U1 |
| ATOM | 454 | OD1 | ASN | 80 | 3.176 | −3.491 | 47.594 | 1.00 | 56.00 U1 |
| ATOM | 455 | ND2 | ASN | 80 | 4.342 | −1.627 | 47.160 | 1.00 | 56.00 U1 |
| ATOM | 458 | C | ASN | 80 | 2.885 | −4.410 | 43.480 | 1.00 | 39.67 U1 |
| ATOM | 459 | O | ASN | 80 | 1.672 | −4.554 | 43.451 | 1.00 | 39.67 U1 |
| ATOM | 460 | N | LEU | 81 | 3.629 | −4.362 | 42.368 | 1.00 | 29.49 U1 |
| ATOM | 462 | CA | LEU | 81 | 3.010 | −4.558 | 41.045 | 1.00 | 29.49 U1 |
| ATOM | 463 | CB | LEU | 81 | 3.691 | −3.716 | 39.947 | 1.00 | 2.00 U1 |
| ATOM | 464 | CG | LEU | 81 | 3.511 | −2.188 | 40.006 | 1.00 | 2.00 U1 |
| ATOM | 465 | CD1 | LEU | 81 | 4.342 | −1.491 | 38.944 | 1.00 | 2.00 U1 |

TABLE 1-continued

Structure coordinates of CPP32

| ATOM | 466 | CD2 | LEU | 81 | 2.055 | −1.819 | 39.838 | 1.00 | 2.00 | U1 |
|---|---|---|---|---|---|---|---|---|---|---|
| ATOM | 467 | C | LEU | 81 | 2.967 | −6.045 | 40.644 | 1.00 | 29.49 | U1 |
| ATOM | 468 | O | LEU | 81 | 2.478 | −6.392 | 39.570 | 1.00 | 29.49 | U1 |
| ATOM | 469 | N | LYS | 82 | 3.469 | −6.905 | 41.525 | 1.00 | 21.84 | U1 |
| ATOM | 471 | CA | LYS | 82 | 3.500 | −8.342 | 41.315 | 1.00 | 21.84 | U1 |
| ATOM | 472 | CB | LYS | 82 | 2.127 | −8.848 | 40.898 | 1.00 | 45.72 | U1 |
| ATOM | 473 | CG | LYS | 82 | 1.004 | −8.438 | 41.844 | 1.00 | 45.72 | U1 |
| ATOM | 474 | CD | LYS | 82 | 1.217 | −8.994 | 43.243 | 1.00 | 45.72 | U1 |
| ATOM | 475 | CE | LYS | 82 | −0.040 | −8.855 | 44.097 | 1.00 | 45.72 | U1 |
| ATOM | 476 | NZ | LYS | 82 | −0.366 | −7.452 | 44.496 | 1.00 | 45.72 | U1 |
| ATOM | 480 | C | LYS | 82 | 4.579 | −8.884 | 40.369 | 1.00 | 21.84 | U1 |
| ATOM | 481 | O | LYS | 82 | 4.383 | −9.930 | 39.712 | 1.00 | 21.84 | U1 |
| ATOM | 482 | N | TYR | 83 | 5.734 | −8.218 | 40.324 | 1.00 | 26.90 | U1 |
| ATOM | 484 | CA | TYR | 83 | 6.838 | −8.671 | 39.475 | 1.00 | 26.90 | U1 |
| ATOM | 485 | CB | TYR | 83 | 7.610 | −7.476 | 38.896 | 1.00 | 26.64 | U1 |
| ATOM | 486 | CG | TYR | 83 | 6.958 | −6.860 | 37.675 | 1.00 | 26.64 | U1 |
| ATOM | 487 | CD1 | TYR | 83 | 5.980 | −5.871 | 37.787 | 1.00 | 26.64 | U1 |
| ATOM | 488 | CE1 | TYR | 83 | 5.310 | −5.386 | 36.665 | 1.00 | 26.64 | U1 |
| ATOM | 489 | CD2 | TYR | 83 | 7.247 | −7.324 | 36.408 | 1.00 | 26.64 | U1 |
| ATOM | 490 | CE2 | TYR | 83 | 6.584 | −6.838 | 35.289 | 1.00 | 26.64 | U1 |
| ATOM | 491 | CZ | TYR | 83 | 5.627 | −5.889 | 35.429 | 1.00 | 26.64 | U1 |
| ATOM | 492 | OH | TYR | 83 | 4.962 | −5.459 | 34.321 | 1.00 | 26.64 | U1 |
| ATOM | 494 | C | TYR | 83 | 7.764 | −9.503 | 40.343 | 1.00 | 26.90 | U1 |
| ATOM | 495 | O | TYR | 83 | 7.722 | −9.408 | 41.566 | 1.00 | 26.90 | U1 |
| ATOM | 496 | N | GLU | 84 | 8.529 | −10.398 | 39.745 | 1.00 | 28.00 | U1 |
| ATOM | 498 | CA | GLU | 84 | 9.482 | −11.171 | 40.522 | 1.00 | 28.00 | U1 |
| ATOM | 499 | CB | GLU | 84 | 9.755 | −12.514 | 39.845 | 1.00 | 46.80 | U1 |
| ATOM | 500 | CG | GLU | 84 | 10.779 | −13.351 | 40.558 | 1.00 | 46.80 | U1 |
| ATOM | 501 | CD | GLU | 84 | 11.153 | −14.613 | 39.797 | 1.00 | 46.80 | U1 |
| ATOM | 502 | OE1 | GLU | 84 | 12.373 | −14.907 | 39.710 | 1.00 | 46.80 | U1 |
| ATOM | 503 | OE2 | GLU | 84 | 10.241 | −15.321 | 39.295 | 1.00 | 46.80 | U1 |
| ATOM | 504 | C | GLU | 84 | 10.743 | −10.307 | 40.476 | 1.00 | 28.00 | U1 |
| ATOM | 505 | O | GLU | 84 | 11.467 | −10.330 | 39.483 | 1.00 | 28.00 | U1 |
| ATOM | 506 | N | VAL | 85 | 10.982 | −9.478 | 41.484 | 1.00 | 32.11 | U1 |
| ATOM | 508 | CA | VAL | 85 | 12.182 | −8.640 | 41.451 | 1.00 | 32.11 | U1 |
| ATOM | 509 | CB | VAL | 85 | 12.061 | −7.499 | 42.390 | 1.00 | 17.64 | U1 |
| ATOM | 510 | CG1 | VAL | 85 | 13.052 | −6.440 | 42.014 | 1.00 | 17.64 | U1 |
| ATOM | 511 | CG2 | VAL | 85 | 10.682 | −6.971 | 42.366 | 1.00 | 17.64 | U1 |
| ATOM | 512 | C | VAL | 85 | 13.486 | −9.379 | 41.779 | 1.00 | 32.11 | U1 |
| ATOM | 513 | O | VAL | 85 | 13.491 | −10.336 | 42.557 | 1.00 | 32.11 | U1 |
| ATOM | 514 | N | ARG | 86 | 14.595 | −8.937 | 41.186 | 1.00 | 26.62 | U1 |
| ATOM | 516 | CA | ARG | 86 | 15.901 | −9.539 | 41.437 | 1.00 | 26.62 | U1 |
| ATOM | 517 | CB | ARG | 86 | 16.252 | −10.585 | 40.368 | 1.00 | 28.30 | U1 |
| ATOM | 518 | CG | ARG | 86 | 15.304 | −11.779 | 40.226 | 1.00 | 28.30 | U1 |
| ATOM | 519 | CD | ARG | 86 | 15.853 | −12.776 | 39.188 | 1.00 | 28.30 | U1 |
| ATOM | 520 | NE | ARG | 86 | 14.865 | −13.762 | 38.708 | 1.00 | 28.30 | U1 |
| ATOM | 522 | CZ | ARG | 86 | 15.101 | −14.650 | 37.728 | 1.00 | 28.30 | U1 |
| ATOM | 523 | NH1 | ARG | 86 | 16.285 | −14.684 | 37.130 | 1.00 | 28.30 | U1 |
| ATOM | 526 | NH2 | ARG | 86 | 14.147 | −15.473 | 37.308 | 1.00 | 28.30 | U1 |
| ATOM | 529 | C | ARG | 86 | 16.915 | −8.419 | 41.346 | 1.00 | 26.62 | U1 |
| ATOM | 530 | O | ARG | 86 | 17.084 | −7.865 | 40.289 | 1.00 | 26.62 | U1 |
| ATOM | 531 | N | ASN | 87 | 17.576 | −8.044 | 42.428 | 1.00 | 32.21 | U1 |
| ATOM | 533 | CA | ASN | 87 | 18.557 | −6.967 | 42.316 | 1.00 | 32.21 | U1 |
| ATOM | 534 | CB | ASN | 87 | 18.655 | −6.148 | 43.595 | 1.00 | 31.97 | U1 |
| ATOM | 535 | CG | ASN | 87 | 17.430 | −5.325 | 43.861 | 1.00 | 31.97 | U1 |
| ATOM | 536 | OD1 | ASN | 87 | 16.304 | −5.827 | 43.832 | 1.00 | 31.97 | U1 |
| ATOM | 537 | ND2 | ASN | 87 | 17.639 | −4.049 | 44.154 | 1.00 | 31.97 | U1 |
| ATOM | 540 | C | ASN | 87 | 19.898 | −7.590 | 42.104 | 1.00 | 32.21 | U1 |
| ATOM | 541 | O | ASN | 87 | 20.134 | −8.690 | 42.578 | 1.00 | 32.21 | U1 |
| ATOM | 542 | N | LYS | 88 | 20.789 | −6.879 | 41.426 | 1.00 | 35.09 | U1 |
| ATOM | 544 | CA | LYS | 88 | 22.154 | −7.354 | 41.186 | 1.00 | 35.09 | U1 |
| ATOM | 545 | CB | LYS | 88 | 22.332 | −7.813 | 39.737 | 1.00 | 45.02 | U1 |
| ATOM | 546 | CG | LYS | 88 | 21.358 | −8.878 | 39.298 | 1.00 | 45.02 | U1 |
| ATOM | 547 | CD | LYS | 88 | 21.646 | −10.193 | 39.973 | 1.00 | 45.02 | U1 |
| ATOM | 548 | CE | LYS | 88 | 22.888 | −10.832 | 39.376 | 1.00 | 45.02 | U1 |
| ATOM | 549 | NZ | LYS | 88 | 23.291 | −12.097 | 40.067 | 1.00 | 45.02 | U1 |
| ATOM | 553 | C | LYS | 88 | 22.953 | −6.089 | 41.417 | 1.00 | 35.09 | U1 |
| ATOM | 554 | O | LYS | 88 | 22.545 | −5.030 | 40.943 | 1.00 | 35.09 | U1 |
| ATOM | 555 | N | ASN | 89 | 24.072 | −6.160 | 42.132 | 1.00 | 38.94 | U1 |
| ATOM | 557 | CA | ASN | 89 | 24.853 | −4.942 | 42.399 | 1.00 | 38.94 | U1 |
| ATOM | 558 | CB | ASN | 89 | 24.877 | −4.658 | 43.896 | 1.00 | 44.97 | U1 |
| ATOM | 559 | CG | ASN | 89 | 23.508 | −4.722 | 44.502 | 1.00 | 44.97 | U1 |
| ATOM | 560 | OD1 | ASN | 89 | 22.658 | −3.876 | 44.237 | 1.00 | 44.97 | U1 |
| ATOM | 561 | ND2 | ASN | 89 | 23.252 | −5.773 | 45.254 | 1.00 | 44.97 | U1 |
| ATOM | 564 | C | ASN | 89 | 26.272 | −4.987 | 41.877 | 1.00 | 38.94 | U1 |
| ATOM | 565 | O | ASN | 89 | 26.905 | −6.038 | 41.879 | 1.00 | 38.94 | U1 |
| ATOM | 566 | N | ASP | 90 | 26.772 | −3.847 | 41.426 | 1.00 | 34.10 | U1 |

TABLE 1-continued

Structure coordinates of CPP32

| | | | | | | | | | |
|---|---|---|---|---|---|---|---|---|---|
| ATOM | 568 | CA | ASP | 90 | 28.138 | −3.769 | 40.922 | 1.00 | 34.10 U1 |
| ATOM | 569 | CB | ASP | 90 | 29.132 | −3.713 | 42.095 | 1.00 | 38.49 U1 |
| ATOM | 570 | CG | ASP | 90 | 29.025 | −2.445 | 42.907 | 1.00 | 38.49 U1 |
| ATOM | 571 | OD1 | ASP | 90 | 28.691 | −1.390 | 42.350 | 1.00 | 38.49 U1 |
| ATOM | 572 | OD2 | ASP | 90 | 29.319 | −2.489 | 44.109 | 1.00 | 38.49 U1 |
| ATOM | 573 | C | ASP | 90 | 28.574 | −4.917 | 39.996 | 1.00 | 34.10 U1 |
| ATOM | 574 | O | ASP | 90 | 29.472 | −5.677 | 40.357 | 1.00 | 34.10 U1 |
| ATOM | 575 | N | LEU | 91 | 27.982 | −5.063 | 38.817 | 1.00 | 27.76 U1 |
| ATOM | 577 | CA | LEU | 91 | 28.419 | −6.138 | 37.915 | 1.00 | 27.76 U1 |
| ATOM | 578 | CB | LEU | 91 | 27.238 | −6.787 | 37.221 | 1.00 | 25.62 U1 |
| ATOM | 579 | CG | LEU | 91 | 26.070 | −7.277 | 38.057 | 1.00 | 25.62 U1 |
| ATOM | 580 | CD1 | LEU | 91 | 25.029 | −7.887 | 37.137 | 1.00 | 25.62 U1 |
| ATOM | 581 | CD2 | LEU | 91 | 26.540 | −8.303 | 39.032 | 1.00 | 25.62 U1 |
| ATOM | 582 | C | LEU | 91 | 29.357 | −5.556 | 36.851 | 1.00 | 27.76 U1 |
| ATOM | 583 | O | LEU | 91 | 29.293 | −4.360 | 36.532 | 1.00 | 27.76 U1 |
| ATOM | 584 | N | THR | 92 | 30.236 | −6.400 | 36.313 | 1.00 | 38.90 U1 |
| ATOM | 586 | CA | THR | 92 | 31.192 | −5.989 | 35.272 | 1.00 | 38.90 U1 |
| ATOM | 587 | CB | THR | 92 | 32.318 | −7.014 | 35.175 | 1.00 | 47.98 U1 |
| ATOM | 588 | OG1 | THR | 92 | 31.746 | −8.333 | 35.022 | 1.00 | 47.98 U1 |
| ATOM | 590 | CG2 | THR | 92 | 33.178 | −6.965 | 36.436 | 1.00 | 47.98 U1 |
| ATOM | 591 | C | THR | 92 | 30.480 | −5.947 | 33.924 | 1.00 | 38.90 U1 |
| ATOM | 592 | O | THR | 92 | 29.304 | −6.294 | 33.852 | 1.00 | 38.90 U1 |
| ATOM | 593 | N | ARG | 93 | 31.164 | −5.574 | 32.847 | 1.00 | 32.89 U1 |
| ATOM | 595 | CA | ARG | 93 | 30.481 | −5.551 | 31.562 | 1.00 | 32.89 U1 |
| ATOM | 596 | CB | ARG | 93 | 31.281 | −4.800 | 30.500 | 1.00 | 83.59 U1 |
| ATOM | 597 | CG | ARG | 93 | 32.699 | −5.298 | 30.254 | 1.00 | 83.59 U1 |
| ATOM | 598 | CD | ARG | 93 | 33.156 | −4.923 | 28.845 | 1.00 | 83.59 U1 |
| ATOM | 599 | NE | ARG | 93 | 32.280 | −5.529 | 27.839 | 1.00 | 83.59 U1 |
| ATOM | 601 | CZ | ARG | 93 | 32.128 | −5.088 | 26.593 | 1.00 | 83.59 U1 |
| ATOM | 602 | NH1 | ARG | 93 | 32.796 | −4.024 | 26.166 | 1.00 | 83.59 U1 |
| ATOM | 605 | NH2 | ARG | 93 | 31.288 | −5.710 | 25.775 | 1.00 | 83.59 U1 |
| ATOM | 608 | C | ARG | 93 | 30.176 | −6.980 | 31.128 | 1.00 | 32.89 U1 |
| ATOM | 609 | O | ARG | 93 | 29.079 | −7.284 | 30.665 | 1.00 | 32.89 U1 |
| ATOM | 610 | N | GLU | 94 | 31.104 | −7.893 | 31.370 | 1.00 | 48.91 U1 |
| ATOM | 612 | CA | GLU | 94 | 30.867 | −9.277 | 30.982 | 1.00 | 48.91 U1 |
| ATOM | 613 | CB | GLU | 94 | 32.160 | −10.113 | 30.976 | 1.00 | 56.07 U1 |
| ATOM | 614 | CG | GLU | 94 | 33.110 | −9.900 | 32.144 | 1.00 | 56.07 U1 |
| ATOM | 615 | CD | GLU | 94 | 33.984 | −8.663 | 31.975 | 1.00 | 56.07 U1 |
| ATOM | 616 | OE1 | GLU | 94 | 34.287 | −8.022 | 33.005 | 1.00 | 56.07 U1 |
| ATOM | 617 | OE2 | GLU | 94 | 34.364 | −8.334 | 30.822 | 1.00 | 56.07 U1 |
| ATOM | 618 | C | GLU | 94 | 29.810 | −9.937 | 31.854 | 1.00 | 48.91 U1 |
| ATOM | 619 | O | GLU | 94 | 29.112 | −10.854 | 31.406 | 1.00 | 48.91 U1 |
| ATOM | 620 | N | GLU | 95 | 29.696 | −9.485 | 33.102 | 1.00 | 40.21 U1 |
| ATOM | 622 | CA | GLU | 95 | 28.695 | −10.063 | 33.993 | 1.00 | 40.21 U1 |
| ATOM | 623 | CB | GLU | 95 | 28.987 | −9.729 | 35.448 | 1.00 | 46.14 U1 |
| ATOM | 624 | CG | GLU | 95 | 30.021 | −10.656 | 36.097 | 1.00 | 46.14 U1 |
| ATOM | 625 | CD | GLU | 95 | 30.260 | −10.312 | 37.558 | 1.00 | 46.14 U1 |
| ATOM | 626 | OE1 | GLU | 95 | 29.832 | −11.104 | 38.439 | 1.00 | 46.14 U1 |
| ATOM | 627 | OE2 | GLU | 95 | 30.857 | −9.235 | 37.803 | 1.00 | 46.14 U1 |
| ATOM | 628 | C | GLU | 95 | 27.310 | −9.600 | 33.596 | 1.00 | 40.21 U1 |
| ATOM | 629 | O | GLU | 95 | 26.346 | −10.344 | 33.726 | 1.00 | 40.21 U1 |
| ATOM | 630 | N | ILE | 96 | 27.220 | −8.372 | 33.100 | 1.00 | 42.90 U1 |
| ATOM | 632 | CA | ILE | 96 | 25.953 | −7.830 | 32.636 | 1.00 | 42.90 U1 |
| ATOM | 633 | CB | ILE | 96 | 26.061 | −6.337 | 32.317 | 1.00 | 16.85 U1 |
| ATOM | 634 | CG2 | ILE | 96 | 24.831 | −5.864 | 31.570 | 1.00 | 16.85 U1 |
| ATOM | 635 | CG1 | ILE | 96 | 26.184 | −5.540 | 33.605 | 1.00 | 16.85 U1 |
| ATOM | 636 | CD1 | ILE | 96 | 26.477 | −4.101 | 33.368 | 1.00 | 16.85 U1 |
| ATOM | 637 | C | ILE | 96 | 25.585 | −8.591 | 31.360 | 1.00 | 42.90 U1 |
| ATOM | 638 | O | ILE | 96 | 24.426 | −8.990 | 31.167 | 1.00 | 42.90 U1 |
| ATOM | 639 | N | VAL | 97 | 26.565 | −8.826 | 30.492 | 1.00 | 42.58 U1 |
| ATOM | 641 | CA | VAL | 97 | 26.256 | −9.560 | 29.282 | 1.00 | 42.58 U1 |
| ATOM | 642 | CB | VAL | 97 | 27.404 | −9.561 | 28.299 | 1.00 | 32.08 U1 |
| ATOM | 643 | CG1 | VAL | 97 | 26.946 | −10.202 | 26.993 | 1.00 | 32.08 U1 |
| ATOM | 644 | CG2 | VAL | 97 | 27.868 | −8.154 | 28.071 | 1.00 | 32.08 U1 |
| ATOM | 645 | C | VAL | 97 | 25.864 | −10.992 | 29.636 | 1.00 | 42.58 U1 |
| ATOM | 646 | O | VAL | 97 | 24.852 | −11.507 | 29.147 | 1.00 | 42.58 U1 |
| ATOM | 647 | N | GLU | 98 | 26.607 | −11.621 | 30.536 | 1.00 | 35.15 U1 |
| ATOM | 649 | CA | GLU | 98 | 26.280 | −12.987 | 30.909 | 1.00 | 35.15 U1 |
| ATOM | 650 | CB | GLU | 98 | 27.336 | −13.557 | 31.853 | 1.00 | 93.99 U1 |
| ATOM | 651 | CG | GLU | 98 | 28.471 | −14.272 | 31.140 | 1.00 | 93.99 U1 |
| ATOM | 652 | CD | GLU | 98 | 28.005 | −15.511 | 30.385 | 1.00 | 93.99 U1 |
| ATOM | 653 | OE1 | GLU | 98 | 26.997 | −16.137 | 30.791 | 1.00 | 93.99 U1 |
| ATOM | 654 | OE2 | GLU | 98 | 28.655 | −15.866 | 29.380 | 1.00 | 93.99 U1 |
| ATOM | 655 | C | GLU | 98 | 24.873 | −13.129 | 31.501 | 1.00 | 35.15 U1 |
| ATOM | 656 | O | GLU | 98 | 24.127 | −14.047 | 31.138 | 1.00 | 35.15 U1 |
| ATOM | 657 | N | LEU | 99 | 24.497 | −12.202 | 32.380 | 1.00 | 34.91 U1 |
| ATOM | 659 | CA | LEU | 99 | 23.182 | −12.229 | 33.014 | 1.00 | 34.91 U1 |

TABLE 1-continued

Structure coordinates of CPP32

| | | | | | | | | | | |
|---|---|---|---|---|---|---|---|---|---|---|
| ATOM | 660 | CB | LEU | 99 | 23.047 | −11.079 | 34.023 | 1.00 | 33.40 | U1 |
| ATOM | 661 | CG | LEU | 99 | 21.707 | −10.842 | 34.738 | 1.00 | 33.40 | U1 |
| ATOM | 662 | CD1 | LEU | 99 | 21.242 | −12.082 | 35.432 | 1.00 | 33.40 | U1 |
| ATOM | 663 | CD2 | LEU | 99 | 21.823 | −9.691 | 35.733 | 1.00 | 33.40 | U1 |
| ATOM | 664 | C | LEU | 99 | 22.079 | −12.156 | 31.968 | 1.00 | 34.91 | U1 |
| ATOM | 665 | O | LEU | 99 | 21.291 | −13.082 | 31.837 | 1.00 | 34.91 | U1 |
| ATOM | 666 | N | MET | 100 | 22.062 | −11.082 | 31.188 | 1.00 | 29.87 | U1 |
| ATOM | 668 | CA | MET | 100 | 21.048 | −10.888 | 30.153 | 1.00 | 29.87 | U1 |
| ATOM | 669 | CB | MET | 100 | 21.425 | −9.690 | 29.298 | 1.00 | 33.35 | U1 |
| ATOM | 670 | CG | MET | 100 | 21.472 | −8.391 | 30.083 | 1.00 | 33.35 | U1 |
| ATOM | 671 | SD | MET | 100 | 19.869 | −7.915 | 30.752 | 1.00 | 33.35 | U1 |
| ATOM | 672 | CE | MET | 100 | 20.055 | −8.339 | 32.383 | 1.00 | 33.35 | U1 |
| ATOM | 673 | C | MET | 100 | 20.876 | −12.123 | 29.278 | 1.00 | 29.87 | U1 |
| ATOM | 674 | O | MET | 100 | 19.760 | −12.593 | 29.049 | 1.00 | 29.87 | U1 |
| ATOM | 675 | N | ARG | 101 | 21.996 | −12.675 | 28.832 | 1.00 | 41.51 | U1 |
| ATOM | 677 | CA | ARG | 101 | 22.014 | −13.869 | 27.990 | 1.00 | 41.51 | U1 |
| ATOM | 678 | CB | ARG | 101 | 23.463 | −14.313 | 27.783 | 1.00 | 77.75 | U1 |
| ATOM | 679 | CG | ARG | 101 | 23.678 | −15.589 | 26.988 | 1.00 | 77.75 | U1 |
| ATOM | 680 | CD | ARG | 101 | 25.184 | −15.884 | 26.847 | 1.00 | 77.75 | U1 |
| ATOM | 681 | NE | ARG | 101 | 25.901 | −14.774 | 26.214 | 1.00 | 77.75 | U1 |
| ATOM | 683 | CZ | ARG | 101 | 27.224 | −14.683 | 26.114 | 1.00 | 77.75 | U1 |
| ATOM | 684 | NH1 | ARG | 101 | 28.000 | −15.638 | 26.608 | 1.00 | 77.75 | U1 |
| ATOM | 687 | NH2 | ARG | 101 | 27.772 | −13.637 | 25.506 | 1.00 | 77.75 | U1 |
| ATOM | 690 | C | ARG | 101 | 21.217 | −14.976 | 28.661 | 1.00 | 41.51 | U1 |
| ATOM | 691 | O | ARG | 101 | 20.260 | −15.483 | 28.089 | 1.00 | 41.51 | U1 |
| ATOM | 692 | N | ASP | 102 | 21.555 | −15.283 | 29.912 | 1.00 | 43.30 | U1 |
| ATOM | 694 | CA | ASP | 102 | 20.868 | −16.345 | 30.647 | 1.00 | 43.30 | U1 |
| ATOM | 695 | CB | ASP | 102 | 21.572 | −16.653 | 31.972 | 1.00 | 74.78 | U1 |
| ATOM | 696 | CG | ASP | 102 | 23.088 | −16.711 | 31.837 | 1.00 | 74.78 | U1 |
| ATOM | 697 | OD1 | ASP | 102 | 23.760 | −16.234 | 32.770 | 1.00 | 74.78 | U1 |
| ATOM | 698 | OD2 | ASP | 102 | 23.615 | −17.208 | 30.812 | 1.00 | 74.78 | U1 |
| ATOM | 699 | C | ASP | 102 | 19.404 | −16.024 | 30.905 | 1.00 | 43.30 | U1 |
| ATOM | 700 | O | ASP | 102 | 18.561 | −16.924 | 30.830 | 1.00 | 43.30 | U1 |
| ATOM | 701 | N | VAL | 103 | 19.090 | −14.760 | 31.203 | 1.00 | 41.55 | U1 |
| ATOM | 703 | CA | VAL | 103 | 17.706 | −14.353 | 31.452 | 1.00 | 41.55 | U1 |
| ATOM | 704 | CB | VAL | 103 | 17.612 | −12.919 | 32.018 | 1.00 | 34.14 | U1 |
| ATOM | 705 | CG1 | VAL | 103 | 16.267 | −12.291 | 31.681 | 1.00 | 34.14 | U1 |
| ATOM | 706 | CG2 | VAL | 103 | 17.766 | −12.953 | 33.525 | 1.00 | 34.14 | U1 |
| ATOM | 707 | C | VAL | 103 | 16.841 | −14.506 | 30.196 | 1.00 | 41.55 | U1 |
| ATOM | 708 | O | VAL | 103 | 15.636 | −14.786 | 30.294 | 1.00 | 41.55 | U1 |
| ATOM | 709 | N | SER | 104 | 17.445 | −14.348 | 29.017 | 1.00 | 43.61 | U1 |
| ATOM | 711 | CA | SER | 104 | 16.701 | −14.519 | 27.762 | 1.00 | 43.61 | U1 |
| ATOM | 712 | CB | SER | 104 | 17.422 | −13.849 | 26.581 | 1.00 | 45.37 | U1 |
| ATOM | 713 | OG | SER | 104 | 18.790 | −14.212 | 26.491 | 1.00 | 45.37 | U1 |
| ATOM | 715 | C | SER | 104 | 16.455 | −15.998 | 27.475 | 1.00 | 43.61 | U1 |
| ATOM | 716 | O | SER | 104 | 15.592 | −16.354 | 26.666 | 1.00 | 43.61 | U1 |
| ATOM | 717 | N | LYS | 105 | 17.224 | −16.851 | 28.148 | 1.00 | 61.00 | U1 |
| ATOM | 719 | CA | LYS | 105 | 17.113 | −18.300 | 28.014 | 1.00 | 61.00 | U1 |
| ATOM | 720 | CB | LYS | 105 | 18.406 | −18.974 | 28.505 | 1.00 | 108.85 | U1 |
| ATOM | 721 | CG | LYS | 105 | 18.327 | −20.491 | 28.721 | 1.00 | 108.85 | U1 |
| ATOM | 722 | CD | LYS | 105 | 17.731 | −20.856 | 30.094 | 1.00 | 108.85 | U1 |
| ATOM | 723 | CE | LYS | 105 | 16.855 | −22.113 | 30.011 | 1.00 | 108.85 | U1 |
| ATOM | 724 | NZ | LYS | 105 | 15.825 | −22.200 | 31.100 | 1.00 | 108.85 | U1 |
| ATOM | 728 | C | LYS | 105 | 15.908 | −18.801 | 28.805 | 1.00 | 61.00 | U1 |
| ATOM | 729 | O | LYS | 105 | 15.247 | −19.757 | 28.394 | 1.00 | 61.00 | U1 |
| ATOM | 730 | N | GLU | 106 | 15.656 | −18.191 | 29.963 | 1.00 | 52.38 | U1 |
| ATOM | 732 | CA | GLU | 106 | 14.529 | −18.582 | 30.806 | 1.00 | 52.38 | U1 |
| ATOM | 733 | CB | GLU | 106 | 14.280 | −17.555 | 31.900 | 1.00 | 42.85 | U1 |
| ATOM | 734 | CG | GLU | 106 | 15.297 | −17.567 | 33.003 | 1.00 | 42.85 | U1 |
| ATOM | 735 | CD | GLU | 106 | 14.796 | −16.873 | 34.256 | 1.00 | 42.85 | U1 |
| ATOM | 736 | OE1 | GLU | 106 | 15.644 | −16.402 | 35.041 | 1.00 | 42.85 | U1 |
| ATOM | 737 | OE2 | GLU | 106 | 13.562 | −16.803 | 34.464 | 1.00 | 42.85 | U1 |
| ATOM | 738 | C | GLU | 106 | 13.265 | −18.723 | 29.984 | 1.00 | 52.38 | U1 |
| ATOM | 739 | O | GLU | 106 | 13.041 | −17.983 | 29.025 | 1.00 | 52.38 | U1 |
| ATOM | 740 | N | ASP | 107 | 12.442 | −19.687 | 30.342 | 1.00 | 45.40 | U1 |
| ATOM | 742 | CA | ASP | 107 | 11.211 | −19.900 | 29.624 | 1.00 | 45.40 | U1 |
| ATOM | 743 | CB | ASP | 107 | 10.697 | −21.297 | 29.927 | 1.00 | 70.17 | U1 |
| ATOM | 744 | CG | ASP | 107 | 9.375 | −21.570 | 29.284 | 1.00 | 70.17 | U1 |
| ATOM | 745 | OD1 | ASP | 107 | 8.395 | −21.806 | 30.017 | 1.00 | 70.17 | U1 |
| ATOM | 746 | OD2 | ASP | 107 | 9.317 | −21.542 | 28.043 | 1.00 | 70.17 | U1 |
| ATOM | 747 | C | ASP | 107 | 10.241 | −18.860 | 30.141 | 1.00 | 45.40 | U1 |
| ATOM | 748 | O | ASP | 107 | 9.788 | −18.961 | 31.272 | 1.00 | 45.40 | U1 |
| ATOM | 749 | N | HIS | 108 | 9.938 | −17.839 | 29.354 | 1.00 | 38.43 | U1 |
| ATOM | 751 | CA | HIS | 108 | 9.012 | −16.823 | 29.834 | 1.00 | 38.43 | U1 |
| ATOM | 752 | CB | HIS | 108 | 9.436 | −15.431 | 29.391 | 1.00 | 32.58 | U1 |
| ATOM | 753 | CG | HIS | 108 | 10.789 | −15.014 | 29.879 | 1.00 | 32.58 | U1 |
| ATOM | 754 | CD2 | HIS | 108 | 12.031 | −15.320 | 29.427 | 1.00 | 32.58 | U1 |

TABLE 1-continued

Structure coordinates of CPP32

| ATOM | 755 | ND1 | HIS | 108 | 10.966 | −14.093 | 30.891 | 1.00 | 32.58 | U1 |
|------|-----|-----|-----|-----|--------|---------|--------|------|-------|-----|
| ATOM | 757 | CE1 | HIS | 108 | 12.257 | −13.847 | 31.037 | 1.00 | 32.58 | U1 |
| ATOM | 758 | NE2 | HIS | 108 | 12.924 | −14.578 | 30.160 | 1.00 | 32.58 | U1 |
| ATOM | 760 | C | HIS | 108 | 7.579 | −17.072 | 29.409 | 1.00 | 38.43 | U1 |
| ATOM | 761 | O | HIS | 108 | 6.746 | −16.169 | 29.435 | 1.00 | 38.43 | U1 |
| ATOM | 762 | N | SER | 109 | 7.262 | −18.318 | 29.112 | 1.00 | 52.54 | U1 |
| ATOM | 764 | CA | SER | 109 | 5.923 | −18.669 | 28.680 | 1.00 | 52.54 | U1 |
| ATOM | 765 | CB | SER | 109 | 5.818 | −20.178 | 28.541 | 1.00 | 63.72 | U1 |
| ATOM | 766 | OG | SER | 109 | 6.869 | −20.663 | 27.725 | 1.00 | 63.72 | U1 |
| ATOM | 768 | C | SER | 109 | 4.775 | −18.155 | 29.537 | 1.00 | 52.54 | U1 |
| ATOM | 769 | O | SER | 109 | 3.840 | −17.560 | 29.016 | 1.00 | 52.54 | U1 |
| ATOM | 770 | N | LYS | 110 | 4.842 | −18.365 | 30.844 | 1.00 | 38.95 | U1 |
| ATOM | 772 | CA | LYS | 110 | 3.757 | −17.938 | 31.714 | 1.00 | 38.95 | U1 |
| ATOM | 773 | CB | LYS | 110 | 3.527 | −18.987 | 32.798 | 1.00 | 91.15 | U1 |
| ATOM | 774 | CG | LYS | 110 | 3.707 | −20.429 | 32.349 | 1.00 | 91.15 | U1 |
| ATOM | 775 | CD | LYS | 110 | 3.265 | −21.410 | 33.445 | 1.00 | 91.15 | U1 |
| ATOM | 776 | CE | LYS | 110 | 1.754 | −21.316 | 33.684 | 1.00 | 91.15 | U1 |
| ATOM | 777 | NZ | LYS | 110 | 1.216 | −22.165 | 34.790 | 1.00 | 91.15 | U1 |
| ATOM | 781 | C | LYS | 110 | 3.914 | −16.557 | 32.371 | 1.00 | 38.95 | U1 |
| ATOM | 782 | O | LYS | 110 | 3.359 | −16.314 | 33.453 | 1.00 | 38.95 | U1 |
| ATOM | 783 | N | ARG | 111 | 4.662 | −15.652 | 31.749 | 1.00 | 31.49 | U1 |
| ATOM | 785 | CA | ARG | 111 | 4.834 | −14.321 | 32.315 | 1.00 | 31.49 | U1 |
| ATOM | 786 | CB | ARG | 111 | 6.303 | −13.984 | 32.490 | 1.00 | 37.94 | U1 |
| ATOM | 787 | CG | ARG | 111 | 7.127 | −15.025 | 33.177 | 1.00 | 37.94 | U1 |
| ATOM | 788 | CD | ARG | 111 | 8.450 | −14.417 | 33.463 | 1.00 | 37.94 | U1 |
| ATOM | 789 | NE | ARG | 111 | 9.527 | −15.384 | 33.571 | 1.00 | 37.94 | U1 |
| ATOM | 791 | CZ | ARG | 111 | 9.877 | −15.980 | 34.698 | 1.00 | 37.94 | U1 |
| ATOM | 792 | NH1 | ARG | 111 | 9.215 | −15.725 | 35.820 | 1.00 | 37.94 | U1 |
| ATOM | 795 | NH2 | ARG | 111 | 10.958 | −16.745 | 34.725 | 1.00 | 37.94 | U1 |
| ATOM | 798 | C | ARG | 111 | 4.253 | −13.332 | 31.344 | 1.00 | 31.49 | U1 |
| ATOM | 799 | O | ARG | 111 | 4.422 | −13.473 | 30.150 | 1.00 | 31.49 | U1 |
| ATOM | 800 | N | SER | 112 | 3.617 | −12.298 | 31.848 | 1.00 | 26.48 | U1 |
| ATOM | 802 | CA | SER | 112 | 3.044 | −11.308 | 30.981 | 1.00 | 26.48 | U1 |
| ATOM | 803 | CB | SER | 112 | 1.946 | −10.583 | 31.735 | 1.00 | 38.19 | U1 |
| ATOM | 804 | OG | SER | 112 | 1.058 | −11.527 | 32.333 | 1.00 | 38.19 | U1 |
| ATOM | 806 | C | SER | 112 | 4.060 | −10.313 | 30.390 | 1.00 | 26.48 | U1 |
| ATOM | 807 | O | SER | 112 | 3.948 | −9.970 | 29.204 | 1.00 | 26.48 | U1 |
| ATOM | 808 | N | SER | 113 | 5.021 | −9.827 | 31.200 | 1.00 | 33.02 | U1 |
| ATOM | 810 | CA | SER | 113 | 6.059 | −8.871 | 30.734 | 1.00 | 33.02 | U1 |
| ATOM | 811 | CB | SER | 113 | 5.657 | −7.421 | 31.065 | 1.00 | 23.22 | U1 |
| ATOM | 812 | OG | SER | 113 | 5.272 | −7.290 | 32.412 | 1.00 | 23.22 | U1 |
| ATOM | 814 | C | SER | 113 | 7.507 | −9.124 | 31.207 | 1.00 | 33.02 | U1 |
| ATOM | 815 | O | SER | 113 | 7.814 | −10.162 | 31.794 | 1.00 | 33.02 | U1 |
| ATOM | 816 | N | PHE | 114 | 8.412 | −8.210 | 30.859 | 1.00 | 27.59 | U1 |
| ATOM | 818 | CA | PHE | 114 | 9.806 | −8.296 | 31.259 | 1.00 | 27.59 | U1 |
| ATOM | 819 | CB | PHE | 114 | 10.690 | −8.897 | 30.175 | 1.00 | 22.83 | U1 |
| ATOM | 820 | CG | PHE | 114 | 12.179 | −8.802 | 30.489 | 1.00 | 22.83 | U1 |
| ATOM | 821 | CD1 | PHE | 114 | 12.757 | −9.603 | 31.496 | 1.00 | 22.83 | U1 |
| ATOM | 822 | CD2 | PHE | 114 | 12.993 | −7.903 | 29.815 | 1.00 | 22.83 | U1 |
| ATOM | 823 | CE1 | PHE | 114 | 14.112 | −9.495 | 31.818 | 1.00 | 22.83 | U1 |
| ATOM | 824 | CE2 | PHE | 114 | 14.354 | −7.795 | 30.132 | 1.00 | 22.83 | U1 |
| ATOM | 825 | CZ | PHE | 114 | 14.905 | −8.588 | 31.132 | 1.00 | 22.83 | U1 |
| ATOM | 826 | C | PHE | 114 | 10.297 | −6.901 | 31.493 | 1.00 | 27.59 | U1 |
| ATOM | 827 | O | PHE | 114 | 10.231 | −6.070 | 30.580 | 1.00 | 27.59 | U1 |
| ATOM | 828 | N | VAL | 115 | 10.816 | −6.629 | 32.690 | 1.00 | 26.17 | U1 |
| ATOM | 830 | CA | VAL | 115 | 11.341 | −5.300 | 32.995 | 1.00 | 26.17 | U1 |
| ATOM | 831 | CB | VAL | 115 | 10.587 | −4.643 | 34.154 | 1.00 | 15.31 | U1 |
| ATOM | 832 | CG1 | VAL | 115 | 11.155 | −3.271 | 34.417 | 1.00 | 15.31 | U1 |
| ATOM | 833 | CG2 | VAL | 115 | 9.106 | −4.523 | 33.836 | 1.00 | 15.31 | U1 |
| ATOM | 834 | C | VAL | 115 | 12.813 | −5.385 | 33.373 | 1.00 | 26.17 | U1 |
| ATOM | 835 | O | VAL | 115 | 13.212 | −6.278 | 34.109 | 1.00 | 26.17 | U1 |
| ATOM | 836 | N | CYS | 116 | 13.621 | −4.455 | 32.888 | 1.00 | 14.15 | U1 |
| ATOM | 838 | CA | CYS | 116 | 15.038 | −4.446 | 33.221 | 1.00 | 14.15 | U1 |
| ATOM | 839 | CB | CYS | 116 | 15.852 | −4.995 | 32.065 | 1.00 | 32.15 | U1 |
| ATOM | 840 | SG | CYS | 116 | 17.609 | −5.059 | 32.386 | 1.00 | 32.15 | U1 |
| ATOM | 841 | C | CYS | 116 | 15.405 | −3.003 | 33.486 | 1.00 | 14.15 | U1 |
| ATOM | 842 | O | CYS | 116 | 15.140 | −2.144 | 32.650 | 1.00 | 14.15 | U1 |
| ATOM | 843 | N | VAL | 117 | 15.892 | −2.719 | 34.694 | 1.00 | 25.35 | U1 |
| ATOM | 845 | CA | VAL | 117 | 16.276 | −1.351 | 35.072 | 1.00 | 25.35 | U1 |
| ATOM | 846 | CB | VAL | 117 | 15.757 | −0.982 | 36.457 | 1.00 | 19.60 | U1 |
| ATOM | 847 | CG1 | VAL | 117 | 15.883 | 0.477 | 36.659 | 1.00 | 19.60 | U1 |
| ATOM | 848 | CG2 | VAL | 117 | 14.305 | −1.391 | 36.642 | 1.00 | 19.60 | U1 |
| ATOM | 849 | C | VAL | 117 | 17.792 | −1.342 | 35.162 | 1.00 | 25.35 | U1 |
| ATOM | 850 | O | VAL | 117 | 18.378 | −2.275 | 35.715 | 1.00 | 25.35 | U1 |
| ATOM | 851 | N | LEU | 118 | 18.445 | −0.331 | 34.606 | 1.00 | 22.47 | U1 |
| ATOM | 853 | CA | LEU | 118 | 19.902 | −0.281 | 34.648 | 1.00 | 22.47 | U1 |
| ATOM | 854 | CB | LEU | 118 | 20.472 | −0.278 | 33.234 | 1.00 | 23.18 | U1 |

TABLE 1-continued

Structure coordinates of CPP32

| ATOM | 855 | CG | LEU | 118 | 20.218 | −1.461 | 32.305 | 1.00 | 23.18 | U1 |
|---|---|---|---|---|---|---|---|---|---|---|
| ATOM | 856 | CD1 | LEU | 118 | 20.428 | −0.993 | 30.895 | 1.00 | 23.18 | U1 |
| ATOM | 857 | CD2 | LEU | 118 | 21.138 | −2.637 | 32.612 | 1.00 | 23.18 | U1 |
| ATOM | 858 | C | LEU | 118 | 20.282 | 1.019 | 35.328 | 1.00 | 22.47 | U1 |
| ATOM | 859 | O | LEU | 118 | 19.943 | 2.095 | 34.828 | 1.00 | 22.47 | U1 |
| ATOM | 860 | N | LEU | 119 | 20.944 | 0.943 | 36.480 | 1.00 | 22.41 | U1 |
| ATOM | 862 | CA | LEU | 119 | 21.352 | 2.159 | 37.184 | 1.00 | 22.41 | U1 |
| ATOM | 863 | CB | LEU | 119 | 20.774 | 2.163 | 38.589 | 1.00 | 18.82 | U1 |
| ATOM | 864 | CG | LEU | 119 | 19.260 | 1.974 | 38.565 | 1.00 | 18.82 | U1 |
| ATOM | 865 | CD1 | LEU | 119 | 18.771 | 1.478 | 39.889 | 1.00 | 18.82 | U1 |
| ATOM | 866 | CD2 | LEU | 119 | 18.601 | 3.258 | 38.186 | 1.00 | 18.82 | U1 |
| ATOM | 867 | C | LEU | 119 | 22.866 | 2.146 | 37.211 | 1.00 | 22.41 | U1 |
| ATOM | 868 | O | LEU | 119 | 23.485 | 1.262 | 37.860 | 1.00 | 22.41 | U1 |
| ATOM | 869 | N | SER | 120 | 23.469 | 3.069 | 36.461 | 1.00 | 21.77 | U1 |
| ATOM | 871 | CA | SER | 120 | 24.912 | 3.138 | 36.377 | 1.00 | 21.77 | U1 |
| ATOM | 872 | CB | SER | 120 | 25.408 | 1.916 | 35.634 | 1.00 | 29.08 | U1 |
| ATOM | 873 | OG | SER | 120 | 26.787 | 1.996 | 35.388 | 1.00 | 29.08 | U1 |
| ATOM | 875 | C | SER | 120 | 25.296 | 4.386 | 35.633 | 1.00 | 21.77 | U1 |
| ATOM | 876 | O | SER | 120 | 24.444 | 5.247 | 35.419 | 1.00 | 21.77 | U1 |
| ATOM | 877 | N | HIS | 121 | 26.578 | 4.533 | 35.307 | 1.00 | 23.45 | U1 |
| ATOM | 879 | CA | HIS | 121 | 27.069 | 5.690 | 34.550 | 1.00 | 23.45 | U1 |
| ATOM | 880 | CB | HIS | 121 | 28.577 | 5.878 | 34.764 | 1.00 | 29.01 | U1 |
| ATOM | 881 | CG | HIS | 121 | 28.946 | 6.552 | 36.047 | 1.00 | 29.01 | U1 |
| ATOM | 882 | CD2 | HIS | 121 | 29.441 | 6.053 | 37.211 | 1.00 | 29.01 | U1 |
| ATOM | 883 | ND1 | HIS | 121 | 28.867 | 7.917 | 36.221 | 1.00 | 29.01 | U1 |
| ATOM | 885 | CE1 | HIS | 121 | 29.294 | 8.229 | 37.434 | 1.00 | 29.01 | U1 |
| ATOM | 886 | NE2 | HIS | 121 | 29.648 | 7.114 | 38.053 | 1.00 | 29.01 | U1 |
| ATOM | 888 | C | HIS | 121 | 26.877 | 5.367 | 33.063 | 1.00 | 23.45 | U1 |
| ATOM | 889 | O | HIS | 121 | 26.653 | 4.204 | 32.680 | 1.00 | 23.45 | U1 |
| ATOM | 890 | N | GLY | 122 | 27.058 | 6.356 | 32.204 | 1.00 | 27.37 | U1 |
| ATOM | 892 | CA | GLY | 122 | 26.923 | 6.062 | 30.803 | 1.00 | 27.37 | U1 |
| ATOM | 893 | C | GLY | 122 | 27.175 | 7.196 | 29.844 | 1.00 | 27.37 | U1 |
| ATOM | 894 | O | GLY | 122 | 27.521 | 8.316 | 30.232 | 1.00 | 27.37 | U1 |
| ATOM | 895 | N | GLU | 123 | 26.998 | 6.859 | 28.572 | 1.00 | 35.34 | U1 |
| ATOM | 897 | CA | GLU | 123 | 27.166 | 7.745 | 27.437 | 1.00 | 35.34 | U1 |
| ATOM | 898 | CB | GLU | 123 | 28.528 | 7.522 | 26.785 | 1.00 | 67.96 | U1 |
| ATOM | 899 | CC | GLU | 123 | 29.706 | 7.994 | 27.605 | 1.00 | 67.96 | U1 |
| ATOM | 900 | CD | GLU | 123 | 31.037 | 7.637 | 26.973 | 1.00 | 67.96 | U1 |
| ATOM | 901 | OE1 | GLU | 123 | 31.093 | 7.484 | 25.732 | 1.00 | 67.96 | U1 |
| ATOM | 902 | OE2 | GLU | 123 | 32.029 | 7.506 | 27.721 | 1.00 | 67.96 | U1 |
| ATOM | 903 | C | GLU | 123 | 26.078 | 7.305 | 26.455 | 1.00 | 35.34 | U1 |
| ATOM | 904 | O | GLU | 123 | 25.373 | 6.313 | 26.698 | 1.00 | 35.34 | U1 |
| ATOM | 905 | N | GLU | 124 | 25.957 | 8.001 | 25.330 | 1.00 | 37.39 | U1 |
| ATOM | 907 | CA | GLU | 124 | 24.940 | 7.626 | 24.381 | 1.00 | 37.39 | U1 |
| ATOM | 908 | CB | GLU | 124 | 24.966 | 8.502 | 23.146 | 1.00 | 34.88 | U1 |
| ATOM | 909 | CG | GLU | 124 | 23.769 | 8.253 | 22.251 | 1.00 | 34.88 | U1 |
| ATOM | 910 | CD | GLU | 124 | 22.461 | 8.584 | 22.913 | 1.00 | 34.88 | U1 |
| ATOM | 911 | OE1 | GLU | 124 | 22.074 | 9.765 | 22.835 | 1.00 | 34.88 | U1 |
| ATOM | 912 | OE2 | GLU | 124 | 21.824 | 7.674 | 23.500 | 1.00 | 34.88 | U1 |
| ATOM | 913 | C | GLU | 124 | 25.122 | 6.174 | 24.004 | 1.00 | 37.39 | U1 |
| ATOM | 914 | O | GLU | 124 | 26.243 | 5.704 | 23.781 | 1.00 | 37.39 | U1 |
| ATOM | 915 | N | GLY | 125 | 24.017 | 5.444 | 24.063 | 1.00 | 33.78 | U1 |
| ATOM | 917 | CA | GLY | 125 | 24.028 | 4.033 | 23.741 | 1.00 | 33.78 | U1 |
| ATOM | 918 | C | GLY | 125 | 25.023 | 3.226 | 24.539 | 1.00 | 33.78 | U1 |
| ATOM | 919 | O | GLY | 125 | 25.251 | 2.050 | 24.224 | 1.00 | 33.78 | U1 |
| ATOM | 920 | N | ILE | 126 | 25.520 | 3.795 | 25.631 | 1.00 | 34.22 | U1 |
| ATOM | 922 | CA | ILE | 126 | 26.516 | 3.120 | 26.460 | 1.00 | 34.22 | U1 |
| ATOM | 923 | CB | ILE | 126 | 27.919 | 3.782 | 26.228 | 1.00 | 39.22 | U1 |
| ATOM | 924 | CG2 | ILE | 126 | 28.935 | 3.366 | 27.299 | 1.00 | 39.22 | U1 |
| ATOM | 925 | CG1 | ILE | 126 | 28.428 | 3.475 | 24.821 | 1.00 | 39.22 | U1 |
| ATOM | 926 | CD1 | ILE | 126 | 29.514 | 4.404 | 24.396 | 1.00 | 39.22 | U1 |
| ATOM | 927 | C | ILE | 126 | 26.209 | 3.183 | 27.947 | 1.00 | 34.22 | U1 |
| ATOM | 928 | O | ILE | 126 | 25.787 | 4.232 | 28.432 | 1.00 | 34.22 | U1 |
| ATOM | 929 | N | ILE | 127 | 26.303 | 2.037 | 28.634 | 1.00 | 26.98 | U1 |
| ATOM | 931 | CA | ILE | 127 | 26.159 | 2.011 | 30.094 | 1.00 | 26.98 | U1 |
| ATOM | 932 | CB | ILE | 127 | 24.902 | 1.335 | 30.661 | 1.00 | 40.58 | U1 |
| ATOM | 933 | CG2 | ILE | 127 | 23.660 | 1.984 | 30.146 | 1.00 | 40.58 | U1 |
| ATOM | 934 | CG1 | ILE | 127 | 24.954 | −0.170 | 30.483 | 1.00 | 40.58 | U1 |
| ATOM | 935 | CD1 | ILE | 127 | 24.159 | −0.885 | 31.559 | 1.00 | 40.58 | U1 |
| ATOM | 936 | C | ILE | 127 | 27.370 | 1.279 | 30.637 | 1.00 | 26.98 | U1 |
| ATOM | 937 | O | ILE | 127 | 27.837 | 0.315 | 30.040 | 1.00 | 26.98 | U1 |
| ATOM | 938 | N | PHE | 128 | 27.877 | 1.746 | 31.772 | 1.00 | 30.45 | U1 |
| ATOM | 940 | CA | PHE | 128 | 29.061 | 1.156 | 32.392 | 1.00 | 30.45 | U1 |
| ATOM | 941 | CB | PHE | 128 | 29.861 | 2.201 | 33.178 | 1.00 | 31.96 | U1 |
| ATOM | 942 | CG | PHE | 128 | 30.687 | 3.098 | 32.331 | 1.00 | 31.96 | U1 |
| ATOM | 943 | CD1 | PHE | 128 | 30.099 | 3.935 | 31.405 | 1.00 | 31.96 | U1 |
| ATOM | 944 | CD2 | PHE | 128 | 32.058 | 3.087 | 32.444 | 1.00 | 31.96 | U1 |

TABLE 1-continued

Structure coordinates of CPP32

| ATOM | 945 | CE1 | PHE | 128 | 30.859 | 4.748 | 30.596 | 1.00 | 31.96 | U1 |
|---|---|---|---|---|---|---|---|---|---|---|
| ATOM | 946 | CE2 | PHE | 128 | 32.827 | 3.898 | 31.636 | 1.00 | 31.96 | U1 |
| ATOM | 947 | CZ | PHE | 128 | 32.220 | 4.731 | 30.707 | 1.00 | 31.96 | U1 |
| ATOM | 948 | C | PHE | 128 | 28.857 | 0.010 | 33.343 | 1.00 | 30.45 | U1 |
| ATOM | 949 | O | PHE | 128 | 27.905 | −0.030 | 34.136 | 1.00 | 30.45 | U1 |
| ATOM | 950 | N | GLY | 129 | 29.794 | −0.921 | 33.250 | 1.00 | 28.56 | U1 |
| ATOM | 952 | CA | GLY | 129 | 29.853 | −2.038 | 34.167 | 1.00 | 28.56 | U1 |
| ATOM | 953 | C | GLY | 129 | 30.855 | −1.451 | 35.155 | 1.00 | 28.56 | U1 |
| ATOM | 954 | O | GLY | 129 | 31.361 | −0.327 | 34.942 | 1.00 | 28.56 | U1 |
| ATOM | 955 | N | THR | 130 | 31.179 | −2.186 | 36.211 | 1.00 | 42.87 | U1 |
| ATOM | 957 | CA | THR | 130 | 32.125 | −1.691 | 37.210 | 1.00 | 42.87 | U1 |
| ATOM | 958 | CB | THR | 130 | 32.187 | −2.603 | 38.371 | 1.00 | 23.57 | U1 |
| ATOM | 959 | OG1 | TER | 130 | 32.557 | −3.900 | 37.885 | 1.00 | 23.57 | U1 |
| ATOM | 961 | CG2 | THR | 130 | 30.831 | −2.664 | 39.066 | 1.00 | 23.57 | U1 |
| ATOM | 962 | C | THR | 130 | 33.542 | −1.624 | 36.673 | 1.00 | 42.87 | U1 |
| ATOM | 963 | O | THR | 130 | 34.412 | −1.020 | 37.300 | 1.00 | 42.87 | U1 |
| ATOM | 964 | N | ASN | 131 | 33.790 | −2.258 | 35.535 | 1.00 | 45.88 | U1 |
| ATOM | 966 | CA | ASN | 131 | 35.126 | −2.248 | 34.973 | 1.00 | 45.88 | U1 |
| ATOM | 967 | CB | ASN | 131 | 35.712 | −3.644 | 35.046 | 1.00 | 41.02 | U1 |
| ATOM | 968 | CG | ASN | 131 | 35.036 | −4.589 | 34.094 | 1.00 | 41.02 | U1 |
| ATOM | 969 | OD1 | ASN | 131 | 33.890 | −4.387 | 33.712 | 1.00 | 41.02 | U1 |
| ATOM | 970 | ND2 | ASN | 131 | 35.741 | −5.623 | 33.697 | 1.00 | 41.02 | U1 |
| ATOM | 973 | C | ASN | 131 | 35.200 | −1.763 | 33.537 | 1.00 | 45.88 | U1 |
| ATOM | 974 | O | ASN | 131 | 36.201 | −2.005 | 32.870 | 1.00 | 45.88 | U1 |
| ATOM | 975 | N | GLY | 132 | 34.161 | −1.083 | 33.057 | 1.00 | 37.49 | U1 |
| ATOM | 977 | CA | GLY | 132 | 34.178 | −0.590 | 31.679 | 1.00 | 37.49 | U1 |
| ATOM | 978 | C | GLY | 132 | 32.842 | −0.574 | 30.954 | 1.00 | 37.49 | U1 |
| ATOM | 979 | O | GLY | 132 | 31.939 | −1.336 | 31.294 | 1.00 | 37.49 | U1 |
| ATOM | 980 | N | PRO | 133 | 32.715 | 0.212 | 29.883 | 1.00 | 38.59 | U1 |
| ATOM | 981 | CD | PRO | 133 | 33.821 | 0.872 | 29.171 | 1.00 | 36.92 | U1 |
| ATOM | 982 | CA | PRO | 133 | 31.476 | 0.321 | 29.113 | 1.00 | 38.59 | U1 |
| ATOM | 983 | CB | PRO | 133 | 31.866 | 1.303 | 28.025 | 1.00 | 36.92 | U1 |
| ATOM | 984 | CG | PRO | 133 | 33.300 | 0.937 | 27.784 | 1.00 | 36.92 | U1 |
| ATOM | 985 | C | PRO | 133 | 30.953 | −0.969 | 28.511 | 1.00 | 38.59 | U1 |
| ATOM | 986 | O | PRO | 133 | 31.664 | −1.953 | 28.439 | 1.00 | 38.59 | U1 |
| ATOM | 987 | N | VAL | 134 | 29.669 | −0.980 | 28.172 | 1.00 | 36.90 | U1 |
| ATOM | 989 | CA | VAL | 134 | 29.020 | −2.108 | 27.513 | 1.00 | 36.90 | U1 |
| ATOM | 990 | CB | VAL | 134 | 28.507 | −3.181 | 28.463 | 1.00 | 36.16 | U1 |
| ATOM | 991 | CG1 | VAL | 134 | 27.348 | −2.689 | 29.272 | 1.00 | 36.16 | U1 |
| ATOM | 992 | CG2 | VAL | 134 | 28.107 | −4.376 | 27.658 | 1.00 | 36.16 | U1 |
| ATOM | 993 | C | VAL | 134 | 27.881 | −1.523 | 26.683 | 1.00 | 36.90 | U1 |
| ATOM | 994 | O | VAL | 134 | 27.047 | −0.756 | 27.171 | 1.00 | 36.90 | U1 |
| ATOM | 995 | N | ASP | 135 | 27.909 | −1.810 | 25.395 | 1.00 | 48.82 | U1 |
| ATOM | 997 | CA | ASP | 135 | 26.929 | −1.280 | 24.469 | 1.00 | 48.82 | U1 |
| ATOM | 998 | CB | ASP | 135 | 27.308 | −1.724 | 23.060 | 1.00 | 78.66 | U1 |
| ATOM | 999 | CG | ASP | 135 | 26.518 | −1.022 | 22.005 | 1.00 | 78.66 | U1 |
| ATOM | 1000 | OD1 | ASP | 135 | 25.704 | −1.697 | 21.343 | 1.00 | 78.66 | U1 |
| ATOM | 1001 | OD2 | ASP | 135 | 26.710 | 0.203 | 21.842 | 1.00 | 78.66 | U1 |
| ATOM | 1002 | C | ASP | 135 | 25.519 | −1.741 | 24.794 | 1.00 | 48.82 | U1 |
| ATOM | 1003 | O | ASP | 135 | 25.321 | −2.915 | 25.104 | 1.00 | 48.82 | U1 |
| ATOM | 1004 | N | LEU | 136 | 24.547 | −0.828 | 24.711 | 1.00 | 31.71 | U1 |
| ATOM | 1006 | CA | LEU | 136 | 23.138 | −1.166 | 24.962 | 1.00 | 31.71 | U1 |
| ATOM | 1007 | CB | LEU | 136 | 22.285 | 0.101 | 25.022 | 1.00 | 29.10 | U1 |
| ATOM | 1008 | CG | LEU | 136 | 21.970 | 0.614 | 26.427 | 1.00 | 29.10 | U1 |
| ATOM | 1009 | CD1 | LEU | 136 | 21.551 | 2.068 | 26.385 | 1.00 | 29.10 | U1 |
| ATOM | 1010 | CD2 | LEU | 136 | 20.897 | −0.245 | 27.055 | 1.00 | 29.10 | U1 |
| ATOM | 1011 | C | LEU | 136 | 22.536 | −2.147 | 23.929 | 1.00 | 31.71 | U1 |
| ATOM | 1012 | O | LEU | 136 | 21.708 | −3.001 | 24.277 | 1.00 | 31.71 | U1 |
| ATOM | 1013 | N | LYS | 137 | 22.940 | −2.041 | 22.666 | 1.00 | 33.22 | U1 |
| ATOM | 1015 | CA | LYS | 137 | 22.412 | −2.935 | 21.651 | 1.00 | 33.22 | U1 |
| ATOM | 1016 | CB | LYS | 137 | 22.871 | −2.535 | 20.254 | 1.00 | 98.07 | U1 |
| ATOM | 1017 | CG | LYS | 137 | 21.740 | −2.390 | 19.250 | 1.00 | 98.07 | U1 |
| ATOM | 1018 | CD | LYS | 137 | 20.940 | −1.099 | 19.465 | 1.00 | 98.07 | U1 |
| ATOM | 1019 | CE | LYS | 137 | 20.015 | −1.144 | 20.687 | 1.00 | 98.07 | U1 |
| ATOM | 1020 | NZ | LYS | 137 | 19.375 | 0.176 | 20.970 | 1.00 | 98.07 | U1 |
| ATOM | 1024 | C | LYS | 137 | 22.805 | −4.362 | 21.935 | 1.00 | 33.22 | U1 |
| ATOM | 1025 | O | LYS | 137 | 22.122 | −5.290 | 21.511 | 1.00 | 33.22 | U1 |
| ATOM | 1026 | N | LYS | 138 | 23.892 | −4.551 | 22.669 | 1.00 | 28.73 | U1 |
| ATOM | 1028 | CA | LYS | 138 | 24.340 | −5.898 | 23.002 | 1.00 | 28.73 | U1 |
| ATOM | 1029 | CB | LYS | 138 | 25.754 | −5.878 | 23.575 | 1.00 | 62.80 | U1 |
| ATOM | 1030 | CG | LYS | 138 | 26.470 | −7.220 | 23.561 | 1.00 | 62.80 | U1 |
| ATOM | 1031 | CD | LYS | 138 | 27.908 | −7.039 | 24.005 | 1.00 | 62.80 | U1 |
| ATOM | 1032 | CE | LYS | 138 | 28.843 | −8.023 | 23.322 | 1.00 | 62.80 | U1 |
| ATOM | 1033 | NZ | LYS | 138 | 30.279 | −7.789 | 23.690 | 1.00 | 62.80 | U1 |
| ATOM | 1037 | C | LYS | 138 | 23.405 | −6.520 | 24.004 | 1.00 | 28.73 | U1 |
| ATOM | 1038 | O | LYS | 138 | 23.087 | −7.688 | 23.885 | 1.00 | 28.73 | U1 |
| ATOM | 1039 | N | ILE | 139 | 22.931 | −5.711 | 24.952 | 1.00 | 29.19 | U1 |

TABLE 1-continued

Structure coordinates of CPP32

| | | | | | | | | | |
|---|---|---|---|---|---|---|---|---|---|
| ATOM | 1041 | CA | ILE | 139 | 22.026 | −6.140 | 26.027 | 1.00 | 29.19 U1 |
| ATOM | 1042 | CB | ILE | 139 | 21.878 | −5.032 | 27.102 | 1.00 | 33.91 U1 |
| ATOM | 1043 | CG2 | ILE | 139 | 20.853 | −5.436 | 28.159 | 1.00 | 33.91 U1 |
| ATOM | 1044 | CG1 | ILE | 139 | 23.215 | −4.732 | 27.767 | 1.00 | 33.91 U1 |
| ATOM | 1045 | CD1 | ILE | 139 | 23.097 | −3.725 | 28.900 | 1.00 | 33.91 U1 |
| ATOM | 1046 | C | ILE | 139 | 20.629 | −6.420 | 25.498 | 1.00 | 29.19 U1 |
| ATOM | 1047 | O | ILE | 139 | 20.053 | −7.482 | 25.722 | 1.00 | 29.19 U1 |
| ATOM | 1048 | N | THR | 140 | 20.080 | −5.393 | 24.865 | 1.00 | 32.07 U1 |
| ATOM | 1050 | CA | THR | 140 | 18.757 | −5.355 | 24.256 | 1.00 | 32.07 U1 |
| ATOM | 1051 | CB | THR | 140 | 18.634 | −4.000 | 23.548 | 1.00 | 37.13 U1 |
| ATOM | 1052 | OG1 | THR | 140 | 18.025 | −3.057 | 24.427 | 1.00 | 37.13 U1 |
| ATOM | 1054 | CG2 | THR | 140 | 17.878 | −4.089 | 22.249 | 1.00 | 37.13 U1 |
| ATOM | 1055 | C | THR | 140 | 18.438 | −6.483 | 23.266 | 1.00 | 32.07 U1 |
| ATOM | 1056 | O | THR | 140 | 17.357 | −7.066 | 23.288 | 1.00 | 32.07 U1 |
| ATOM | 1057 | N | ASN | 141 | 19.387 | −6.802 | 22.401 | 1.00 | 39.82 U1 |
| ATOM | 1059 | CA | ASN | 141 | 19.155 | −7.816 | 21.384 | 1.00 | 39.82 U1 |
| ATOM | 1060 | CB | ASN | 141 | 20.294 | −7.842 | 20.351 | 1.00 | 60.27 U1 |
| ATOM | 1061 | CG | ASN | 141 | 20.341 | −6.578 | 19.472 | 1.00 | 60.27 U1 |
| ATOM | 1062 | OD1 | ASN | 141 | 21.339 | −6.326 | 18.803 | 1.00 | 60.27 U1 |
| ATOM | 1063 | ND2 | ASN | 141 | 19.267 | −5.793 | 19.468 | 1.00 | 60.27 U1 |
| ATOM | 1066 | C | ASN | 141 | 18.823 | −9.212 | 21.859 | 1.00 | 39.82 U1 |
| ATOM | 1067 | O | ASN | 141 | 18.104 | −9.926 | 21.173 | 1.00 | 39.82 U1 |
| ATOM | 1068 | N | PHE | 142 | 19.294 | −9.613 | 23.030 | 1.00 | 35.54 U1 |
| ATOM | 1070 | CA | PHE | 142 | 18.985 | −10.964 | 23.502 | 1.00 | 35.54 U1 |
| ATOM | 1071 | CB | PHE | 142 | 19.565 | −11.252 | 24.906 | 1.00 | 36.20 U1 |
| ATOM | 1072 | CG | PHE | 142 | 21.070 | −11.315 | 24.968 | 1.00 | 36.20 U1 |
| ATOM | 1073 | CD1 | PHE | 142 | 21.800 | −10.262 | 25.488 | 1.00 | 36.20 U1 |
| ATOM | 1074 | CD2 | PHE | 142 | 21.750 | −12.428 | 24.528 | 1.00 | 36.20 U1 |
| ATOM | 1075 | CE1 | PHE | 142 | 23.186 | −10.321 | 25.565 | 1.00 | 36.20 U1 |
| ATOM | 1076 | CE2 | PHE | 142 | 23.135 | −12.489 | 24.603 | 1.00 | 36.20 U1 |
| ATOM | 1077 | CZ | PHE | 142 | 23.853 | −11.435 | 25.121 | 1.00 | 36.20 U1 |
| ATOM | 1078 | C | PHE | 142 | 17.473 | −11.070 | 23.576 | 1.00 | 35.54 U1 |
| ATOM | 1079 | O | PHE | 142 | 16.912 | −12.156 | 23.491 | 1.00 | 35.54 U1 |
| ATOM | 1080 | N | PHE | 143 | 16.813 | −9.925 | 23.701 | 1.00 | 34.98 U1 |
| ATOM | 1082 | CA | PHE | 143 | 15.366 | −9.896 | 23.823 | 1.00 | 34.98 U1 |
| ATOM | 1083 | CB | PHE | 143 | 14.983 | −8.894 | 24.908 | 1.00 | 23.95 U1 |
| ATOM | 1084 | CG | PHE | 143 | 15.491 | −9.287 | 26.244 | 1.00 | 23.95 U1 |
| ATOM | 1085 | CD1 | PHE | 143 | 16.667 | −8.752 | 26.732 | 1.00 | 23.95 U1 |
| ATOM | 1086 | CD2 | PHE | 143 | 14.875 | −10.317 | 26.952 | 1.00 | 23.95 U1 |
| ATOM | 1087 | CE1 | PHE | 143 | 17.225 | −9.238 | 27.883 | 1.00 | 23.95 U1 |
| ATOM | 1088 | CE2 | PHE | 143 | 15.429 | −10.811 | 28.107 | 1.00 | 23.95 U1 |
| ATOM | 1089 | CZ | PHE | 143 | 16.609 | −10.274 | 28.574 | 1.00 | 23.95 U1 |
| ATOM | 1090 | C | PHE | 143 | 14.556 | −9.670 | 22.554 | 1.00 | 34.98 U1 |
| ATOM | 1091 | O | PHE | 143 | 13.357 | −9.450 | 22.625 | 1.00 | 34.98 U1 |
| ATOM | 1092 | N | ARG | 144 | 15.191 | −9.750 | 21.391 | 1.00 | 41.51 U1 |
| ATOM | 1094 | CA | ARG | 144 | 14.470 | −9.539 | 20.148 | 1.00 | 41.51 U1 |
| ATOM | 1095 | CB | ARG | 144 | 15.423 | −9.517 | 18.978 | 1.00 | 49.58 U1 |
| ATOM | 1096 | CG | ARG | 144 | 15.952 | −8.142 | 18.693 | 1.00 | 49.58 U1 |
| ATOM | 1097 | CD | ARG | 144 | 16.949 | −8.192 | 17.588 | 1.00 | 49.58 U1 |
| ATOM | 1098 | NE | ARG | 144 | 16.602 | −9.256 | 16.666 | 1.00 | 49.58 U1 |
| ATOM | 1100 | CZ | ARG | 144 | 17.419 | −9.701 | 15.725 | 1.00 | 49.58 U1 |
| ATOM | 1101 | NH1 | ARG | 144 | 18.626 | −9.155 | 15.589 | 1.00 | 49.58 U1 |
| ATOM | 1104 | NH2 | ARG | 144 | 17.030 | −10.687 | 14.923 | 1.00 | 49.58 U1 |
| ATOM | 1107 | C | ARG | 144 | 13.431 | −10.615 | 19.956 | 1.00 | 41.51 U1 |
| ATOM | 1108 | O | ARG | 144 | 13.643 | −11.768 | 20.326 | 1.00 | 41.51 U1 |
| ATOM | 1109 | N | GLY | 145 | 12.310 | −10.234 | 19.360 | 1.00 | 55.99 U1 |
| ATOM | 1111 | CA | GLY | 145 | 11.210 | −11.158 | 19.148 | 1.00 | 55.99 U1 |
| ATOM | 1112 | C | GLY | 145 | 11.512 | −12.473 | 18.456 | 1.00 | 55.99 U1 |
| ATOM | 1113 | O | GLY | 145 | 10.682 | −13.384 | 18.484 | 1.00 | 55.99 U1 |
| ATOM | 1114 | N | ASP | 146 | 12.666 | −12.573 | 17.814 | 1.00 | 52.04 U1 |
| ATOM | 1116 | CA | ASP | 146 | 13.041 | −13.800 | 17.127 | 1.00 | 52.04 U1 |
| ATOM | 1117 | CB | ASP | 146 | 13.573 | −13.463 | 15.747 | 1.00 | 63.02 U1 |
| ATOM | 1118 | CG | ASP | 146 | 14.857 | −12.663 | 15.799 | 1.00 | 63.02 U1 |
| ATOM | 1119 | OD1 | ASP | 146 | 15.718 | −12.918 | 14.938 | 1.00 | 63.02 U1 |
| ATOM | 1120 | OD2 | ASP | 146 | 15.008 | −11.775 | 16.673 | 1.00 | 63.02 U1 |
| ATOM | 1121 | C | ASP | 146 | 14.114 | −14.545 | 17.898 | 1.00 | 52.04 U1 |
| ATOM | 1122 | O | ASP | 146 | 14.506 | −15.651 | 17.526 | 1.00 | 52.04 U1 |
| ATOM | 1123 | N | ARG | 147 | 14.643 | −13.895 | 18.930 | 1.00 | 43.93 U1 |
| ATOM | 1125 | CA | ARG | 147 | 15.684 | −14.474 | 19.762 | 1.00 | 43.93 U1 |
| ATOM | 1126 | CB | ARG | 147 | 16.701 | −13.410 | 20.139 | 1.00 | 56.55 U1 |
| ATOM | 1127 | CG | ARG | 147 | 18.102 | −13.946 | 20.262 | 1.00 | 56.55 U1 |
| ATOM | 1128 | CD | ARG | 147 | 18.928 | −13.560 | 19.055 | 1.00 | 56.55 U1 |
| ATOM | 1129 | NE | ARG | 147 | 19.163 | −12.128 | 19.035 | 1.00 | 56.55 U1 |
| ATOM | 1131 | CZ | ARG | 147 | 20.016 | −11.527 | 18.219 | 1.00 | 56.55 U1 |
| ATOM | 1132 | NH1 | ARG | 147 | 20.720 | −12.234 | 17.345 | 1.00 | 56.55 U1 |
| ATOM | 1135 | NH2 | ARG | 147 | 20.175 | −10.217 | 18.295 | 1.00 | 56.55 U1 |
| ATOM | 1138 | C | ARG | 147 | 15.078 | −15.055 | 21.026 | 1.00 | 43.93 U1 |

TABLE 1-continued

Structure coordinates of CPP32

| | | | | | | | | | |
|---|---|---|---|---|---|---|---|---|---|
| ATOM | 1139 | O | ARG | 147 | 15.216 | −16.239 | 21.305 | 1.00 | 43.93 U1 |
| ATOM | 1140 | N | CYS | 148 | 14.379 | −14.229 | 21.786 | 1.00 | 51.03 U1 |
| ATOM | 1142 | CA | CYS | 148 | 13.771 | −14.706 | 23.016 | 1.00 | 51.03 U1 |
| ATOM | 1143 | CB | CYS | 148 | 13.897 | −13.649 | 24.112 | 1.00 | 42.58 U1 |
| ATOM | 1144 | SG | CYS | 148 | 13.019 | −14.086 | 25.626 | 1.00 | 42.58 U1 |
| ATOM | 1145 | C | CYS | 148 | 12.308 | −15.067 | 22.755 | 1.00 | 51.03 U1 |
| ATOM | 1146 | O | CYS | 148 | 11.381 | −14.442 | 23.293 | 1.00 | 51.03 U1 |
| ATOM | 1147 | N | ARG | 149 | 12.102 | −16.137 | 21.995 | 1.00 | 48.73 U1 |
| ATOM | 1149 | CA | ARG | 149 | 10.759 | −16.563 | 21.617 | 1.00 | 48.73 U1 |
| ATOM | 1150 | CB | ARG | 149 | 10.804 | −17.944 | 20.970 | 1.00 | 97.02 U1 |
| ATOM | 1151 | CG | ARG | 149 | 10.793 | −17.924 | 19.445 | 1.00 | 97.02 U1 |
| ATOM | 1152 | CD | ARG | 149 | 9.489 | −17.334 | 18.915 | 1.00 | 97.02 U1 |
| ATOM | 1153 | NE | ARG | 149 | 9.293 | −17.622 | 17.497 | 1.00 | 97.02 U1 |
| ATOM | 1155 | CZ | ARG | 149 | 8.120 | −17.558 | 16.876 | 1.00 | 97.02 U1 |
| ATOM | 1156 | NH1 | ARG | 149 | 7.029 | −17.209 | 17.542 | 1.00 | 97.02 U1 |
| ATOM | 1159 | NH2 | ARG | 149 | 8.033 | −17.870 | 15.591 | 1.00 | 97.02 U1 |
| ATOM | 1162 | C | ARG | 149 | 9.625 | −16.498 | 22.636 | 1.00 | 48.73 U1 |
| ATOM | 1163 | O | ARG | 149 | 8.508 | −16.132 | 22.276 | 1.00 | 48.73 U1 |
| ATOM | 1164 | N | SER | 150 | 9.883 | −16.812 | 23.901 | 1.00 | 34.60 U1 |
| ATOM | 1166 | CA | SER | 150 | 8.796 | −16.781 | 24.875 | 1.00 | 34.60 U1 |
| ATOM | 1167 | CB | SER | 150 | 9.085 | −17.694 | 26.058 | 1.00 | 35.23 U1 |
| ATOM | 1168 | OG | SER | 150 | 10.314 | −17.367 | 26.668 | 1.00 | 35.23 U1 |
| ATOM | 1170 | C | SER | 150 | 8.389 | −15.394 | 25.357 | 1.00 | 34.60 U1 |
| ATOM | 1171 | O | SER | 150 | 7.768 | −15.268 | 26.417 | 1.00 | 34.60 U1 |
| ATOM | 1172 | N | LEU | 151 | 8.781 | −14.356 | 24.619 | 1.00 | 41.78 U1 |
| ATOM | 1174 | CA | LEU | 151 | 8.395 | −12.975 | 24.938 | 1.00 | 41.78 U1 |
| ATOM | 1175 | CB | LEU | 151 | 9.554 | −12.143 | 25.495 | 1.00 | 27.20 U1 |
| ATOM | 1176 | CG | LEU | 151 | 9.791 | −12.197 | 26.999 | 1.00 | 27.20 U1 |
| ATOM | 1177 | CD1 | LEU | 151 | 10.863 | −11.199 | 27.330 | 1.00 | 27.20 U1 |
| ATOM | 1178 | CD2 | LEU | 151 | 8.505 | −11.876 | 27.763 | 1.00 | 27.20 U1 |
| ATOM | 1179 | C | LEU | 151 | 7.855 | −12.269 | 23.697 | 1.00 | 41.78 U1 |
| ATOM | 1180 | O | LEU | 151 | 7.529 | −11.076 | 23.757 | 1.00 | 41.78 U1 |
| ATOM | 1181 | N | THR | 152 | 7.774 | −12.994 | 22.578 | 1.00 | 36.01 U1 |
| ATOM | 1183 | CA | THR | 152 | 7.275 | −12.432 | 21.325 | 1.00 | 36.01 U1 |
| ATOM | 1184 | CB | THR | 152 | 7.323 | −13.479 | 20.186 | 1.00 | 32.89 U1 |
| ATOM | 1185 | OG1 | THR | 152 | 8.663 | −13.985 | 20.036 | 1.00 | 32.89 U1 |
| ATOM | 1187 | CG2 | THR | 152 | 6.874 | −12.854 | 18.875 | 1.00 | 32.89 U1 |
| ATOM | 1188 | C | THR | 152 | 5.838 | −12.030 | 21.612 | 1.00 | 36.01 U1 |
| ATOM | 1189 | O | THR | 152 | 5.117 | −12.790 | 22.234 | 1.00 | 36.01 U1 |
| ATOM | 1190 | N | GLY | 153 | 5.445 | −10.814 | 21.237 | 1.00 | 23.22 U1 |
| ATOM | 1192 | CA | GLY | 153 | 4.088 | −10.356 | 21.511 | 1.00 | 23.22 U1 |
| ATOM | 1193 | C | GLY | 153 | 3.915 | −9.796 | 22.922 | 1.00 | 23.22 U1 |
| ATOM | 1194 | O | GLY | 153 | 2.843 | −9.279 | 23.280 | 1.00 | 23.22 U1 |
| ATOM | 1195 | N | LYS | 154 | 4.959 | −9.906 | 23.740 | 1.00 | 23.10 U1 |
| ATOM | 1197 | CA | LYS | 154 | 4.895 | −9.415 | 25.111 | 1.00 | 23.10 U1 |
| ATOM | 1198 | CB | LYS | 154 | 5.407 | −10.486 | 26.086 | 1.00 | 17.21 U1 |
| ATOM | 1199 | CG | LYS | 154 | 4.567 | −11.755 | 26.096 | 1.00 | 17.21 U1 |
| ATOM | 1200 | CD | LYS | 154 | 5.001 | −12.686 | 27.183 | 1.00 | 17.21 U1 |
| ATOM | 1201 | CE | LYS | 154 | 4.302 | −14.030 | 27.029 | 1.00 | 17.21 U1 |
| ATOM | 1202 | NZ | LYS | 154 | 4.782 | −15.063 | 27.985 | 1.00 | 17.21 U1 |
| ATOM | 1206 | C | LYS | 154 | 5.698 | −8.141 | 25.232 | 1.00 | 23.10 U1 |
| ATOM | 1207 | O | LYS | 154 | 6.670 | −7.963 | 24.516 | 1.00 | 23.10 U1 |
| ATOM | 1208 | N | PRO | 155 | 5.326 | −7.246 | 26.150 | 1.00 | 17.32 U1 |
| ATOM | 1209 | CD | PRO | 155 | 4.233 | −7.352 | 27.125 | 1.00 | 14.71 U1 |
| ATOM | 1210 | CA | PRO | 155 | 6.046 | −5.989 | 26.321 | 1.00 | 17.32 U1 |
| ATOM | 1211 | CB | PRO | 155 | 5.155 | −5.220 | 27.295 | 1.00 | 14.71 U1 |
| ATOM | 1212 | CG | PRO | 155 | 3.804 | −5.928 | 27.234 | 1.00 | 14.71 U1 |
| ATOM | 1213 | C | PRO | 155 | 7.417 | −6.195 | 26.944 | 1.00 | 17.32 U1 |
| ATOM | 1214 | O | PRO | 155 | 7.556 | −6.977 | 27.871 | 1.00 | 17.32 U1 |
| ATOM | 1215 | N | LYS | 156 | 8.424 | −5.463 | 26.478 | 1.00 | 21.35 U1 |
| ATOM | 1217 | CA | LYS | 156 | 9.759 | −5.578 | 27.041 | 1.00 | 21.35 U1 |
| ATOM | 1218 | CB | LYS | 156 | 10.691 | −6.188 | 26.026 | 1.00 | 27.26 U1 |
| ATOM | 1219 | CG | LYS | 156 | 10.223 | −7.556 | 25.553 | 1.00 | 27.26 U1 |
| ATOM | 1220 | CD | LYS | 156 | 10.913 | −7.940 | 24.257 | 1.00 | 27.26 U1 |
| ATOM | 1221 | CE | LYS | 156 | 10.154 | −9.031 | 23.513 | 1.00 | 27.26 U1 |
| ATOM | 1222 | NZ | LYS | 156 | 8.801 | −8.622 | 23.165 | 1.00 | 27.26 U1 |
| ATOM | 1226 | C | LYS | 156 | 10.207 | −4.193 | 27.436 | 1.00 | 21.35 U1 |
| ATOM | 1227 | O | LYS | 156 | 10.577 | −3.399 | 26.589 | 1.00 | 21.35 U1 |
| ATOM | 1228 | N | LEU | 157 | 10.159 | −3.900 | 28.732 | 1.00 | 23.32 U1 |
| ATOM | 1230 | CA | LEU | 157 | 10.491 | −2.573 | 29.236 | 1.00 | 23.32 U1 |
| ATOM | 1231 | CB | LEU | 157 | 9.522 | −2.172 | 30.337 | 1.00 | 33.17 U1 |
| ATOM | 1232 | CG | LEU | 157 | 8.044 | −1.936 | 29.998 | 1.00 | 33.17 U1 |
| ATOM | 1233 | CD1 | LEU | 157 | 7.483 | −2.912 | 28.980 | 1.00 | 33.17 U1 |
| ATOM | 1234 | CD2 | LEU | 157 | 7.251 | −2.011 | 31.279 | 1.00 | 33.17 U1 |
| ATOM | 1235 | C | LEU | 157 | 11.903 | −2.439 | 29.742 | 1.00 | 23.32 U1 |
| ATOM | 1236 | O | LEU | 157 | 12.362 | −3.286 | 30.489 | 1.00 | 23.32 U1 |
| ATOM | 1237 | N | PHE | 158 | 12.587 | −1.380 | 29.313 | 1.00 | 18.94 U1 |

TABLE 1-continued

Structure coordinates of CPP32

| | | | | | | | | | |
|---|---|---|---|---|---|---|---|---|---|
| ATOM | 1239 | CA | PHE | 158 | 13.951 | −1.103 | 29.716 | 1.00 | 18.94 U1 |
| ATOM | 1240 | CB | PHE | 158 | 14.921 | −1.199 | 28.532 | 1.00 | 22.16 U1 |
| ATOM | 1241 | CG | PHE | 158 | 15.313 | −2.602 | 28.189 | 1.00 | 22.16 U1 |
| ATOM | 1242 | CD1 | PHE | 158 | 14.542 | −3.360 | 27.290 | 1.00 | 22.16 U1 |
| ATOM | 1243 | CD2 | PHE | 158 | 16.391 | −3.209 | 28.822 | 1.00 | 22.16 U1 |
| ATOM | 1244 | CE1 | PHE | 158 | 14.832 | −4.718 | 27.039 | 1.00 | 22.16 U1 |
| ATOM | 1245 | CE2 | PHE | 158 | 16.687 | −4.558 | 28.579 | 1.00 | 22.16 U1 |
| ATOM | 1246 | CZ | PHE | 158 | 15.901 | −5.308 | 27.688 | 1.00 | 22.16 U1 |
| ATOM | 1247 | C | PHE | 158 | 13.974 | 0.297 | 30.284 | 1.00 | 18.94 U1 |
| ATOM | 1248 | O | PHE | 158 | 13.696 | 1.265 | 29.572 | 1.00 | 18.94 U1 |
| ATOM | 1249 | N | ILE | 159 | 14.201 | 0.398 | 31.586 | 1.00 | 28.54 U1 |
| ATOM | 1251 | CA | ILE | 159 | 14.254 | 1.689 | 32.244 | 1.00 | 28.54 U1 |
| ATOM | 1252 | CB | ILE | 159 | 13.470 | 1.671 | 33.576 | 1.00 | 19.72 U1 |
| ATOM | 1253 | CG2 | ILE | 159 | 13.669 | 2.945 | 34.319 | 1.00 | 19.72 U1 |
| ATOM | 1254 | CG1 | ILE | 159 | 11.973 | 1.537 | 33.297 | 1.00 | 19.72 U1 |
| ATOM | 1255 | CD1 | ILE | 159 | 11.284 | 0.457 | 34.092 | 1.00 | 19.72 U1 |
| ATOM | 1256 | C | ILE | 159 | 15.738 | 1.920 | 32.473 | 1.00 | 28.54 U1 |
| ATOM | 1257 | O | ILE | 159 | 16.418 | 1.080 | 33.074 | 1.00 | 28.54 U1 |
| ATOM | 1258 | N | ILE | 160 | 16.242 | 3.059 | 32.026 | 1.00 | 19.74 U1 |
| ATOM | 1260 | CA | ILE | 160 | 17.651 | 3.344 | 32.129 | 1.00 | 19.74 U1 |
| ATOM | 1261 | CB | ILE | 160 | 18.257 | 3.378 | 30.744 | 1.00 | 21.32 U1 |
| ATOM | 1262 | CG2 | ILE | 160 | 19.729 | 3.647 | 30.822 | 1.00 | 21.32 U1 |
| ATOM | 1263 | CG1 | ILE | 160 | 17.982 | 2.069 | 30.021 | 1.00 | 21.32 U1 |
| ATOM | 1264 | CD1 | ILE | 160 | 17.785 | 2.248 | 28.545 | 1.00 | 21.32 U1 |
| ATOM | 1265 | C | ILE | 160 | 18.007 | 4.670 | 32.758 | 1.00 | 19.74 U1 |
| ATOM | 1266 | O | ILE | 160 | 17.670 | 5.728 | 32.213 | 1.00 | 19.74 U1 |
| ATOM | 1267 | N | GLN | 161 | 18.754 | 4.626 | 33.863 | 1.00 | 21.74 U1 |
| ATOM | 1269 | CA | GLN | 161 | 19.216 | 5.851 | 34.527 | 1.00 | 21.74 U1 |
| ATOM | 1270 | CB | GLN | 161 | 18.934 | 5.793 | 36.032 | 1.00 | 19.19 U1 |
| ATOM | 1271 | CG | GLN | 161 | 19.597 | 6.876 | 36.864 | 1.00 | 19.19 U1 |
| ATOM | 1272 | CD | GLN | 161 | 19.170 | 8.272 | 36.490 | 1.00 | 19.19 U1 |
| ATOM | 1273 | OE1 | GLN | 161 | 18.009 | 8.526 | 36.253 | 1.00 | 19.19 U1 |
| ATOM | 1274 | NE2 | GLN | 161 | 20.121 | 9.184 | 36.426 | 1.00 | 19.19 U1 |
| ATOM | 1277 | C | GLN | 161 | 20.724 | 5.957 | 34.227 | 1.00 | 21.74 U1 |
| ATOM | 1278 | O | GLN | 161 | 21.522 | 5.193 | 34.752 | 1.00 | 21.74 U1 |
| ATOM | 1279 | N | ALA | 162 | 21.092 | 6.870 | 33.335 | 1.00 | 17.69 U1 |
| ATOM | 1281 | CA | ALA | 162 | 22.465 | 7.052 | 32.943 | 1.00 | 17.69 U1 |
| ATOM | 1282 | CB | ALA | 162 | 22.882 | 5.892 | 32.158 | 1.00 | 8.04 U1 |
| ATOM | 1283 | C | ALA | 162 | 22.510 | 8.279 | 32.078 | 1.00 | 17.69 U1 |
| ATOM | 1284 | O | ALA | 162 | 21.493 | 8.661 | 31.497 | 1.00 | 17.69 U1 |
| ATOM | 1285 | N | CYS | 163 | 23.650 | 8.958 | 32.040 | 1.00 | 26.61 U1 |
| ATOM | 1287 | CA | CYS | 163 | 23.778 | 10.140 | 31.193 | 1.00 | 26.61 U1 |
| ATOM | 1288 | C | CYS | 163 | 23.806 | 9.651 | 29.752 | 1.00 | 26.61 U1 |
| ATOM | 1289 | O | CYS | 163 | 24.181 | 8.507 | 29.483 | 1.00 | 26.61 U1 |
| ATOM | 1290 | CB | CYS | 163 | 25.092 | 10.880 | 31.472 | 1.00 | 34.71 U1 |
| ATOM | 1291 | SG | CYS | 163 | 25.326 | 11.511 | 33.142 | 1.00 | 34.71 U1 |
| ATOM | 1292 | N | ARG | 164 | 23.442 | 10.511 | 28.814 | 1.00 | 28.51 U1 |
| ATOM | 1294 | CA | ARG | 164 | 23.478 | 10.122 | 27.404 | 1.00 | 28.51 U1 |
| ATOM | 1295 | CB | ARG | 164 | 22.065 | 10.170 | 26.813 | 1.00 | 27.51 U1 |
| ATOM | 1296 | CG | ARG | 164 | 21.181 | 9.009 | 27.253 | 1.00 | 27.51 U1 |
| ATOM | 1297 | CD | ARG | 164 | 19.752 | 9.184 | 26.777 | 1.00 | 27.51 U1 |
| ATOM | 1298 | NE | ARG | 164 | 19.495 | 8.488 | 25.519 | 1.00 | 27.51 U1 |
| ATOM | 1300 | CZ | ARG | 164 | 18.438 | 8.700 | 24.734 | 1.00 | 27.51 U1 |
| ATOM | 1301 | NH1 | ARG | 164 | 17.512 | 9.592 | 25.050 | 1.00 | 27.51 U1 |
| ATOM | 1304 | NH2 | ARG | 164 | 18.311 | 8.017 | 23.610 | 1.00 | 27.51 U1 |
| ATOM | 1307 | C | ARG | 164 | 24.414 | 11.041 | 26.631 | 1.00 | 28.51 U1 |
| ATOM | 1308 | O | ARG | 164 | 24.238 | 11.239 | 25.443 | 1.00 | 28.51 U1 |
| ATOM | 1309 | N | GLY | 165 | 25.398 | 11.616 | 27.310 | 1.00 | 26.42 U1 |
| ATOM | 1311 | CA | GLY | 165 | 26.318 | 12.541 | 26.671 | 1.00 | 26.42 U1 |
| ATOM | 1312 | C | GLY | 165 | 26.669 | 13.640 | 27.666 | 1.00 | 26.42 U1 |
| ATOM | 1313 | O | GLY | 165 | 26.459 | 13.445 | 28.855 | 1.00 | 26.42 U1 |
| ATOM | 1314 | N | THR | 166 | 27.139 | 14.801 | 27.212 | 1.00 | 38.33 U1 |
| ATOM | 1316 | CA | THR | 166 | 27.521 | 15.870 | 28.133 | 1.00 | 38.33 U1 |
| ATOM | 1317 | CB | THR | 166 | 29.045 | 16.111 | 28.152 | 1.00 | 42.76 U1 |
| ATOM | 1318 | OG1 | THR | 166 | 29.466 | 16.599 | 26.876 | 1.00 | 42.76 U1 |
| ATOM | 1320 | CG2 | THR | 166 | 29.802 | 14.838 | 28.470 | 1.00 | 42.76 U1 |
| ATOM | 1321 | C | THR | 166 | 26.884 | 17.224 | 27.876 | 1.00 | 38.33 U1 |
| ATOM | 1322 | O | THR | 166 | 27.354 | 18.228 | 28.413 | 1.00 | 38.33 U1 |
| ATOM | 1323 | N | GLU | 167 | 25.861 | 17.281 | 27.029 | 1.00 | 33.15 U1 |
| ATOM | 1325 | CA | GLU | 167 | 25.207 | 18.551 | 26.768 | 1.00 | 33.15 U1 |
| ATOM | 1326 | CB | GLU | 167 | 24.207 | 18.425 | 25.622 | 1.00 | 97.95 U1 |
| ATOM | 1327 | CG | GLU | 167 | 24.456 | 19.417 | 24.485 | 1.00 | 97.95 U1 |
| ATOM | 1328 | CD | GLU | 167 | 23.394 | 20.515 | 24.381 | 1.00 | 97.95 U1 |
| ATOM | 1329 | OE1 | GLU | 167 | 23.175 | 21.253 | 25.368 | 1.00 | 97.95 U1 |
| ATOM | 1330 | OE2 | GLU | 167 | 22.783 | 20.649 | 23.296 | 1.00 | 97.95 U1 |
| ATOM | 1331 | C | GLU | 167 | 24.498 | 18.921 | 28.052 | 1.00 | 33.15 U1 |
| ATOM | 1332 | O | GLU | 167 | 24.068 | 18.044 | 28.787 | 1.00 | 33.15 U1 |

TABLE 1-continued

Structure coordinates of CPP32

| | | | | | | | | | |
|---|---|---|---|---|---|---|---|---|---|
| ATOM | 1333 | N | LEU | 168 | 24.432 | 20.209 | 28.354 | 1.00 | 32.47 U1 |
| ATOM | 1335 | CA | LEU | 168 | 23.775 | 20.679 | 29.566 | 1.00 | 32.47 U1 |
| ATOM | 1336 | CB | LEU | 168 | 24.703 | 21.617 | 30.361 | 1.00 | 34.34 U1 |
| ATOM | 1337 | CG | LEU | 168 | 26.010 | 21.103 | 30.978 | 1.00 | 34.34 U1 |
| ATOM | 1338 | CD1 | LEU | 168 | 27.032 | 22.224 | 31.034 | 1.00 | 34.34 U1 |
| ATOM | 1339 | CD2 | LEU | 168 | 25.770 | 20.542 | 32.347 | 1.00 | 34.34 U1 |
| ATOM | 1340 | C | LEU | 168 | 22.528 | 21.449 | 29.184 | 1.00 | 32.47 U1 |
| ATOM | 1341 | O | LEU | 168 | 22.571 | 22.324 | 28.313 | 1.00 | 32.47 U1 |
| ATOM | 1342 | N | ASP | 169 | 21.430 | 21.148 | 29.858 | 1.00 | 29.51 U1 |
| ATOM | 1344 | CA | ASP | 169 | 20.168 | 21.821 | 29.610 | 1.00 | 29.51 U1 |
| ATOM | 1345 | CB | ASP | 169 | 19.020 | 20.798 | 29.654 | 1.00 | 18.98 U1 |
| ATOM | 1346 | CG | ASP | 169 | 17.686 | 21.396 | 29.296 | 1.00 | 18.98 U1 |
| ATOM | 1347 | OD1 | ASP | 169 | 16.789 | 20.669 | 28.827 | 1.00 | 18.98 U1 |
| ATOM | 1348 | OD2 | ASP | 169 | 17.520 | 22.607 | 29.489 | 1.00 | 18.98 U1 |
| ATOM | 1349 | C | ASP | 169 | 20.049 | 22.837 | 30.735 | 1.00 | 29.51 U1 |
| ATOM | 1350 | O | ASP | 169 | 20.012 | 22.475 | 31.910 | 1.00 | 29.51 U1 |
| ATOM | 1351 | N | CYS | 170 | 20.016 | 24.110 | 30.378 | 1.00 | 42.41 U1 |
| ATOM | 1353 | CA | CYS | 170 | 19.923 | 25.207 | 31.353 | 1.00 | 42.41 U1 |
| ATOM | 1354 | CB | CYS | 170 | 20.829 | 26.380 | 30.914 | 1.00 | 52.09 U1 |
| ATOM | 1355 | SG | CYS | 170 | 22.631 | 26.001 | 30.720 | 1.00 | 52.09 U1 |
| ATOM | 1356 | C | CYS | 170 | 18.509 | 25.751 | 31.612 | 1.00 | 42.41 U1 |
| ATOM | 1357 | O | CYS | 170 | 18.372 | 26.836 | 32.163 | 1.00 | 42.41 U1 |
| ATOM | 1358 | N | GLY | 171 | 17.474 | 25.018 | 31.211 | 1.00 | 42.03 U1 |
| ATOM | 1360 | CA | GLY | 171 | 16.096 | 25.462 | 31.416 | 1.00 | 42.03 U1 |
| ATOM | 1361 | C | GLY | 171 | 15.672 | 26.742 | 30.703 | 1.00 | 42.03 U1 |
| ATOM | 1362 | O | GLY | 171 | 16.473 | 27.348 | 29.985 | 1.00 | 42.03 U1 |
| ATOM | 1363 | N | ILE | 172 | 14.410 | 27.141 | 30.871 | 1.00 | 51.65 U1 |
| ATOM | 1365 | CA | ILE | 172 | 13.871 | 28.372 | 30.255 | 1.00 | 51.65 U1 |
| ATOM | 1366 | CB | ILE | 172 | 13.517 | 28.175 | 28.742 | 1.00 | 50.46 U1 |
| ATOM | 1367 | CG2 | ILE | 172 | 12.342 | 27.215 | 28.586 | 1.00 | 50.46 U1 |
| ATOM | 1368 | CG1 | ILE | 172 | 13.130 | 29.512 | 28.086 | 1.00 | 50.46 U1 |
| ATOM | 1369 | CD1 | ILE | 172 | 14.261 | 30.529 | 27.985 | 1.00 | 50.46 U1 |
| ATOM | 1370 | C | ILE | 172 | 12.597 | 28.845 | 30.966 | 1.00 | 51.65 U1 |
| ATOM | 1371 | O | ILE | 172 | 11.984 | 28.083 | 31.716 | 1.00 | 51.65 U1 |
| ATOM | 1372 | N | GLU | 173 | 12.229 | 30.104 | 30.734 | 1.00 | 79.66 U1 |
| ATOM | 1374 | CA | GLU | 173 | 11.028 | 30.708 | 31.292 | 1.00 | 79.66 U1 |
| ATOM | 1375 | CB | GLU | 173 | 9.779 | 30.012 | 30.741 | 1.00 | 125.39 U1 |
| ATOM | 1376 | CG | GLU | 173 | 8.462 | 30.633 | 31.190 | 1.00 | 125.39 U1 |
| ATOM | 1377 | CD | GLU | 173 | 7.298 | 30.266 | 30.276 | 1.00 | 125.39 U1 |
| ATOM | 1378 | OE1 | GLU | 173 | 6.713 | 31.186 | 29.661 | 1.00 | 125.39 U1 |
| ATOM | 1379 | OE2 | GLU | 173 | 6.965 | 29.064 | 30.170 | 1.00 | 125.39 U1 |
| ATOM | 1380 | C | GLU | 173 | 11.024 | 30.717 | 32.809 | 1.00 | 79.66 U1 |
| ATOM | 1381 | O | GLU | 173 | 11.508 | 31.721 | 33.364 | 1.00 | 79.66 U1 |
| ATOM | 1382 | OT | GLU | 173 | 10.558 | 29.731 | 33.423 | 1.00 | 125.39 U1 |
| ATOM | 1383 | CB | LYS | 186 | 5.775 | −12.246 | 10.277 | 1.00 | 56.27 U1 |
| ATOM | 1384 | CG | LYS | 186 | 6.302 | −13.597 | 9.873 | 1.00 | 56.27 U1 |
| ATOM | 1385 | CD | LYS | 186 | 6.874 | −13.546 | 8.475 | 1.00 | 56.27 U1 |
| ATOM | 1386 | CE | LYS | 186 | 8.263 | −12.936 | 8.440 | 1.00 | 56.27 U1 |
| ATOM | 1387 | NZ | LYS | 186 | 8.335 | −11.652 | 9.174 | 1.00 | 56.27 U1 |
| ATOM | 1391 | C | LYS | 186 | 4.861 | −10.802 | 12.064 | 1.00 | 57.91 U1 |
| ATOM | 1392 | O | LYS | 186 | 4.032 | −10.040 | 11.564 | 1.00 | 57.91 U1 |
| ATOM | 1395 | N | LYS | 186 | 3.667 | −12.951 | 11.423 | 1.00 | 57.91 U1 |
| ATOM | 1397 | CA | LYS | 186 | 4.979 | −12.240 | 11.580 | 1.00 | 57.91 U1 |
| ATOM | 1398 | N | ILE | 187 | 5.666 | −10.446 | 13.062 | 1.00 | 46.79 U1 |
| ATOM | 1400 | CA | ILE | 187 | 5.685 | −9.074 | 13.582 | 1.00 | 46.79 U1 |
| ATOM | 1401 | CB | ILE | 187 | 5.112 | −8.972 | 15.006 | 1.00 | 42.94 U1 |
| ATOM | 1402 | CG2 | ILE | 187 | 3.638 | −9.411 | 15.011 | 1.00 | 42.94 U1 |
| ATOM | 1403 | CG1 | ILE | 187 | 5.963 | −9.794 | 15.988 | 1.00 | 42.94 U1 |
| ATOM | 1404 | CD1 | ILE | 187 | 5.513 | −9.617 | 17.441 | 1.00 | 42.94 U1 |
| ATOM | 1405 | C | ILE | 187 | 7.159 | −8.697 | 13.591 | 1.00 | 46.79 U1 |
| ATOM | 1406 | O | ILE | 187 | 8.022 | −9.590 | 13.601 | 1.00 | 46.79 U1 |
| ATOM | 1407 | N | PRO | 188 | 7.481 | −7.391 | 13.575 | 1.00 | 45.20 U1 |
| ATOM | 1408 | CD | PRO | 188 | 6.637 | −6.184 | 13.637 | 1.00 | 24.88 U1 |
| ATOM | 1409 | CA | PRO | 188 | 8.911 | −7.042 | 13.574 | 1.00 | 45.20 U1 |
| ATOM | 1410 | CB | PRO | 188 | 8.888 | −5.511 | 13.543 | 1.00 | 24.88 U1 |
| ATOM | 1411 | CG | PRO | 188 | 7.500 | −5.177 | 12.950 | 1.00 | 24.88 U1 |
| ATOM | 1412 | C | PRO | 188 | 9.644 | −7.608 | 14.814 | 1.00 | 45.20 U1 |
| ATOM | 1413 | O | PRO | 188 | 9.048 | −7.750 | 15.896 | 1.00 | 45.20 U1 |
| ATOM | 1414 | N | VAL | 189 | 10.922 | −7.949 | 14.652 | 1.00 | 36.88 U1 |
| ATOM | 1416 | CA | VAL | 189 | 11.711 | −8.504 | 15.748 | 1.00 | 36.88 U1 |
| ATOM | 1417 | CB | VAL | 189 | 13.032 | −9.088 | 15.244 | 1.00 | 24.17 U1 |
| ATOM | 1418 | CG1 | VAL | 189 | 12.772 | −10.239 | 14.271 | 1.00 | 24.17 U1 |
| ATOM | 1419 | CG2 | VAL | 189 | 13.847 | −8.005 | 14.592 | 1.00 | 24.17 U1 |
| ATOM | 1420 | C | VAL | 189 | 12.015 | −7.470 | 16.825 | 1.00 | 36.88 U1 |
| ATOM | 1421 | O | VAL | 189 | 12.415 | −7.817 | 17.950 | 1.00 | 36.88 U1 |
| ATOM | 1422 | N | ASP | 190 | 11.850 | −6.202 | 16.476 | 1.00 | 29.02 U1 |
| ATOM | 1424 | CA | ASP | 190 | 12.088 | −5.131 | 17.412 | 1.00 | 29.02 U1 |

TABLE 1-continued

Structure coordinates of CPP32

| ATOM | 1425 | CB | ASP | 190 | 13.077 | −4.105 | 16.838 | 1.00 | 45.08 | U1 |
|---|---|---|---|---|---|---|---|---|---|---|
| ATOM | 1426 | CG | ASP | 190 | 14.548 | −4.503 | 17.064 | 1.00 | 45.08 | U1 |
| ATOM | 1427 | OD1 | ASP | 190 | 14.872 | −5.709 | 17.080 | 1.00 | 45.08 | U1 |
| ATOM | 1428 | OD2 | ASP | 190 | 15.391 | −3.605 | 17.221 | 1.00 | 45.08 | U1 |
| ATOM | 1429 | C | ASP | 190 | 10.796 | −4.463 | 17.868 | 1.00 | 29.02 | U1 |
| ATOM | 1430 | O | ASP | 190 | 10.832 | −3.346 | 18.361 | 1.00 | 29.02 | U1 |
| ATOM | 1431 | N | ALA | 191 | 9.657 | −5.135 | 17.736 | 1.00 | 26.07 | U1 |
| ATOM | 1433 | CA | ALA | 191 | 8.389 | −4.549 | 18.187 | 1.00 | 26.07 | U1 |
| ATOM | 1434 | CB | ALA | 191 | 7.222 | −5.090 | 17.383 | 1.00 | 11.55 | U1 |
| ATOM | 1435 | C | ALA | 191 | 8.187 | −4.917 | 19.642 | 1.00 | 26.07 | U1 |
| ATOM | 1436 | O | ALA | 191 | 8.656 | −5.950 | 20.088 | 1.00 | 26.07 | U1 |
| ATOM | 1437 | N | ASP | 192 | 7.390 | −4.131 | 20.342 | 1.00 | 26.56 | U1 |
| ATOM | 1439 | CA | ASP | 192 | 7.102 | −4.384 | 21.742 | 1.00 | 26.56 | U1 |
| ATOM | 1440 | CB | ASP | 192 | 6.624 | −5.831 | 21.931 | 1.00 | 33.77 | U1 |
| ATOM | 1441 | CG | ASP | 192 | 5.499 | −6.222 | 20.965 | 1.00 | 33.77 | U1 |
| ATOM | 1442 | OD1 | ASP | 192 | 5.644 | −7.277 | 20.290 | 1.00 | 33.77 | U1 |
| ATOM | 1443 | OD2 | ASP | 192 | 4.462 | −5.513 | 20.902 | 1.00 | 33.77 | U1 |
| ATOM | 1444 | C | ASP | 192 | 8.246 | −4.079 | 22.728 | 1.00 | 26.56 | U1 |
| ATOM | 1445 | O | ASP | 192 | 8.317 | −4.672 | 23.789 | 1.00 | 26.56 | U1 |
| ATOM | 1446 | N | PHE | 193 | 9.151 | −3.183 | 22.379 | 1.00 | 16.22 | U1 |
| ATOM | 1448 | CA | PHE | 193 | 10.242 | −2.794 | 23.281 | 1.00 | 16.22 | U1 |
| ATOM | 1449 | CB | PHE | 193 | 11.595 | −2.694 | 22.549 | 1.00 | 19.71 | U1 |
| ATOM | 1450 | CG | PHE | 193 | 12.399 | −3.972 | 22.533 | 1.00 | 19.71 | U1 |
| ATOM | 1451 | CD1 | PHE | 193 | 13.434 | −4.154 | 23.411 | 1.00 | 19.71 | U1 |
| ATOM | 1452 | CD2 | PHE | 193 | 12.109 | −4.982 | 21.652 | 1.00 | 19.71 | U1 |
| ATOM | 1453 | CE1 | PHE | 193 | 14.167 | −5.335 | 23.412 | 1.00 | 19.71 | U1 |
| ATOM | 1454 | CE2 | PHE | 193 | 12.831 | −6.149 | 21.651 | 1.00 | 19.71 | U1 |
| ATOM | 1455 | CZ | PHE | 193 | 13.857 | −6.327 | 22.529 | 1.00 | 19.71 | U1 |
| ATOM | 1456 | C | PHE | 193 | 9.899 | −1.379 | 23.690 | 1.00 | 16.22 | U1 |
| ATOM | 1457 | O | PHE | 193 | 9.416 | −0.623 | 22.853 | 1.00 | 16.22 | U1 |
| ATOM | 1458 | N | LEU | 194 | 10.115 | −1.013 | 24.953 | 1.00 | 22.89 | U1 |
| ATOM | 1460 | CA | LEU | 194 | 9.887 | 0.371 | 25.382 | 1.00 | 22.89 | U1 |
| ATOM | 1461 | CB | LEU | 194 | 8.655 | 0.496 | 26.276 | 1.00 | 23.73 | U1 |
| ATOM | 1462 | CG | LEU | 194 | 8.340 | 1.926 | 26.726 | 1.00 | 23.73 | U1 |
| ATOM | 1463 | CD1 | LEU | 194 | 6.873 | 2.298 | 26.483 | 1.00 | 23.73 | U1 |
| ATOM | 1464 | CD2 | LEU | 194 | 8.702 | 2.051 | 28.168 | 1.00 | 23.73 | U1 |
| ATOM | 1465 | C | LEU | 194 | 11.137 | 0.777 | 26.148 | 1.00 | 22.89 | U1 |
| ATOM | 1466 | O | LEU | 194 | 11.642 | −0.017 | 26.926 | 1.00 | 22.89 | U1 |
| ATOM | 1467 | N | TYR | 195 | 11.706 | 1.942 | 25.864 | 1.00 | 27.44 | U1 |
| ATOM | 1469 | CA | TYR | 195 | 12.902 | 2.389 | 26.582 | 1.00 | 27.44 | U1 |
| ATOM | 1470 | CB | TYR | 195 | 14.083 | 2.621 | 25.638 | 1.00 | 28.46 | U1 |
| ATOM | 1471 | CG | TYR | 195 | 14.444 | 1.427 | 24.779 | 1.00 | 28.46 | U1 |
| ATOM | 1472 | CD1 | TYR | 195 | 13.729 | 1.141 | 23.617 | 1.00 | 28.46 | U1 |
| ATOM | 1473 | CE1 | TYR | 195 | 14.025 | 0.037 | 22.847 | 1.00 | 28.46 | U1 |
| ATOM | 1474 | CD2 | TYR | 195 | 15.479 | 0.569 | 25.139 | 1.00 | 28.46 | U1 |
| ATOM | 1475 | CE2 | TYR | 195 | 15.782 | −0.540 | 24.371 | 1.00 | 28.46 | U1 |
| ATOM | 1476 | CZ | TYR | 195 | 15.044 | −0.799 | 23.231 | 1.00 | 28.46 | U1 |
| ATOM | 1477 | OH | TYR | 195 | 15.294 | −1.927 | 22.500 | 1.00 | 28.46 | U1 |
| ATOM | 1479 | C | TYR | 195 | 12.565 | 3.692 | 27.278 | 1.00 | 27.44 | U1 |
| ATOM | 1480 | O | TYR | 195 | 12.217 | 4.680 | 26.632 | 1.00 | 27.44 | U1 |
| ATOM | 1481 | N | ALA | 196 | 12.603 | 3.690 | 28.600 | 1.00 | 17.02 | U1 |
| ATOM | 1483 | CA | ALA | 196 | 12.299 | 4.894 | 29.334 | 1.00 | 17.02 | U1 |
| ATOM | 1484 | CB | ALA | 196 | 11.439 | 4.566 | 30.498 | 1.00 | 12.85 | U1 |
| ATOM | 1485 | C | ALA | 196 | 13.645 | 5.436 | 29.770 | 1.00 | 17.02 | U1 |
| ATOM | 1486 | O | ALA | 196 | 14.337 | 4.853 | 30.589 | 1.00 | 17.02 | U1 |
| ATOM | 1487 | N | TYR | 197 | 14.084 | 6.470 | 29.089 | 1.00 | 15.09 | U1 |
| ATOM | 1489 | CA | TYR | 197 | 15.356 | 7.085 | 29.380 | 1.00 | 15.09 | U1 |
| ATOM | 1490 | CB | TYR | 197 | 15.975 | 7.640 | 28.088 | 1.00 | 26.55 | U1 |
| ATOM | 1491 | CG | TYR | 197 | 16.480 | 6.593 | 27.127 | 1.00 | 26.55 | U1 |
| ATOM | 1492 | CD1 | TYR | 197 | 15.786 | 6.279 | 25.959 | 1.00 | 26.55 | U1 |
| ATOM | 1493 | CE1 | TYR | 197 | 16.280 | 5.299 | 25.073 | 1.00 | 26.55 | U1 |
| ATOM | 1494 | CD2 | TYR | 197 | 17.658 | 5.914 | 27.384 | 1.00 | 26.55 | U1 |
| ATOM | 1495 | CE2 | TYR | 197 | 18.150 | 4.943 | 26.512 | 1.00 | 26.55 | U1 |
| ATOM | 1496 | CZ | TYR | 197 | 17.469 | 4.644 | 25.372 | 1.00 | 26.55 | U1 |
| ATOM | 1497 | OH | TYR | 197 | 18.001 | 3.704 | 24.535 | 1.00 | 26.55 | U1 |
| ATOM | 1499 | C | TYR | 197 | 15.158 | 8.216 | 30.373 | 1.00 | 15.09 | U1 |
| ATOM | 1500 | O | TYR | 197 | 14.174 | 8.962 | 30.316 | 1.00 | 15.09 | U1 |
| ATOM | 1501 | N | SER | 198 | 16.128 | 8.359 | 31.260 | 1.00 | 21.79 | U1 |
| ATOM | 1503 | CA | SER | 198 | 16.079 | 9.395 | 32.256 | 1.00 | 21.79 | U1 |
| ATOM | 1504 | CB | SER | 198 | 17.154 | 9.158 | 33.295 | 1.00 | 29.20 | U1 |
| ATOM | 1505 | OG | SER | 198 | 18.439 | 9.234 | 32.704 | 1.00 | 29.20 | U1 |
| ATOM | 1507 | C | SER | 198 | 16.322 | 10.737 | 31.621 | 1.00 | 21.79 | U1 |
| ATOM | 1508 | O | SER | 198 | 15.987 | 11.757 | 32.229 | 1.00 | 21.79 | U1 |
| ATOM | 1509 | N | THR | 199 | 16.890 | 10.764 | 30.408 | 1.00 | 24.41 | U1 |
| ATOM | 1511 | CA | THR | 199 | 17.204 | 12.040 | 29.730 | 1.00 | 24.41 | U1 |
| ATOM | 1512 | CB | THR | 199 | 18.624 | 12.468 | 30.010 | 1.00 | 21.04 | U1 |
| ATOM | 1513 | OG1 | THR | 199 | 19.288 | 11.458 | 30.783 | 1.00 | 21.04 | U1 |

TABLE 1-continued

Structure coordinates of CPP32

| ATOM | 1515 | CG2 | THR | 199 | 18.650 | 13.789 | 30.684 | 1.00 | 21.04 | U1 |
| --- | --- | --- | --- | --- | --- | --- | --- | --- | --- | --- |
| ATOM | 1516 | C | THR | 199 | 17.160 | 12.028 | 28.217 | 1.00 | 24.41 | U1 |
| ATOM | 1517 | O | THR | 199 | 17.299 | 10.989 | 27.579 | 1.00 | 24.41 | U1 |
| ATOM | 1518 | N | ALA | 200 | 17.136 | 13.221 | 27.646 | 1.00 | 27.10 | U1 |
| ATOM | 1520 | CA | ALA | 200 | 17.117 | 13.369 | 26.207 | 1.00 | 27.10 | U1 |
| ATOM | 1521 | CB | ALA | 200 | 16.877 | 14.827 | 25.841 | 1.00 | 15.91 | U1 |
| ATOM | 1522 | C | ALA | 200 | 18.450 | 12.884 | 25.654 | 1.00 | 27.10 | U1 |
| ATOM | 1523 | O | ALA | 200 | 19.399 | 12.692 | 26.390 | 1.00 | 27.10 | U1 |
| ATOM | 1524 | N | PRO | 201 | 18.529 | 12.654 | 24.347 | 1.00 | 21.43 | U1 |
| ATOM | 1525 | CD | PRO | 201 | 17.434 | 12.594 | 23.361 | 1.00 | 29.33 | U1 |
| ATOM | 1526 | CA | PRO | 201 | 19.777 | 12.188 | 23.756 | 1.00 | 21.43 | U1 |
| ATOM | 1527 | CB | PRO | 201 | 19.379 | 11.978 | 22.313 | 1.00 | 29.33 | U1 |
| ATOM | 1528 | CG | PRO | 201 | 17.924 | 11.555 | 22.437 | 1.00 | 29.33 | U1 |
| ATOM | 1529 | C | PRO | 201 | 20.870 | 13.218 | 23.867 | 1.00 | 21.43 | U1 |
| ATOM | 1530 | O | PRO | 201 | 20.625 | 14.400 | 23.676 | 1.00 | 21.43 | U1 |
| ATOM | 1531 | N | GLY | 202 | 22.065 | 12.787 | 24.230 | 1.00 | 33.85 | U1 |
| ATOM | 1533 | CA | GLY | 202 | 23.174 | 13.712 | 24.330 | 1.00 | 33.85 | U1 |
| ATOM | 1534 | C | GLY | 202 | 23.303 | 14.557 | 25.585 | 1.00 | 33.85 | U1 |
| ATOM | 1535 | O | GLY | 202 | 24.283 | 15.302 | 25.710 | 1.00 | 33.85 | U1 |
| ATOM | 1536 | N | TYR | 203 | 22.388 | 14.395 | 26.542 | 1.00 | 26.76 | U1 |
| ATOM | 1538 | CA | TYR | 203 | 22.413 | 15.181 | 27.775 | 1.00 | 26.76 | U1 |
| ATOM | 1539 | CB | TYR | 203 | 21.048 | 15.788 | 28.022 | 1.00 | 27.37 | U1 |
| ATOM | 1540 | CG | TYR | 203 | 20.765 | 16.950 | 27.157 | 1.00 | 27.37 | U1 |
| ATOM | 1541 | CD1 | TYR | 203 | 20.429 | 16.782 | 25.833 | 1.00 | 27.37 | U1 |
| ATOM | 1542 | CE1 | TYR | 203 | 20.187 | 17.864 | 25.011 | 1.00 | 27.37 | U1 |
| ATOM | 1543 | CD2 | TYR | 203 | 20.854 | 18.225 | 27.653 | 1.00 | 27.37 | U1 |
| ATOM | 1544 | CE2 | TYR | 203 | 20.614 | 19.307 | 26.848 | 1.00 | 27.37 | U1 |
| ATOM | 1545 | CZ | TYR | 203 | 20.279 | 19.119 | 25.525 | 1.00 | 27.37 | U1 |
| ATOM | 1546 | OH | TYR | 203 | 20.016 | 20.203 | 24.724 | 1.00 | 27.37 | U1 |
| ATOM | 1548 | C | TYR | 203 | 22.844 | 14.505 | 29.072 | 1.00 | 26.76 | U1 |
| ATOM | 1549 | O | TYR | 203 | 22.960 | 13.278 | 29.170 | 1.00 | 26.76 | U1 |
| ATOM | 1550 | N | TYR | 204 | 23.083 | 15.338 | 30.075 | 1.00 | 32.47 | U1 |
| ATOM | 1552 | CA | TYR | 204 | 23.448 | 14.879 | 31.406 | 1.00 | 32.47 | U1 |
| ATOM | 1553 | CB | TYR | 204 | 23.979 | 16.040 | 32.241 | 1.00 | 38.70 | U1 |
| ATOM | 1554 | CG | TYR | 204 | 25.446 | 16.308 | 32.151 | 1.00 | 38.70 | U1 |
| ATOM | 1555 | CD1 | TYR | 204 | 25.895 | 17.547 | 31.770 | 1.00 | 38.70 | U1 |
| ATOM | 1556 | CE1 | TYR | 204 | 27.235 | 17.833 | 31.703 | 1.00 | 38.70 | U1 |
| ATOM | 1557 | CD2 | TYR | 204 | 26.381 | 15.337 | 32.472 | 1.00 | 38.70 | U1 |
| ATOM | 1558 | CE2 | TYR | 204 | 27.734 | 15.610 | 32.413 | 1.00 | 38.70 | U1 |
| ATOM | 1559 | CZ | TYR | 204 | 28.154 | 16.870 | 32.023 | 1.00 | 38.70 | U1 |
| ATOM | 1560 | OH | TYR | 204 | 29.491 | 17.201 | 31.935 | 1.00 | 38.70 | U1 |
| ATOM | 1562 | C | TYR | 204 | 22.162 | 14.423 | 32.075 | 1.00 | 32.47 | U1 |
| ATOM | 1563 | O | TYR | 204 | 21.078 | 14.972 | 31.801 | 1.00 | 32.47 | U1 |
| ATOM | 1564 | N | SER | 205 | 22.288 | 13.446 | 32.961 | 1.00 | 14.26 | U1 |
| ATOM | 1566 | CA | SER | 205 | 21.163 | 12.954 | 33.727 | 1.00 | 14.26 | U1 |
| ATOM | 1567 | CB | SER | 205 | 20.963 | 11.506 | 33.460 | 1.00 | 26.22 | U1 |
| ATOM | 1568 | OG | SER | 205 | 20.043 | 11.006 | 34.399 | 1.00 | 26.22 | U1 |
| ATOM | 1570 | C | SER | 205 | 21.635 | 13.132 | 35.153 | 1.00 | 14.26 | U1 |
| ATOM | 1571 | O | SER | 205 | 22.754 | 12.715 | 35.495 | 1.00 | 14.26 | U1 |
| ATOM | 1572 | N | TRP | 206 | 20.801 | 13.756 | 35.979 | 1.00 | 17.64 | U1 |
| ATOM | 1574 | CA | TRP | 206 | 21.142 | 14.071 | 37.368 | 1.00 | 17.64 | U1 |
| ATOM | 1575 | CB | TRP | 206 | 20.588 | 15.441 | 37.698 | 1.00 | 27.36 | U1 |
| ATOM | 1576 | CG | TRP | 206 | 21.306 | 16.472 | 36.943 | 1.00 | 27.36 | U1 |
| ATOM | 1577 | CD2 | TRP | 206 | 22.625 | 16.946 | 37.217 | 1.00 | 27.36 | U1 |
| ATOM | 1578 | CE2 | TRP | 206 | 22.973 | 17.837 | 36.175 | 1.00 | 27.36 | U1 |
| ATOM | 1579 | CE3 | TRP | 206 | 23.552 | 16.704 | 38.233 | 1.00 | 27.36 | U1 |
| ATOM | 1580 | CD1 | TRP | 206 | 20.902 | 17.075 | 35.792 | 1.00 | 27.36 | U1 |
| ATOM | 1581 | NE1 | TRP | 206 | 21.905 | 17.895 | 35.316 | 1.00 | 27.36 | U1 |
| ATOM | 1583 | CZ2 | TRP | 206 | 24.203 | 18.482 | 36.124 | 1.00 | 27.36 | U1 |
| ATOM | 1584 | CZ3 | TRP | 206 | 24.773 | 17.341 | 38.180 | 1.00 | 27.36 | U1 |
| ATOM | 1585 | CH2 | TRP | 206 | 25.088 | 18.225 | 37.129 | 1.00 | 27.36 | U1 |
| ATOM | 1586 | C | TRP | 206 | 20.781 | 13.110 | 38.473 | 1.00 | 17.64 | U1 |
| ATOM | 1587 | O | TRP | 206 | 19.738 | 12.468 | 38.435 | 1.00 | 17.64 | U1 |
| ATOM | 1588 | N | ARG | 207 | 21.600 | 13.094 | 39.514 | 1.00 | 22.31 | U1 |
| ATOM | 1590 | CA | ARG | 207 | 21.396 | 12.209 | 40.663 | 1.00 | 22.31 | U1 |
| ATOM | 1591 | CB | ARG | 207 | 22.312 | 10.986 | 40.544 | 1.00 | 32.02 | U1 |
| ATOM | 1592 | CG | ARG | 207 | 22.179 | 9.957 | 41.641 | 1.00 | 32.02 | U1 |
| ATOM | 1593 | CD | ARG | 207 | 23.314 | 8.965 | 41.606 | 1.00 | 32.02 | U1 |
| ATOM | 1594 | NE | ARG | 207 | 24.548 | 9.560 | 42.127 | 1.00 | 32.02 | U1 |
| ATOM | 1596 | CZ | ARG | 207 | 25.659 | 9.768 | 41.425 | 1.00 | 32.02 | U1 |
| ATOM | 1597 | NH1 | ARG | 207 | 25.727 | 9.436 | 40.153 | 1.00 | 32.02 | U1 |
| ATOM | 1600 | NH2 | ARG | 207 | 26.710 | 10.325 | 41.999 | 1.00 | 32.02 | U1 |
| ATOM | 1603 | C | ARG | 207 | 21.742 | 12.980 | 41.933 | 1.00 | 22.31 | U1 |
| ATOM | 1604 | O | ARG | 207 | 22.717 | 13.705 | 41.968 | 1.00 | 22.31 | U1 |
| ATOM | 1605 | N | ASN | 208 | 20.885 | 12.878 | 42.945 | 1.00 | 27.20 | U1 |
| ATOM | 1607 | CA | ASN | 208 | 21.096 | 13.541 | 44.239 | 1.00 | 27.20 | U1 |
| ATOM | 1608 | CB | ASN | 208 | 19.764 | 14.057 | 44.799 | 1.00 | 40.20 | U1 |

TABLE 1-continued

Structure coordinates of CPP32

| ATOM | 1609 | CG | ASN | 208 | 19.890 | 14.555 | 46.230 | 1.00 | 40.20 | U1 |
|---|---|---|---|---|---|---|---|---|---|---|
| ATOM | 1610 | OD1 | ASN | 208 | 20.182 | 13.782 | 47.143 | 1.00 | 40.20 | U1 |
| ATOM | 1611 | ND2 | ASN | 208 | 19.694 | 15.847 | 46.431 | 1.00 | 40.20 | U1 |
| ATOM | 1614 | C | ASN | 208 | 21.699 | 12.518 | 45.206 | 1.00 | 27.20 | U1 |
| ATOM | 1615 | O | ASN | 208 | 21.065 | 11.496 | 45.492 | 1.00 | 27.20 | U1 |
| ATOM | 1616 | N | SER | 209 | 22.882 | 12.831 | 45.738 | 1.00 | 40.85 | U1 |
| ATOM | 1618 | CA | SER | 209 | 23.630 | 11.965 | 46.669 | 1.00 | 40.85 | U1 |
| ATOM | 1619 | CB | SER | 209 | 24.743 | 12.753 | 47.366 | 1.00 | 48.09 | U1 |
| ATOM | 1620 | OG | SER | 209 | 25.548 | 13.443 | 46.430 | 1.00 | 48.09 | U1 |
| ATOM | 1622 | C | SER | 209 | 22.815 | 11.293 | 47.755 | 1.00 | 40.85 | U1 |
| ATOM | 1623 | O | SER | 209 | 23.097 | 10.162 | 48.134 | 1.00 | 40.85 | U1 |
| ATOM | 1624 | N | LYS | 210 | 21.828 | 12.006 | 48.271 | 1.00 | 42.31 | U1 |
| ATOM | 1626 | CA | LYS | 210 | 21.001 | 11.490 | 49.339 | 1.00 | 42.31 | U1 |
| ATOM | 1627 | CB | LYS | 210 | 20.709 | 12.613 | 50.351 | 1.00 | 67.84 | U1 |
| ATOM | 1628 | CG | LYS | 210 | 19.693 | 12.255 | 51.435 | 1.00 | 67.84 | U1 |
| ATOM | 1629 | CD | LYS | 210 | 19.153 | 13.491 | 52.146 | 1.00 | 67.84 | U1 |
| ATOM | 1630 | CE | LYS | 210 | 18.122 | 13.100 | 53.197 | 1.00 | 67.84 | U1 |
| ATOM | 1631 | NZ | LYS | 210 | 17.655 | 14.265 | 53.998 | 1.00 | 67.84 | U1 |
| ATOM | 1635 | C | LYS | 210 | 19.696 | 10.826 | 48.920 | 1.00 | 42.31 | U1 |
| ATOM | 1636 | O | LYS | 210 | 19.374 | 9.746 | 49.412 | 1.00 | 42.31 | U1 |
| ATOM | 1637 | N | ASP | 211 | 18.939 | 11.462 | 48.030 | 1.00 | 21.04 | U1 |
| ATOM | 1639 | CA | ASP | 211 | 17.639 | 10.929 | 47.620 | 1.00 | 21.04 | U1 |
| ATOM | 1640 | CB | ASP | 211 | 16.690 | 12.085 | 47.340 | 1.00 | 44.60 | U1 |
| ATOM | 1641 | CG | ASP | 211 | 16.606 | 13.056 | 48.494 | 1.00 | 44.60 | U1 |
| ATOM | 1642 | OD1 | ASP | 211 | 16.686 | 12.613 | 49.658 | 1.00 | 44.60 | U1 |
| ATOM | 1643 | OD2 | ASP | 211 | 16.463 | 14.267 | 48.233 | 1.00 | 44.60 | U1 |
| ATOM | 1644 | C | ASP | 211 | 17.565 | 9.933 | 46.471 | 1.00 | 21.04 | U1 |
| ATOM | 1645 | O | ASP | 211 | 16.615 | 9.157 | 46.382 | 1.00 | 21.04 | U1 |
| ATOM | 1646 | N | GLY | 212 | 18.586 | 9.904 | 45.633 | 1.00 | 18.65 | U1 |
| ATOM | 1648 | CA | GLY | 212 | 18.554 | 9.009 | 44.499 | 1.00 | 18.65 | U1 |
| ATOM | 1649 | C | GLY | 212 | 18.314 | 9.841 | 43.251 | 1.00 | 18.65 | U1 |
| ATOM | 1650 | O | GLY | 212 | 18.245 | 11.089 | 43.296 | 1.00 | 18.65 | U1 |
| ATOM | 1651 | N | SER | 213 | 18.169 | 9.167 | 42.122 | 1.00 | 27.10 | U1 |
| ATOM | 1653 | CA | SER | 213 | 17.972 | 9.881 | 40.861 | 1.00 | 27.10 | U1 |
| ATOM | 1654 | CB | SER | 213 | 18.252 | 8.936 | 39.689 | 1.00 | 25.79 | U1 |
| ATOM | 1655 | OG | SER | 213 | 17.700 | 7.648 | 39.922 | 1.00 | 25.79 | U1 |
| ATOM | 1657 | C | SER | 213 | 16.597 | 10.537 | 40.716 | 1.00 | 27.10 | U1 |
| ATOM | 1658 | O | SER | 213 | 15.589 | 9.978 | 41.166 | 1.00 | 27.10 | U1 |
| ATOM | 1659 | N | TRP | 214 | 16.551 | 11.711 | 40.091 | 1.00 | 22.34 | U1 |
| ATOM | 1661 | CA | TRP | 214 | 15.283 | 12.391 | 39.888 | 1.00 | 22.34 | U1 |
| ATOM | 1662 | CB | TRP | 214 | 15.458 | 13.662 | 39.094 | 1.00 | 2.00 | U1 |
| ATOM | 1663 | CG | TRP | 214 | 16.451 | 14.597 | 39.642 | 1.00 | 2.00 | U1 |
| ATOM | 1664 | CD2 | TRP | 214 | 16.974 | 15.742 | 38.974 | 1.00 | 2.00 | U1 |
| ATOM | 1665 | CE2 | TRP | 214 | 17.922 | 16.333 | 39.836 | 1.00 | 2.00 | U1 |
| ATOM | 1666 | CE3 | TRP | 214 | 16.731 | 16.330 | 37.724 | 1.00 | 2.00 | U1 |
| ATOM | 1667 | CD1 | TRP | 214 | 17.067 | 14.537 | 40.858 | 1.00 | 2.00 | U1 |
| ATOM | 1668 | NE1 | TRP | 214 | 17.955 | 15.579 | 40.981 | 1.00 | 2.00 | U1 |
| ATOM | 1670 | CZ2 | TRP | 214 | 18.630 | 17.473 | 39.494 | 1.00 | 2.00 | U1 |
| ATOM | 1671 | CZ3 | TRP | 214 | 17.428 | 17.461 | 37.385 | 1.00 | 2.00 | U1 |
| ATOM | 1672 | CH2 | TRP | 214 | 18.373 | 18.030 | 38.263 | 1.00 | 2.00 | U1 |
| ATOM | 1673 | C | TRP | 214 | 14.363 | 11.487 | 39.105 | 1.00 | 22.34 | U1 |
| ATOM | 1674 | O | TRP | 214 | 13.213 | 11.307 | 39.484 | 1.00 | 22.34 | U1 |
| ATOM | 1675 | N | PHE | 215 | 14.877 | 10.895 | 38.028 | 1.00 | 18.08 | U1 |
| ATOM | 1677 | CA | PHE | 215 | 14.082 | 9.998 | 37.207 | 1.00 | 18.08 | U1 |
| ATOM | 1678 | CB | PHE | 215 | 14.903 | 9.376 | 36.112 | 1.00 | 16.35 | U1 |
| ATOM | 1679 | CG | PHE | 215 | 14.091 | 8.561 | 35.185 | 1.00 | 16.35 | U1 |
| ATOM | 1680 | CD1 | PHE | 215 | 12.919 | 9.079 | 34.650 | 1.00 | 16.35 | U1 |
| ATOM | 1681 | CD2 | PHE | 215 | 14.479 | 7.295 | 34.828 | 1.00 | 16.35 | U1 |
| ATOM | 1682 | CE1 | PHE | 215 | 12.161 | 8.348 | 33.772 | 1.00 | 16.35 | U1 |
| ATOM | 1683 | CE2 | PHE | 215 | 13.715 | 6.563 | 33.950 | 1.00 | 16.35 | U1 |
| ATOM | 1684 | CZ | PHE | 215 | 12.558 | 7.091 | 33.423 | 1.00 | 16.35 | U1 |
| ATOM | 1685 | C | PHE | 215 | 13.438 | 8.872 | 37.983 | 1.00 | 18.08 | U1 |
| ATOM | 1686 | O | PHE | 215 | 12.227 | 8.763 | 38.009 | 1.00 | 18.08 | U1 |
| ATOM | 1687 | N | ILE | 216 | 14.246 | 8.014 | 38.597 | 1.00 | 18.54 | U1 |
| ATOM | 1689 | CA | ILE | 216 | 13.727 | 6.899 | 39.392 | 1.00 | 18.54 | U1 |
| ATOM | 1690 | CB | ILE | 216 | 14.838 | 6.025 | 39.889 | 1.00 | 15.44 | U1 |
| ATOM | 1691 | CG2 | ILE | 216 | 14.251 | 4.853 | 40.684 | 1.00 | 15.44 | U1 |
| ATOM | 1692 | CG1 | ILE | 216 | 15.646 | 5.517 | 38.687 | 1.00 | 15.44 | U1 |
| ATOM | 1693 | CD1 | ILE | 216 | 14.822 | 4.775 | 37.585 | 1.00 | 15.44 | U1 |
| ATOM | 1694 | C | ILE | 216 | 12.827 | 7.308 | 40.563 | 1.00 | 18.54 | U1 |
| ATOM | 1695 | O | ILE | 216 | 11.838 | 6.641 | 40.833 | 1.00 | 18.54 | U1 |
| ATOM | 1696 | N | GLN | 217 | 13.141 | 8.405 | 41.246 | 1.00 | 15.80 | U1 |
| ATOM | 1698 | CA | GLN | 217 | 12.275 | 8.863 | 42.326 | 1.00 | 15.80 | U1 |
| ATOM | 1699 | CB | GLN | 217 | 12.719 | 10.224 | 42.861 | 1.00 | 29.98 | U1 |
| ATOM | 1700 | CG | GLN | 217 | 13.878 | 10.275 | 43.824 | 1.00 | 29.98 | U1 |
| ATOM | 1701 | CD | GLN | 217 | 14.197 | 11.728 | 44.228 | 1.00 | 29.98 | U1 |
| ATOM | 1702 | OE1 | GLN | 217 | 15.349 | 12.205 | 44.097 | 1.00 | 29.98 | U1 |

TABLE 1-continued

Structure coordinates of CPP32

| ATOM | 1703 | NE2 | GLN | 217 | 13.169 | 12.446 | 44.699 | 1.00 | 29.98 | U1 |
| ATOM | 1706 | C | GLN | 217 | 10.885 | 9.069 | 41.742 | 1.00 | 15.80 | U1 |
| ATOM | 1707 | O | GLN | 217 | 9.902 | 8.579 | 42.296 | 1.00 | 15.80 | U1 |
| ATOM | 1708 | N | SER | 218 | 10.805 | 9.859 | 40.658 | 1.00 | 21.60 | U1 |
| ATOM | 1710 | CA | SER | 218 | 9.529 | 10.162 | 39.970 | 1.00 | 21.60 | U1 |
| ATOM | 1711 | CB | SER | 218 | 9.717 | 11.191 | 38.880 | 1.00 | 24.77 | U1 |
| ATOM | 1712 | OG | SER | 218 | 10.330 | 12.350 | 39.400 | 1.00 | 24.77 | U1 |
| ATOM | 1714 | C | SER | 218 | 8.841 | 8.955 | 39.360 | 1.00 | 21.60 | U1 |
| ATOM | 1715 | O | SER | 218 | 7.620 | 8.898 | 39.347 | 1.00 | 21.60 | U1 |
| ATOM | 1716 | N | LEU | 219 | 9.605 | 8.012 | 38.820 | 1.00 | 19.35 | U1 |
| ATOM | 1718 | CA | LEU | 219 | 9.027 | 6.817 | 38.234 | 1.00 | 19.35 | U1 |
| ATOM | 1719 | CB | LEU | 219 | 10.136 | 5.918 | 37.658 | 1.00 | 2.00 | U1 |
| ATOM | 1720 | CG | LEU | 219 | 9.720 | 4.579 | 37.086 | 1.00 | 2.00 | U1 |
| ATOM | 1721 | CD1 | LEU | 219 | 8.954 | 4.813 | 35.826 | 1.00 | 2.00 | U1 |
| ATOM | 1722 | CD2 | LEU | 219 | 10.932 | 3.752 | 36.812 | 1.00 | 2.00 | U1 |
| ATOM | 1723 | C | LEU | 219 | 8.279 | 6.067 | 39.328 | 1.00 | 19.35 | U1 |
| ATOM | 1724 | O | LEU | 219 | 7.106 | 5.762 | 39.195 | 1.00 | 19.35 | U1 |
| ATOM | 1725 | N | CYS | 220 | 8.954 | 5.788 | 40.434 | 1.00 | 13.98 | U1 |
| ATOM | 1727 | CA | CYS | 220 | 8.332 | 5.069 | 41.525 | 1.00 | 13.98 | U1 |
| ATOM | 1728 | CB | CYS | 220 | 9.367 | 4.777 | 42.577 | 1.00 | 21.34 | U1 |
| ATOM | 1729 | SG | CYS | 220 | 10.596 | 3.626 | 41.993 | 1.00 | 21.34 | U1 |
| ATOM | 1730 | C | CYS | 220 | 7.130 | 5.797 | 42.108 | 1.00 | 13.98 | U1 |
| ATOM | 1731 | O | CYS | 220 | 6.073 | 5.212 | 42.242 | 1.00 | 13.98 | U1 |
| ATOM | 1732 | N | ALA | 221 | 7.264 | 7.071 | 42.434 | 1.00 | 14.56 | U1 |
| ATOM | 1734 | CA | ALA | 221 | 6.129 | 7.796 | 42.965 | 1.00 | 14.56 | U1 |
| ATOM | 1735 | CB | ALA | 221 | 6.439 | 9.296 | 43.062 | 1.00 | 2.00 | U1 |
| ATOM | 1736 | C | ALA | 221 | 4.923 | 7.577 | 42.070 | 1.00 | 14.56 | U1 |
| ATOM | 1737 | O | ALA | 221 | 3.965 | 6.901 | 42.441 | 1.00 | 14.56 | U1 |
| ATOM | 1738 | N | MET | 222 | 5.030 | 8.080 | 40.844 | 1.00 | 22.83 | U1 |
| ATOM | 1740 | CA | MET | 222 | 3.969 | 7.999 | 39.837 | 1.00 | 22.83 | U1 |
| ATOM | 1741 | CB | MET | 222 | 4.423 | 8.606 | 38.523 | 1.00 | 27.02 | U1 |
| ATOM | 1742 | CG | MET | 222 | 3.446 | 9.631 | 38.042 | 1.00 | 27.02 | U1 |
| ATOM | 1743 | SD | MET | 222 | 3.648 | 11.150 | 38.881 | 1.00 | 27.02 | U1 |
| ATOM | 1744 | CE | MET | 222 | 2.750 | 10.880 | 40.310 | 1.00 | 27.02 | U1 |
| ATOM | 1745 | C | MET | 222 | 3.396 | 6.629 | 39.612 | 1.00 | 22.83 | U1 |
| ATOM | 1746 | O | MET | 222 | 2.184 | 6.477 | 39.549 | 1.00 | 22.83 | U1 |
| ATOM | 1747 | N | LEU | 223 | 4.255 | 5.628 | 39.495 | 1.00 | 30.97 | U1 |
| ATOM | 1749 | CA | LEU | 223 | 3.778 | 4.264 | 39.325 | 1.00 | 30.97 | U1 |
| ATOM | 1750 | CB | LEU | 223 | 4.953 | 3.314 | 39.080 | 1.00 | 27.52 | U1 |
| ATOM | 1751 | CG | LEU | 223 | 5.201 | 2.895 | 37.630 | 1.00 | 27.52 | U1 |
| ATOM | 1752 | CD1 | LEU | 223 | 6.148 | 1.722 | 37.585 | 1.00 | 27.52 | U1 |
| ATOM | 1753 | CD2 | LEU | 223 | 3.898 | 2.506 | 37.006 | 1.00 | 27.52 | U1 |
| ATOM | 1754 | C | LEU | 223 | 3.003 | 3.831 | 40.591 | 1.00 | 30.97 | U1 |
| ATOM | 1755 | O | LEU | 223 | 2.003 | 3.112 | 40.507 | 1.00 | 30.97 | U1 |
| ATOM | 1756 | N | LYS | 224 | 3.459 | 4.279 | 41.757 | 1.00 | 46.06 | U1 |
| ATOM | 1758 | CA | LYS | 224 | 2.822 | 3.958 | 43.032 | 1.00 | 46.06 | U1 |
| ATOM | 1759 | CB | LYS | 224 | 3.690 | 4.496 | 44.170 | 1.00 | 69.87 | U1 |
| ATOM | 1760 | CG | LYS | 224 | 3.036 | 4.536 | 45.527 | 1.00 | 69.87 | U1 |
| ATOM | 1761 | CD | LYS | 224 | 3.903 | 5.311 | 46.518 | 1.00 | 69.87 | U1 |
| ATOM | 1762 | CE | LYS | 224 | 5.044 | 4.464 | 47.088 | 1.00 | 69.87 | U1 |
| ATOM | 1763 | NZ | LYS | 224 | 6.144 | 4.116 | 46.127 | 1.00 | 69.87 | U1 |
| ATOM | 1767 | C | LYS | 224 | 1.436 | 4.587 | 43.123 | 1.00 | 46.06 | U1 |
| ATOM | 1768 | O | LYS | 224 | 0.483 | 3.996 | 43.626 | 1.00 | 46.06 | U1 |
| ATOM | 1769 | N | GLN | 225 | 1.329 | 5.797 | 42.620 | 1.00 | 37.14 | U1 |
| ATOM | 1771 | CA | GLN | 225 | 0.095 | 6.538 | 42.652 | 1.00 | 37.14 | U1 |
| ATOM | 1772 | CB | GLN | 225 | 0.446 | 8.010 | 42.662 | 1.00 | 43.14 | U1 |
| ATOM | 1773 | CG | GLN | 225 | −0.731 | 8.912 | 42.670 | 1.00 | 43.14 | U1 |
| ATOM | 1774 | CD | GLN | 225 | −0.321 | 10.341 | 42.827 | 1.00 | 43.14 | U1 |
| ATOM | 1775 | OE1 | GLN | 225 | 0.867 | 10.673 | 42.770 | 1.00 | 43.14 | U1 |
| ATOM | 1776 | NE2 | GLN | 225 | −1.297 | 11.207 | 43.051 | 1.00 | 43.14 | U1 |
| ATOM | 1779 | C | GLN | 225 | −0.927 | 6.257 | 41.544 | 1.00 | 37.14 | U1 |
| ATOM | 1780 | O | GLN | 225 | −2.128 | 6.370 | 41.795 | 1.00 | 37.14 | U1 |
| ATOM | 1781 | N | TYR | 226 | −0.476 | 5.889 | 40.337 | 1.00 | 22.31 | U1 |
| ATOM | 1783 | CA | TYR | 226 | −1.389 | 5.664 | 39.201 | 1.00 | 22.31 | U1 |
| ATOM | 1784 | CB | TYR | 226 | −1.109 | 6.679 | 38.096 | 1.00 | 2.00 | U1 |
| ATOM | 1785 | CG | TYR | 226 | −1.308 | 8.108 | 38.504 | 1.00 | 2.00 | U1 |
| ATOM | 1786 | CD1 | TYR | 226 | −2.578 | 8.620 | 38.736 | 1.00 | 2.00 | U1 |
| ATOM | 1787 | CE1 | TYR | 226 | −2.761 | 9.943 | 39.096 | 1.00 | 2.00 | U1 |
| ATOM | 1788 | CD2 | TYR | 226 | −0.234 | 8.956 | 38.647 | 1.00 | 2.00 | U1 |
| ATOM | 1789 | CE2 | TYR | 226 | −0.408 | 10.295 | 39.019 | 1.00 | 2.00 | U1 |
| ATOM | 1790 | CZ | TYR | 226 | −1.673 | 10.772 | 39.234 | 1.00 | 2.00 | U1 |
| ATOM | 1791 | OH | TYR | 226 | −1.864 | 12.089 | 39.555 | 1.00 | 2.00 | U1 |
| ATOM | 1793 | C | TYR | 226 | −1.416 | 4.304 | 38.551 | 1.00 | 22.31 | U1 |
| ATOM | 1794 | O | TYR | 226 | −2.279 | 4.032 | 37.736 | 1.00 | 22.31 | U1 |
| ATOM | 1795 | N | ALA | 227 | −0.520 | 3.422 | 38.925 | 1.00 | 29.11 | U1 |
| ATOM | 1797 | CA | ALA | 227 | −0.483 | 2.133 | 38.293 | 1.00 | 29.11 | U1 |
| ATOM | 1798 | CB | ALA | 227 | 0.463 | 1.236 | 39.015 | 1.00 | 9.83 | U1 |

TABLE 1-continued

Structure coordinates of CPP32

| ATOM | 1799 | C   | ALA | 227 | −1.823 | 1.448 | 38.120 | 1.00 | 29.11 | U1 |
|------|------|-----|-----|-----|--------|-------|--------|------|-------|----|
| ATOM | 1800 | O   | ALA | 227 | −1.950 | 0.612 | 37.238 | 1.00 | 29.11 | U1 |
| ATOM | 1801 | N   | ASP | 228 | −2.836 | 1.833 | 38.896 | 1.00 | 35.10 | U1 |
| ATOM | 1803 | CA  | ASP | 228 | −4.155 | 1.184 | 38.819 | 1.00 | 35.10 | U1 |
| ATOM | 1804 | CB  | ASP | 228 | −4.600 | 0.683 | 40.198 | 1.00 | 47.00 | U1 |
| ATOM | 1805 | CG  | ASP | 228 | −4.740 | 1.806 | 41.221 | 1.00 | 47.00 | U1 |
| ATOM | 1806 | OD1 | ASP | 228 | −4.773 | 3.001 | 40.833 | 1.00 | 47.00 | U1 |
| ATOM | 1807 | OD2 | ASP | 228 | −4.818 | 1.484 | 42.427 | 1.00 | 47.00 | U1 |
| ATOM | 1808 | C   | ASP | 228 | −5.309 | 1.952 | 38.200 | 1.00 | 35.10 | U1 |
| ATOM | 1809 | O   | ASP | 228 | −6.469 | 1.695 | 38.531 | 1.00 | 35.10 | U1 |
| ATOM | 1810 | N   | LYS | 229 | −4.991 | 2.927 | 37.355 | 1.00 | 49.66 | U1 |
| ATOM | 1812 | CA  | LYS | 229 | −6.011 | 3.704 | 36.662 | 1.00 | 49.66 | U1 |
| ATOM | 1813 | CB  | LYS | 229 | −6.621 | 4.765 | 37.580 | 1.00 | 66.64 | U1 |
| ATOM | 1814 | CG  | LYS | 229 | −5.664 | 5.367 | 38.577 | 1.00 | 66.64 | U1 |
| ATOM | 1815 | CD  | LYS | 229 | −6.250 | 6.603 | 39.237 | 1.00 | 66.64 | U1 |
| ATOM | 1816 | CE  | LYS | 229 | −5.365 | 7.073 | 40.386 | 1.00 | 66.64 | U1 |
| ATOM | 1817 | NZ  | LYS | 229 | −5.773 | 8.387 | 40.968 | 1.00 | 66.64 | U1 |
| ATOM | 1821 | C   | LYS | 229 | −5.520 | 4.320 | 35.347 | 1.00 | 49.66 | U1 |
| ATOM | 1822 | O   | LYS | 229 | −6.336 | 4.729 | 34.524 | 1.00 | 49.66 | U1 |
| ATOM | 1823 | N   | LEU | 230 | −4.205 | 4.365 | 35.131 | 1.00 | 32.42 | U1 |
| ATOM | 1825 | CA  | LEU | 230 | −3.650 | 4.936 | 33.905 | 1.00 | 32.42 | U1 |
| ATOM | 1826 | CB  | LEU | 230 | −2.723 | 6.129 | 34.199 | 1.00 | 23.07 | U1 |
| ATOM | 1827 | CG  | LEU | 230 | −3.366 | 7.431 | 34.689 | 1.00 | 23.07 | U1 |
| ATOM | 1828 | CD1 | LEU | 230 | −2.359 | 8.536 | 34.797 | 1.00 | 23.07 | U1 |
| ATOM | 1829 | CD2 | LEU | 230 | −4.460 | 7.849 | 33.751 | 1.00 | 23.07 | U1 |
| ATOM | 1830 | C   | LEU | 230 | −2.859 | 3.924 | 33.101 | 1.00 | 32.42 | U1 |
| ATOM | 1831 | O   | LEU | 230 | −2.203 | 3.033 | 33.661 | 1.00 | 32.42 | U1 |
| ATOM | 1832 | N   | GLU | 231 | −2.920 | 4.068 | 31.781 | 1.00 | 25.77 | U1 |
| ATOM | 1834 | CA  | GLU | 231 | −2.173 | 3.220 | 30.862 | 1.00 | 25.77 | U1 |
| ATOM | 1835 | CB  | GLU | 231 | −2.687 | 3.466 | 29.442 | 1.00 | 20.59 | U1 |
| ATOM | 1836 | CG  | GLU | 231 | −2.204 | 2.523 | 28.392 | 1.00 | 20.59 | U1 |
| ATOM | 1837 | CD  | GLU | 231 | −0.925 | 2.975 | 27.812 | 1.00 | 20.59 | U1 |
| ATOM | 1838 | OE1 | GLU | 231 | −0.755 | 4.186 | 27.610 | 1.00 | 20.59 | U1 |
| ATOM | 1839 | OE2 | GLU | 231 | −0.062 | 2.124 | 27.558 | 1.00 | 20.59 | U1 |
| ATOM | 1840 | C   | GLU | 231 | −0.729 | 3.691 | 31.025 | 1.00 | 25.77 | U1 |
| ATOM | 1841 | O   | GLU | 231 | −0.482 | 4.883 | 31.267 | 1.00 | 25.77 | U1 |
| ATOM | 1842 | N   | PHE | 232 | 0.219  | 2.779 | 30.871 | 1.00 | 28.74 | U1 |
| ATOM | 1844 | CA  | PHE | 232 | 1.637  | 3.082 | 31.051 | 1.00 | 28.74 | U1 |
| ATOM | 1845 | CB  | PHE | 232 | 2.497  | 1.900 | 30.582 | 1.00 | 40.16 | U1 |
| ATOM | 1846 | CG  | PHE | 232 | 3.910  | 1.923 | 31.098 | 1.00 | 40.16 | U1 |
| ATOM | 1847 | CD1 | PHE | 232 | 4.215  | 2.483 | 32.331 | 1.00 | 40.16 | U1 |
| ATOM | 1848 | CD2 | PHE | 232 | 4.938  | 1.375 | 30.352 | 1.00 | 40.16 | U1 |
| ATOM | 1849 | CE1 | PHE | 232 | 5.535  | 2.493 | 32.811 | 1.00 | 40.16 | U1 |
| ATOM | 1850 | CE2 | PHE | 232 | 6.240  | 1.385 | 30.824 | 1.00 | 40.16 | U1 |
| ATOM | 1851 | CZ  | PHE | 232 | 6.538  | 1.949 | 32.060 | 1.00 | 40.16 | U1 |
| ATOM | 1852 | C   | PHE | 232 | 2.171  | 4.398 | 30.488 | 1.00 | 28.74 | U1 |
| ATOM | 1853 | O   | PHE | 232 | 2.818  | 5.154 | 31.216 | 1.00 | 28.74 | U1 |
| ATOM | 1854 | N   | MET | 233 | 1.888  | 4.697 | 29.219 | 1.00 | 23.92 | U1 |
| ATOM | 1856 | CA  | MET | 233 | 2.376  | 5.935 | 28.573 | 1.00 | 23.92 | U1 |
| ATOM | 1857 | CB  | MET | 233 | 1.914  | 5.979 | 27.110 | 1.00 | 43.91 | U1 |
| ATOM | 1858 | CG  | MET | 233 | 2.382  | 4.780 | 26.290 | 1.00 | 43.91 | U1 |
| ATOM | 1859 | SD  | NET | 233 | 4.184  | 4.633 | 26.373 | 1.00 | 43.91 | U1 |
| ATOM | 1860 | CE  | MET | 233 | 4.670  | 6.200 | 25.525 | 1.00 | 43.91 | U1 |
| ATOM | 1861 | C   | MET | 233 | 1.948  | 7.222 | 29.288 | 1.00 | 23.92 | U1 |
| ATOM | 1862 | O   | MET | 233 | 2.691  | 8.222 | 29.332 | 1.00 | 23.92 | U1 |
| ATOM | 1863 | N   | HIS | 234 | 0.731  | 7.210 | 29.825 | 1.00 | 29.68 | U1 |
| ATOM | 1865 | CA  | HIS | 234 | 0.230  | 8.363 | 30.545 | 1.00 | 29.68 | U1 |
| ATOM | 1866 | CB  | HIS | 234 | −1.278 | 8.315 | 30.672 | 1.00 | 32.32 | U1 |
| ATOM | 1867 | CG  | HIS | 234 | −1.970 | 8.427 | 29.358 | 1.00 | 32.32 | U1 |
| ATOM | 1868 | CD2 | HIS | 234 | −1.485 | 8.730 | 28.132 | 1.00 | 32.32 | U1 |
| ATOM | 1869 | ND1 | HIS | 234 | −3.323 | 8.235 | 29.202 | 1.00 | 32.32 | U1 |
| ATOM | 1871 | CE1 | HIS | 234 | −3.645 | 8.420 | 27.935 | 1.00 | 32.32 | U1 |
| ATOM | 1872 | NE2 | HIS | 234 | −2.549 | 8.721 | 27.267 | 1.00 | 32.32 | U1 |
| ATOM | 1874 | C   | HIS | 234 | 0.896  | 8.439 | 31.891 | 1.00 | 29.68 | U1 |
| ATOM | 1875 | O   | HIS | 234 | 1.020  | 9.516 | 32.463 | 1.00 | 29.68 | U1 |
| ATOM | 1876 | N   | ILE | 235 | 1.316  | 7.311 | 32.430 | 1.00 | 31.69 | U1 |
| ATOM | 1878 | CA  | ILE | 235 | 2.021  | 7.400 | 33.695 | 1.00 | 31.69 | U1 |
| ATOM | 1879 | CB  | ILE | 235 | 2.204  | 6.053 | 34.361 | 1.00 | 18.51 | U1 |
| ATOM | 1880 | CG2 | ILE | 235 | 3.086  | 6.203 | 35.571 | 1.00 | 18.51 | U1 |
| ATOM | 1881 | CG1 | ILE | 235 | 0.846  | 5.486 | 34.756 | 1.00 | 18.51 | U1 |
| ATOM | 1882 | CD1 | ILE | 235 | 0.956  | 4.075 | 35.161 | 1.00 | 18.51 | U1 |
| ATOM | 1883 | C   | ILE | 235 | 3.386  | 8.020 | 33.384 | 1.00 | 31.69 | U1 |
| ATOM | 1884 | O   | ILE | 235 | 3.743  | 9.043 | 33.983 | 1.00 | 31.69 | U1 |
| ATOM | 1885 | N   | LEU | 236 | 4.075  | 7.497 | 32.361 | 1.00 | 20.04 | U1 |
| ATOM | 1887 | CA  | LEU | 236 | 5.392  | 8.003 | 31.994 | 1.00 | 20.04 | U1 |
| ATOM | 1888 | CB  | LEU | 236 | 6.036  | 7.149 | 30.934 | 1.00 | 2.00  | U1 |
| ATOM | 1889 | CG  | LEU | 236 | 6.583  | 5.839 | 31.466 | 1.00 | 2.00  | U1 |

TABLE 1-continued

Structure coordinates of CPP32

| ATOM | 1890 | CD1 | LEU | 236 | 6.945 | 4.966 | 30.298 | 1.00 | 2.00 | U1 |
|---|---|---|---|---|---|---|---|---|---|---|
| ATOM | 1891 | CD2 | LEU | 236 | 7.769 | 6.073 | 32.375 | 1.00 | 2.00 | U1 |
| ATOM | 1892 | C | LEU | 236 | 5.373 | 9.438 | 31.567 | 1.00 | 20.04 | U1 |
| ATOM | 1893 | O | LEU | 236 | 6.387 | 10.127 | 31.647 | 1.00 | 20.04 | U1 |
| ATOM | 1894 | N | THR | 237 | 4.231 | 9.918 | 31.111 | 1.00 | 16.72 | U1 |
| ATOM | 1896 | CA | THR | 237 | 4.137 | 11.319 | 30.720 | 1.00 | 16.72 | U1 |
| ATOM | 1897 | CB | THR | 237 | 2.892 | 11.546 | 29.895 | 1.00 | 2.00 | U1 |
| ATOM | 1898 | OG1 | THR | 237 | 3.050 | 10.888 | 28.636 | 1.00 | 2.00 | U1 |
| ATOM | 1900 | CG2 | THR | 237 | 2.654 | 12.978 | 29.675 | 1.00 | 2.00 | U1 |
| ATOM | 1901 | C | THR | 237 | 4.109 | 12.164 | 31.982 | 1.00 | 16.72 | U1 |
| ATOM | 1902 | O | THR | 237 | 4.665 | 13.269 | 32.026 | 1.00 | 16.72 | U1 |
| ATOM | 1903 | N | ARG | 238 | 3.489 | 11.624 | 33.029 | 1.00 | 28.44 | U1 |
| ATOM | 1905 | CA | ARG | 238 | 3.417 | 12.334 | 34.299 | 1.00 | 28.44 | U1 |
| ATOM | 1906 | CB | ARG | 238 | 2.382 | 11.712 | 35.225 | 1.00 | 56.35 | U1 |
| ATOM | 1907 | CG | ARG | 238 | 0.957 | 12.216 | 34.910 | 1.00 | 56.35 | U1 |
| ATOM | 1908 | CD | ARG | 238 | −0.091 | 11.289 | 35.462 | 1.00 | 56.35 | U1 |
| ATOM | 1909 | NE | ARG | 238 | −1.391 | 11.454 | 34.824 | 1.00 | 56.35 | U1 |
| ATOM | 1911 | CZ | ARG | 238 | −2.363 | 12.230 | 35.292 | 1.00 | 56.35 | U1 |
| ATOM | 1912 | NH1 | ARG | 238 | −2.196 | 12.932 | 36.406 | 1.00 | 56.35 | U1 |
| ATOM | 1915 | NH2 | ARG | 238 | −3.518 | 12.290 | 34.649 | 1.00 | 56.35 | U1 |
| ATOM | 1918 | C | ARG | 238 | 4.798 | 12.389 | 34.907 | 1.00 | 28.44 | U1 |
| ATOM | 1919 | O | ARG | 238 | 5.165 | 13.392 | 35.512 | 1.00 | 28.44 | U1 |
| ATOM | 1920 | N | VAL | 239 | 5.595 | 11.348 | 34.684 | 1.00 | 19.08 | U1 |
| ATOM | 1922 | CA | VAL | 239 | 6.974 | 11.346 | 35.170 | 1.00 | 19.08 | U1 |
| ATOM | 1923 | CB | VAL | 239 | 7.678 | 10.036 | 34.887 | 1.00 | 2.00 | U1 |
| ATOM | 1924 | CG1 | VAL | 239 | 9.163 | 10.165 | 35.137 | 1.00 | 2.00 | U1 |
| ATOM | 1925 | CG2 | VAL | 239 | 7.087 | 8.959 | 35.752 | 1.00 | 2.00 | U1 |
| ATOM | 1926 | C | VAL | 239 | 7.696 | 12.463 | 34.443 | 1.00 | 19.08 | U1 |
| ATOM | 1927 | O | VAL | 239 | 8.397 | 13.245 | 35.064 | 1.00 | 19.08 | U1 |
| ATOM | 1928 | N | ASN | 240 | 7.476 | 12.585 | 33.136 | 1.00 | 21.86 | U1 |
| ATOM | 1930 | CA | ASN | 240 | 8.114 | 13.643 | 32.359 | 1.00 | 21.86 | U1 |
| ATOM | 1931 | CB | ASN | 240 | 7.638 | 13.636 | 30.900 | 1.00 | 23.01 | U1 |
| ATOM | 1932 | CG | ASN | 240 | 8.285 | 12.534 | 30.057 | 1.00 | 23.01 | U1 |
| ATOM | 1933 | OD1 | ASN | 240 | 9.094 | 11.747 | 30.545 | 1.00 | 23.01 | U1 |
| ATOM | 1934 | ND2 | ASN | 240 | 7.910 | 12.467 | 28.792 | 1.00 | 23.01 | U1 |
| ATOM | 1937 | C | ASN | 240 | 7.800 | 14.986 | 32.967 | 1.00 | 21.86 | U1 |
| ATOM | 1938 | O | ASN | 240 | 8.682 | 15.801 | 33.159 | 1.00 | 21.86 | U1 |
| ATOM | 1939 | N | ARG | 241 | 6.536 | 15.249 | 33.260 | 1.00 | 29.09 | U1 |
| ATOM | 1941 | CA | ARG | 241 | 6.178 | 16.545 | 33.843 | 1.00 | 29.09 | U1 |
| ATOM | 1942 | CB | ARG | 241 | 4.655 | 16.702 | 33.935 | 1.00 | 37.83 | U1 |
| ATOM | 1943 | CG | ARG | 241 | 4.175 | 18.112 | 34.214 | 1.00 | 37.83 | U1 |
| ATOM | 1944 | CD | ARG | 241 | 2.751 | 18.329 | 33.714 | 1.00 | 37.83 | U1 |
| ATOM | 1945 | NE | ARG | 241 | 1.726 | 17.599 | 34.468 | 1.00 | 37.83 | U1 |
| ATOM | 1947 | CZ | ARG | 241 | 0.922 | 16.656 | 33.968 | 1.00 | 37.83 | U1 |
| ATOM | 1948 | NH1 | ARG | 241 | 1.006 | 16.284 | 32.700 | 1.00 | 37.83 | U1 |
| ATOM | 1951 | NH2 | ARG | 241 | −0.008 | 16.105 | 34.737 | 1.00 | 37.83 | U1 |
| ATOM | 1954 | C | ARG | 241 | 6.836 | 16.716 | 35.221 | 1.00 | 29.09 | U1 |
| ATOM | 1955 | O | ARG | 241 | 7.384 | 17.779 | 35.526 | 1.00 | 29.09 | U1 |
| ATOM | 1956 | N | LYS | 242 | 6.870 | 15.651 | 36.017 | 1.00 | 25.30 | U1 |
| ATOM | 1958 | CA | LYS | 242 | 7.463 | 15.746 | 37.329 | 1.00 | 25.30 | U1 |
| ATOM | 1959 | CB | LYS | 242 | 7.298 | 14.461 | 38.120 | 1.00 | 42.15 | U1 |
| ATOM | 1960 | CG | LYS | 242 | 7.861 | 14.589 | 39.525 | 1.00 | 42.15 | U1 |
| ATOM | 1961 | CD | LYS | 242 | 7.171 | 13.675 | 40.507 | 1.00 | 42.15 | U1 |
| ATOM | 1962 | CE | LYS | 242 | 7.557 | 14.068 | 41.936 | 1.00 | 42.15 | U1 |
| ATOM | 1963 | NZ | LYS | 242 | 6.855 | 13.188 | 42.908 | 1.00 | 42.15 | U1 |
| ATOM | 1967 | C | LYS | 242 | 8.919 | 16.120 | 37.304 | 1.00 | 25.30 | U1 |
| ATOM | 1968 | O | LYS | 242 | 9.318 | 17.078 | 37.986 | 1.00 | 25.30 | U1 |
| ATOM | 1969 | N | VAL | 243 | 9.734 | 15.391 | 36.543 | 1.00 | 27.61 | U1 |
| ATOM | 1971 | CA | VAL | 243 | 11.154 | 15.732 | 36.536 | 1.00 | 27.61 | U1 |
| ATOM | 1972 | CB | VAL | 243 | 12.103 | 14.584 | 36.093 | 1.00 | 12.51 | U1 |
| ATOM | 1973 | CG1 | VAL | 243 | 11.359 | 13.312 | 35.925 | 1.00 | 12.51 | U1 |
| ATOM | 1974 | CG2 | VAL | 243 | 12.860 | 14.942 | 34.900 | 1.00 | 12.51 | U1 |
| ATOM | 1975 | C | VAL | 243 | 11.484 | 17.023 | 35.829 | 1.00 | 27.61 | U1 |
| ATOM | 1976 | O | VAL | 243 | 12.482 | 17.666 | 36.161 | 1.00 | 27.61 | U1 |
| ATOM | 1977 | N | ALA | 244 | 10.596 | 17.461 | 34.948 | 1.00 | 22.16 | U1 |
| ATOM | 1979 | CA | ALA | 244 | 10.827 | 18.689 | 34.184 | 1.00 | 22.16 | U1 |
| ATOM | 1980 | CB | ALA | 244 | 10.051 | 18.636 | 32.881 | 1.00 | 26.26 | U1 |
| ATOM | 1981 | C | ALA | 244 | 10.449 | 19.944 | 34.951 | 1.00 | 22.16 | U1 |
| ATOM | 1982 | O | ALA | 244 | 11.145 | 20.952 | 34.910 | 1.00 | 22.16 | U1 |
| ATOM | 1983 | N | THR | 245 | 9.334 | 19.884 | 35.646 | 1.00 | 33.88 | U1 |
| ATOM | 1985 | CA | THR | 245 | 8.880 | 21.032 | 36.377 | 1.00 | 33.88 | U1 |
| ATOM | 1986 | CB | THR | 245 | 7.342 | 21.074 | 36.379 | 1.00 | 30.81 | U1 |
| ATOM | 1987 | OG1 | THR | 245 | 6.839 | 19.959 | 37.123 | 1.00 | 30.81 | U1 |
| ATOM | 1989 | CG2 | THR | 245 | 6.808 | 20.954 | 34.966 | 1.00 | 30.81 | U1 |
| ATOM | 1990 | C | THR | 245 | 9.400 | 21.039 | 37.810 | 1.00 | 33.88 | U1 |
| ATOM | 1991 | O | THR | 245 | 9.764 | 22.086 | 38.324 | 1.00 | 33.88 | U1 |
| ATOM | 1992 | N | GLU | 246 | 9.528 | 19.867 | 38.425 | 1.00 | 30.45 | U1 |

TABLE 1-continued

Structure coordinates of CPP32

| | | | | | | | | | |
|---|---|---|---|---|---|---|---|---|---|
| ATOM | 1994 | CA | GLU | 246 | 9.955 | 19.803 | 39.811 | 1.00 | 30.45 U1 |
| ATOM | 1995 | CB | GLU | 246 | 9.163 | 18.740 | 40.543 | 1.00 | 44.10 U1 |
| ATOM | 1996 | CG | GLU | 246 | 7.693 | 19.052 | 40.570 | 1.00 | 44.10 U1 |
| ATOM | 1997 | CD | GLU | 246 | 6.893 | 18.052 | 41.352 | 1.00 | 44.10 U1 |
| ATOM | 1998 | OE1 | GLU | 246 | 5.652 | 18.180 | 41.358 | 1.00 | 44.10 U1 |
| ATOM | 1999 | OE2 | GLU | 246 | 7.491 | 17.138 | 41.959 | 1.00 | 44.10 U1 |
| ATOM | 2000 | C | GLU | 246 | 11.401 | 19.744 | 40.253 | 1.00 | 30.45 U1 |
| ATOM | 2001 | O | GLU | 246 | 11.667 | 19.968 | 41.424 | 1.00 | 30.45 U1 |
| ATOM | 2002 | N | PHE | 247 | 12.345 | 19.462 | 39.375 | 1.00 | 27.63 U1 |
| ATOM | 2004 | CA | PHE | 247 | 13.725 | 19.405 | 39.817 | 1.00 | 27.63 U1 |
| ATOM | 2005 | CB | PHE | 247 | 14.294 | 18.036 | 39.560 | 1.00 | 23.40 U1 |
| ATOM | 2006 | CG | PHE | 247 | 13.568 | 16.929 | 40.255 | 1.00 | 23.40 U1 |
| ATOM | 2007 | CD1 | PHE | 247 | 12.309 | 16.531 | 39.838 | 1.00 | 23.40 U1 |
| ATOM | 2008 | CD2 | PHE | 247 | 14.176 | 16.226 | 41.289 | 1.00 | 23.40 U1 |
| ATOM | 2009 | CE1 | PHE | 247 | 11.665 | 15.450 | 40.433 | 1.00 | 23.40 U1 |
| ATOM | 2010 | CE2 | PHE | 247 | 13.543 | 15.135 | 41.898 | 1.00 | 23.40 U1 |
| ATOM | 2011 | CZ | PHE | 247 | 12.283 | 14.751 | 41.465 | 1.00 | 23.40 U1 |
| ATOM | 2012 | C | PHE | 247 | 14.614 | 20.446 | 39.150 | 1.00 | 27.63 U1 |
| ATOM | 2013 | O | PHE | 247 | 14.300 | 20.919 | 38.064 | 1.00 | 27.63 U1 |
| ATOM | 2014 | N | GLU | 248 | 15.694 | 20.820 | 39.839 | 1.00 | 36.28 U1 |
| ATOM | 2016 | CA | GLU | 248 | 16.704 | 21.789 | 39.384 | 1.00 | 36.28 U1 |
| ATOM | 2017 | CB | GLU | 248 | 16.280 | 23.217 | 39.719 | 1.00 | 44.15 U1 |
| ATOM | 2018 | CG | GLU | 248 | 17.181 | 24.276 | 39.130 | 1.00 | 44.15 U1 |
| ATOM | 2019 | CD | GLU | 248 | 16.509 | 25.636 | 39.012 | 1.00 | 44.15 U1 |
| ATOM | 2020 | OE1 | GLU | 248 | 17.156 | 26.654 | 39.329 | 1.00 | 44.15 U1 |
| ATOM | 2021 | OE2 | GLU | 248 | 15.336 | 25.696 | 38.577 | 1.00 | 44.15 U1 |
| ATOM | 2022 | C | GLU | 248 | 17.952 | 21.411 | 40.171 | 1.00 | 36.28 U1 |
| ATOM | 2023 | O | GLU | 248 | 17.877 | 21.265 | 41.387 | 1.00 | 36.28 U1 |
| ATOM | 2024 | N | SER | 249 | 19.083 | 21.207 | 39.504 | 1.00 | 35.87 U1 |
| ATOM | 2026 | CA | SER | 249 | 20.290 | 20.773 | 40.210 | 1.00 | 35.87 U1 |
| ATOM | 2027 | CB | SER | 249 | 21.392 | 20.439 | 39.231 | 1.00 | 22.66 U1 |
| ATOM | 2028 | OG | SER | 249 | 21.900 | 21.650 | 38.680 | 1.00 | 22.66 U1 |
| ATOM | 2030 | C | SER | 249 | 20.827 | 21.817 | 41.161 | 1.00 | 35.87 U1 |
| ATOM | 2031 | O | SER | 249 | 20.580 | 23.001 | 40.991 | 1.00 | 35.87 U1 |
| ATOM | 2032 | N | PHE | 250 | 21.617 | 21.386 | 42.133 | 1.00 | 32.37 U1 |
| ATOM | 2034 | CA | PHE | 250 | 22.212 | 22.311 | 43.072 | 1.00 | 32.37 U1 |
| ATOM | 2035 | CB | PHE | 250 | 21.483 | 22.276 | 44.431 | 1.00 | 30.28 U1 |
| ATOM | 2036 | CG | PHE | 250 | 22.058 | 23.241 | 45.448 | 1.00 | 30.28 U1 |
| ATOM | 2037 | CD1 | PHE | 250 | 21.595 | 24.543 | 45.520 | 1.00 | 30.28 U1 |
| ATOM | 2038 | CD2 | PHE | 250 | 23.137 | 22.878 | 46.244 | 1.00 | 30.28 U1 |
| ATOM | 2039 | CE1 | PHE | 250 | 22.206 | 25.455 | 46.354 | 1.00 | 30.28 U1 |
| ATOM | 2040 | CE2 | PHE | 250 | 23.748 | 23.794 | 47.081 | 1.00 | 30.28 U1 |
| ATOM | 2041 | CZ | PHE | 250 | 23.286 | 25.076 | 47.133 | 1.00 | 30.28 U1 |
| ATOM | 2042 | C | PHE | 250 | 23.631 | 21.831 | 43.251 | 1.00 | 32.37 U1 |
| ATOM | 2043 | O | PHE | 250 | 23.850 | 20.696 | 43.660 | 1.00 | 32.37 U1 |
| ATOM | 2044 | N | SER | 251 | 24.591 | 22.670 | 42.892 | 1.00 | 32.63 U1 |
| ATOM | 2046 | CA | SER | 251 | 25.987 | 22.314 | 43.055 | 1.00 | 32.63 U1 |
| ATOM | 2047 | CB | SER | 251 | 26.490 | 21.609 | 41.803 | 1.00 | 48.84 U1 |
| ATOM | 2048 | OG | SER | 251 | 27.644 | 20.831 | 42.075 | 1.00 | 48.84 U1 |
| ATOM | 2050 | C | SER | 251 | 26.789 | 23.584 | 43.313 | 1.00 | 32.63 U1 |
| ATOM | 2051 | O | SER | 251 | 26.340 | 24.686 | 42.965 | 1.00 | 32.63 U1 |
| ATOM | 2052 | N | PHE | 252 | 27.927 | 23.424 | 43.993 | 1.00 | 51.16 U1 |
| ATOM | 2054 | CA | PHE | 252 | 28.845 | 24.515 | 44.333 | 1.00 | 51.16 U1 |
| ATOM | 2055 | CB | PHE | 252 | 29.781 | 24.096 | 45.470 | 1.00 | 38.32 U1 |
| ATOM | 2056 | CG | PHE | 252 | 29.068 | 23.745 | 46.737 | 1.00 | 38.32 U1 |
| ATOM | 2057 | CD1 | PHE | 252 | 29.384 | 22.588 | 47.422 | 1.00 | 38.32 U1 |
| ATOM | 2058 | CD2 | PHE | 252 | 28.037 | 24.552 | 47.215 | 1.00 | 38.32 U1 |
| ATOM | 2059 | CE1 | PHE | 252 | 28.671 | 22.234 | 48.571 | 1.00 | 38.32 U1 |
| ATOM | 2060 | CE2 | PHE | 252 | 27.322 | 24.207 | 48.361 | 1.00 | 38.32 U1 |
| ATOM | 2061 | CZ | PHE | 252 | 27.634 | 23.052 | 49.038 | 1.00 | 38.32 U1 |
| ATOM | 2062 | C | PHE | 252 | 29.676 | 24.878 | 43.114 | 1.00 | 51.16 U1 |
| ATOM | 2063 | O | PHE | 252 | 30.450 | 25.843 | 43.133 | 1.00 | 51.16 U1 |
| ATOM | 2064 | N | ASP | 253 | 29.558 | 24.055 | 42.076 | 1.00 | 43.04 U1 |
| ATOM | 2066 | CA | ASP | 253 | 30.261 | 24.286 | 40.827 | 1.00 | 43.04 U1 |
| ATOM | 2067 | CB | ASP | 253 | 30.669 | 22.957 | 40.190 | 1.00 | 70.49 U1 |
| ATOM | 2068 | CG | ASP | 253 | 32.020 | 23.027 | 39.502 | 1.00 | 70.49 U1 |
| ATOM | 2069 | OD1 | ASP | 253 | 32.809 | 22.064 | 39.670 | 1.00 | 70.49 U1 |
| ATOM | 2070 | OD2 | ASP | 253 | 32.298 | 24.041 | 38.809 | 1.00 | 70.49 U1 |
| ATOM | 2071 | C | ASP | 253 | 29.263 | 25.010 | 39.926 | 1.00 | 43.04 U1 |
| ATOM | 2072 | O | ASP | 253 | 28.256 | 24.427 | 39.514 | 1.00 | 43.04 U1 |
| ATOM | 2073 | N | ALA | 254 | 29.524 | 26.285 | 39.664 | 1.00 | 37.77 U1 |
| ATOM | 2075 | CA | ALA | 254 | 28.657 | 27.099 | 38.829 | 1.00 | 37.77 U1 |
| ATOM | 2076 | CB | ALA | 254 | 29.381 | 28.353 | 38.402 | 1.00 | 38.75 U1 |
| ATOM | 2077 | C | ALA | 254 | 28.255 | 26.312 | 37.610 | 1.00 | 37.77 U1 |
| ATOM | 2078 | O | ALA | 254 | 27.106 | 26.352 | 37.183 | 1.00 | 37.77 U1 |
| ATOM | 2079 | N | THR | 255 | 29.209 | 25.555 | 37.083 | 1.00 | 58.35 U1 |
| ATOM | 2081 | CA | THR | 255 | 28.983 | 24.752 | 35.894 | 1.00 | 58.35 U1 |

TABLE 1-continued

Structure coordinates of CPP32

| ATOM | 2082 | CB | THR | 255 | 30.255 | 23.968 | 35.523 | 1.00 | 60.21 | U1 |
|---|---|---|---|---|---|---|---|---|---|---|
| ATOM | 2083 | OG1 | THR | 255 | 30.828 | 23.416 | 36.714 | 1.00 | 60.21 | U1 |
| ATOM | 2085 | CG2 | THR | 255 | 31.272 | 24.875 | 34.861 | 1.00 | 60.21 | U1 |
| ATOM | 2086 | C | THR | 255 | 27.791 | 23.789 | 35.967 | 1.00 | 58.35 | U1 |
| ATOM | 2087 | O | THR | 255 | 26.923 | 23.819 | 35.092 | 1.00 | 58.35 | U1 |
| ATOM | 2088 | N | PHE | 256 | 27.723 | 22.979 | 37.022 | 1.00 | 30.49 | U1 |
| ATOM | 2090 | CA | PHE | 256 | 26.659 | 21.992 | 37.151 | 1.00 | 30.49 | U1 |
| ATOM | 2091 | CB | PHE | 256 | 27.216 | 20.734 | 37.809 | 1.00 | 55.89 | U1 |
| ATOM | 2092 | CG | PHE | 256 | 28.336 | 20.088 | 37.050 | 1.00 | 55.89 | U1 |
| ATOM | 2093 | CD1 | PHE | 256 | 29.355 | 20.846 | 36.495 | 1.00 | 55.89 | U1 |
| ATOM | 2094 | CD2 | PHE | 256 | 28.364 | 18.705 | 36.878 | 1.00 | 55.89 | U1 |
| ATOM | 2095 | CE1 | PHE | 256 | 30.386 | 20.248 | 35.776 | 1.00 | 55.89 | U1 |
| ATOM | 2096 | CE2 | PHE | 256 | 29.392 | 18.092 | 36.162 | 1.00 | 55.89 | U1 |
| ATOM | 2097 | CZ | PHE | 256 | 30.404 | 18.867 | 35.609 | 1.00 | 55.89 | U1 |
| ATOM | 2098 | C | PHE | 256 | 25.460 | 22.484 | 37.962 | 1.00 | 30.49 | U1 |
| ATOM | 2099 | O | PHE | 256 | 24.569 | 21.706 | 38.301 | 1.00 | 30.49 | U1 |
| ATOM | 2100 | N | HIS | 257 | 25.386 | 23.786 | 38.190 | 1.00 | 25.68 | U1 |
| ATOM | 2102 | CA | HIS | 257 | 24.337 | 24.350 | 39.023 | 1.00 | 25.68 | U1 |
| ATOM | 2103 | CB | HIS | 257 | 24.991 | 25.359 | 39.991 | 1.00 | 22.46 | U1 |
| ATOM | 2104 | CG | HIS | 257 | 24.042 | 25.972 | 40.972 | 1.00 | 22.46 | U1 |
| ATOM | 2105 | CD2 | HIS | 257 | 23.318 | 27.118 | 40.913 | 1.00 | 22.46 | U1 |
| ATOM | 2106 | ND1 | HIS | 257 | 23.640 | 25.324 | 42.120 | 1.00 | 22.46 | U1 |
| ATOM | 2108 | CE1 | HIS | 257 | 22.687 | 26.030 | 42.709 | 1.00 | 22.46 | U1 |
| ATOM | 2109 | NE2 | HIS | 257 | 22.478 | 27.123 | 41.997 | 1.00 | 22.46 | U1 |
| ATOM | 2111 | C | HIS | 257 | 23.165 | 24.983 | 38.288 | 1.00 | 25.68 | U1 |
| ATOM | 2112 | O | HIS | 257 | 23.355 | 25.871 | 37.475 | 1.00 | 25.68 | U1 |
| ATOM | 2113 | N | ALA | 258 | 21.951 | 24.565 | 38.633 | 1.00 | 32.27 | U1 |
| ATOM | 2115 | CA | ALA | 258 | 20.706 | 25.100 | 38.051 | 1.00 | 32.27 | U1 |
| ATOM | 2116 | CB | ALA | 258 | 20.768 | 26.608 | 37.963 | 1.00 | 23.66 | U1 |
| ATOM | 2117 | C | ALA | 258 | 20.290 | 24.517 | 36.693 | 1.00 | 32.27 | U1 |
| ATOM | 2118 | O | ALA | 258 | 19.567 | 25.172 | 35.924 | 1.00 | 32.27 | U1 |
| ATOM | 2119 | N | LYS | 259 | 20.712 | 23.283 | 36.427 | 1.00 | 41.96 | U1 |
| ATOM | 2121 | CA | LYS | 259 | 20.406 | 22.599 | 35.184 | 1.00 | 41.96 | U1 |
| ATOM | 2122 | CB | LYS | 259 | 21.494 | 21.585 | 34.864 | 1.00 | 32.26 | U1 |
| ATOM | 2123 | CG | LYS | 259 | 22.880 | 22.169 | 34.890 | 1.00 | 32.26 | U1 |
| ATOM | 2124 | CD | LYS | 259 | 22.941 | 23.485 | 34.122 | 1.00 | 32.26 | U1 |
| ATOM | 2125 | CE | LYS | 259 | 24.313 | 24.079 | 34.258 | 1.00 | 32.26 | U1 |
| ATOM | 2126 | NZ | LYS | 259 | 24.378 | 25.489 | 33.834 | 1.00 | 32.26 | U1 |
| ATOM | 2130 | C | LYS | 259 | 19.097 | 21.873 | 35.323 | 1.00 | 41.96 | U1 |
| ATOM | 2131 | O | LYS | 259 | 18.683 | 21.537 | 36.431 | 1.00 | 41.96 | U1 |
| ATOM | 2132 | N | LYS | 260 | 18.507 | 21.521 | 34.193 | 1.00 | 31.28 | U1 |
| ATOM | 2134 | CA | LYS | 260 | 17.227 | 20.831 | 34.192 | 1.00 | 31.28 | U1 |
| ATOM | 2135 | CB | LYS | 260 | 16.173 | 21.745 | 33.582 | 1.00 | 22.91 | U1 |
| ATOM | 2136 | CG | LYS | 260 | 16.117 | 23.143 | 34.229 | 1.00 | 22.91 | U1 |
| ATOM | 2137 | CD | LYS | 260 | 15.290 | 23.130 | 35.504 | 1.00 | 22.91 | U1 |
| ATOM | 2138 | CE | LYS | 260 | 13.846 | 22.813 | 35.189 | 1.00 | 22.91 | U1 |
| ATOM | 2139 | NZ | LYS | 260 | 12.971 | 22.871 | 36.368 | 1.00 | 22.91 | U1 |
| ATOM | 2143 | C | LYS | 260 | 17.327 | 19.501 | 33.431 | 1.00 | 31.28 | U1 |
| ATOM | 2144 | O | LYS | 260 | 18.388 | 19.165 | 32.882 | 1.00 | 31.28 | U1 |
| ATOM | 2145 | N | GLN | 261 | 16.234 | 18.753 | 33.369 | 1.00 | 21.27 | U1 |
| ATOM | 2147 | CA | GLN | 261 | 16.256 | 17.464 | 32.707 | 1.00 | 21.27 | U1 |
| ATOM | 2148 | CB | GLN | 261 | 16.791 | 16.425 | 33.692 | 1.00 | 22.61 | U1 |
| ATOM | 2149 | CG | GLN | 261 | 16.603 | 14.967 | 33.317 | 1.00 | 22.61 | U1 |
| ATOM | 2150 | CD | GLN | 261 | 17.218 | 14.016 | 34.333 | 1.00 | 22.61 | U1 |
| ATOM | 2151 | OE1 | GLN | 261 | 18.285 | 14.275 | 34.880 | 1.00 | 22.61 | U1 |
| ATOM | 2152 | NE2 | GLN | 261 | 16.553 | 12.913 | 34.579 | 1.00 | 22.61 | U1 |
| ATOM | 2155 | C | GLN | 261 | 14.863 | 17.089 | 32.287 | 1.00 | 21.27 | U1 |
| ATOM | 2156 | O | GLN | 261 | 13.901 | 17.423 | 32.971 | 1.00 | 21.27 | U1 |
| ATOM | 2157 | N | ILE | 262 | 14.756 | 16.385 | 31.170 | 1.00 | 27.96 | U1 |
| ATOM | 2159 | CA | ILE | 262 | 13.473 | 15.929 | 30.656 | 1.00 | 27.96 | U1 |
| ATOM | 2160 | CB | ILE | 262 | 13.043 | 16.758 | 29.393 | 1.00 | 18.54 | U1 |
| ATOM | 2161 | CG2 | ILE | 262 | 14.139 | 16.779 | 28.380 | 1.00 | 18.54 | U1 |
| ATOM | 2162 | CG1 | ILE | 262 | 11.775 | 16.191 | 28.755 | 1.00 | 18.54 | U1 |
| ATOM | 2163 | CD1 | ILE | 262 | 10.518 | 16.418 | 29.535 | 1.00 | 18.54 | U1 |
| ATOM | 2164 | C | ILE | 262 | 13.674 | 14.464 | 30.290 | 1.00 | 27.96 | U1 |
| ATOM | 2165 | O | ILE | 262 | 14.630 | 14.123 | 29.586 | 1.00 | 27.96 | U1 |
| ATOM | 2166 | N | PRO | 263 | 12.896 | 13.561 | 30.881 | 1.00 | 23.51 | U1 |
| ATOM | 2167 | CD | PRO | 263 | 11.996 | 13.746 | 32.019 | 1.00 | 12.23 | U1 |
| ATOM | 2168 | CA | PRO | 263 | 13.039 | 12.142 | 30.561 | 1.00 | 23.51 | U1 |
| ATOM | 2169 | CB | PRO | 263 | 11.946 | 11.514 | 31.398 | 1.00 | 12.23 | U1 |
| ATOM | 2170 | CG | PRO | 263 | 11.951 | 12.391 | 32.609 | 1.00 | 12.23 | U1 |
| ATOM | 2171 | C | PRO | 263 | 12.763 | 11.978 | 29.077 | 1.00 | 23.51 | U1 |
| ATOM | 2172 | O | PRO | 263 | 12.389 | 12.935 | 28.432 | 1.00 | 23.51 | U1 |
| ATOM | 2173 | N | CYS | 264 | 12.845 | 10.765 | 28.552 | 1.00 | 22.57 | U1 |
| ATOM | 2175 | CA | CYS | 264 | 12.633 | 10.547 | 27.125 | 1.00 | 22.57 | U1 |
| ATOM | 2176 | CB | CYS | 264 | 13.954 | 10.745 | 26.402 | 1.00 | 21.62 | U1 |
| ATOM | 2177 | SG | CYS | 264 | 13.964 | 10.202 | 24.717 | 1.00 | 21.62 | U1 |

TABLE 1-continued

Structure coordinates of CPP32

| | | | | | | | | | |
|---|---|---|---|---|---|---|---|---|---|
| ATOM | 2178 | C | CYS | 264 | 12.103 | 9.139 | 26.870 | 1.00 | 22.57 U1 |
| ATOM | 2179 | O | CYS | 264 | 12.835 | 8.172 | 26.989 | 1.00 | 22.57 U1 |
| ATOM | 2180 | N | ILE | 265 | 10.830 | 9.040 | 26.507 | 1.00 | 22.45 U1 |
| ATOM | 2182 | CA | ILE | 265 | 10.165 | 7.766 | 26.258 | 1.00 | 22.45 U1 |
| ATOM | 2183 | CB | ILE | 265 | 8.639 | 7.915 | 26.424 | 1.00 | 21.45 U1 |
| ATOM | 2184 | CG2 | ILE | 265 | 8.009 | 6.581 | 26.595 | 1.00 | 21.45 U1 |
| ATOM | 2185 | CG1 | ILE | 265 | 8.295 | 8.791 | 27.620 | 1.00 | 21.45 U1 |
| ATOM | 2186 | CD1 | ILE | 265 | 6.837 | 9.174 | 27.674 | 1.00 | 21.45 U1 |
| ATOM | 2187 | C | ILE | 265 | 10.320 | 7.325 | 24.809 | 1.00 | 22.45 U1 |
| ATOM | 2188 | O | ILE | 265 | 9.928 | 8.068 | 23.900 | 1.00 | 22.45 U1 |
| ATOM | 2189 | N | VAL | 266 | 10.838 | 6.122 | 24.585 | 1.00 | 17.42 U1 |
| ATOM | 2191 | CA | VAL | 266 | 10.948 | 5.591 | 23.229 | 1.00 | 17.42 U1 |
| ATOM | 2192 | CB | VAL | 266 | 12.364 | 5.234 | 22.855 | 1.00 | 18.51 U1 |
| ATOM | 2193 | CG1 | VAL | 266 | 12.388 | 4.762 | 21.431 | 1.00 | 18.51 U1 |
| ATOM | 2194 | CG2 | VAL | 266 | 13.263 | 6.416 | 23.041 | 1.00 | 18.51 U1 |
| ATOM | 2195 | C | VAL | 266 | 10.120 | 4.314 | 23.159 | 1.00 | 17.42 U1 |
| ATOM | 2196 | O | VAL | 266 | 10.554 | 3.279 | 23.649 | 1.00 | 17.42 U1 |
| ATOM | 2197 | N | SER | 267 | 8.914 | 4.398 | 22.606 | 1.00 | 17.67 U1 |
| ATOM | 2199 | CA | SER | 267 | 8.025 | 3.245 | 22.504 | 1.00 | 17.67 U1 |
| ATOM | 2200 | CB | SER | 267 | 6.612 | 3.604 | 22.950 | 1.00 | 13.78 U1 |
| ATOM | 2201 | OG | SER | 267 | 5.743 | 2.527 | 22.633 | 1.00 | 13.78 U1 |
| ATOM | 2203 | C | SER | 267 | 7.899 | 2.660 | 21.122 | 1.00 | 17.67 U1 |
| ATOM | 2204 | O | SER | 267 | 7.782 | 3.380 | 20.142 | 1.00 | 17.67 U1 |
| ATOM | 2205 | N | MET | 268 | 7.854 | 1.347 | 21.061 | 1.00 | 19.85 U1 |
| ATOM | 2207 | CA | MET | 268 | 7.683 | 0.594 | 19.815 | 1.00 | 19.85 U1 |
| ATOM | 2208 | CB | MET | 268 | 9.017 | 0.021 | 19.344 | 1.00 | 33.34 U1 |
| ATOM | 2209 | CG | MET | 268 | 10.047 | 1.104 | 19.177 | 1.00 | 33.34 U1 |
| ATOM | 2210 | SD | MET | 268 | 11.668 | 0.603 | 18.669 | 1.00 | 33.34 U1 |
| ATOM | 2211 | CE | MET | 268 | 12.630 | 1.349 | 19.930 | 1.00 | 33.34 U1 |
| ATOM | 2212 | C | MET | 268 | 6.736 | −0.500 | 20.284 | 1.00 | 19.85 U1 |
| ATOM | 2213 | O | MET | 268 | 6.878 | −1.677 | 19.989 | 1.00 | 19.85 U1 |
| ATOM | 2214 | N | LEU | 269 | 5.857 | −0.082 | 21.181 | 1.00 | 33.63 U1 |
| ATOM | 2216 | CA | LEU | 269 | 4.854 | −0.941 | 21.783 | 1.00 | 33.63 U1 |
| ATOM | 2217 | CB | LEU | 269 | 4.372 | −0.345 | 23.128 | 1.00 | 23.46 U1 |
| ATOM | 2218 | CG | LEU | 269 | 5.220 | −0.419 | 24.403 | 1.00 | 23.46 U1 |
| ATOM | 2219 | CD1 | LEU | 269 | 4.392 | 0.069 | 25.587 | 1.00 | 23.46 U1 |
| ATOM | 2220 | CD2 | LEU | 269 | 5.581 | −1.838 | 24.648 | 1.00 | 23.46 U1 |
| ATOM | 2221 | C | LEU | 269 | 3.739 | −0.892 | 20.767 | 1.00 | 33.63 U1 |
| ATOM | 2222 | O | LEU | 269 | 3.560 | 0.125 | 20.101 | 1.00 | 33.63 U1 |
| ATOM | 2223 | N | THR | 270 | 2.996 | −1.977 | 20.630 | 1.00 | 34.08 U1 |
| ATOM | 2225 | CA | THR | 270 | 1.930 | −1.977 | 19.668 | 1.00 | 34.08 U1 |
| ATOM | 2226 | CB | THR | 270 | 2.091 | −3.125 | 18.694 | 1.00 | 24.54 U1 |
| ATOM | 2227 | OG1 | THR | 270 | 2.066 | −4.342 | 19.417 | 1.00 | 24.54 U1 |
| ATOM | 2229 | CG2 | THR | 270 | 3.428 | −3.073 | 18.016 | 1.00 | 24.54 U1 |
| ATOM | 2230 | C | THR | 270 | 0.587 | −2.067 | 20.373 | 1.00 | 34.08 U1 |
| ATOM | 2231 | O | THR | 270 | −0.435 | −2.283 | 19.737 | 1.00 | 34.08 U1 |
| ATOM | 2232 | N | LYS | 271 | 0.571 | −1.886 | 21.686 | 1.00 | 23.96 U1 |
| ATOM | 2234 | CA | LYS | 271 | −0.686 | −1.953 | 22.421 | 1.00 | 23.96 U1 |
| ATOM | 2235 | CB | LYS | 271 | −1.036 | −3.388 | 22.768 | 1.00 | 25.95 U1 |
| ATOM | 2236 | CG | LYS | 271 | −1.473 | −4.217 | 21.601 | 1.00 | 25.95 U1 |
| ATOM | 2237 | CD | LYS | 271 | −1.761 | −5.642 | 22.010 | 1.00 | 25.95 U1 |
| ATOM | 2238 | CE | LYS | 271 | −1.923 | −6.487 | 20.777 | 1.00 | 25.95 U1 |
| ATOM | 2239 | NZ | LYS | 271 | −1.964 | −7.905 | 21.175 | 1.00 | 25.95 U1 |
| ATOM | 2243 | C | LYS | 271 | −0.635 | −1.162 | 23.695 | 1.00 | 23.96 U1 |
| ATOM | 2244 | O | LYS | 271 | 0.438 | −0.843 | 24.190 | 1.00 | 23.96 U1 |
| ATOM | 2245 | N | GLU | 272 | −1.800 | −0.856 | 24.249 | 1.00 | 22.29 U1 |
| ATOM | 2247 | CA | GLU | 272 | −1.852 | −0.095 | 25.492 | 1.00 | 22.29 U1 |
| ATOM | 2248 | CB | GLU | 272 | −3.255 | 0.424 | 25.720 | 1.00 | 33.29 U1 |
| ATOM | 2249 | CG | GLU | 272 | −3.809 | 1.248 | 24.608 | 1.00 | 33.29 U1 |
| ATOM | 2250 | CD | GLU | 272 | −5.199 | 1.750 | 24.934 | 1.00 | 33.29 U1 |
| ATOM | 2251 | OE1 | GLU | 272 | −6.085 | 0.932 | 25.241 | 1.00 | 33.29 U1 |
| ATOM | 2252 | OE2 | GLU | 272 | −5.413 | 2.977 | 24.928 | 1.00 | 33.29 U1 |
| ATOM | 2253 | C | GLU | 272 | −1.414 | −1.041 | 26.633 | 1.00 | 22.29 U1 |
| ATOM | 2254 | O | GLU | 272 | −1.719 | −2.249 | 26.611 | 1.00 | 22.29 U1 |
| ATOM | 2255 | N | LEU | 273 | −0.679 | −0.499 | 27.602 | 1.00 | 20.70 U1 |
| ATOM | 2257 | CA | LEU | 273 | −0.171 | −1.277 | 28.730 | 1.00 | 20.70 U1 |
| ATOM | 2258 | CB | LEU | 273 | 1.355 | −1.085 | 28.870 | 1.00 | 22.24 U1 |
| ATOM | 2259 | CG | LEU | 273 | 2.219 | −1.781 | 29.946 | 1.00 | 22.24 U1 |
| ATOM | 2260 | CD1 | LEU | 273 | 1.947 | −3.259 | 30.028 | 1.00 | 22.24 U1 |
| ATOM | 2261 | CD2 | LEU | 273 | 3.695 | −1.558 | 29.623 | 1.00 | 22.24 U1 |
| ATOM | 2262 | C | LEU | 273 | −0.858 | −0.840 | 30.000 | 1.00 | 20.70 U1 |
| ATOM | 2263 | O | LEU | 273 | −0.876 | 0.356 | 30.318 | 1.00 | 20.70 U1 |
| ATOM | 2264 | N | TYR | 274 | −1.448 | −1.811 | 30.698 | 1.00 | 26.65 U1 |
| ATOM | 2266 | CA | TYR | 274 | −2.129 | −1.565 | 31.957 | 1.00 | 26.65 U1 |
| ATOM | 2267 | CB | TYR | 274 | −3.640 | −1.755 | 31.800 | 1.00 | 23.10 U1 |
| ATOM | 2268 | CG | TYR | 274 | −4.296 | −0.689 | 30.949 | 1.00 | 23.10 U1 |
| ATOM | 2269 | CD1 | TYR | 274 | −4.694 | −0.969 | 29.652 | 1.00 | 23.10 U1 |

TABLE 1-continued

Structure coordinates of CPP32

| ATOM | 2270 | CE1 | TYR | 274 | −5.236 | −0.003 | 28.841 | 1.00 | 23.10 | U1 |
|------|------|-----|-----|-----|--------|--------|--------|------|-------|-----|
| ATOM | 2271 | CD2 | TYR | 274 | −4.473 | 0.601 | 31.418 | 1.00 | 23.10 | U1 |
| ATOM | 2272 | CE2 | TYR | 274 | −5.015 | 1.570 | 30.612 | 1.00 | 23.10 | U1 |
| ATOM | 2273 | CZ | TYR | 274 | −5.389 | 1.253 | 29.312 | 1.00 | 23.10 | U1 |
| ATOM | 2274 | OH | TYR | 274 | −5.877 | 2.207 | 28.443 | 1.00 | 23.10 | U1 |
| ATOM | 2276 | C | TYR | 274 | −1.576 | −2.554 | 32.968 | 1.00 | 26.65 | U1 |
| ATOM | 2277 | O | TYR | 274 | −1.431 | −3.739 | 32.662 | 1.00 | 26.65 | U1 |
| ATOM | 2278 | N | PHE | 275 | −1.242 | −2.067 | 34.160 | 1.00 | 48.00 | U1 |
| ATOM | 2280 | CA | PHE | 275 | −0.709 | −2.913 | 35.226 | 1.00 | 48.00 | U1 |
| ATOM | 2281 | CB | PHE | 275 | 0.287 | −2.123 | 36.078 | 1.00 | 27.47 | U1 |
| ATOM | 2282 | CG | PHE | 275 | 1.609 | −1.879 | 35.399 | 1.00 | 27.47 | U1 |
| ATOM | 2283 | CD1 | PHE | 275 | 2.002 | −0.596 | 35.050 | 1.00 | 27.47 | U1 |
| ATOM | 2284 | CD2 | PHE | 275 | 2.464 | −2.931 | 35.115 | 1.00 | 27.47 | U1 |
| ATOM | 2285 | CE1 | PHE | 275 | 3.222 | −0.362 | 34.434 | 1.00 | 27.47 | U1 |
| ATOM | 2286 | CE2 | PHE | 275 | 3.685 | −2.703 | 34.496 | 1.00 | 27.47 | U1 |
| ATOM | 2287 | CZ | PHE | 275 | 4.059 | −1.411 | 34.159 | 1.00 | 27.47 | U1 |
| ATOM | 2288 | C | PHE | 275 | −1.796 | −3.516 | 36.123 | 1.00 | 48.00 | U1 |
| ATOM | 2289 | O | PHE | 275 | −1.531 | −3.867 | 37.272 | 1.00 | 48.00 | U1 |
| ATOM | 2290 | N | TYR | 276 | −3.017 | −3.637 | 35.608 | 1.00 | 63.94 | U1 |
| ATOM | 2292 | CA | TYR | 276 | −4.111 | −4.211 | 36.389 | 1.00 | 63.94 | U1 |
| ATOM | 2293 | CB | TYR | 276 | −4.960 | −3.128 | 37.054 | 1.00 | 34.25 | U1 |
| ATOM | 2294 | CG | TYR | 276 | −5.581 | −2.140 | 36.112 | 1.00 | 34.25 | U1 |
| ATOM | 2295 | CD1 | TYR | 276 | −6.780 | −2.414 | 35.473 | 1.00 | 34.25 | U1 |
| ATOM | 2296 | CE1 | TYR | 276 | −7.353 | −1.496 | 34.612 | 1.00 | 34.25 | U1 |
| ATOM | 2297 | CD2 | TYR | 276 | −4.976 | −0.915 | 35.867 | 1.00 | 34.25 | U1 |
| ATOM | 2298 | CE2 | TYR | 276 | −5.549 | 0.008 | 35.018 | 1.00 | 34.25 | U1 |
| ATOM | 2299 | CZ | TYR | 276 | −6.727 | −0.291 | 34.393 | 1.00 | 34.25 | U1 |
| ATOM | 2300 | OH | TYR | 276 | −7.259 | 0.627 | 33.514 | 1.00 | 34.25 | U1 |
| ATOM | 2302 | C | TYR | 276 | −4.994 | −5.133 | 35.573 | 1.00 | 63.94 | U1 |
| ATOM | 2303 | O | TYR | 276 | −5.000 | −5.059 | 34.331 | 1.00 | 63.94 | U1 |
| ATOM | 2304 | N | HIS | 277 | −5.728 | −5.993 | 36.284 | 1.00 | 79.77 | U1 |
| ATOM | 2306 | CA | HIS | 277 | −6.635 | −6.970 | 35.691 | 1.00 | 79.77 | U1 |
| ATOM | 2307 | CB | HIS | 277 | −7.722 | −6.273 | 34.885 | 1.00 | 97.72 | U1 |
| ATOM | 2308 | CG | HIS | 277 | −8.942 | −5.951 | 35.680 | 1.00 | 97.72 | U1 |
| ATOM | 2309 | CD2 | HIS | 277 | −9.417 | −6.471 | 36.835 | 1.00 | 97.72 | U1 |
| ATOM | 2310 | ND1 | HIS | 277 | −9.862 | −5.009 | 35.277 | 1.00 | 97.72 | U1 |
| ATOM | 2312 | CE1 | HIS | 277 | −10.857 | −4.965 | 36.143 | 1.00 | 97.72 | U1 |
| ATOM | 2313 | NE2 | HIS | 277 | −10.611 | −5.842 | 37.100 | 1.00 | 97.72 | U1 |
| ATOM | 2315 | C | HIS | 277 | −5.929 | −8.014 | 34.829 | 1.00 | 79.77 | U1 |
| ATOM | 2316 | O | HIS | 277 | −4.726 | −8.257 | 35.067 | 1.00 | 79.77 | U1 |
| ATOM | 2317 | OT | HIS | 277 | −6.595 | −8.596 | 33.943 | 1.00 | 97.72 | U1 |
| ATOM | 2318 | CB | ASN | 1035 | −4.002 | 16.235 | 33.095 | 1.00 | 95.51 | U2 |
| ATOM | 2319 | CG | ASN | 1035 | −4.040 | 16.167 | 34.604 | 1.00 | 95.51 | U2 |
| ATOM | 2320 | OD1 | ASN | 1035 | −2.997 | 16.108 | 35.259 | 1.00 | 95.51 | U2 |
| ATOM | 2321 | ND2 | ASN | 1035 | −5.241 | 16.197 | 35.168 | 1.00 | 95.51 | U2 |
| ATOM | 2324 | C | ASN | 1035 | −2.776 | 16.919 | 31.044 | 1.00 | 45.12 | U2 |
| ATOM | 2325 | O | ASN | 1035 | −2.188 | 16.057 | 30.401 | 1.00 | 45.12 | U2 |
| ATOM | 2328 | N | ASN | 1035 | −2.622 | 18.288 | 33.137 | 1.00 | 45.12 | U2 |
| ATOM | 2330 | CA | ASN | 1035 | −2.739 | 16.916 | 32.569 | 1.00 | 45.12 | U2 |
| ATOM | 2331 | N | SER | 1036 | −3.440 | 17.916 | 30.472 | 1.00 | 46.29 | U2 |
| ATOM | 2333 | CA | SER | 1036 | −3.592 | 18.022 | 29.030 | 1.00 | 46.29 | U2 |
| ATOM | 2334 | CB | SER | 1036 | −5.066 | 17.848 | 28.642 | 1.00 | 32.42 | U2 |
| ATOM | 2335 | OG | SER | 1036 | −5.631 | 16.667 | 29.196 | 1.00 | 32.42 | U2 |
| ATOM | 2337 | C | SER | 1036 | −3.155 | 19.383 | 28.556 | 1.00 | 46.29 | U2 |
| ATOM | 2338 | O | SER | 1036 | −3.401 | 20.401 | 29.225 | 1.00 | 46.29 | U2 |
| ATOM | 2339 | N | TYR | 1037 | −2.521 | 19.410 | 27.393 | 1.00 | 39.20 | U2 |
| ATOM | 2341 | CA | TYR | 1037 | −2.083 | 20.665 | 26.815 | 1.00 | 39.20 | U2 |
| ATOM | 2342 | CB | TYR | 1037 | −1.343 | 20.384 | 25.530 | 1.00 | 25.55 | U2 |
| ATOM | 2343 | CG | TYR | 1037 | 0.049 | 19.908 | 25.731 | 1.00 | 25.55 | U2 |
| ATOM | 2344 | CD1 | TYR | 1037 | 0.412 | 18.612 | 25.404 | 1.00 | 25.55 | U2 |
| ATOM | 2345 | CE1 | TYR | 1037 | 1.737 | 18.207 | 25.495 | 1.00 | 25.55 | U2 |
| ATOM | 2346 | CD2 | TYR | 1037 | 1.038 | 20.780 | 26.162 | 1.00 | 25.55 | U2 |
| ATOM | 2347 | CE2 | TYR | 1037 | 2.359 | 20.382 | 26.252 | 1.00 | 25.55 | U2 |
| ATOM | 2348 | CZ | TYR | 1037 | 2.697 | 19.098 | 25.919 | 1.00 | 25.55 | U2 |
| ATOM | 2349 | OH | TYR | 1037 | 4.012 | 18.701 | 26.025 | 1.00 | 25.55 | U2 |
| ATOM | 2351 | C | TYR | 1037 | −3.308 | 21.530 | 26.497 | 1.00 | 39.20 | U2 |
| ATOM | 2352 | O | TYR | 1037 | −4.437 | 21.021 | 26.388 | 1.00 | 39.20 | U2 |
| ATOM | 2353 | N | LYS | 1038 | −3.081 | 22.827 | 26.306 | 1.00 | 39.68 | U2 |
| ATOM | 2355 | CA | LYS | 1038 | −4.157 | 23.752 | 25.984 | 1.00 | 39.68 | U2 |
| ATOM | 2356 | CB | LYS | 1038 | −3.795 | 25.176 | 26.435 | 1.00 | 70.27 | U2 |
| ATOM | 2357 | CG | LYS | 1038 | −4.963 | 26.176 | 26.383 | 1.00 | 70.27 | U2 |
| ATOM | 2358 | CD | LYS | 1038 | −4.649 | 27.478 | 27.132 | 1.00 | 70.27 | U2 |
| ATOM | 2359 | CE | LYS | 1038 | −5.914 | 28.318 | 27.432 | 1.00 | 70.27 | U2 |
| ATOM | 2360 | NZ | LYS | 1038 | −6.520 | 29.009 | 26.247 | 1.00 | 70.27 | U2 |
| ATOM | 2364 | C | LYS | 1038 | −4.309 | 23.736 | 24.479 | 1.00 | 39.68 | U2 |
| ATOM | 2365 | O | LYS | 1038 | −3.352 | 24.021 | 23.756 | 1.00 | 39.68 | U2 |
| ATOM | 2366 | N | MET | 1039 | −5.467 | 23.290 | 24.006 | 1.00 | 53.12 | U2 |

TABLE 1-continued

Structure coordinates of CPP32

| ATOM | 2368 | CA | MET | 1039 | −5.741 | 23.286 | 22.575 | 1.00 | 53.12 | U2 |
|---|---|---|---|---|---|---|---|---|---|---|
| ATOM | 2369 | CB | MET | 1039 | −6.116 | 21.887 | 22.070 | 1.00 | 42.34 | U2 |
| ATOM | 2370 | CG | MET | 1039 | −5.011 | 20.843 | 22.181 | 1.00 | 42.34 | U2 |
| ATOM | 2371 | SD | MET | 1039 | −3.402 | 21.353 | 21.501 | 1.00 | 42.34 | U2 |
| ATOM | 2372 | CE | MET | 1039 | −3.269 | 20.292 | 20.080 | 1.00 | 42.34 | U2 |
| ATOM | 2373 | C | NET | 1039 | −6.907 | 24.250 | 22.359 | 1.00 | 53.12 | U2 |
| ATOM | 2374 | O | MET | 1039 | −7.714 | 24.068 | 21.459 | 1.00 | 53.12 | U2 |
| ATOM | 2375 | N | ASP | 1040 | −6.990 | 25.263 | 23.216 | 1.00 | 50.19 | U2 |
| ATOM | 2377 | CA | ASP | 1040 | −8.043 | 26.270 | 23.168 | 1.00 | 50.19 | U2 |
| ATOM | 2378 | CB | ASP | 1040 | −8.383 | 26.756 | 24.580 | 1.00 | 73.39 | U2 |
| ATOM | 2379 | CG | ASP | 1040 | −9.172 | 25.743 | 25.380 | 1.00 | 73.39 | U2 |
| ATOM | 2380 | OD1 | ASP | 1040 | −10.188 | 26.149 | 25.986 | 1.00 | 73.39 | U2 |
| ATOM | 2381 | OD2 | ASP | 1040 | −8.785 | 24.548 | 25.418 | 1.00 | 73.39 | U2 |
| ATOM | 2382 | C | ASP | 1040 | −7.653 | 27.485 | 22.356 | 1.00 | 50.19 | U2 |
| ATOM | 2383 | O | ASP | 1040 | −8.523 | 28.236 | 21.953 | 1.00 | 50.19 | U2 |
| ATOM | 2384 | N | TYR | 1041 | −6.355 | 27.711 | 22.162 | 1.00 | 58.75 | U2 |
| ATOM | 2386 | CA | TYR | 1041 | −5.869 | 28.887 | 21.422 | 1.00 | 58.75 | U2 |
| ATOM | 2387 | CB | TYR | 1041 | −4.362 | 28.764 | 21.126 | 1.00 | 49.23 | U2 |
| ATOM | 2388 | CG | TYR | 1041 | −3.471 | 28.856 | 22.346 | 1.00 | 49.23 | U2 |
| ATOM | 2389 | CD1 | TYR | 1041 | −3.271 | 27.758 | 23.165 | 1.00 | 49.23 | U2 |
| ATOM | 2390 | CE1 | TYR | 1041 | −2.439 | 27.834 | 24.272 | 1.00 | 49.23 | U2 |
| ATOM | 2391 | CD2 | TYR | 1041 | −2.814 | 30.038 | 22.666 | 1.00 | 49.23 | U2 |
| ATOM | 2392 | CE2 | TYR | 1041 | −1.980 | 30.126 | 23.772 | 1.00 | 49.23 | U2 |
| ATOM | 2393 | CZ | TYR | 1041 | −1.795 | 29.020 | 24.573 | 1.00 | 49.23 | U2 |
| ATOM | 2394 | OH | TYR | 1041 | −0.969 | 29.089 | 25.682 | 1.00 | 49.23 | U2 |
| ATOM | 2396 | C | TYR | 1041 | −6.660 | 29.174 | 20.135 | 1.00 | 58.75 | U2 |
| ATOM | 2397 | O | TYR | 1041 | −7.250 | 28.260 | 19.553 | 1.00 | 58.75 | U2 |
| ATOM | 2398 | N | PRO | 1042 | −6.676 | 30.451 | 19.681 | 1.00 | 58.91 | U2 |
| ATOM | 2399 | CD | PRO | 1042 | −5.903 | 31.554 | 20.283 | 1.00 | 58.15 | U2 |
| ATOM | 2400 | CA | PRO | 1042 | −7.374 | 30.933 | 18.483 | 1.00 | 58.91 | U2 |
| ATOM | 2401 | CB | PRO | 1042 | −6.715 | 32.288 | 18.237 | 1.00 | 58.15 | U2 |
| ATOM | 2402 | CG | PRO | 1042 | −6.479 | 32.773 | 19.601 | 1.00 | 58.15 | U2 |
| ATOM | 2403 | C | PRO | 1042 | −7.238 | 30.037 | 17.263 | 1.00 | 58.91 | U2 |
| ATOM | 2404 | O | PRO | 1042 | −8.166 | 29.920 | 16.455 | 1.00 | 58.91 | U2 |
| ATOM | 2405 | N | GLU | 1043 | −6.077 | 29.411 | 17.130 | 1.00 | 59.91 | U2 |
| ATOM | 2407 | CA | GLU | 1043 | −5.815 | 28.532 | 16.005 | 1.00 | 59.91 | U2 |
| ATOM | 2408 | CB | GLU | 1043 | −5.220 | 29.361 | 14.867 | 1.00 | 80.30 | U2 |
| ATOM | 2409 | CG | GLU | 1043 | −4.499 | 30.624 | 15.347 | 1.00 | 80.30 | U2 |
| ATOM | 2410 | CD | GLU | 1043 | −3.880 | 31.427 | 14.212 | 1.00 | 80.30 | U2 |
| ATOM | 2411 | OE1 | GLU | 1043 | −3.312 | 30.813 | 13.280 | 1.00 | 80.30 | U2 |
| ATOM | 2412 | OE2 | GLU | 1043 | −3.947 | 32.675 | 14.267 | 1.00 | 80.30 | U2 |
| ATOM | 2413 | C | GLU | 1043 | −4.887 | 27.374 | 16.396 | 1.00 | 59.91 | U2 |
| ATOM | 2414 | O | GLU | 1043 | −3.842 | 27.594 | 17.012 | 1.00 | 59.91 | U2 |
| ATOM | 2415 | N | MET | 1044 | −5.274 | 26.148 | 16.031 | 1.00 | 53.27 | U2 |
| ATOM | 2417 | CA | MET | 1044 | −4.507 | 24.930 | 16.339 | 1.00 | 53.27 | U2 |
| ATOM | 2418 | CB | MET | 1044 | −5.044 | 23.737 | 15.555 | 1.00 | 49.95 | U2 |
| ATOM | 2419 | CG | MET | 1044 | −6.408 | 23.225 | 16.003 | 1.00 | 49.95 | U2 |
| ATOM | 2420 | SD | MET | 1044 | −6.341 | 22.288 | 17.544 | 1.00 | 49.95 | U2 |
| ATOM | 2421 | CE | MET | 1044 | −5.545 | 20.764 | 16.976 | 1.00 | 49.95 | U2 |
| ATOM | 2422 | C | MET | 1044 | −3.012 | 25.041 | 16.088 | 1.00 | 53.27 | U2 |
| ATOM | 2423 | O | MET | 1044 | −2.222 | 24.415 | 16.797 | 1.00 | 53.27 | U2 |
| ATOM | 2424 | N | GLY | 1045 | −2.630 | 25.832 | 15.087 | 1.00 | 42.99 | U2 |
| ATOM | 2426 | CA | GLY | 1045 | −1.224 | 26.019 | 14.753 | 1.00 | 42.99 | U2 |
| ATOM | 2427 | C | GLY | 1045 | −0.933 | 25.586 | 13.318 | 1.00 | 42.99 | U2 |
| ATOM | 2428 | O | GLY | 1045 | −1.861 | 25.299 | 12.547 | 1.00 | 42.99 | U2 |
| ATOM | 2429 | N | LEU | 1046 | 0.337 | 25.522 | 12.936 | 1.00 | 42.06 | U2 |
| ATOM | 2431 | CA | LEU | 1046 | 0.628 | 25.121 | 11.584 | 1.00 | 42.06 | U2 |
| ATOM | 2432 | CB | LEU | 1046 | 1.267 | 26.258 | 10.798 | 1.00 | 41.71 | U2 |
| ATOM | 2433 | CG | LEU | 1046 | 2.460 | 27.030 | 11.324 | 1.00 | 41.71 | U2 |
| ATOM | 2434 | CD1 | LEU | 1046 | 3.705 | 26.654 | 10.533 | 1.00 | 41.71 | U2 |
| ATOM | 2435 | CD2 | LEU | 1046 | 2.155 | 28.523 | 11.144 | 1.00 | 41.71 | U2 |
| ATOM | 2436 | C | LEU | 1046 | 1.391 | 23.832 | 11.402 | 1.00 | 42.06 | U2 |
| ATOM | 2437 | O | LEU | 1046 | 2.283 | 23.496 | 12.178 | 1.00 | 42.06 | U2 |
| ATOM | 2438 | N | CYS | 1047 | 0.977 | 23.094 | 10.380 | 1.00 | 49.83 | U2 |
| ATOM | 2440 | CA | CYS | 1047 | 1.569 | 21.821 | 10.010 | 1.00 | 49.83 | U2 |
| ATOM | 2441 | CB | CYS | 1047 | 0.458 | 20.789 | 9.828 | 1.00 | 32.48 | U2 |
| ATOM | 2442 | SG | CYS | 1047 | 0.930 | 19.373 | 8.840 | 1.00 | 32.48 | U2 |
| ATOM | 2443 | C | CYS | 1047 | 2.318 | 22.039 | 8.696 | 1.00 | 49.83 | U2 |
| ATOM | 2444 | O | CYS | 1047 | 1.712 | 22.375 | 7.688 | 1.00 | 49.83 | U2 |
| ATOM | 2445 | N | ILE | 1048 | 3.641 | 21.982 | 8.743 | 1.00 | 43.14 | U2 |
| ATOM | 2447 | CA | ILE | 1048 | 4.455 | 22.162 | 7.557 | 1.00 | 43.14 | U2 |
| ATOM | 2448 | CB | ILE | 1048 | 5.820 | 22.801 | 7.888 | 1.00 | 36.96 | U2 |
| ATOM | 2449 | CG2 | ILE | 1048 | 6.693 | 22.841 | 6.659 | 1.00 | 36.96 | U2 |
| ATOM | 2450 | CG1 | ILE | 1048 | 5.641 | 24.231 | 8.381 | 1.00 | 36.96 | U2 |
| ATOM | 2451 | CD1 | ILE | 1048 | 6.949 | 24.923 | 8.676 | 1.00 | 36.96 | U2 |
| ATOM | 2452 | C | ILE | 1048 | 4.718 | 20.784 | 6.981 | 1.00 | 43.14 | U2 |
| ATOM | 2453 | O | ILE | 1048 | 4.978 | 19.847 | 7.736 | 1.00 | 43.14 | U2 |

TABLE 1-continued

Structure coordinates of CPP32

| ATOM | 2454 | N | ILE | 1049 | 4.599 | 20.643 | 5.662 | 1.00 | 46.40 | U2 |
|------|------|------|-----|------|--------|--------|--------|------|-------|-----|
| ATOM | 2456 | CA | ILE | 1049 | 4.878 | 19.369 | 5.018 | 1.00 | 46.40 | U2 |
| ATOM | 2457 | CB | ILE | 1049 | 3.697 | 18.827 | 4.220 | 1.00 | 28.36 | U2 |
| ATOM | 2458 | CG2 | ILE | 1049 | 3.986 | 17.394 | 3.813 | 1.00 | 28.36 | U2 |
| ATOM | 2459 | CG1 | ILE | 1049 | 2.424 | 18.853 | 5.061 | 1.00 | 28.36 | U2 |
| ATOM | 2460 | CD1 | ILE | 1049 | 1.314 | 18.010 | 4.489 | 1.00 | 28.36 | U2 |
| ATOM | 2461 | C | ILE | 1049 | 6.014 | 19.650 | 4.067 | 1.00 | 46.40 | U2 |
| ATOM | 2462 | O | ILE | 1049 | 5.968 | 20.639 | 3.330 | 1.00 | 46.40 | U2 |
| ATOM | 2463 | N | ILE | 1050 | 7.067 | 18.845 | 4.141 | 1.00 | 38.51 | U2 |
| ATOM | 2465 | CA | ILE | 1050 | 8.221 | 19.019 | 3.276 | 1.00 | 38.51 | U2 |
| ATOM | 2466 | CB | ILE | 1050 | 9.488 | 19.364 | 4.071 | 1.00 | 29.37 | U2 |
| ATOM | 2467 | CG2 | ILE | 1050 | 10.711 | 19.279 | 3.178 | 1.00 | 29.37 | U2 |
| ATOM | 2468 | CG1 | ILE | 1050 | 9.371 | 20.767 | 4.660 | 1.00 | 29.37 | U2 |
| ATOM | 2469 | CD1 | ILE | 1050 | 10.507 | 21.148 | 5.588 | 1.00 | 29.37 | U2 |
| ATOM | 2470 | C | ILE | 1050 | 8.406 | 17.705 | 2.575 | 1.00 | 38.51 | U2 |
| ATOM | 2471 | O | ILE | 1050 | 8.912 | 16.761 | 3.167 | 1.00 | 38.51 | U2 |
| ATOM | 2472 | N | ASN | 1051 | 7.938 | 17.627 | 1.330 | 1.00 | 47.06 | U2 |
| ATOM | 2474 | CA | ASN | 1051 | 8.030 | 16.400 | 0.541 | 1.00 | 47.06 | U2 |
| ATOM | 2475 | CB | ASN | 1051 | 6.733 | 16.144 | −0.235 | 1.00 | 49.08 | U2 |
| ATOM | 2476 | CG | ASN | 1051 | 6.670 | 14.722 | −0.826 | 1.00 | 49.08 | U2 |
| ATOM | 2477 | OD1 | ASN | 1051 | 5.634 | 14.042 | −0.740 | 1.00 | 49.08 | U2 |
| ATOM | 2478 | ND2 | ASN | 1051 | 7.770 | 14.271 | −1.440 | 1.00 | 49.08 | U2 |
| ATOM | 2481 | C | ASN | 1051 | 9.180 | 16.499 | −0.437 | 1.00 | 47.06 | U2 |
| ATOM | 2482 | O | ASN | 1051 | 9.231 | 17.431 | −1.237 | 1.00 | 47.06 | U2 |
| ATOM | 2483 | N | ASN | 1052 | 10.090 | 15.533 | −0.390 | 1.00 | 44.24 | U2 |
| ATOM | 2485 | CA | ASN | 1052 | 11.216 | 15.513 | −1.305 | 1.00 | 44.24 | U2 |
| ATOM | 2486 | CB | ASN | 1052 | 12.539 | 15.457 | −0.557 | 1.00 | 55.95 | U2 |
| ATOM | 2487 | CG | ASN | 1052 | 13.033 | 16.831 | −0.164 | 1.00 | 55.95 | U2 |
| ATOM | 2488 | OD1 | ASN | 1052 | 12.324 | 17.838 | −0.322 | 1.00 | 55.95 | U2 |
| ATOM | 2489 | ND2 | ASN | 1052 | 14.263 | 16.893 | 0.338 | 1.00 | 55.95 | U2 |
| ATOM | 2492 | C | ASN | 1052 | 11.083 | 14.328 | −2.221 | 1.00 | 44.24 | U2 |
| ATOM | 2493 | O | ASN | 1052 | 11.398 | 13.203 | −1.845 | 1.00 | 44.24 | U2 |
| ATOM | 2494 | N | LYS | 1053 | 10.576 | 14.583 | −3.422 | 1.00 | 63.36 | U2 |
| ATOM | 2496 | CA | LYS | 1053 | 10.383 | 13.525 | −4.406 | 1.00 | 63.36 | U2 |
| ATOM | 2497 | CB | LYS | 1053 | 9.028 | 13.684 | −5.096 | 1.00 | 74.02 | U2 |
| ATOM | 2498 | CG | LYS | 1053 | 8.725 | 12.579 | −6.098 | 1.00 | 74.02 | U2 |
| ATOM | 2499 | CD | LYS | 1053 | 7.358 | 12.799 | −6.718 | 1.00 | 74.02 | U2 |
| ATOM | 2500 | CE | LYS | 1053 | 7.071 | 11.851 | −7.880 | 1.00 | 74.02 | U2 |
| ATOM | 2501 | NZ | LYS | 1053 | 5.716 | 12.116 | −8.461 | 1.00 | 74.02 | U2 |
| ATOM | 2505 | C | LYS | 1053 | 11.474 | 13.403 | −5.464 | 1.00 | 63.36 | U2 |
| ATOM | 2506 | O | LYS | 1053 | 11.797 | 12.295 | −5.891 | 1.00 | 63.36 | U2 |
| ATOM | 2507 | N | ASN | 1054 | 12.057 | 14.526 | −5.868 | 1.00 | 58.28 | U2 |
| ATOM | 2509 | CA | ASN | 1054 | 13.072 | 14.509 | −6.913 | 1.00 | 58.28 | U2 |
| ATOM | 2510 | CB | ASN | 1054 | 12.644 | 15.457 | −8.024 | 1.00 | 48.39 | U2 |
| ATOM | 2511 | CG | ASN | 1054 | 11.358 | 15.009 | −8.683 | 1.00 | 48.39 | U2 |
| ATOM | 2512 | OD1 | ASN | 1054 | 11.294 | 13.912 | −9.249 | 1.00 | 48.39 | U2 |
| ATOM | 2513 | ND2 | ASN | 1054 | 10.313 | 15.823 | −8.577 | 1.00 | 48.39 | U2 |
| ATOM | 2516 | C | ASN | 1054 | 14.499 | 14.778 | −6.463 | 1.00 | 58.28 | U2 |
| ATOM | 2517 | O | ASN | 1054 | 14.813 | 15.855 | −5.953 | 1.00 | 58.28 | U2 |
| ATOM | 2518 | N | PHE | 1055 | 15.380 | 13.812 | −6.701 | 1.00 | 79.61 | U2 |
| ATOM | 2520 | CA | PHE | 1055 | 16.768 | 13.944 | −6.268 | 1.00 | 79.61 | U2 |
| ATOM | 2521 | CB | PHE | 1055 | 17.157 | 12.751 | −5.393 | 1.00 | 81.48 | U2 |
| ATOM | 2522 | CG | PHE | 1055 | 16.377 | 12.685 | −4.121 | 1.00 | 81.48 | U2 |
| ATOM | 2523 | CD1 | PHE | 1055 | 16.720 | 13.504 | −3.043 | 1.00 | 81.48 | U2 |
| ATOM | 2524 | CD2 | PHE | 1055 | 15.239 | 11.888 | −4.030 | 1.00 | 81.48 | U2 |
| ATOM | 2525 | CE1 | PHE | 1055 | 15.937 | 13.538 | −1.899 | 1.00 | 81.48 | U2 |
| ATOM | 2526 | CE2 | PHE | 1055 | 14.449 | 11.914 | −2.892 | 1.00 | 81.48 | U2 |
| ATOM | 2527 | CZ | PHE | 1055 | 14.796 | 12.744 | −1.823 | 1.00 | 81.48 | U2 |
| ATOM | 2528 | C | PHE | 1055 | 17.815 | 14.184 | −7.341 | 1.00 | 79.61 | U2 |
| ATOM | 2529 | O | PHE | 1055 | 17.798 | 13.553 | −8.400 | 1.00 | 79.61 | U2 |
| ATOM | 2530 | N | HIS | 1056 | 18.748 | 15.081 | −7.028 | 1.00 | 74.33 | U2 |
| ATOM | 2532 | CA | HIS | 1056 | 19.824 | 15.452 | −7.937 | 1.00 | 74.33 | U2 |
| ATOM | 2533 | CB | HIS | 1056 | 20.615 | 16.631 | −7.379 | 1.00 | 82.76 | U2 |
| ATOM | 2534 | CG | HIS | 1056 | 19.784 | 17.847 | −7.132 | 1.00 | 82.76 | U2 |
| ATOM | 2535 | CD2 | HIS | 1056 | 18.454 | 18.063 | −7.271 | 1.00 | 82.76 | U2 |
| ATOM | 2536 | ND1 | HIS | 1056 | 20.317 | 19.028 | −6.666 | 1.00 | 82.76 | U2 |
| ATOM | 2538 | CE1 | HIS | 1056 | 19.352 | 19.921 | −6.527 | 1.00 | 82.76 | U2 |
| ATOM | 2539 | NE2 | HIS | 1056 | 18.212 | 19.360 | −6.887 | 1.00 | 82.76 | U2 |
| ATOM | 2541 | C | HIS | 1056 | 20.787 | 14.319 | −8.239 | 1.00 | 74.33 | U2 |
| ATOM | 2542 | O | HIS | 1056 | 20.825 | 13.296 | −7.551 | 1.00 | 74.33 | U2 |
| ATOM | 2543 | N | LYS | 1057 | 21.575 | 14.529 | −9.285 | 1.00 | 94.39 | U2 |
| ATOM | 2545 | CA | LYS | 1057 | 22.581 | 13.573 | −9.714 | 1.00 | 94.39 | U2 |
| ATOM | 2546 | CB | LYS | 1057 | 23.129 | 14.008 | −11.082 | 1.00 | 98.21 | U2 |
| ATOM | 2547 | CG | LYS | 1057 | 23.666 | 12.893 | −11.975 | 1.00 | 98.21 | U2 |
| ATOM | 2548 | CD | LYS | 1057 | 22.542 | 12.088 | −12.608 | 1.00 | 98.21 | U2 |
| ATOM | 2549 | CE | LYS | 1057 | 23.086 | 11.103 | −13.626 | 1.00 | 98.21 | U2 |
| ATOM | 2550 | NZ | LYS | 1057 | 21.982 | 10.360 | −14.280 | 1.00 | 98.21 | U2 |

TABLE 1-continued

Structure coordinates of CPP32

| ATOM | 2554 | C | LYS | 1057 | 23.684 | 13.644 | −8.641 | 1.00 | 94.39 | U2 |
|---|---|---|---|---|---|---|---|---|---|---|
| ATOM | 2555 | O | LYS | 1057 | 24.260 | 12.625 | −8.236 | 1.00 | 94.39 | U2 |
| ATOM | 2556 | N | SER | 1058 | 23.910 | 14.858 | −8.142 | 1.00 | 81.81 | U2 |
| ATOM | 2558 | CA | SER | 1058 | 24.909 | 15.138 | −7.119 | 1.00 | 81.81 | U2 |
| ATOM | 2559 | CB | SER | 1058 | 24.752 | 16.591 | −6.668 | 1.00 | 71.85 | U2 |
| ATOM | 2560 | OG | SER | 1058 | 24.326 | 17.406 | −7.750 | 1.00 | 71.85 | U2 |
| ATOM | 2562 | C | SER | 1058 | 24.800 | 14.210 | −5.899 | 1.00 | 81.81 | U2 |
| ATOM | 2563 | O | SER | 1058 | 25.814 | 13.776 | −5.353 | 1.00 | 81.81 | U2 |
| ATOM | 2564 | N | THR | 1059 | 23.567 | 13.906 | −5.495 | 1.00 | 76.51 | U2 |
| ATOM | 2566 | CA | THR | 1059 | 23.289 | 13.061 | −4.332 | 1.00 | 76.51 | U2 |
| ATOM | 2567 | CB | THR | 1059 | 21.902 | 13.394 | −3.739 | 1.00 | 71.63 | U2 |
| ATOM | 2568 | OG1 | THR | 1059 | 21.687 | 14.808 | −3.777 | 1.00 | 71.63 | U2 |
| ATOM | 2570 | CG2 | THR | 1059 | 21.826 | 12.943 | −2.301 | 1.00 | 71.63 | U2 |
| ATOM | 2571 | C | THR | 1059 | 23.350 | 11.544 | −4.569 | 1.00 | 76.51 | U2 |
| ATOM | 2572 | O | THR | 1059 | 23.770 | 10.791 | −3.686 | 1.00 | 76.51 | U2 |
| ATOM | 2573 | N | GLY | 1060 | 22.909 | 11.097 | −5.743 | 1.00 | 85.15 | U2 |
| ATOM | 2575 | CA | GLY | 1060 | 22.908 | 9.672 | −6.040 | 1.00 | 85.15 | U2 |
| ATOM | 2576 | C | GLY | 1060 | 21.668 | 8.969 | −5.496 | 1.00 | 85.15 | U2 |
| ATOM | 2577 | O | GLY | 1060 | 21.628 | 7.737 | −5.389 | 1.00 | 85.15 | U2 |
| ATOM | 2578 | N | MET | 1061 | 20.638 | 9.750 | −5.185 | 1.00 | 61.20 | U2 |
| ATOM | 2580 | CA | MET | 1061 | 19.408 | 9.202 | −4.647 | 1.00 | 61.20 | U2 |
| ATOM | 2581 | CB | MET | 1061 | 18.850 | 10.101 | −3.533 | 1.00 | 60.03 | U2 |
| ATOM | 2582 | CG | MET | 1061 | 19.742 | 10.305 | −2.300 | 1.00 | 60.03 | U2 |
| ATOM | 2583 | SD | MET | 1061 | 20.415 | 8.782 | −1.600 | 1.00 | 60.03 | U2 |
| ATOM | 2584 | CE | MET | 1061 | 18.930 | 7.980 | −1.043 | 1.00 | 60.03 | U2 |
| ATOM | 2585 | C | MET | 1061 | 18.364 | 9.080 | −5.736 | 1.00 | 61.20 | U2 |
| ATOM | 2586 | O | MET | 1061 | 18.295 | 9.920 | −6.628 | 1.00 | 61.20 | U2 |
| ATOM | 2587 | N | THR | 1062 | 17.564 | 8.023 | −5.656 | 1.00 | 52.63 | U2 |
| ATOM | 2589 | CA | THR | 1062 | 16.479 | 7.776 | −6.594 | 1.00 | 52.63 | U2 |
| ATOM | 2590 | CB | THR | 1062 | 15.969 | 6.327 | −6.477 | 1.00 | 71.49 | U2 |
| ATOM | 2591 | OG1 | THR | 1062 | 16.242 | 5.828 | −5.161 | 1.00 | 71.49 | U2 |
| ATOM | 2593 | CG2 | THR | 1062 | 16.630 | 5.424 | −7.500 | 1.00 | 71.49 | U2 |
| ATOM | 2594 | C | THR | 1062 | 15.315 | 8.676 | −6.209 | 1.00 | 52.63 | U2 |
| ATOM | 2595 | O | THR | 1062 | 15.190 | 9.060 | −5.047 | 1.00 | 52.63 | U2 |
| ATOM | 2596 | N | SER | 1063 | 14.483 | 9.055 | −7.168 | 1.00 | 48.19 | U2 |
| ATOM | 2598 | CA | SER | 1063 | 13.333 | 9.869 | −6.823 | 1.00 | 48.19 | U2 |
| ATOM | 2599 | CB | SER | 1063 | 12.688 | 10.498 | −8.057 | 1.00 | 64.16 | U2 |
| ATOM | 2600 | OG | SER | 1063 | 13.341 | 11.723 | −8.375 | 1.00 | 64.16 | U2 |
| ATOM | 2602 | C | SER | 1063 | 12.360 | 8.976 | −6.057 | 1.00 | 48.19 | U2 |
| ATOM | 2603 | O | SER | 1063 | 12.414 | 7.746 | −6.157 | 1.00 | 48.19 | U2 |
| ATOM | 2604 | N | ARG | 1064 | 11.472 | 9.601 | −5.296 | 1.00 | 62.43 | U2 |
| ATOM | 2606 | CA | ARG | 1064 | 10.539 | 8.878 | −4.446 | 1.00 | 62.43 | U2 |
| ATOM | 2607 | CB | ARG | 1064 | 10.567 | 9.505 | −3.041 | 1.00 | 47.58 | U2 |
| ATOM | 2608 | CG | ARG | 1064 | 11.966 | 9.485 | −2.414 | 1.00 | 47.58 | U2 |
| ATOM | 2609 | CD | ARG | 1064 | 11.982 | 9.994 | −0.989 | 1.00 | 47.58 | U2 |
| ATOM | 2610 | NE | ARG | 1064 | 10.953 | 9.345 | −0.178 | 1.00 | 47.58 | U2 |
| ATOM | 2612 | CZ | ARG | 1064 | 9.824 | 9.951 | 0.185 | 1.00 | 47.58 | U2 |
| ATOM | 2613 | NH1 | ARG | 1064 | 9.604 | 11.216 | −0.183 | 1.00 | 47.58 | U2 |
| ATOM | 2616 | NH2 | ARG | 1064 | 8.879 | 9.271 | 0.830 | 1.00 | 47.58 | U2 |
| ATOM | 2619 | C | ARG | 1064 | 9.113 | 8.772 | −4.960 | 1.00 | 62.43 | U2 |
| ATOM | 2620 | O | ARG | 1064 | 8.289 | 9.669 | −4.740 | 1.00 | 62.43 | U2 |
| ATOM | 2621 | N | SER | 1065 | 8.805 | 7.645 | −5.588 | 1.00 | 47.73 | U2 |
| ATOM | 2623 | CA | SER | 1065 | 7.468 | 7.421 | −6.129 | 1.00 | 47.73 | U2 |
| ATOM | 2624 | CB | SER | 1065 | 7.495 | 6.255 | −7.118 | 1.00 | 73.85 | U2 |
| ATOM | 2625 | OG | SER | 1065 | 8.578 | 6.392 | −8.024 | 1.00 | 73.85 | U2 |
| ATOM | 2627 | C | SER | 1065 | 6.438 | 7.139 | −5.039 | 1.00 | 47.73 | U2 |
| ATOM | 2628 | O | SER | 1065 | 6.672 | 6.311 | −4.164 | 1.00 | 47.73 | U2 |
| ATOM | 2629 | N | GLY | 1066 | 5.301 | 7.829 | −5.105 | 1.00 | 58.69 | U2 |
| ATOM | 2631 | CA | GLY | 1066 | 4.240 | 7.623 | −4.132 | 1.00 | 58.69 | U2 |
| ATOM | 2632 | C | GLY | 1066 | 4.141 | 8.696 | −3.063 | 1.00 | 58.69 | U2 |
| ATOM | 2633 | O | GLY | 1066 | 3.058 | 8.978 | −2.539 | 1.00 | 58.69 | U2 |
| ATOM | 2634 | N | THR | 1067 | 5.258 | 9.348 | −2.780 | 1.00 | 56.19 | U2 |
| ATOM | 2636 | CA | THR | 1067 | 5.313 | 10.377 | −1.756 | 1.00 | 56.19 | U2 |
| ATOM | 2637 | CB | THR | 1067 | 6.715 | 10.985 | −1.699 | 1.00 | 54.04 | U2 |
| ATOM | 2638 | OG1 | THR | 1067 | 6.796 | 11.925 | −0.628 | 1.00 | 54.04 | U2 |
| ATOM | 2640 | CG2 | THR | 1067 | 7.049 | 11.664 | −3.003 | 1.00 | 54.04 | U2 |
| ATOM | 2641 | C | THR | 1067 | 4.253 | 11.481 | −1.863 | 1.00 | 56.19 | U2 |
| ATOM | 2642 | O | THR | 1067 | 3.796 | 11.989 | −0.835 | 1.00 | 56.19 | U2 |
| ATOM | 2643 | N | ASP | 1068 | 3.854 | 11.849 | −3.083 | 1.00 | 51.44 | U2 |
| ATOM | 2645 | CA | ASP | 1068 | 2.835 | 12.892 | −3.268 | 1.00 | 51.44 | U2 |
| ATOM | 2646 | CB | ASP | 1068 | 2.555 | 13.171 | −4.753 | 1.00 | 64.98 | U2 |
| ATOM | 2647 | CG | ASP | 1068 | 3.662 | 13.950 | −5.433 | 1.00 | 64.98 | U2 |
| ATOM | 2648 | OD1 | ASP | 1068 | 3.830 | 15.146 | −5.126 | 1.00 | 64.98 | U2 |
| ATOM | 2649 | OD2 | ASP | 1068 | 4.339 | 13.371 | −6.305 | 1.00 | 64.98 | U2 |
| ATOM | 2650 | C | ASP | 1068 | 1.534 | 12.457 | −2.600 | 1.00 | 51.44 | U2 |
| ATOM | 2651 | O | ASP | 1068 | 0.817 | 13.287 | −2.036 | 1.00 | 51.44 | U2 |
| ATOM | 2652 | N | VAL | 1069 | 1.233 | 11.157 | −2.668 | 1.00 | 42.14 | U2 |

TABLE 1-continued

Structure coordinates of CPP32

| ATOM | 2654 | CA | VAL | 1069 | 0.024 | 10.622 | -2.059 | 1.00 | 42.14 | U2 |
|------|------|----|-----|------|-------|--------|--------|------|-------|-----|
| ATOM | 2655 | CB | VAL | 1069 | -0.002 | 9.097 | -2.143 | 1.00 | 39.88 | U2 |
| ATOM | 2656 | CG1 | VAL | 1069 | -1.263 | 8.563 | -1.513 | 1.00 | 39.88 | U2 |
| ATOM | 2657 | CG2 | VAL | 1069 | 0.111 | 8.644 | -3.576 | 1.00 | 39.88 | U2 |
| ATOM | 2658 | C | VAL | 1069 | 0.073 | 11.004 | -0.579 | 1.00 | 42.14 | U2 |
| ATOM | 2659 | O | VAL | 1069 | -0.870 | 11.619 | -0.034 | 1.00 | 42.14 | U2 |
| ATOM | 2660 | N | ASP | 1070 | 1.204 | 10.674 | 0.048 | 1.00 | 43.12 | U2 |
| ATOM | 2662 | CA | ASP | 1070 | 1.424 | 10.978 | 1.450 | 1.00 | 43.12 | U2 |
| ATOM | 2663 | CB | ASP | 1070 | 2.860 | 10.637 | 1.870 | 1.00 | 29.11 | U2 |
| ATOM | 2664 | CG | ASP | 1070 | 3.129 | 9.136 | 1.950 | 1.00 | 29.11 | U2 |
| ATOM | 2665 | OD1 | ASP | 1070 | 2.176 | 8.341 | 2.047 | 1.00 | 29.11 | U2 |
| ATOM | 2666 | OD2 | ASP | 1070 | 4.323 | 8.766 | 1.926 | 1.00 | 29.11 | U2 |
| ATOM | 2667 | C | ASP | 1070 | 1.171 | 12.473 | 1.667 | 1.00 | 43.12 | U2 |
| ATOM | 2668 | O | ASP | 1070 | 0.247 | 12.852 | 2.397 | 1.00 | 43.12 | U2 |
| ATOM | 2669 | N | ALA | 1071 | 1.911 | 13.322 | 0.959 | 1.00 | 40.76 | U2 |
| ATOM | 2671 | CA | ALA | 1071 | 1.759 | 14.760 | 1.134 | 1.00 | 40.76 | U2 |
| ATOM | 2672 | CB | ALA | 1071 | 2.617 | 15.499 | 0.156 | 1.00 | 27.30 | U2 |
| ATOM | 2673 | C | ALA | 1071 | 0.315 | 15.211 | 1.023 | 1.00 | 40.76 | U2 |
| ATOM | 2674 | O | ALA | 1071 | -0.159 | 16.010 | 1.835 | 1.00 | 40.76 | U2 |
| ATOM | 2675 | N | ALA | 1072 | -0.404 | 14.644 | 0.064 | 1.00 | 47.59 | U2 |
| ATOM | 2677 | CA | ALA | 1072 | -1.797 | 15.006 | -0.155 | 1.00 | 47.59 | U2 |
| ATOM | 2678 | CB | ALA | 1072 | -2.319 | 14.353 | -1.414 | 1.00 | 48.54 | U2 |
| ATOM | 2679 | C | ALA | 1072 | -2.630 | 14.591 | 1.033 | 1.00 | 47.59 | U2 |
| ATOM | 2680 | O | ALA | 1072 | -3.287 | 15.430 | 1.652 | 1.00 | 47.59 | U2 |
| ATOM | 2681 | N | ASN | 1073 | -2.600 | 13.301 | 1.356 | 1.00 | 43.75 | U2 |
| ATOM | 2683 | CA | ASN | 1073 | -3.356 | 12.787 | 2.497 | 1.00 | 43.75 | U2 |
| ATOM | 2684 | CB | ASN | 1073 | -3.093 | 11.303 | 2.673 | 1.00 | 84.08 | U2 |
| ATOM | 2685 | CG | ASN | 1073 | -3.523 | 10.507 | 1.466 | 1.00 | 84.08 | U2 |
| ATOM | 2686 | OD1 | ASN | 1073 | -4.344 | 10.970 | 0.670 | 1.00 | 84.08 | U2 |
| ATOM | 2687 | ND2 | ASN | 1073 | -2.961 | 9.316 | 1.304 | 1.00 | 84.08 | U2 |
| ATOM | 2690 | C | ASN | 1073 | -3.031 | 13.543 | 3.784 | 1.00 | 43.75 | U2 |
| ATOM | 2691 | O | ASN | 1073 | -3.924 | 13.818 | 4.593 | 1.00 | 43.75 | U2 |
| ATOM | 2692 | N | LEU | 1074 | -1.767 | 13.926 | 3.950 | 1.00 | 36.36 | U2 |
| ATOM | 2694 | CA | LEU | 1074 | -1.359 | 14.670 | 5.133 | 1.00 | 36.36 | U2 |
| ATOM | 2695 | CB | LEU | 1074 | 0.155 | 14.868 | 5.157 | 1.00 | 39.28 | U2 |
| ATOM | 2696 | CG | LEU | 1074 | 0.834 | 13.563 | 5.564 | 1.00 | 39.28 | U2 |
| ATOM | 2697 | CD1 | LEU | 1074 | 2.241 | 13.520 | 5.049 | 1.00 | 39.28 | U2 |
| ATOM | 2698 | CD2 | LEU | 1074 | 0.772 | 13.384 | 7.076 | 1.00 | 39.28 | U2 |
| ATOM | 2699 | C | LEU | 1074 | -2.090 | 15.993 | 5.148 | 1.00 | 36.36 | U2 |
| ATOM | 2700 | O | LEU | 1074 | -2.757 | 16.326 | 6.132 | 1.00 | 36.36 | U2 |
| ATOM | 2701 | N | ARG | 1075 | -2.057 | 16.685 | 4.016 | 1.00 | 42.11 | U2 |
| ATOM | 2703 | CA | ARG | 1075 | -2.726 | 17.975 | 3.869 | 1.00 | 42.11 | U2 |
| ATOM | 2704 | CB | ARG | 1075 | -2.556 | 18.482 | 2.433 | 1.00 | 67.31 | U2 |
| ATOM | 2705 | CG | ARG | 1075 | -3.052 | 19.897 | 2.205 | 1.00 | 67.31 | U2 |
| ATOM | 2706 | CD | ARG | 1075 | -3.033 | 20.275 | 0.741 | 1.00 | 67.31 | U2 |
| ATOM | 2707 | NE | ARG | 1075 | -3.436 | 21.664 | 0.557 | 1.00 | 67.31 | U2 |
| ATOM | 2709 | CZ | ARG | 1075 | -2.594 | 22.657 | 0.289 | 1.00 | 67.31 | U2 |
| ATOM | 2710 | NH1 | ARG | 1075 | -1.298 | 22.417 | 0.168 | 1.00 | 67.31 | U2 |
| ATOM | 2713 | NH2 | ARG | 1075 | -3.045 | 23.897 | 0.155 | 1.00 | 67.31 | U2 |
| ATOM | 2716 | C | ARG | 1075 | -4.217 | 17.935 | 4.242 | 1.00 | 42.11 | U2 |
| ATOM | 2717 | O | ARG | 1075 | -4.728 | 18.838 | 4.905 | 1.00 | 42.11 | U2 |
| ATOM | 2718 | N | GLU | 1076 | -4.915 | 16.881 | 3.852 | 1.00 | 39.57 | U2 |
| ATOM | 2720 | CA | GLU | 1076 | -6.342 | 16.784 | 4.165 | 1.00 | 39.57 | U2 |
| ATOM | 2721 | CB | GLU | 1076 | -7.025 | 15.758 | 3.266 | 1.00 | 81.49 | U2 |
| ATOM | 2722 | CG | GLU | 1076 | -8.024 | 16.384 | 2.301 | 1.00 | 81.49 | U2 |
| ATOM | 2723 | CD | GLU | 1076 | -9.235 | 17.010 | 2.996 | 1.00 | 81.49 | U2 |
| ATOM | 2724 | OE1 | GLU | 1076 | -9.619 | 18.142 | 2.612 | 1.00 | 81.49 | U2 |
| ATOM | 2725 | OE2 | GLU | 1076 | -9.810 | 16.363 | 3.909 | 1.00 | 81.49 | U2 |
| ATOM | 2726 | C | GLU | 1076 | -6.619 | 16.415 | 5.605 | 1.00 | 39.57 | U2 |
| ATOM | 2727 | O | GLU | 1076 | -7.629 | 16.826 | 6.177 | 1.00 | 39.57 | U2 |
| ATOM | 2728 | N | THR | 1077 | -5.743 | 15.586 | 6.169 | 1.00 | 43.17 | U2 |
| ATOM | 2730 | CA | THR | 1077 | -5.869 | 15.118 | 7.541 | 1.00 | 43.17 | U2 |
| ATOM | 2731 | CB | THR | 1077 | -4.892 | 13.958 | 7.789 | 1.00 | 40.04 | U2 |
| ATOM | 2732 | OG1 | THR | 1077 | -5.224 | 12.860 | 6.916 | 1.00 | 40.04 | U2 |
| ATOM | 2734 | CG2 | THR | 1077 | -4.940 | 13.507 | 9.230 | 1.00 | 40.04 | U2 |
| ATOM | 2735 | C | THR | 1077 | -5.619 | 16.284 | 8.489 | 1.00 | 43.17 | U2 |
| ATOM | 2736 | O | THR | 1077 | -6.432 | 16.571 | 9.365 | 1.00 | 43.17 | U2 |
| ATOM | 2737 | N | PHE | 1078 | -4.545 | 17.022 | 8.259 | 1.00 | 44.77 | U2 |
| ATOM | 2739 | CA | PHE | 1078 | -4.264 | 18.150 | 9.118 | 1.00 | 44.77 | U2 |
| ATOM | 2740 | CB | PHE | 1078 | -2.763 | 18.460 | 9.157 | 1.00 | 43.40 | U2 |
| ATOM | 2741 | CG | PHE | 1078 | -1.986 | 17.480 | 10.000 | 1.00 | 43.40 | U2 |
| ATOM | 2742 | CD1 | PHE | 1078 | -1.616 | 16.248 | 9.493 | 1.00 | 43.40 | U2 |
| ATOM | 2743 | CD2 | PHE | 1078 | -1.714 | 17.753 | 11.331 | 1.00 | 43.40 | U2 |
| ATOM | 2744 | CE1 | PHE | 1078 | -0.996 | 15.303 | 10.301 | 1.00 | 43.40 | U2 |
| ATOM | 2745 | CE2 | PHE | 1078 | -1.097 | 16.820 | 12.138 | 1.00 | 43.40 | U2 |
| ATOM | 2746 | CZ | PHE | 1078 | -0.740 | 15.595 | 11.627 | 1.00 | 43.40 | U2 |
| ATOM | 2747 | C | PHE | 1078 | -5.125 | 19.368 | 8.809 | 1.00 | 44.77 | U2 |

TABLE 1-continued

Structure coordinates of CPP32

| ATOM | 2748 | O   | PHE | 1078 | −5.081  | 20.363 | 9.531  | 1.00 | 44.77 | U2 |
|------|------|-----|-----|------|---------|--------|--------|------|-------|----|
| ATOM | 2749 | N   | ARG | 1079 | −5.934  | 19.282 | 7.756  | 1.00 | 32.82 | U2 |
| ATOM | 2751 | CA  | ARG | 1079 | −6.837  | 20.372 | 7.415  | 1.00 | 32.82 | U2 |
| ATOM | 2752 | CB  | ARG | 1079 | −7.119  | 20.412 | 5.913  | 1.00 | 39.73 | U2 |
| ATOM | 2753 | CG  | ARG | 1079 | −7.825  | 21.697 | 5.474  | 1.00 | 39.73 | U2 |
| ATOM | 2754 | CD  | ARG | 1079 | −8.278  | 21.624 | 4.040  | 1.00 | 39.73 | U2 |
| ATOM | 2755 | NE  | ARG | 1079 | −9.368  | 20.672 | 3.856  | 1.00 | 39.73 | U2 |
| ATOM | 2757 | CZ  | ARG | 1079 | −10.656 | 20.928 | 4.085  | 1.00 | 39.73 | U2 |
| ATOM | 2758 | NH1 | ARG | 1079 | −11.062 | 22.122 | 4.516  | 1.00 | 39.73 | U2 |
| ATOM | 2761 | NH2 | ARG | 1079 | −11.550 | 19.971 | 3.880  | 1.00 | 39.73 | U2 |
| ATOM | 2764 | C   | ARG | 1079 | −8.123  | 20.081 | 8.180  | 1.00 | 32.82 | U2 |
| ATOM | 2765 | O   | ARG | 1079 | −8.737  | 20.972 | 8.766  | 1.00 | 32.82 | U2 |
| ATOM | 2766 | N   | ASN | 1080 | −8.517  | 18.814 | 8.188  | 1.00 | 48.19 | U2 |
| ATOM | 2768 | CA  | ASN | 1080 | −9.712  | 18.399 | 8.909  | 1.00 | 48.19 | U2 |
| ATOM | 2769 | CB  | ASN | 1080 | −10.015 | 16.920 | 8.679  | 1.00 | 80.76 | U2 |
| ATOM | 2770 | CG  | ASN | 1080 | −10.615 | 16.652 | 7.305  | 1.00 | 80.76 | U2 |
| ATOM | 2771 | OD1 | ASN | 1080 | −11.158 | 17.556 | 6.652  | 1.00 | 80.76 | U2 |
| ATOM | 2772 | ND2 | ASN | 1080 | −10.537 | 15.397 | 6.865  | 1.00 | 80.76 | U2 |
| ATOM | 2775 | C   | ASN | 1080 | −9.552  | 18.658 | 10.396 | 1.00 | 48.19 | U2 |
| ATOM | 2776 | O   | ASN | 1080 | −10.523 | 18.982 | 11.068 | 1.00 | 48.19 | U2 |
| ATOM | 2777 | N   | LEU | 1081 | −8.325  | 18.526 | 10.907 | 1.00 | 55.27 | U2 |
| ATOM | 2779 | CA  | LEU | 1081 | −8.042  | 18.755 | 12.332 | 1.00 | 55.27 | U2 |
| ATOM | 2780 | CB  | LEU | 1081 | −6.751  | 18.038 | 12.748 | 1.00 | 36.11 | U2 |
| ATOM | 2781 | CG  | LEU | 1081 | −6.726  | 16.527 | 12.468 | 1.00 | 36.11 | U2 |
| ATOM | 2782 | CD1 | LEU | 1081 | −5.355  | 15.987 | 12.832 | 1.00 | 36.11 | U2 |
| ATOM | 2783 | CD2 | LEU | 1081 | −7.857  | 15.790 | 13.237 | 1.00 | 36.11 | U2 |
| ATOM | 2784 | C   | LEU | 1081 | −7.919  | 20.249 | 12.613 | 1.00 | 55.27 | U2 |
| ATOM | 2785 | O   | LEU | 1081 | −7.679  | 20.661 | 13.751 | 1.00 | 55.27 | U2 |
| ATOM | 2786 | N   | LYS | 1082 | −8.076  | 21.045 | 11.560 | 1.00 | 38.99 | U2 |
| ATOM | 2788 | CA  | LYS | 1082 | −8.010  | 22.492 | 11.621 | 1.00 | 38.99 | U2 |
| ATOM | 2789 | CB  | LYS | 1082 | −9.060  | 23.041 | 12.575 | 1.00 | 62.25 | U2 |
| ATOM | 2790 | CG  | LYS | 1082 | −10.470 | 22.741 | 12.090 | 1.00 | 62.25 | U2 |
| ATOM | 2791 | CD  | LYS | 1082 | −11.489 | 23.701 | 12.675 | 1.00 | 62.25 | U2 |
| ATOM | 2792 | CE  | LYS | 1082 | −12.887 | 23.393 | 12.165 | 1.00 | 62.25 | U2 |
| ATOM | 2793 | NZ  | LYS | 1082 | −12.989 | 23.496 | 10.683 | 1.00 | 62.25 | U2 |
| ATOM | 2797 | C   | LYS | 1082 | −6.642  | 23.130 | 11.822 | 1.00 | 38.99 | U2 |
| ATOM | 2798 | O   | LYS | 1082 | −6.502  | 24.177 | 12.470 | 1.00 | 38.99 | U2 |
| ATOM | 2799 | N   | TYR | 1083 | −5.652  | 22.533 | 11.172 | 1.00 | 44.24 | U2 |
| ATOM | 2801 | CA  | TYR | 1083 | −4.282  | 23.030 | 11.194 | 1.00 | 44.24 | U2 |
| ATOM | 2802 | CB  | TYR | 1083 | −3.282  | 21.859 | 11.297 | 1.00 | 44.18 | U2 |
| ATOM | 2803 | CG  | TYR | 1083 | −2.917  | 21.396 | 12.708 | 1.00 | 44.18 | U2 |
| ATOM | 2804 | CD1 | TYR | 1083 | −3.682  | 20.439 | 13.380 | 1.00 | 44.18 | U2 |
| ATOM | 2805 | CE1 | TYR | 1083 | −3.327  | 19.996 | 14.650 | 1.00 | 44.18 | U2 |
| ATOM | 2806 | CD2 | TYR | 1083 | −1.785  | 21.897 | 13.353 | 1.00 | 44.18 | U2 |
| ATOM | 2807 | CE2 | TYR | 1083 | −1.425  | 21.465 | 14.619 | 1.00 | 44.18 | U2 |
| ATOM | 2808 | CZ  | TYR | 1083 | −2.196  | 20.518 | 15.261 | 1.00 | 44.18 | U2 |
| ATOM | 2809 | OH  | TYR | 1083 | −1.833  | 20.090 | 16.509 | 1.00 | 44.18 | U2 |
| ATOM | 2811 | C   | TYR | 1083 | −4.044  | 23.800 | 9.872  | 1.00 | 44.24 | U2 |
| ATOM | 2812 | O   | TYR | 1083 | −4.628  | 23.472 | 8.837  | 1.00 | 44.24 | U2 |
| ATOM | 2813 | N   | GLU | 1084 | −3.220  | 24.838 | 9.904  | 1.00 | 47.90 | U2 |
| ATOM | 2815 | CA  | GLU | 1084 | −2.912  | 25.600 | 8.701  | 1.00 | 47.90 | U2 |
| ATOM | 2816 | CB  | GLU | 1084 | −2.379  | 26.966 | 9.098  | 1.00 | 75.39 | U2 |
| ATOM | 2817 | CG  | GLU | 1084 | −1.993  | 27.861 | 7.941  | 1.00 | 75.39 | U2 |
| ATOM | 2818 | CD  | GLU | 1084 | −1.204  | 29.084 | 8.397  | 1.00 | 75.39 | U2 |
| ATOM | 2819 | OE1 | GLU | 1084 | −1.592  | 29.713 | 9.416  | 1.00 | 75.39 | U2 |
| ATOM | 2820 | OE2 | GLU | 1084 | −0.186  | 29.408 | 7.739  | 1.00 | 75.39 | U2 |
| ATOM | 2821 | C   | GLU | 1084 | −1.826  | 24.816 | 7.971  | 1.00 | 47.90 | U2 |
| ATOM | 2822 | O   | GLU | 1084 | −0.658  | 24.885 | 8.352  | 1.00 | 47.90 | U2 |
| ATOM | 2823 | N   | VAL | 1085 | −2.201  | 24.053 | 6.945  | 1.00 | 45.35 | U2 |
| ATOM | 2825 | CA  | VAL | 1085 | −1.228  | 23.233 | 6.207  | 1.00 | 45.35 | U2 |
| ATOM | 2826 | CB  | VAL | 1085 | −1.920  | 22.037 | 5.519  | 1.00 | 36.26 | U2 |
| ATOM | 2827 | CG1 | VAL | 1085 | −0.886  | 21.063 | 4.973  | 1.00 | 36.26 | U2 |
| ATOM | 2828 | CG2 | VAL | 1085 | −2.852  | 21.323 | 6.508  | 1.00 | 36.26 | U2 |
| ATOM | 2829 | C   | VAL | 1085 | −0.391  | 24.000 | 5.185  | 1.00 | 45.35 | U2 |
| ATOM | 2830 | O   | VAL | 1085 | −0.864  | 24.971 | 4.598  | 1.00 | 45.35 | U2 |
| ATOM | 2831 | N   | ARG | 1086 | 0.858   | 23.573 | 5.000  | 1.00 | 33.06 | U2 |
| ATOM | 2833 | CA  | ARG | 1086 | 1.764   | 24.205 | 4.048  | 1.00 | 33.06 | U2 |
| ATOM | 2834 | CB  | ARG | 1086 | 2.636   | 25.269 | 4.724  | 1.00 | 34.72 | U2 |
| ATOM | 2835 | CG  | ARG | 1086 | 1.907   | 26.459 | 5.333  | 1.00 | 34.72 | U2 |
| ATOM | 2836 | CD  | ARG | 1086 | 2.929   | 27.476 | 5.845  | 1.00 | 34.72 | U2 |
| ATOM | 2837 | NE  | ARG | 1086 | 2.338   | 28.488 | 6.731  | 1.00 | 34.72 | U2 |
| ATOM | 2839 | CZ  | ARG | 1086 | 3.050   | 29.432 | 7.347  | 1.00 | 34.72 | U2 |
| ATOM | 2840 | NH1 | ARG | 1086 | 4.363   | 29.477 | 7.168  | 1.00 | 34.72 | U2 |
| ATOM | 2843 | NH2 | ARG | 1086 | 2.456   | 30.357 | 8.100  | 1.00 | 34.72 | U2 |
| ATOM | 2846 | C   | ARG | 1086 | 2.691   | 23.205 | 3.379  | 1.00 | 33.06 | U2 |
| ATOM | 2847 | O   | ARG | 1086 | 3.720   | 22.843 | 3.937  | 1.00 | 33.06 | U2 |
| ATOM | 2848 | N   | ASN | 1087 | 2.346   | 22.763 | 2.176  | 1.00 | 54.01 | U2 |

TABLE 1-continued

Structure coordinates of CPP32

| | | | | | | | | | |
|---|---|---|---|---|---|---|---|---|---|
| ATOM | 2850 | CA | ASN | 1087 | 3.196 | 21.821 | 1.453 | 1.00 | 54.01 U2 |
| ATOM | 2851 | CB | ASN | 1087 | 2.386 | 21.028 | 0.431 | 1.00 | 51.20 U2 |
| ATOM | 2852 | CG | ASN | 1087 | 1.419 | 20.045 | 1.079 | 1.00 | 51.20 U2 |
| ATOM | 2853 | OD1 | ASN | 1087 | 0.298 | 20.404 | 1.463 | 1.00 | 51.20 U2 |
| ATOM | 2854 | ND2 | ASN | 1087 | 1.839 | 18.788 | 1.177 | 1.00 | 51.20 U2 |
| ATOM | 2857 | C | ASN | 1087 | 4.317 | 22.561 | 0.736 | 1.00 | 54.01 U2 |
| ATOM | 2858 | O | ASN | 1087 | 4.080 | 23.608 | 0.141 | 1.00 | 54.01 U2 |
| ATOM | 2859 | N | LYS | 1088 | 5.537 | 22.039 | 0.837 | 1.00 | 56.82 U2 |
| ATOM | 2861 | CA | LYS | 1088 | 6.715 | 22.611 | 0.175 | 1.00 | 56.82 U2 |
| ATOM | 2862 | CB | LYS | 1088 | 7.660 | 23.281 | 1.178 | 1.00 | 58.78 U2 |
| ATOM | 2863 | CG | LYS | 1088 | 7.405 | 24.763 | 1.369 | 1.00 | 58.78 U2 |
| ATOM | 2864 | CD | LYS | 1088 | 7.209 | 25.106 | 2.830 | 1.00 | 58.78 U2 |
| ATOM | 2865 | CE | LYS | 1088 | 6.734 | 26.554 | 2.985 | 1.00 | 58.78 U2 |
| ATOM | 2866 | NZ | LYS | 1088 | 6.218 | 26.871 | 4.361 | 1.00 | 58.78 U2 |
| ATOM | 2870 | C | LYS | 1088 | 7.415 | 21.430 | −0.473 | 1.00 | 56.82 U2 |
| ATOM | 2871 | O | LYS | 1088 | 7.993 | 20.601 | −0.229 | 1.00 | 56.82 U2 |
| ATOM | 2872 | N | ASN | 1089 | 7.361 | 21.352 | −1.804 | 1.00 | 48.49 U2 |
| ATOM | 2874 | CA | ASN | 1089 | 7.953 | 20.237 | −2.541 | 1.00 | 48.49 U2 |
| ATOM | 2875 | CB | ASN | 1089 | 7.090 | 19.892 | −3.745 | 1.00 | 56.43 U2 |
| ATOM | 2876 | CG | ASN | 1089 | 5.646 | 19.652 | −3.371 | 1.00 | 56.43 U2 |
| ATOM | 2877 | OD1 | ASN | 1089 | 5.210 | 18.515 | −3.248 | 1.00 | 56.43 U2 |
| ATOM | 2878 | ND2 | ASN | 1089 | 4.893 | 20.728 | −3.184 | 1.00 | 56.43 U2 |
| ATOM | 2881 | C | ASN | 1089 | 9.388 | 20.471 | −2.984 | 1.00 | 48.49 U2 |
| ATOM | 2882 | O | ASN | 1089 | 9.774 | 21.598 | −3.284 | 1.00 | 48.49 U2 |
| ATOM | 2883 | N | ASP | 1090 | 10.172 | 19.394 | −2.973 | 1.00 | 52.98 U2 |
| ATOM | 2885 | CA | ASP | 1090 | 11.579 | 19.412 | −3.367 | 1.00 | 52.98 U2 |
| ATOM | 2886 | CB | ASP | 1090 | 11.709 | 19.269 | −4.884 | 1.00 | 83.48 U2 |
| ATOM | 2887 | CG | ASP | 1090 | 11.317 | 17.896 | −5.379 | 1.00 | 83.48 U2 |
| ATOM | 2888 | OD1 | ASP | 1090 | 11.040 | 17.760 | −6.589 | 1.00 | 83.48 U2 |
| ATOM | 2889 | OD2 | ASP | 1090 | 11.297 | 16.952 | −4.564 | 1.00 | 83.48 U2 |
| ATOM | 2890 | C | ASP | 1090 | 12.375 | 20.625 | −2.902 | 1.00 | 52.98 U2 |
| ATOM | 2891 | O | ASP | 1090 | 12.557 | 21.587 | −3.650 | 1.00 | 52.98 U2 |
| ATOM | 2892 | N | LEU | 1091 | 12.884 | 20.556 | −1.678 | 1.00 | 48.11 U2 |
| ATOM | 2894 | CA | LEU | 1091 | 13.675 | 21.637 | −1.108 | 1.00 | 48.11 U2 |
| ATOM | 2895 | CB | LEU | 1091 | 13.108 | 22.030 | 0.259 | 1.00 | 58.03 U2 |
| ATOM | 2896 | CG | LEU | 1091 | 11.984 | 23.059 | 0.428 | 1.00 | 58.03 U2 |
| ATOM | 2897 | CD1 | LEU | 1091 | 10.845 | 22.818 | −0.532 | 1.00 | 58.03 U2 |
| ATOM | 2898 | CD2 | LEU | 1091 | 11.486 | 23.011 | 1.854 | 1.00 | 58.03 U2 |
| ATOM | 2899 | C | LEU | 1091 | 15.111 | 21.153 | −0.944 | 1.00 | 48.11 U2 |
| ATOM | 2900 | O | LEU | 1091 | 15.356 | 19.947 | −0.829 | 1.00 | 48.11 U2 |
| ATOM | 2901 | N | THR | 1092 | 16.065 | 22.077 | −0.977 | 1.00 | 55.21 U2 |
| ATOM | 2903 | CA | THR | 1092 | 17.465 | 21.714 | −0.797 | 1.00 | 55.21 U2 |
| ATOM | 2904 | CB | THR | 1092 | 18.404 | 22.642 | −1.572 | 1.00 | 58.77 U2 |
| ATOM | 2905 | OG1 | THR | 1092 | 18.041 | 24.009 | −1.339 | 1.00 | 58.77 U2 |
| ATOM | 2907 | CG2 | THR | 1092 | 18.365 | 22.331 | −3.039 | 1.00 | 58.77 U2 |
| ATOM | 2908 | C | THR | 1092 | 17.811 | 21.845 | 0.678 | 1.00 | 55.21 U2 |
| ATOM | 2909 | O | THR | 1092 | 17.136 | 22.568 | 1.415 | 1.00 | 55.21 U2 |
| ATOM | 2910 | N | ARG | 1093 | 18.905 | 21.213 | 1.090 | 1.00 | 59.06 U2 |
| ATOM | 2912 | CA | ARG | 1093 | 19.332 | 21.266 | 2.476 | 1.00 | 59.06 U2 |
| ATOM | 2913 | CB | ARG | 1093 | 20.605 | 20.434 | 2.687 | 1.00 | 104.89 U2 |
| ATOM | 2914 | CG | ARG | 1093 | 21.916 | 21.060 | 2.260 | 1.00 | 104.89 U2 |
| ATOM | 2915 | CD | ARG | 1093 | 22.669 | 21.634 | 3.460 | 1.00 | 104.89 U2 |
| ATOM | 2916 | NE | ARG | 1093 | 22.849 | 20.653 | 4.532 | 1.00 | 104.89 U2 |
| ATOM | 2918 | CZ | ARG | 1093 | 23.151 | 20.959 | 5.793 | 1.00 | 104.89 U2 |
| ATOM | 2919 | NH1 | ARG | 1093 | 23.319 | 22.226 | 6.159 | 1.00 | 104.89 U2 |
| ATOM | 2922 | NH2 | ARG | 1093 | 23.255 | 19.995 | 6.701 | 1.00 | 104.89 U2 |
| ATOM | 2925 | C | ARG | 1093 | 19.488 | 22.709 | 2.949 | 1.00 | 59.06 U2 |
| ATOM | 2926 | O | ARG | 1093 | 19.250 | 23.009 | 4.115 | 1.00 | 59.06 U2 |
| ATOM | 2927 | N | GLU | 1094 | 19.784 | 23.611 | 2.018 | 1.00 | 51.35 U2 |
| ATOM | 2929 | CA | GLU | 1094 | 19.945 | 25.033 | 2.330 | 1.00 | 51.35 U2 |
| ATOM | 2930 | CB | GLU | 1094 | 20.526 | 25.790 | 1.130 | 1.00 | 58.30 U2 |
| ATOM | 2931 | CG | GLU | 1094 | 21.283 | 24.949 | 0.104 | 1.00 | 58.30 U2 |
| ATOM | 2932 | CD | GLU | 1094 | 22.652 | 24.491 | 0.588 | 1.00 | 58.30 U2 |
| ATOM | 2933 | OE1 | GLU | 1094 | 23.169 | 23.500 | 0.025 | 1.00 | 58.30 U2 |
| ATOM | 2934 | OE2 | GLU | 1094 | 23.222 | 25.128 | 1.507 | 1.00 | 58.30 U2 |
| ATOM | 2935 | C | GLU | 1094 | 18.562 | 25.614 | 2.597 | 1.00 | 51.35 U2 |
| ATOM | 2936 | O | GLU | 1094 | 18.356 | 26.416 | 3.515 | 1.00 | 51.35 U2 |
| ATOM | 2937 | N | GLU | 1095 | 17.620 | 25.213 | 1.752 | 1.00 | 57.38 U2 |
| ATOM | 2939 | CA | GLU | 1095 | 16.255 | 25.688 | 1.846 | 1.00 | 57.38 U2 |
| ATOM | 2940 | CB | GLU | 1095 | 15.472 | 25.307 | 0.587 | 1.00 | 78.81 U2 |
| ATOM | 2941 | CG | GLU | 1095 | 15.910 | 26.091 | −0.656 | 1.00 | 78.81 U2 |
| ATOM | 2942 | CD | GLU | 1095 | 15.122 | 25.733 | −1.907 | 1.00 | 78.81 U2 |
| ATOM | 2943 | OE1 | GLU | 1095 | 15.203 | 24.563 | −2.356 | 1.00 | 78.81 U2 |
| ATOM | 2944 | OE2 | GLU | 1095 | 14.433 | 26.631 | −2.446 | 1.00 | 78.81 U2 |
| ATOM | 2945 | C | GLU | 1095 | 15.536 | 25.209 | 3.090 | 1.00 | 57.38 U2 |
| ATOM | 2946 | O | GLU | 1095 | 14.778 | 25.972 | 3.690 | 1.00 | 57.38 U2 |
| ATOM | 2947 | N | ILE | 1096 | 15.794 | 23.969 | 3.500 | 1.00 | 53.69 U2 |

TABLE 1-continued

Structure coordinates of CPP32

| ATOM | 2949 | CA  | ILE | 1096 | 15.145 | 23.416 | 4.691  | 1.00 | 53.69  | U2 |
|------|------|-----|-----|------|--------|--------|--------|------|--------|----|
| ATOM | 2950 | CB  | ILE | 1096 | 15.430 | 21.912 | 4.861  | 1.00 | 39.85  | U2 |
| ATOM | 2951 | CG2 | ILE | 1096 | 14.965 | 21.449 | 6.217  | 1.00 | 39.85  | U2 |
| ATOM | 2952 | CG1 | ILE | 1096 | 14.709 | 21.126 | 3.762  | 1.00 | 39.85  | U2 |
| ATOM | 2953 | CD1 | ILE | 1096 | 15.092 | 19.663 | 3.702  | 1.00 | 39.85  | U2 |
| ATOM | 2954 | C   | ILE | 1096 | 15.572 | 24.189 | 5.931  | 1.00 | 53.69  | U2 |
| ATOM | 2955 | O   | ILE | 1096 | 14.732 | 24.745 | 6.646  | 1.00 | 53.69  | U2 |
| ATOM | 2956 | N   | VAL | 1097 | 16.877 | 24.278 | 6.152  | 1.00 | 41.93  | U2 |
| ATOM | 2958 | CA  | VAL | 1097 | 17.394 | 25.015 | 7.295  | 1.00 | 41.93  | U2 |
| ATOM | 2959 | CB  | VAL | 1097 | 18.899 | 25.159 | 7.190  | 1.00 | 51.54  | U2 |
| ATOM | 2960 | CG1 | VAL | 1097 | 19.420 | 26.015 | 8.310  | 1.00 | 51.54  | U2 |
| ATOM | 2961 | CG2 | VAL | 1097 | 19.543 | 23.794 | 7.211  | 1.00 | 51.54  | U2 |
| ATOM | 2962 | C   | VAL | 1097 | 16.775 | 26.407 | 7.375  | 1.00 | 41.93  | U2 |
| ATOM | 2963 | O   | VAL | 1097 | 16.278 | 26.812 | 8.421  | 1.00 | 41.93  | U2 |
| ATOM | 2964 | N   | GLU | 1098 | 16.745 | 27.103 | 6.244  | 1.00 | 56.62  | U2 |
| ATOM | 2966 | CA  | GLU | 1098 | 16.200 | 28.460 | 6.178  | 1.00 | 56.62  | U2 |
| ATOM | 2967 | CB  | GLU | 1098 | 16.486 | 29.096 | 4.815  | 1.00 | 107.38 | U2 |
| ATOM | 2968 | CG  | GLU | 1098 | 17.955 | 29.360 | 4.534  | 1.00 | 107.38 | U2 |
| ATOM | 2969 | CD  | GLU | 1098 | 18.614 | 30.228 | 5.594  | 1.00 | 107.38 | U2 |
| ATOM | 2970 | OE1 | GLU | 1098 | 17.983 | 31.210 | 6.054  | 1.00 | 107.38 | U2 |
| ATOM | 2971 | OE2 | GLU | 1098 | 19.768 | 29.921 | 5.966  | 1.00 | 107.38 | U2 |
| ATOM | 2972 | C   | GLU | 1098 | 14.714 | 28.552 | 6.461  | 1.00 | 56.62  | U2 |
| ATOM | 2973 | O   | GLU | 1098 | 14.262 | 29.479 | 7.120  | 1.00 | 56.62  | U2 |
| ATOM | 2974 | N   | LEU | 1099 | 13.952 | 27.613 | 5.916  | 1.00 | 56.96  | U2 |
| ATOM | 2976 | CA  | LEU | 1099 | 12.511 | 27.580 | 6.112  | 1.00 | 56.96  | U2 |
| ATOM | 2977 | CB  | LEU | 1099 | 11.924 | 26.366 | 5.396  | 1.00 | 40.56  | U2 |
| ATOM | 2978 | CG  | LEU | 1099 | 10.439 | 26.034 | 5.572  | 1.00 | 40.56  | U2 |
| ATOM | 2979 | CD1 | LEU | 1099 | 9.571  | 27.241 | 5.218  | 1.00 | 40.56  | U2 |
| ATOM | 2980 | CD2 | LEU | 1099 | 10.096 | 24.832 | 4.674  | 1.00 | 40.56  | U2 |
| ATOM | 2981 | C   | LEU | 1099 | 12.235 | 27.475 | 7.603  | 1.00 | 56.96  | U2 |
| ATOM | 2982 | O   | LEU | 1099 | 11.429 | 28.227 | 8.155  | 1.00 | 56.96  | U2 |
| ATOM | 2983 | N   | MET | 1100 | 12.939 | 26.550 | 8.248  | 1.00 | 54.19  | U2 |
| ATOM | 2985 | CA  | MET | 1100 | 12.807 | 26.314 | 9.678  | 1.00 | 54.19  | U2 |
| ATOM | 2986 | CB  | MET | 1100 | 13.690 | 25.133 | 10.073 | 1.00 | 55.60  | U2 |
| ATOM | 2987 | CG  | MET | 1100 | 13.298 | 23.834 | 9.380  | 1.00 | 55.60  | U2 |
| ATOM | 2988 | SD  | MET | 1100 | 11.640 | 23.221 | 9.836  | 1.00 | 55.60  | U2 |
| ATOM | 2989 | CE  | MET | 1100 | 10.497 | 24.379 | 9.055  | 1.00 | 55.60  | U2 |
| ATOM | 2990 | C   | MET | 1100 | 13.160 | 27.575 | 10.468 | 1.00 | 54.19  | U2 |
| ATOM | 2991 | O   | MET | 1100 | 12.390 | 28.025 | 11.317 | 1.00 | 54.19  | U2 |
| ATOM | 2992 | N   | ARG | 1101 | 14.302 | 28.168 | 10.146 | 1.00 | 55.66  | U2 |
| ATOM | 2994 | CA  | ARG | 1101 | 14.744 | 29.386 | 10.798 | 1.00 | 55.66  | U2 |
| ATOM | 2995 | CB  | ARG | 1101 | 15.945 | 29.955 | 10.039 | 1.00 | 79.51  | U2 |
| ATOM | 2996 | CG  | ARG | 1101 | 16.724 | 31.052 | 10.762 | 1.00 | 79.51  | U2 |
| ATOM | 2997 | CD  | ARG | 1101 | 17.856 | 31.615 | 9.886  | 1.00 | 79.51  | U2 |
| ATOM | 2998 | NE  | ARG | 1101 | 18.760 | 30.578 | 9.376  | 1.00 | 79.51  | U2 |
| ATOM | 3000 | CZ  | ARG | 1101 | 19.723 | 29.992 | 10.086 | 1.00 | 79.51  | U2 |
| ATOM | 3001 | NH1 | ARG | 1101 | 19.926 | 30.332 | 11.353 | 1.00 | 79.51  | U2 |
| ATOM | 3004 | NH2 | ARG | 1101 | 20.482 | 29.057 | 9.532  | 1.00 | 79.51  | U2 |
| ATOM | 3007 | C   | ARG | 1101 | 13.591 | 30.384 | 10.775 | 1.00 | 55.66  | U2 |
| ATOM | 3008 | O   | ARG | 1101 | 13.147 | 30.851 | 11.816 | 1.00 | 55.66  | U2 |
| ATOM | 3009 | N   | ASP | 1102 | 13.039 | 30.616 | 9.591  | 1.00 | 49.84  | U2 |
| ATOM | 3011 | CA  | ASP | 1102 | 11.945 | 31.568 | 9.404  | 1.00 | 49.84  | U2 |
| ATOM | 3012 | CB  | ASP | 1102 | 11.683 | 31.793 | 7.904  | 1.00 | 97.23  | U2 |
| ATOM | 3013 | CG  | ASP | 1102 | 12.919 | 32.306 | 7.140  | 1.00 | 97.23  | U2 |
| ATOM | 3014 | OD1 | ASP | 1102 | 13.965 | 32.603 | 7.764  | 1.00 | 97.23  | U2 |
| ATOM | 3015 | OD2 | ASP | 1102 | 12.836 | 32.406 | 5.895  | 1.00 | 97.23  | U2 |
| ATOM | 3016 | C   | ASP | 1102 | 10.638 | 31.204 | 10.100 | 1.00 | 49.84  | U2 |
| ATOM | 3017 | O   | ASP | 1102 | 9.986  | 32.066 | 10.687 | 1.00 | 49.84  | U2 |
| ATOM | 3018 | N   | VAL | 1103 | 10.246 | 29.937 | 10.019 | 1.00 | 66.80  | U2 |
| ATOM | 3020 | CA  | VAL | 1103 | 9.005  | 29.469 | 10.645 | 1.00 | 66.80  | U2 |
| ATOM | 3021 | CB  | VAL | 1103 | 8.591  | 28.074 | 10.087 | 1.00 | 67.60  | U2 |
| ATOM | 3022 | CG1 | VAL | 1103 | 7.312  | 27.567 | 10.758 | 1.00 | 67.60  | U2 |
| ATOM | 3023 | CG2 | VAL | 1103 | 8.366  | 28.174 | 8.587  | 1.00 | 67.60  | U2 |
| ATOM | 3024 | C   | VAL | 1103 | 9.154  | 29.450 | 12.180 | 1.00 | 66.80  | U2 |
| ATOM | 3025 | O   | VAL | 1103 | 8.164  | 29.468 | 12.937 | 1.00 | 66.80  | U2 |
| ATOM | 3026 | N   | SER | 1104 | 10.405 | 29.443 | 12.622 | 1.00 | 61.61  | U2 |
| ATOM | 3028 | CA  | SER | 1104 | 10.744 | 29.470 | 14.023 | 1.00 | 61.61  | U2 |
| ATOM | 3029 | CB  | SER | 1104 | 12.245 | 29.255 | 14.154 | 1.00 | 57.43  | U2 |
| ATOM | 3030 | OG  | SER | 1104 | 12.730 | 29.627 | 15.428 | 1.00 | 57.43  | U2 |
| ATOM | 3032 | C   | SER | 1104 | 10.357 | 30.839 | 14.592 | 1.00 | 61.61  | U2 |
| ATOM | 3033 | O   | SER | 1104 | 9.895  | 30.947 | 15.736 | 1.00 | 61.61  | U2 |
| ATOM | 3034 | N   | LYS | 1105 | 10.496 | 31.884 | 13.781 | 1.00 | 72.08  | U2 |
| ATOM | 3036 | CA  | LYS | 1105 | 10.177 | 33.227 | 14.248 | 1.00 | 72.08  | U2 |
| ATOM | 3037 | CB  | LYS | 1105 | 11.252 | 34.221 | 13.816 | 1.00 | 91.80  | U2 |
| ATOM | 3038 | CG  | LYS | 1105 | 12.447 | 34.253 | 14.765 | 1.00 | 91.80  | U2 |
| ATOM | 3039 | CD  | LYS | 1105 | 12.038 | 34.609 | 16.206 | 1.00 | 91.80  | U2 |
| ATOM | 3040 | CE  | LYS | 1105 | 11.512 | 36.037 | 16.312 | 1.00 | 91.80  | U2 |

TABLE 1-continued

Structure coordinates of CPP32

| ATOM | 3041 | NZ | LYS | 1105 | 11.224 | 36.436 | 17.716 | 1.00 | 91.80 | U2 |
| --- | --- | --- | --- | --- | --- | --- | --- | --- | --- | --- |
| ATOM | 3045 | C | LYS | 1105 | 8.786 | 33.810 | 14.030 | 1.00 | 72.08 | U2 |
| ATOM | 3046 | O | LYS | 1105 | 8.475 | 34.861 | 14.590 | 1.00 | 72.08 | U2 |
| ATOM | 3047 | N | GLU | 1106 | 7.944 | 33.174 | 13.222 | 1.00 | 63.91 | U2 |
| ATOM | 3049 | CA | GLU | 1106 | 6.597 | 33.706 | 13.042 | 1.00 | 63.91 | U2 |
| ATOM | 3050 | CB | GLU | 1106 | 5.743 | 32.744 | 12.233 | 1.00 | 55.60 | U2 |
| ATOM | 3051 | CG | GLU | 1106 | 6.294 | 32.391 | 10.884 | 1.00 | 55.60 | U2 |
| ATOM | 3052 | CD | GLU | 1106 | 5.330 | 31.524 | 10.090 | 1.00 | 55.60 | U2 |
| ATOM | 3053 | OE1 | GLU | 1106 | 5.801 | 30.785 | 9.205 | 1.00 | 55.60 | U2 |
| ATOM | 3054 | OE2 | GLU | 1106 | 4.102 | 31.571 | 10.349 | 1.00 | 55.60 | U2 |
| ATOM | 3055 | C | GLU | 1106 | 6.024 | 33.796 | 14.452 | 1.00 | 63.91 | U2 |
| ATOM | 3056 | O | GLU | 1106 | 6.423 | 33.021 | 15.314 | 1.00 | 63.91 | U2 |
| ATOM | 3057 | N | ASP | 1107 | 5.123 | 34.739 | 14.708 | 1.00 | 65.46 | U2 |
| ATOM | 3059 | CA | ASP | 1107 | 4.522 | 34.887 | 16.044 | 1.00 | 65.46 | U2 |
| ATOM | 3060 | CB | ASP | 1107 | 3.821 | 36.253 | 16.154 | 1.00 | 72.49 | U2 |
| ATOM | 3061 | CG | ASP | 1107 | 3.236 | 36.518 | 17.538 | 1.00 | 72.49 | U2 |
| ATOM | 3062 | OD1 | ASP | 1107 | 2.131 | 36.010 | 17.837 | 1.00 | 72.49 | U2 |
| ATOM | 3063 | OD2 | ASP | 1107 | 3.877 | 37.260 | 18.311 | 1.00 | 72.49 | U2 |
| ATOM | 3064 | C | ASP | 1107 | 3.525 | 33.738 | 16.283 | 1.00 | 65.46 | U2 |
| ATOM | 3065 | O | ASP | 1107 | 2.403 | 33.765 | 15.762 | 1.00 | 65.46 | U2 |
| ATOM | 3066 | N | HIS | 1108 | 3.932 | 32.742 | 17.075 | 1.00 | 55.29 | U2 |
| ATOM | 3068 | CA | HIS | 1108 | 3.098 | 31.569 | 17.347 | 1.00 | 55.29 | U2 |
| ATOM | 3069 | CB | HIS | 1108 | 3.963 | 30.337 | 17.587 | 1.00 | 41.28 | U2 |
| ATOM | 3070 | CG | HIS | 1108 | 4.715 | 29.868 | 16.380 | 1.00 | 41.28 | U2 |
| ATOM | 3071 | CD2 | HIS | 1108 | 5.960 | 30.164 | 15.935 | 1.00 | 41.28 | U2 |
| ATOM | 3072 | ND1 | HIS | 1108 | 4.216 | 28.915 | 15.512 | 1.00 | 41.28 | U2 |
| ATOM | 3074 | CE1 | HIS | 1108 | 5.125 | 28.646 | 14.592 | 1.00 | 41.28 | U2 |
| ATOM | 3075 | NE2 | HIS | 1108 | 6.193 | 29.390 | 14.825 | 1.00 | 41.28 | U2 |
| ATOM | 3077 | C | HIS | 1108 | 2.143 | 31.709 | 18.512 | 1.00 | 55.29 | U2 |
| ATOM | 3078 | O | HIS | 1108 | 1.298 | 30.855 | 18.712 | 1.00 | 55.29 | U2 |
| ATOM | 3079 | N | SER | 1109 | 2.281 | 32.788 | 19.263 | 1.00 | 53.54 | U2 |
| ATOM | 3081 | CA | SER | 1109 | 1.470 | 33.074 | 20.448 | 1.00 | 53.54 | U2 |
| ATOM | 3082 | CB | SER | 1109 | 1.650 | 34.537 | 20.810 | 1.00 | 83.01 | U2 |
| ATOM | 3083 | OG | SER | 1109 | 2.933 | 34.977 | 20.384 | 1.00 | 83.01 | U2 |
| ATOM | 3085 | C | SER | 1109 | −0.025 | 32.757 | 20.468 | 1.00 | 53.54 | U2 |
| ATOM | 3086 | O | SER | 1109 | −0.617 | 32.679 | 21.543 | 1.00 | 53.54 | U2 |
| ATOM | 3087 | N | LYS | 1110 | −0.652 | 32.626 | 19.304 | 1.00 | 56.09 | U2 |
| ATOM | 3089 | CA | LYS | 1110 | −2.087 | 32.345 | 19.262 | 1.00 | 56.09 | U2 |
| ATOM | 3090 | CB | LYS | 1110 | −2.791 | 33.354 | 18.352 | 1.00 | 92.70 | U2 |
| ATOM | 3091 | CG | LYS | 1110 | −2.385 | 34.792 | 18.610 | 1.00 | 92.70 | U2 |
| ATOM | 3092 | CD | LYS | 1110 | −2.571 | 35.634 | 17.367 | 1.00 | 92.70 | U2 |
| ATOM | 3093 | CE | LYS | 1110 | −1.810 | 36.948 | 17.481 | 1.00 | 92.70 | U2 |
| ATOM | 3094 | NZ | LYS | 1110 | −0.338 | 36.749 | 17.589 | 1.00 | 92.70 | U2 |
| ATOM | 3098 | C | LYS | 1110 | −2.322 | 30.935 | 18.746 | 1.00 | 56.09 | U2 |
| ATOM | 3099 | O | LYS | 1110 | −3.463 | 30.527 | 18.476 | 1.00 | 56.09 | U2 |
| ATOM | 3100 | N | ARG | 1111 | −1.228 | 30.190 | 18.640 | 1.00 | 44.40 | U2 |
| ATOM | 3102 | CA | ARG | 1111 | −1.245 | 28.826 | 18.146 | 1.00 | 44.40 | U2 |
| ATOM | 3103 | CB | ARG | 1111 | −0.125 | 28.616 | 17.118 | 1.00 | 64.99 | U2 |
| ATOM | 3104 | CG | ARG | 1111 | −0.279 | 29.501 | 15.877 | 1.00 | 64.99 | U2 |
| ATOM | 3105 | CD | ARG | 1111 | 0.975 | 29.524 | 14.991 | 1.00 | 64.99 | U2 |
| ATOM | 3106 | NE | ARG | 1111 | 0.906 | 30.568 | 13.961 | 1.00 | 64.99 | U2 |
| ATOM | 3108 | CZ | ARG | 1111 | 1.924 | 30.934 | 13.187 | 1.00 | 64.99 | U2 |
| ATOM | 3109 | NH1 | ARG | 1111 | 3.104 | 30.348 | 13.305 | 1.00 | 64.99 | U2 |
| ATOM | 3112 | NH2 | ARG | 1111 | 1.768 | 31.899 | 12.298 | 1.00 | 64.99 | U2 |
| ATOM | 3115 | C | ARG | 1111 | −1.090 | 27.879 | 19.315 | 1.00 | 44.40 | U2 |
| ATOM | 3116 | O | ARG | 1111 | −0.388 | 28.158 | 20.277 | 1.00 | 44.40 | U2 |
| ATOM | 3117 | N | SER | 1112 | −1.785 | 26.764 | 19.229 | 1.00 | 43.39 | U2 |
| ATOM | 3119 | CA | SER | 1112 | −1.752 | 25.770 | 20.263 | 1.00 | 43.39 | U2 |
| ATOM | 3120 | CB | SER | 1112 | −3.079 | 25.027 | 20.226 | 1.00 | 45.11 | U2 |
| ATOM | 3121 | OG | SER | 1112 | −4.155 | 25.942 | 20.072 | 1.00 | 45.11 | U2 |
| ATOM | 3123 | C | SER | 1112 | −0.576 | 24.789 | 20.126 | 1.00 | 43.39 | U2 |
| ATOM | 3124 | O | SER | 1112 | −0.090 | 24.256 | 21.127 | 1.00 | 43.39 | U2 |
| ATOM | 3125 | N | SER | 1113 | −0.089 | 24.580 | 18.904 | 1.00 | 50.61 | U2 |
| ATOM | 3127 | CA | SER | 1113 | 0.995 | 23.628 | 18.667 | 1.00 | 50.61 | U2 |
| ATOM | 3128 | CB | SER | 1113 | 0.410 | 22.224 | 18.616 | 1.00 | 41.52 | U2 |
| ATOM | 3129 | OG | SER | 1113 | −0.530 | 22.146 | 17.546 | 1.00 | 41.52 | U2 |
| ATOM | 3131 | C | SER | 1113 | 1.724 | 23.877 | 17.352 | 1.00 | 50.61 | U2 |
| ATOM | 3132 | O | SER | 1113 | 1.510 | 24.898 | 16.702 | 1.00 | 50.61 | U2 |
| ATOM | 3133 | N | PHE | 1114 | 2.533 | 22.902 | 16.941 | 1.00 | 34.92 | U2 |
| ATOM | 3135 | CA | PHE | 1114 | 3.308 | 22.969 | 15.710 | 1.00 | 34.92 | U2 |
| ATOM | 3136 | CB | PHE | 1114 | 4.649 | 23.666 | 15.959 | 1.00 | 41.76 | U2 |
| ATOM | 3137 | CG | PHE | 1114 | 5.673 | 23.481 | 14.848 | 1.00 | 41.76 | U2 |
| ATOM | 3138 | CD1 | PHE | 1114 | 5.733 | 24.365 | 13.775 | 1.00 | 41.76 | U2 |
| ATOM | 3139 | CD2 | PHE | 1114 | 6.605 | 22.443 | 14.903 | 1.00 | 41.76 | U2 |
| ATOM | 3140 | CE1 | PHE | 1114 | 6.707 | 24.217 | 12.780 | 1.00 | 41.76 | U2 |
| ATOM | 3141 | CE2 | PHE | 1114 | 7.576 | 22.291 | 13.915 | 1.00 | 41.76 | U2 |
| ATOM | 3142 | CZ | PHE | 1114 | 7.624 | 23.182 | 12.853 | 1.00 | 41.76 | U2 |

TABLE 1-continued

Structure coordinates of CPP32

| ATOM | 3143 | C   | PHE | 1114 | 3.548  | 21.555 | 15.234 | 1.00 | 34.92 | U2 |
|------|------|-----|-----|------|--------|--------|--------|------|-------|----|
| ATOM | 3144 | O   | PHE | 1114 | 3.865  | 20.675 | 16.033 | 1.00 | 34.92 | U2 |
| ATOM | 3145 | N   | VAL | 1115 | 3.433  | 21.335 | 13.933 | 1.00 | 32.19 | U2 |
| ATOM | 3147 | CA  | VAL | 1115 | 3.640  | 20.013 | 13.352 | 1.00 | 32.19 | U2 |
| ATOM | 3148 | CB  | VAL | 1115 | 2.298  | 19.433 | 12.889 | 1.00 | 30.85 | U2 |
| ATOM | 3149 | CG1 | VAL | 1115 | 2.462  | 18.043 | 12.304 | 1.00 | 30.85 | U2 |
| ATOM | 3150 | CG2 | VAL | 1115 | 1.307  | 19.455 | 14.060 | 1.00 | 30.85 | U2 |
| ATOM | 3151 | C   | VAL | 1115 | 4.541  | 20.224 | 12.148 | 1.00 | 32.19 | U2 |
| ATOM | 3152 | O   | VAL | 1115 | 4.373  | 21.205 | 11.432 | 1.00 | 32.19 | U2 |
| ATOM | 3153 | N   | CYS | 1116 | 5.530  | 19.357 | 11.967 | 1.00 | 32.72 | U2 |
| ATOM | 3155 | CA  | CYS | 1116 | 6.450  | 19.443 | 10.849 | 1.00 | 32.72 | U2 |
| ATOM | 3156 | CB  | CYS | 1116 | 7.812  | 19.934 | 11.298 | 1.00 | 36.63 | U2 |
| ATOM | 3157 | SG  | CYS | 1116 | 9.097  | 19.743 | 10.060 | 1.00 | 36.63 | U2 |
| ATOM | 3158 | C   | CYS | 1116 | 6.580  | 18.034 | 10.383 | 1.00 | 32.72 | U2 |
| ATOM | 3159 | O   | CYS | 1116 | 6.936  | 17.167 | 11.176 | 1.00 | 32.72 | U2 |
| ATOM | 3160 | N   | VAL | 1117 | 6.276  | 17.785 | 9.113  | 1.00 | 37.10 | U2 |
| ATOM | 3162 | CA  | VAL | 1117 | 6.332  | 16.442 | 8.548  | 1.00 | 37.10 | U2 |
| ATOM | 3163 | CB  | VAL | 1117 | 5.034  | 16.124 | 7.847  | 1.00 | 19.05 | U2 |
| ATOM | 3164 | CG1 | VAL | 1117 | 4.977  | 14.670 | 7.455  | 1.00 | 19.05 | U2 |
| ATOM | 3165 | CG2 | VAL | 1117 | 3.862  | 16.516 | 8.734  | 1.00 | 19.05 | U2 |
| ATOM | 3166 | C   | VAL | 1117 | 7.421  | 16.447 | 7.516  | 1.00 | 37.10 | U2 |
| ATOM | 3167 | O   | VAL | 1117 | 7.464  | 17.344 | 6.689  | 1.00 | 37.10 | U2 |
| ATOM | 3168 | N   | LEU | 1118 | 8.323  | 15.481 | 7.578  | 1.00 | 32.04 | U2 |
| ATOM | 3170 | CA  | LEU | 1118 | 9.427  | 15.403 | 6.635  | 1.00 | 32.04 | U2 |
| ATOM | 3171 | CB  | LEU | 1118 | 10.753 | 15.477 | 7.371  | 1.00 | 38.07 | U2 |
| ATOM | 3172 | CG  | LEU | 1118 | 11.201 | 16.842 | 7.877  | 1.00 | 38.07 | U2 |
| ATOM | 3173 | CD1 | LEU | 1118 | 11.992 | 16.682 | 9.166  | 1.00 | 38.07 | U2 |
| ATOM | 3174 | CD2 | LEU | 1118 | 12.070 | 17.495 | 6.838  | 1.00 | 38.07 | U2 |
| ATOM | 3175 | C   | LEU | 1118 | 9.334  | 14.070 | 5.933  | 1.00 | 32.04 | U2 |
| ATOM | 3176 | O   | LEU | 1118 | 9.297  | 13.016 | 6.589  | 1.00 | 32.04 | U2 |
| ATOM | 3177 | N   | LEU | 1119 | 9.283  | 14.115 | 4.600  | 1.00 | 35.98 | U2 |
| ATOM | 3179 | CA  | LEU | 1119 | 9.186  | 12.907 | 3.768  | 1.00 | 35.98 | U2 |
| ATOM | 3180 | CB  | LEU | 1119 | 7.876  | 12.928 | 2.978  | 1.00 | 25.60 | U2 |
| ATOM | 3181 | CG  | LEU | 1119 | 6.635  | 13.219 | 3.837  | 1.00 | 25.60 | U2 |
| ATOM | 3182 | CD1 | LEU | 1119 | 5.499  | 13.708 | 3.003  | 1.00 | 25.60 | U2 |
| ATOM | 3183 | CD2 | LEU | 1119 | 6.219  | 12.026 | 4.647  | 1.00 | 25.60 | U2 |
| ATOM | 3184 | C   | LEU | 1119 | 10.388 | 12.992 | 2.861  | 1.00 | 35.98 | U2 |
| ATOM | 3185 | O   | LEU | 1119 | 10.549 | 13.968 | 2.145  | 1.00 | 35.98 | U2 |
| ATOM | 3186 | N   | SER | 1120 | 11.284 | 12.023 | 2.962  | 1.00 | 37.84 | U2 |
| ATOM | 3188 | CA  | SER | 1120 | 12.505 | 12.037 | 2.162  | 1.00 | 37.84 | U2 |
| ATOM | 3189 | CB  | SER | 1120 | 13.298 | 13.311 | 2.458  | 1.00 | 40.19 | U2 |
| ATOM | 3190 | OG  | SER | 1120 | 14.565 | 13.300 | 1.831  | 1.00 | 40.19 | U2 |
| ATOM | 3192 | C   | SER | 1120 | 13.367 | 10.819 | 2.476  | 1.00 | 37.84 | U2 |
| ATOM | 3193 | O   | SER | 1120 | 12.924 | 9.860  | 3.128  | 1.00 | 37.84 | U2 |
| ATOM | 3194 | N   | HIS | 1121 | 14.578 | 10.816 | 1.941  | 1.00 | 36.46 | U2 |
| ATOM | 3196 | CA  | HIS | 1121 | 15.494 | 9.727  | 2.203  | 1.00 | 36.46 | U2 |
| ATOM | 3197 | CB  | HIS | 1121 | 16.489 | 9.578  | 1.051  | 1.00 | 43.34 | U2 |
| ATOM | 3198 | CG  | HIS | 1121 | 15.948 | 8.809  | −0.114 | 1.00 | 43.34 | U2 |
| ATOM | 3199 | CD2 | HIS | 1121 | 15.386 | 9.223  | −1.273 | 1.00 | 43.34 | U2 |
| ATOM | 3200 | ND1 | HIS | 1121 | 15.934 | 7.431  | −0.151 | 1.00 | 43.34 | U2 |
| ATOM | 3202 | CE1 | HIS | 1121 | 15.383 | 7.029  | −1.280 | 1.00 | 43.34 | U2 |
| ATOM | 3203 | NE2 | HIS | 1121 | 15.042 | 8.097  | −1.978 | 1.00 | 43.34 | U2 |
| ATOM | 3205 | C   | HIS | 1121 | 16.232 | 10.100 | 3.476  | 1.00 | 36.46 | U2 |
| ATOM | 3206 | O   | HIS | 1121 | 16.236 | 11.276 | 3.872  | 1.00 | 36.46 | U2 |
| ATOM | 3207 | N   | GLY | 1122 | 16.877 | 9.125  | 4.108  | 1.00 | 37.67 | U2 |
| ATOM | 3209 | CA  | GLY | 1122 | 17.601 | 9.429  | 5.321  | 1.00 | 37.67 | U2 |
| ATOM | 3210 | C   | GLY | 1122 | 18.536 | 8.373  | 5.856  | 1.00 | 37.67 | U2 |
| ATOM | 3211 | O   | GLY | 1122 | 18.725 | 7.295  | 5.279  | 1.00 | 37.67 | U2 |
| ATOM | 3212 | N   | GLU | 1123 | 19.144 | 8.730  | 6.977  | 1.00 | 40.61 | U2 |
| ATOM | 3214 | CA  | GLU | 1123 | 20.082 | 7.893  | 7.710  | 1.00 | 40.61 | U2 |
| ATOM | 3215 | CB  | GLU | 1123 | 21.511 | 8.161  | 7.235  | 1.00 | 89.62 | U2 |
| ATOM | 3216 | CG  | GLU | 1123 | 21.768 | 7.692  | 5.808  | 1.00 | 89.62 | U2 |
| ATOM | 3217 | CD  | GLU | 1123 | 23.031 | 8.273  | 5.201  | 1.00 | 89.62 | U2 |
| ATOM | 3218 | OE1 | GLU | 1123 | 23.712 | 9.077  | 5.873  | 1.00 | 89.62 | U2 |
| ATOM | 3219 | OE2 | GLU | 1123 | 23.335 | 7.930  | 4.038  | 1.00 | 89.62 | U2 |
| ATOM | 3220 | C   | GLU | 1123 | 19.891 | 8.315  | 9.172  | 1.00 | 40.61 | U2 |
| ATOM | 3221 | O   | GLU | 1123 | 19.265 | 9.356  | 9.449  | 1.00 | 40.61 | U2 |
| ATOM | 3222 | N   | GLU | 1124 | 20.415 | 7.535  | 10.110 | 1.00 | 33.36 | U2 |
| ATOM | 3224 | CA  | GLU | 1124 | 20.201 | 7.880  | 11.495 | 1.00 | 33.36 | U2 |
| ATOM | 3225 | CB  | GLU | 1124 | 20.957 | 6.960  | 12.434 | 1.00 | 46.40 | U2 |
| ATOM | 3226 | CG  | GLU | 1124 | 20.575 | 7.187  | 13.895 | 1.00 | 46.40 | U2 |
| ATOM | 3227 | CD  | GLU | 1124 | 19.067 | 7.149  | 14.123 | 1.00 | 46.40 | U2 |
| ATOM | 3228 | OE1 | GLU | 1124 | 18.568 | 6.055  | 14.447 | 1.00 | 46.40 | U2 |
| ATOM | 3229 | OE2 | GLU | 1124 | 18.380 | 8.192  | 13.978 | 1.00 | 46.40 | U2 |
| ATOM | 3230 | C   | GLU | 1124 | 20.534 | 9.313  | 11.791 | 1.00 | 33.36 | U2 |
| ATOM | 3231 | O   | GLU | 1124 | 21.645 | 9.771  | 11.545 | 1.00 | 33.36 | U2 |
| ATOM | 3232 | N   | GLY | 1125 | 19.513 | 10.038 | 12.221 | 1.00 | 45.33 | U2 |

TABLE 1-continued

Structure coordinates of CPP32

| ATOM | 3234 | CA | GLY | 1125 | 19.674 | 11.435 | 12.581 | 1.00 | 45.33 | U2 |
|---|---|---|---|---|---|---|---|---|---|---|
| ATOM | 3235 | C | GLY | 1125 | 19.897 | 12.353 | 11.404 | 1.00 | 45.33 | U2 |
| ATOM | 3236 | O | GLY | 1125 | 20.148 | 13.549 | 11.596 | 1.00 | 45.33 | U2 |
| ATOM | 3237 | N | ILE | 1126 | 19.672 | 11.829 | 10.200 | 1.00 | 51.43 | U2 |
| ATOM | 3239 | CA | ILE | 1126 | 19.877 | 12.566 | 8.950 | 1.00 | 51.43 | U2 |
| ATOM | 3240 | CB | ILE | 1126 | 21.135 | 12.008 | 8.226 | 1.00 | 42.02 | U2 |
| ATOM | 3241 | CG2 | ILE | 1126 | 21.180 | 12.474 | 6.791 | 1.00 | 42.02 | U2 |
| ATOM | 3242 | CG1 | ILE | 1126 | 22.406 | 12.394 | 8.969 | 1.00 | 42.02 | U2 |
| ATOM | 3243 | CD1 | ILE | 1126 | 23.656 | 11.767 | 8.387 | 1.00 | 42.02 | U2 |
| ATOM | 3244 | C | ILE | 1126 | 18.718 | 12.472 | 7.941 | 1.00 | 51.43 | U2 |
| ATOM | 3245 | O | ILE | 1126 | 18.180 | 11.386 | 7.703 | 1.00 | 51.43 | U2 |
| ATOM | 3246 | N | ILE | 1127 | 18.333 | 13.607 | 7.359 | 1.00 | 56.91 | U2 |
| ATOM | 3248 | CA | ILE | 1127 | 17.316 | 13.623 | 6.305 | 1.00 | 56.91 | U2 |
| ATOM | 3249 | CB | ILE | 1127 | 15.906 | 14.125 | 6.744 | 1.00 | 49.08 | U2 |
| ATOM | 3250 | CG2 | ILE | 1127 | 15.155 | 13.016 | 7.441 | 1.00 | 49.08 | U2 |
| ATOM | 3251 | CG1 | ILE | 1127 | 15.987 | 15.397 | 7.576 | 1.00 | 49.08 | U2 |
| ATOM | 3252 | CD1 | ILE | 1127 | 15.849 | 16.659 | 6.783 | 1.00 | 49.08 | U2 |
| ATOM | 3253 | C | ILE | 1127 | 17.871 | 14.457 | 5.151 | 1.00 | 56.91 | U2 |
| ATOM | 3254 | O | ILE | 1127 | 18.497 | 15.499 | 5.369 | 1.00 | 56.91 | U2 |
| ATOM | 3255 | N | PHE | 1128 | 17.710 | 13.950 | 3.934 | 1.00 | 51.63 | U2 |
| ATOM | 3257 | CA | PHE | 1128 | 18.217 | 14.613 | 2.740 | 1.00 | 51.63 | U2 |
| ATOM | 3258 | CB | PHE | 1128 | 18.427 | 13.606 | 1.606 | 1.00 | 49.61 | U2 |
| ATOM | 3259 | CG | PHE | 1128 | 19.545 | 12.652 | 1.826 | 1.00 | 49.61 | U2 |
| ATOM | 3260 | CD1 | PHE | 1128 | 19.292 | 11.362 | 2.259 | 1.00 | 49.61 | U2 |
| ATOM | 3261 | CD2 | PHE | 1128 | 20.841 | 13.014 | 1.542 | 1.00 | 49.61 | U2 |
| ATOM | 3262 | CE1 | PHE | 1128 | 20.318 | 10.440 | 2.404 | 1.00 | 49.61 | U2 |
| ATOM | 3263 | CE2 | PHE | 1128 | 21.875 | 12.098 | 1.686 | 1.00 | 49.61 | U2 |
| ATOM | 3264 | CZ | PHE | 1128 | 21.609 | 10.805 | 2.118 | 1.00 | 49.61 | U2 |
| ATOM | 3265 | C | PHE | 1128 | 17.357 | 15.712 | 2.156 | 1.00 | 51.63 | U2 |
| ATOM | 3266 | O | PHE | 1128 | 16.123 | 15.618 | 2.105 | 1.00 | 51.63 | U2 |
| ATOM | 3267 | N | GLY | 1129 | 18.040 | 16.752 | 1.706 | 1.00 | 54.00 | U2 |
| ATOM | 3269 | CA | GLY | 1129 | 17.395 | 17.833 | 0.997 | 1.00 | 54.00 | U2 |
| ATOM | 3270 | C | GLY | 1129 | 17.683 | 17.333 | −0.417 | 1.00 | 54.00 | U2 |
| ATOM | 3271 | O | GLY | 1129 | 18.375 | 16.309 | −0.556 | 1.00 | 54.00 | U2 |
| ATOM | 3272 | N | THR | 1130 | 17.231 | 18.018 | −1.466 | 1.00 | 56.46 | U2 |
| ATOM | 3274 | CA | THR | 1130 | 17.496 | 17.526 | −2.825 | 1.00 | 56.46 | U2 |
| ATOM | 3275 | CB | THR | 1130 | 16.732 | 18.307 | −3.880 | 1.00 | 50.48 | U2 |
| ATOM | 3276 | OG1 | THR | 1130 | 17.020 | 19.700 | −3.725 | 1.00 | 50.48 | U2 |
| ATOM | 3278 | CG2 | THR | 1130 | 15.240 | 18.067 | −3.759 | 1.00 | 50.48 | U2 |
| ATOM | 3279 | C | THR | 1130 | 18.969 | 17.563 | −3.203 | 1.00 | 56.46 | U2 |
| ATOM | 3280 | O | THR | 1130 | 19.387 | 16.908 | −4.157 | 1.00 | 56.46 | U2 |
| ATOM | 3281 | N | ASN | 1131 | 19.745 | 18.356 | −2.476 | 1.00 | 66.71 | U2 |
| ATOM | 3283 | CA | ASN | 1131 | 21.172 | 18.477 | −2.751 | 1.00 | 66.71 | U2 |
| ATOM | 3284 | CB | ASN | 1131 | 21.567 | 19.949 | −2.849 | 1.00 | 70.58 | U2 |
| ATOM | 3285 | CG | ASN | 1131 | 21.184 | 20.730 | −1.622 | 1.00 | 70.58 | U2 |
| ATOM | 3286 | OD1 | ASN | 1131 | 20.665 | 20.167 | −0.662 | 1.00 | 70.58 | U2 |
| ATOM | 3287 | ND2 | ASN | 1131 | 21.404 | 22.042 | −1.653 | 1.00 | 70.58 | U2 |
| ATOM | 3290 | C | ASN | 1131 | 22.083 | 17.771 | −1.749 | 1.00 | 66.71 | U2 |
| ATOM | 3291 | O | ASN | 1131 | 23.275 | 17.604 | −2.011 | 1.00 | 66.71 | U2 |
| ATOM | 3292 | N | GLY | 1132 | 21.549 | 17.372 | −0.601 | 1.00 | 71.58 | U2 |
| ATOM | 3294 | CA | GLY | 1132 | 22.391 | 16.697 | 0.373 | 1.00 | 71.58 | U2 |
| ATOM | 3295 | C | GLY | 1132 | 21.808 | 16.522 | 1.760 | 1.00 | 71.58 | U2 |
| ATOM | 3296 | O | GLY | 1132 | 20.735 | 17.048 | 2.062 | 1.00 | 71.58 | U2 |
| ATOM | 3297 | N | PRO | 1133 | 22.515 | 15.786 | 2.632 | 1.00 | 64.05 | U2 |
| ATOM | 3298 | CD | PRO | 1133 | 23.775 | 15.110 | 2.280 | 1.00 | 65.87 | U2 |
| ATOM | 3299 | CA | PRO | 1133 | 22.141 | 15.483 | 4.020 | 1.00 | 64.05 | U2 |
| ATOM | 3300 | CB | PRO | 1133 | 23.164 | 14.417 | 4.419 | 1.00 | 65.87 | U2 |
| ATOM | 3301 | CG | PRO | 1133 | 24.359 | 14.798 | 3.642 | 1.00 | 65.87 | U2 |
| ATOM | 3302 | C | PRO | 1133 | 22.125 | 16.645 | 5.015 | 1.00 | 64.05 | U2 |
| ATOM | 3303 | O | PRO | 1133 | 23.021 | 17.487 | 5.034 | 1.00 | 64.05 | U2 |
| ATOM | 3304 | N | VAL | 1134 | 21.083 | 16.668 | 5.835 | 1.00 | 65.10 | U2 |
| ATOM | 3306 | CA | VAL | 1134 | 20.908 | 17.675 | 6.870 | 1.00 | 65.10 | U2 |
| ATOM | 3307 | CB | VAL | 1134 | 19.540 | 18.355 | 6.771 | 1.00 | 50.22 | U2 |
| ATOM | 3308 | CG1 | VAL | 1134 | 19.422 | 19.468 | 7.789 | 1.00 | 50.22 | 132 |
| ATOM | 3309 | CG2 | VAL | 1134 | 19.321 | 18.872 | 5.389 | 1.00 | 50.22 | U2 |
| ATOM | 3310 | C | VAL | 1134 | 20.881 | 16.875 | 8.152 | 1.00 | 65.10 | U2 |
| ATOM | 3311 | O | VAL | 1134 | 20.490 | 15.702 | 8.155 | 1.00 | 65.10 | U2 |
| ATOM | 3312 | N | ASP | 1135 | 21.330 | 17.485 | 9.235 | 1.00 | 47.69 | U2 |
| ATOM | 3314 | CA | ASP | 1135 | 21.303 | 16.814 | 10.516 | 1.00 | 47.69 | U2 |
| ATOM | 3315 | CB | ASP | 1135 | 22.495 | 17.236 | 11.377 | 1.00 | 83.88 | U2 |
| ATOM | 3316 | CG | ASP | 1135 | 22.876 | 16.182 | 12.398 | 1.00 | 83.88 | U2 |
| ATOM | 3317 | OD1 | ASP | 1135 | 22.151 | 16.029 | 13.405 | 1.00 | 83.88 | U2 |
| ATOM | 3318 | OD2 | ASP | 1135 | 23.897 | 15.492 | 12.183 | 1.00 | 83.88 | U2 |
| ATOM | 3319 | C | ASP | 1135 | 19.994 | 17.284 | 11.134 | 1.00 | 47.69 | U2 |
| ATOM | 3320 | O | ASP | 1135 | 19.739 | 18.492 | 11.216 | 1.00 | 47.69 | U2 |
| ATOM | 3321 | N | LEU | 1136 | 19.143 | 16.335 | 11.511 | 1.00 | 33.06 | U2 |
| ATOM | 3323 | CA | LEU | 1136 | 17.844 | 16.646 | 12.114 | 1.00 | 33.06 | U2 |

TABLE 1-continued

Structure coordinates of CPP32

| ATOM | 3324 | CB | LEU | 1136 | 17.143 | 15.351 | 12.539 | 1.00 | 43.63 | U2 |
|---|---|---|---|---|---|---|---|---|---|---|
| ATOM | 3325 | CG | LEU | 1136 | 16.240 | 14.644 | 11.531 | 1.00 | 43.63 | U2 |
| ATOM | 3326 | CD1 | LEU | 1136 | 15.988 | 13.207 | 11.939 | 1.00 | 43.63 | U2 |
| ATOM | 3327 | CD2 | LEU | 1136 | 14.941 | 15.388 | 11.443 | 1.00 | 43.63 | U2 |
| ATOM | 3328 | C | LEU | 1136 | 17.977 | 17.593 | 13.312 | 1.00 | 33.06 | U2 |
| ATOM | 3329 | O | LEU | 1136 | 17.102 | 18.429 | 13.566 | 1.00 | 33.06 | U2 |
| ATOM | 3330 | N | LYS | 1137 | 19.098 | 17.459 | 14.020 | 1.00 | 60.31 | U2 |
| ATOM | 3332 | CA | LYS | 1137 | 19.410 | 18.259 | 15.199 | 1.00 | 60.31 | U2 |
| ATOM | 3333 | CB | LYS | 1137 | 20.816 | 17.912 | 15.696 | 1.00 | 97.53 | U2 |
| ATOM | 3334 | CG | LYS | 1137 | 21.165 | 18.429 | 17.076 | 1.00 | 97.53 | U2 |
| ATOM | 3335 | CD | LYS | 1137 | 20.300 | 17.789 | 18.151 | 1.00 | 97.53 | U2 |
| ATOM | 3336 | CE | LYS | 1137 | 20.846 | 18.064 | 19.551 | 1.00 | 97.53 | U2 |
| ATOM | 3337 | NZ | LYS | 1137 | 20.945 | 19.519 | 19.881 | 1.00 | 97.53 | U2 |
| ATOM | 3341 | C | LYS | 1137 | 19.314 | 19.740 | 14.871 | 1.00 | 60.31 | U2 |
| ATOM | 3342 | O | LYS | 1137 | 18.742 | 20.514 | 15.630 | 1.00 | 60.31 | U2 |
| ATOM | 3343 | N | LYS | 1138 | 19.805 | 20.117 | 13.698 | 1.00 | 60.37 | U2 |
| ATOM | 3345 | CA | LYS | 1138 | 19.771 | 21.508 | 13.284 | 1.00 | 60.37 | U2 |
| ATOM | 3346 | CB | LYS | 1138 | 20.679 | 21.740 | 12.077 | 1.00 | 82.00 | U2 |
| ATOM | 3347 | CG | LYS | 1138 | 22.167 | 21.681 | 12.378 | 1.00 | 82.00 | U2 |
| ATOM | 3348 | CD | LYS | 1138 | 22.986 | 22.102 | 11.162 | 1.00 | 82.00 | U2 |
| ATOM | 3349 | CE | LYS | 1138 | 22.679 | 23.542 | 10.748 | 1.00 | 82.00 | U2 |
| ATOM | 3350 | NZ | LYS | 1138 | 23.399 | 23.948 | 9.508 | 1.00 | 82.00 | U2 |
| ATOM | 3354 | C | LYS | 1138 | 18.367 | 22.025 | 12.980 | 1.00 | 60.37 | U2 |
| ATOM | 3355 | O | LYS | 1138 | 18.043 | 23.158 | 13.320 | 1.00 | 60.37 | U2 |
| ATOM | 3356 | N | ILE | 1139 | 17.516 | 21.206 | 12.376 | 1.00 | 57.35 | U2 |
| ATOM | 3358 | CA | ILE | 1139 | 16.181 | 21.686 | 12.047 | 1.00 | 57.35 | U2 |
| ATOM | 3359 | CB | ILE | 1139 | 15.587 | 20.939 | 10.845 | 1.00 | 66.34 | U2 |
| ATOM | 3360 | CG2 | ILE | 1139 | 16.631 | 20.818 | 9.737 | 1.00 | 66.34 | U2 |
| ATOM | 3361 | CG1 | ILE | 1139 | 15.140 | 19.542 | 11.237 | 1.00 | 66.34 | U2 |
| ATOM | 3362 | CD1 | ILE | 1139 | 14.722 | 18.715 | 10.040 | 1.00 | 66.34 | U2 |
| ATOM | 3363 | C | ILE | 1139 | 15.223 | 21.677 | 13.230 | 1.00 | 57.35 | U2 |
| ATOM | 3364 | O | ILE | 1139 | 14.218 | 22.394 | 13.228 | 1.00 | 57.35 | U2 |
| ATOM | 3365 | N | THR | 1140 | 15.541 | 20.878 | 14.246 | 1.00 | 39.31 | U2 |
| ATOM | 3367 | CA | THR | 1140 | 14.720 | 20.795 | 15.451 | 1.00 | 39.31 | U2 |
| ATOM | 3368 | CB | THR | 1140 | 14.839 | 19.414 | 16.093 | 1.00 | 50.23 | U2 |
| ATOM | 3369 | OG1 | THR | 1140 | 16.220 | 19.121 | 16.281 | 1.00 | 50.23 | U2 |
| ATOM | 3371 | CG2 | THR | 1140 | 14.261 | 18.341 | 15.188 | 1.00 | 50.23 | U2 |
| ATOM | 3372 | C | THR | 1140 | 15.179 | 21.872 | 16.442 | 1.00 | 39.31 | U2 |
| ATOM | 3373 | O | THR | 1140 | 14.355 | 22.547 | 17.074 | 1.00 | 39.31 | U2 |
| ATOM | 3374 | N | ASN | 1141 | 16.487 | 22.081 | 16.532 | 1.00 | 38.25 | U2 |
| ATOM | 3376 | CA | ASN | 1141 | 17.023 | 23.088 | 17.431 | 1.00 | 38.25 | U2 |
| ATOM | 3377 | CB | ASN | 1141 | 18.515 | 23.292 | 17.214 | 1.00 | 53.47 | U2 |
| ATOM | 3378 | CG | ASN | 1141 | 19.358 | 22.208 | 17.858 | 1.00 | 53.47 | U2 |
| ATOM | 3379 | OD1 | ASN | 1141 | 20.573 | 22.135 | 17.633 | 1.00 | 53.47 | U2 |
| ATOM | 3380 | ND2 | ASN | 1141 | 18.729 | 21.362 | 18.667 | 1.00 | 53.47 | U2 |
| ATOM | 3383 | C | ASN | 1141 | 16.338 | 24.440 | 17.373 | 1.00 | 38.25 | U2 |
| ATOM | 3384 | O | ASN | 1141 | 16.180 | 25.084 | 18.401 | 1.00 | 38.25 | U2 |
| ATOM | 3385 | N | PHE | 1142 | 15.915 | 24.894 | 16.201 | 1.00 | 32.69 | U2 |
| ATOM | 3387 | CA | PHE | 1142 | 15.268 | 26.210 | 16.120 | 1.00 | 32.69 | U2 |
| ATOM | 3388 | CB | PHE | 1142 | 14.904 | 26.549 | 14.674 | 1.00 | 48.05 | U2 |
| ATOM | 3389 | CG | PHE | 1142 | 16.088 | 26.726 | 13.767 | 1.00 | 48.05 | U2 |
| ATOM | 3390 | CD1 | PHE | 1142 | 16.588 | 25.659 | 13.037 | 1.00 | 48.05 | U2 |
| ATOM | 3391 | CD2 | PHE | 1142 | 16.689 | 27.963 | 13.628 | 1.00 | 48.05 | U2 |
| ATOM | 3392 | CE1 | PHE | 1142 | 17.676 | 25.827 | 12.177 | 1.00 | 48.05 | U2 |
| ATOM | 3393 | CE2 | PHE | 1142 | 17.775 | 28.137 | 12.770 | 1.00 | 48.05 | U2 |
| ATOM | 3394 | CZ | PHE | 1142 | 18.267 | 27.069 | 12.047 | 1.00 | 48.05 | U2 |
| ATOM | 3395 | C | PHE | 1142 | 14.020 | 26.299 | 16.992 | 1.00 | 32.69 | U2 |
| ATOM | 3396 | O | PHE | 1142 | 13.566 | 27.376 | 17.355 | 1.00 | 32.69 | U2 |
| ATOM | 3397 | N | PHE | 1143 | 13.485 | 25.156 | 17.369 | 1.00 | 43.33 | U2 |
| ATOM | 3399 | CA | PHE | 1143 | 12.289 | 25.157 | 18.184 | 1.00 | 43.33 | U2 |
| ATOM | 3400 | CB | PHE | 1143 | 11.290 | 24.156 | 17.602 | 1.00 | 44.62 | U2 |
| ATOM | 3401 | CG | PHE | 1143 | 10.931 | 24.455 | 16.181 | 1.00 | 44.62 | U2 |
| ATOM | 3402 | CD1 | PHE | 1143 | 11.721 | 23.982 | 15.137 | 1.00 | 44.62 | U2 |
| ATOM | 3403 | CD2 | PHE | 1143 | 9.855 | 25.279 | 15.883 | 1.00 | 44.62 | U2 |
| ATOM | 3404 | CE1 | PHE | 1143 | 11.453 | 24.330 | 13.820 | 1.00 | 44.62 | U2 |
| ATOM | 3405 | CE2 | PHE | 1143 | 9.578 | 25.634 | 14.564 | 1.00 | 44.62 | U2 |
| ATOM | 3406 | CZ | PHE | 1143 | 10.381 | 25.157 | 13.535 | 1.00 | 44.62 | U2 |
| ATOM | 3407 | C | PHE | 1143 | 12.489 | 24.973 | 19.698 | 1.00 | 43.33 | U2 |
| ATOM | 3408 | O | PHE | 1143 | 11.525 | 25.056 | 20.465 | 1.00 | 43.33 | U2 |
| ATOM | 3409 | N | ARG | 1144 | 13.726 | 24.746 | 20.135 | 1.00 | 35.08 | U2 |
| ATOM | 3411 | CA | ARG | 1144 | 13.998 | 24.584 | 21.556 | 1.00 | 35.08 | U2 |
| ATOM | 3412 | CB | ARG | 1144 | 15.498 | 24.595 | 21.809 | 1.00 | 39.40 | U2 |
| ATOM | 3413 | CG | ARG | 1144 | 16.218 | 23.291 | 21.557 | 1.00 | 39.40 | U2 |
| ATOM | 3414 | CD | ARG | 1144 | 17.735 | 23.474 | 21.615 | 1.00 | 39.40 | U2 |
| ATOM | 3415 | NE | ARG | 1144 | 18.177 | 24.360 | 22.692 | 1.00 | 39.40 | U2 |
| ATOM | 3417 | CZ | ARG | 1144 | 19.452 | 24.543 | 23.013 | 1.00 | 39.40 | U2 |
| ATOM | 3418 | NH1 | ARG | 1144 | 20.403 | 23.898 | 22.350 | 1.00 | 39.40 | U2 |

TABLE 1-continued

Structure coordinates of CPP32

| ATOM | 3421 | NH2 | ARG | 1144 | 19.788 | 25.390 | 23.977 | 1.00 | 39.40 | U2 |
|---|---|---|---|---|---|---|---|---|---|---|
| ATOM | 3424 | C | ARG | 1144 | 13.367 | 25.776 | 22.257 | 1.00 | 35.08 | U2 |
| ATOM | 3425 | O | ARG | 1144 | 13.487 | 26.904 | 21.797 | 1.00 | 35.08 | U2 |
| ATOM | 3426 | N | GLY | 1145 | 12.721 | 25.525 | 23.384 | 1.00 | 46.31 | U2 |
| ATOM | 3428 | CA | GLY | 1145 | 12.046 | 26.581 | 24.123 | 1.00 | 46.31 | U2 |
| ATOM | 3429 | C | GLY | 1145 | 12.834 | 27.829 | 24.471 | 1.00 | 46.31 | U2 |
| ATOM | 3430 | O | GLY | 1145 | 12.265 | 28.784 | 25.005 | 1.00 | 46.31 | U2 |
| ATOM | 3431 | N | ASP | 1146 | 14.145 | 27.801 | 24.246 | 1.00 | 53.67 | U2 |
| ATOM | 3433 | CA | ASP | 1146 | 14.988 | 28.954 | 24.527 | 1.00 | 53.67 | U2 |
| ATOM | 3434 | CB | ASP | 1146 | 16.342 | 28.538 | 25.117 | 1.00 | 65.88 | U2 |
| ATOM | 3435 | CG | ASP | 1146 | 17.142 | 27.627 | 24.203 | 1.00 | 65.88 | U2 |
| ATOM | 3436 | OD1 | ASP | 1146 | 18.380 | 27.590 | 24.348 | 1.00 | 65.88 | U2 |
| ATOM | 3437 | OD2 | ASP | 1146 | 16.545 | 26.927 | 23.366 | 1.00 | 65.88 | U2 |
| ATOM | 3438 | C | ASP | 1146 | 15.171 | 29.763 | 23.261 | 1.00 | 53.67 | U2 |
| ATOM | 3439 | O | ASP | 1146 | 15.569 | 30.926 | 23.309 | 1.00 | 53.67 | U2 |
| ATOM | 3440 | N | ARG | 1147 | 14.924 | 29.130 | 22.121 | 1.00 | 60.41 | U2 |
| ATOM | 3442 | CA | ARG | 1147 | 15.020 | 29.815 | 20.847 | 1.00 | 60.41 | U2 |
| ATOM | 3443 | CB | ARG | 1147 | 15.593 | 28.900 | 19.775 | 1.00 | 57.05 | U2 |
| ATOM | 3444 | CG | ARG | 1147 | 17.101 | 28.780 | 19.804 | 1.00 | 57.05 | U2 |
| ATOM | 3445 | CD | ARG | 1147 | 17.546 | 27.700 | 20.736 | 1.00 | 57.05 | U2 |
| ATOM | 3446 | NE | ARG | 1147 | 18.990 | 27.495 | 20.722 | 1.00 | 57.05 | U2 |
| ATOM | 3448 | CZ | ARG | 1147 | 19.694 | 27.145 | 19.649 | 1.00 | 57.05 | U2 |
| ATOM | 3449 | NH1 | ARG | 1147 | 19.096 | 26.966 | 18.478 | 1.00 | 57.05 | U2 |
| ATOM | 3452 | NH2 | ARG | 1147 | 20.994 | 26.911 | 19.762 | 1.00 | 57.05 | U2 |
| ATOM | 3455 | C | ARG | 1147 | 13.642 | 30.325 | 20.428 | 1.00 | 60.41 | U2 |
| ATOM | 3456 | O | ARG | 1147 | 13.360 | 31.529 | 20.502 | 1.00 | 60.41 | U2 |
| ATOM | 3457 | N | CYS | 1148 | 12.764 | 29.403 | 20.050 | 1.00 | 49.95 | U2 |
| ATOM | 3459 | CA | CYS | 1148 | 11.416 | 29.750 | 19.612 | 1.00 | 49.95 | U2 |
| ATOM | 3460 | CB | CYS | 1148 | 10.869 | 28.663 | 18.681 | 1.00 | 49.22 | U2 |
| ATOM | 3461 | SG | CYS | 1148 | 9.145 | 28.906 | 18.194 | 1.00 | 49.22 | U2 |
| ATOM | 3462 | C | CYS | 1148 | 10.483 | 29.986 | 20.796 | 1.00 | 49.95 | U2 |
| ATOM | 3463 | O | CYS | 1148 | 9.418 | 29.377 | 20.911 | 1.00 | 49.95 | U2 |
| ATOM | 3464 | N | ARG | 1149 | 10.851 | 30.958 | 21.619 | 1.00 | 64.82 | U2 |
| ATOM | 3466 | CA | ARG | 1149 | 10.114 | 31.336 | 22.826 | 1.00 | 64.82 | U2 |
| ATOM | 3467 | CB | ARG | 1149 | 10.647 | 32.681 | 23.324 | 1.00 | 97.38 | U2 |
| ATOM | 3468 | CG | ARG | 1149 | 10.263 | 33.061 | 24.735 | 1.00 | 97.38 | U2 |
| ATOM | 3469 | CD | ARG | 1149 | 11.237 | 32.475 | 25.738 | 1.00 | 97.38 | U2 |
| ATOM | 3470 | NE | ARG | 1149 | 10.907 | 32.877 | 27.102 | 1.00 | 97.38 | U2 |
| ATOM | 3472 | CZ | ARG | 1149 | 9.923 | 32.351 | 27.829 | 1.00 | 97.38 | U2 |
| ATOM | 3473 | NH1 | ARG | 1149 | 9.155 | 31.387 | 27.335 | 1.00 | 97.38 | U2 |
| ATOM | 3476 | NH2 | ARG | 1149 | 9.704 | 32.797 | 29.058 | 1.00 | 97.38 | U2 |
| ATOM | 3479 | C | ARG | 1149 | 8.592 | 31.422 | 22.674 | 1.00 | 64.82 | U2 |
| ATOM | 3480 | O | ARG | 1149 | 7.867 | 31.412 | 23.676 | 1.00 | 64.82 | U2 |
| ATOM | 3481 | N | SER | 1150 | 8.108 | 31.510 | 21.435 | 1.00 | 48.79 | U2 |
| ATOM | 3483 | CA | SER | 1150 | 6.675 | 31.630 | 21.181 | 1.00 | 48.79 | U2 |
| ATOM | 3484 | CB | SER | 1150 | 6.439 | 32.330 | 19.837 | 1.00 | 41.24 | U2 |
| ATOM | 3485 | OG | SER | 1150 | 5.092 | 32.752 | 19.704 | 1.00 | 41.24 | U2 |
| ATOM | 3487 | C | SER | 1150 | 5.930 | 30.294 | 21.250 | 1.00 | 48.79 | U2 |
| ATOM | 3488 | O | SER | 1150 | 4.696 | 30.266 | 21.272 | 1.00 | 48.79 | U2 |
| ATOM | 3489 | N | LEU | 1151 | 6.682 | 29.195 | 21.309 | 1.00 | 38.01 | U2 |
| ATOM | 3491 | CA | LEU | 1151 | 6.105 | 27.855 | 21.379 | 1.00 | 38.01 | U2 |
| ATOM | 3492 | CB | LEU | 1151 | 6.678 | 26.993 | 20.265 | 1.00 | 27.90 | U2 |
| ATOM | 3493 | CG | LEU | 1151 | 6.047 | 27.114 | 18.890 | 1.00 | 27.90 | U2 |
| ATOM | 3494 | CD1 | LEU | 1151 | 6.853 | 26.328 | 17.876 | 1.00 | 27.90 | U2 |
| ATOM | 3495 | CD2 | LEU | 1151 | 4.620 | 26.596 | 18.998 | 1.00 | 27.90 | U2 |
| ATOM | 3496 | C | LEU | 1151 | 6.389 | 27.161 | 22.711 | 1.00 | 38.01 | U2 |
| ATOM | 3497 | O | LEU | 1151 | 5.960 | 26.016 | 22.927 | 1.00 | 38.01 | U2 |
| ATOM | 3498 | N | THR | 1152 | 7.127 | 27.844 | 23.588 | 1.00 | 39.29 | U2 |
| ATOM | 3500 | CA | THR | 1152 | 7.510 | 27.321 | 24.894 | 1.00 | 39.29 | U2 |
| ATOM | 3501 | CB | THR | 1152 | 8.242 | 28.398 | 25.703 | 1.00 | 39.68 | U2 |
| ATOM | 3502 | OG1 | THR | 1152 | 9.478 | 28.716 | 25.053 | 1.00 | 39.68 | U2 |
| ATOM | 3504 | CG2 | THR | 1152 | 8.555 | 27.908 | 27.080 | 1.00 | 39.68 | U2 |
| ATOM | 3505 | C | THR | 1152 | 6.320 | 26.786 | 25.664 | 1.00 | 39.29 | U2 |
| ATOM | 3506 | O | THR | 1152 | 5.359 | 27.499 | 25.883 | 1.00 | 39.29 | U2 |
| ATOM | 3507 | N | GLY | 1153 | 6.385 | 25.516 | 26.051 | 1.00 | 28.13 | U2 |
| ATOM | 3509 | CA | GLY | 1153 | 5.298 | 24.904 | 26.788 | 1.00 | 28.13 | U2 |
| ATOM | 3510 | C | GLY | 1153 | 4.225 | 24.325 | 25.889 | 1.00 | 28.13 | U2 |
| ATOM | 3511 | O | GLY | 1153 | 3.167 | 23.861 | 26.366 | 1.00 | 28.13 | U2 |
| ATOM | 3512 | N | LYS | 1154 | 4.486 | 24.325 | 24.584 | 1.00 | 25.78 | U2 |
| ATOM | 3514 | CA | LYS | 1154 | 3.521 | 23.807 | 23.619 | 1.00 | 25.78 | U2 |
| ATOM | 3515 | CB | LYS | 1154 | 3.125 | 24.879 | 22.605 | 1.00 | 38.49 | U2 |
| ATOM | 3516 | CG | LYS | 1154 | 2.291 | 26.019 | 23.137 | 1.00 | 38.49 | U2 |
| ATOM | 3517 | CD | LYS | 1154 | 2.281 | 27.142 | 22.124 | 1.00 | 38.49 | U2 |
| ATOM | 3518 | CE | LYS | 1154 | 1.526 | 28.350 | 22.612 | 1.00 | 38.49 | U2 |
| ATOM | 3519 | NZ | LYS | 1154 | 1.730 | 29.504 | 21.691 | 1.00 | 38.49 | U2 |
| ATOM | 3523 | C | LYS | 1154 | 4.118 | 22.647 | 22.878 | 1.00 | 25.78 | U2 |
| ATOM | 3524 | O | LYS | 1154 | 5.319 | 22.590 | 22.673 | 1.00 | 25.78 | U2 |

TABLE 1-continued

Structure coordinates of CPP32

| ATOM | 3525 | N   | PRO | 1155 | 3.270  | 21.722 | 22.436 | 1.00 | 22.46 | U2 |
|------|------|-----|-----|------|--------|--------|--------|------|-------|----|
| ATOM | 3526 | CD  | PRO | 1155 | 1.814  | 21.816 | 22.604 | 1.00 | 18.45 | U2 |
| ATOM | 3527 | CA  | PRO | 1155 | 3.628  | 20.518 | 21.695 | 1.00 | 22.46 | U2 |
| ATOM | 3528 | CB  | PRO | 1155 | 2.271  | 19.887 | 21.420 | 1.00 | 18.45 | U2 |
| ATOM | 3529 | CG  | PRO | 1155 | 1.420  | 20.399 | 22.507 | 1.00 | 18.45 | U2 |
| ATOM | 3530 | C   | PRO | 1155 | 4.308  | 20.867 | 20.369 | 1.00 | 22.46 | U2 |
| ATOM | 3531 | O   | PRO | 1155 | 3.824  | 21.707 | 19.630 | 1.00 | 22.46 | U2 |
| ATOM | 3532 | N   | LYS | 1156 | 5.397  | 20.180 | 20.053 | 1.00 | 27.04 | U2 |
| ATOM | 3534 | CA  | LYS | 1156 | 6.141  | 20.390 | 18.829 | 1.00 | 27.04 | U2 |
| ATOM | 3535 | CB  | LYS | 1156 | 7.498  | 21.003 | 19.156 | 1.00 | 37.09 | U2 |
| ATOM | 3536 | CG  | LYS | 1156 | 7.414  | 22.462 | 19.577 | 1.00 | 37.09 | U2 |
| ATOM | 3537 | CD  | LYS | 1156 | 8.667  | 22.904 | 20.302 | 1.00 | 37.09 | U2 |
| ATOM | 3538 | CE  | LYS | 1156 | 8.452  | 22.878 | 21.808 | 1.00 | 37.09 | U2 |
| ATOM | 3539 | NZ  | LYS | 1156 | 7.428  | 23.863 | 22.218 | 1.00 | 37.09 | U2 |
| ATOM | 3543 | C   | LYS | 1156 | 6.308  | 19.007 | 18.257 | 1.00 | 27.04 | U2 |
| ATOM | 3544 | O   | LYS | 1156 | 7.157  | 18.234 | 18.700 | 1.00 | 27.04 | U2 |
| ATOM | 3545 | N   | LEU | 1157 | 5.426  | 18.673 | 17.320 | 1.00 | 48.23 | U2 |
| ATOM | 3547 | CA  | LEU | 1157 | 5.402  | 17.352 | 16.677 | 1.00 | 48.23 | U2 |
| ATOM | 3548 | CB  | LEU | 1157 | 3.940  | 16.924 | 16.421 | 1.00 | 27.40 | U2 |
| ATOM | 3549 | CG  | LEU | 1157 | 2.916  | 16.718 | 17.572 | 1.00 | 27.40 | U2 |
| ATOM | 3550 | CD1 | LEU | 1157 | 3.399  | 17.235 | 18.922 | 1.00 | 27.40 | U2 |
| ATOM | 3551 | CD2 | LEU | 1157 | 1.606  | 17.380 | 17.229 | 1.00 | 27.40 | U2 |
| ATOM | 3552 | C   | LEU | 1157 | 6.227  | 17.300 | 15.386 | 1.00 | 48.23 | U2 |
| ATOM | 3553 | O   | LEU | 1157 | 6.168  | 18.203 | 14.560 | 1.00 | 48.23 | U2 |
| ATOM | 3554 | N   | PHE | 1158 | 7.057  | 16.276 | 15.262 | 1.00 | 38.29 | U2 |
| ATOM | 3556 | CA  | PHE | 1158 | 7.889  | 16.084 | 14.096 | 1.00 | 38.29 | U2 |
| ATOM | 3557 | CB  | PHE | 1158 | 9.367  | 16.276 | 14.442 | 1.00 | 35.26 | U2 |
| ATOM | 3558 | CG  | PHE | 1158 | 9.751  | 17.710 | 14.704 | 1.00 | 35.26 | U2 |
| ATOM | 3559 | CD1 | PHE | 1158 | 9.297  | 18.375 | 15.835 | 1.00 | 35.26 | U2 |
| ATOM | 3560 | CD2 | PHE | 1158 | 10.545 | 18.405 | 13.803 | 1.00 | 35.26 | U2 |
| ATOM | 3561 | CE1 | PHE | 1158 | 9.626  | 19.719 | 16.060 | 1.00 | 35.26 | U2 |
| ATOM | 3562 | CE2 | PHE | 1158 | 10.876 | 19.742 | 14.014 | 1.00 | 35.26 | U2 |
| ATOM | 3563 | CZ  | PHE | 1158 | 10.415 | 20.402 | 15.142 | 1.00 | 35.26 | U2 |
| ATOM | 3564 | C   | PHE | 1158 | 7.656  | 14.662 | 13.628 | 1.00 | 38.29 | U2 |
| ATOM | 3565 | O   | PHE | 1158 | 7.984  | 13.716 | 14.334 | 1.00 | 38.29 | U2 |
| ATOM | 3566 | N   | ILE | 1159 | 7.055  | 14.507 | 12.458 | 1.00 | 27.37 | U2 |
| ATOM | 3568 | CA  | ILE | 1159 | 6.773  | 13.195 | 11.908 | 1.00 | 27.37 | U2 |
| ATOM | 3569 | CB  | ILE | 1159 | 5.345  | 13.179 | 11.368 | 1.00 | 31.54 | U2 |
| ATOM | 3570 | CG2 | ILE | 1159 | 4.995  | 11.827 | 10.808 | 1.00 | 31.54 | U2 |
| ATOM | 3571 | CG1 | ILE | 1159 | 4.396  | 13.493 | 12.527 | 1.00 | 31.54 | U2 |
| ATOM | 3572 | CD1 | ILE | 1159 | 3.086  | 14.112 | 12.129 | 1.00 | 31.54 | U2 |
| ATOM | 3573 | C   | ILE | 1159 | 7.845  | 12.988 | 10.847 | 1.00 | 27.37 | U2 |
| ATOM | 3574 | O   | ILE | 1159 | 8.142  | 13.902 | 10.087 | 1.00 | 27.37 | U2 |
| ATOM | 3575 | N   | ILE | 1160 | 8.468  | 11.819 | 10.810 | 1.00 | 23.79 | U2 |
| ATOM | 3577 | CA  | ILE | 1160 | 9.558  | 11.598 | 9.878  | 1.00 | 23.79 | U2 |
| ATOM | 3578 | CB  | ILE | 1160 | 10.902 | 11.744 | 10.611 | 1.00 | 20.45 | U2 |
| ATOM | 3579 | CG2 | ILE | 1160 | 12.078 | 11.600 | 9.663  | 1.00 | 20.45 | U2 |
| ATOM | 3580 | CG1 | ILE | 1160 | 10.965 | 13.102 | 11.299 | 1.00 | 20.45 | U2 |
| ATOM | 3581 | CD1 | ILE | 1160 | 12.198 | 13.308 | 12.078 | 1.00 | 20.45 | U2 |
| ATOM | 3582 | C   | ILE | 1160 | 9.535  | 10.254 | 9.181  | 1.00 | 23.79 | U2 |
| ATOM | 3583 | O   | ILE | 1160 | 9.671  | 9.198  | 9.820  | 1.00 | 23.79 | U2 |
| ATOM | 3584 | N   | GLN | 1161 | 9.347  | 10.295 | 7.859  | 1.00 | 30.18 | U2 |
| ATOM | 3586 | CA  | GLN | 1161 | 9.337  | 9.091  | 7.029  | 1.00 | 30.18 | U2 |
| ATOM | 3587 | CB  | GLN | 1161 | 8.159  | 9.144  | 6.052  | 1.00 | 26.73 | U2 |
| ATOM | 3588 | CG  | GLN | 1161 | 8.218  | 8.211  | 4.865  | 1.00 | 26.73 | U2 |
| ATOM | 3589 | CD  | GLN | 1161 | 8.295  | 6.746  | 5.229  | 1.00 | 26.73 | U2 |
| ATOM | 3590 | OE1 | GLN | 1161 | 7.467  | 6.227  | 5.957  | 1.00 | 26.73 | U2 |
| ATOM | 3591 | NE2 | GLN | 1161 | 9.270  | 6.062  | 4.669  | 1.00 | 26.73 | U2 |
| ATOM | 3594 | C   | GLN | 1161 | 10.693 | 9.181  | 6.334  | 1.00 | 30.18 | U2 |
| ATOM | 3595 | O   | GLN | 1161 | 11.038 | 10.201 | 5.747  | 1.00 | 30.18 | U2 |
| ATOM | 3596 | N   | ALA | 1162 | 11.514 | 8.169  | 6.548  | 1.00 | 25.67 | U2 |
| ATOM | 3598 | CA  | ALA | 1162 | 12.846 | 8.126  | 5.995  | 1.00 | 25.67 | U2 |
| ATOM | 3599 | CB  | ALA | 1162 | 13.606 | 9.362  | 6.380  | 1.00 | 15.72 | U2 |
| ATOM | 3600 | C   | ALA | 1162 | 13.489 | 6.926  | 6.635  | 1.00 | 25.67 | U2 |
| ATOM | 3601 | O   | ALA | 1162 | 12.963 | 6.356  | 7.593  | 1.00 | 25.67 | U2 |
| ATOM | 3602 | N   | CYS | 1163 | 14.590 | 6.483  | 6.059  | 1.00 | 45.67 | U2 |
| ATOM | 3604 | CA  | CYS | 1163 | 15.302 | 5.342  | 6.602  | 1.00 | 45.67 | U2 |
| ATOM | 3605 | C   | CYS | 1163 | 16.174 | 5.891  | 7.696  | 1.00 | 45.67 | U2 |
| ATOM | 3606 | O   | CYS | 1163 | 16.465 | 7.098  | 7.723  | 1.00 | 45.67 | U2 |
| ATOM | 3607 | CB  | CYS | 1163 | 16.170 | 4.658  | 5.539  | 1.00 | 54.25 | U2 |
| ATOM | 3608 | SG  | CYS | 1163 | 15.284 | 3.524  | 4.523  | 1.00 | 54.25 | U2 |
| ATOM | 3609 | N   | ARG | 1164 | 16.532 | 5.022  | 8.630  | 1.00 | 41.24 | U2 |
| ATOM | 3611 | CA  | ARG | 1164 | 17.384 | 5.400  | 9.738  | 1.00 | 41.24 | U2 |
| ATOM | 3612 | CB  | ARG | 1164 | 16.598 | 5.330  | 11.046 | 1.00 | 30.28 | U2 |
| ATOM | 3613 | CG  | ARG | 1164 | 15.365 | 6.179  | 11.037 | 1.00 | 30.28 | U2 |
| ATOM | 3614 | CD  | ARG | 1164 | 14.650 | 6.079  | 12.340 | 1.00 | 30.28 | U2 |
| ATOM | 3615 | NE  | ARG | 1164 | 15.434 | 6.701  | 13.392 | 1.00 | 30.28 | U2 |

TABLE 1-continued

Structure coordinates of CPP32

| ATOM | 3617 | CZ | ARG | 1164 | 15.236 | 6.486 | 14.685 | 1.00 | 30.28 | U2 |
|------|------|-----|-----|------|--------|--------|--------|------|-------|-----|
| ATOM | 3618 | NH1 | ARG | 1164 | 14.280 | 5.657 | 15.081 | 1.00 | 30.28 | U2 |
| ATOM | 3621 | NH2 | ARG | 1164 | 15.992 | 7.106 | 15.583 | 1.00 | 30.28 | U2 |
| ATOM | 3624 | C | ARG | 1164 | 18.550 | 4.424 | 9.767 | 1.00 | 41.24 | U2 |
| ATOM | 3625 | O | ARG | 1164 | 19.095 | 4.134 | 10.831 | 1.00 | 41.24 | U2 |
| ATOM | 3626 | N | GLY | 1165 | 18.914 | 3.910 | 8.595 | 1.00 | 33.21 | U2 |
| ATOM | 3628 | CA | GLY | 1165 | 20.002 | 2.963 | 8.506 | 1.00 | 33.21 | U2 |
| ATOM | 3629 | C | GLY | 1165 | 19.741 | 1.963 | 7.409 | 1.00 | 33.21 | U2 |
| ATOM | 3630 | O | GLY | 1165 | 18.843 | 2.155 | 6.589 | 1.00 | 33.21 | U2 |
| ATOM | 3631 | N | THR | 1166 | 20.492 | 0.874 | 7.398 | 1.00 | 41.57 | U2 |
| ATOM | 3633 | CA | THR | 1166 | 20.317 | −0.121 | 6.358 | 1.00 | 41.57 | U2 |
| ATOM | 3634 | CB | THR | 1166 | 21.489 | −0.106 | 5.370 | 1.00 | 50.89 | U2 |
| ATOM | 3635 | OG1 | THR | 1166 | 22.729 | −0.148 | 6.089 | 1.00 | 50.89 | U2 |
| ATOM | 3637 | CG2 | THR | 1166 | 21.446 | 1.155 | 4.533 | 1.00 | 50.89 | U2 |
| ATOM | 3638 | C | THR | 1166 | 20.137 | −1.514 | 6.895 | 1.00 | 41.57 | U2 |
| ATOM | 3639 | O | THR | 1166 | 20.519 | −2.488 | 6.249 | 1.00 | 41.57 | U2 |
| ATOM | 3640 | N | GLU | 1167 | 19.607 | −1.613 | 8.105 | 1.00 | 34.38 | U2 |
| ATOM | 3642 | CA | GLU | 1167 | 19.359 | −2.911 | 8.692 | 1.00 | 34.38 | U2 |
| ATOM | 3643 | CB | GLU | 1167 | 19.449 | −2.845 | 10.220 | 1.00 | 89.81 | U2 |
| ATOM | 3644 | CG | GLU | 1167 | 20.873 | −2.903 | 10.771 | 1.00 | 89.81 | U2 |
| ATOM | 3645 | CD | GLU | 1167 | 21.283 | −1.633 | 11.507 | 1.00 | 89.81 | U2 |
| ATOM | 3646 | OE1 | GLU | 1167 | 20.858 | −1.452 | 12.672 | 1.00 | 89.81 | U2 |
| ATOM | 3647 | OE2 | GLU | 1167 | 22.035 | −0.820 | 10.920 | 1.00 | 89.81 | U2 |
| ATOM | 3648 | C | GLU | 1167 | 17.960 | −3.314 | 8.248 | 1.00 | 34.38 | U2 |
| ATOM | 3649 | O | GLU | 1167 | 17.079 | −2.455 | 8.089 | 1.00 | 34.38 | U2 |
| ATOM | 3650 | N | LEU | 1168 | 17.756 | −4.610 | 8.037 | 1.00 | 37.13 | U2 |
| ATOM | 3652 | CA | LEU | 1168 | 16.468 | −5.115 | 7.605 | 1.00 | 37.13 | U2 |
| ATOM | 3653 | CB | LEU | 1168 | 16.636 | −5.900 | 6.307 | 1.00 | 47.86 | U2 |
| ATOM | 3654 | CG | LEU | 1168 | 17.209 | −5.051 | 5.179 | 1.00 | 47.86 | U2 |
| ATOM | 3655 | CD1 | LEU | 1168 | 18.628 | −5.458 | 4.899 | 1.00 | 47.86 | U2 |
| ATOM | 3656 | CD2 | LEU | 1168 | 16.366 | −5.207 | 3.945 | 1.00 | 47.86 | U2 |
| ATOM | 3657 | C | LEU | 1168 | 15.867 | −6.000 | 8.682 | 1.00 | 37.13 | U2 |
| ATOM | 3658 | O | LEU | 1168 | 16.534 | −6.894 | 9.203 | 1.00 | 37.13 | U2 |
| ATOM | 3659 | N | ASP | 1169 | 14.602 | −5.755 | 9.007 | 1.00 | 40.41 | U2 |
| ATOM | 3661 | CA | ASP | 1169 | 13.908 | −6.530 | 10.038 | 1.00 | 40.41 | U2 |
| ATOM | 3662 | CB | ASP | 1169 | 13.019 | −5.577 | 10.871 | 1.00 | 27.64 | U2 |
| ATOM | 3663 | CG | ASP | 1169 | 12.406 | −6.236 | 12.086 | 1.00 | 27.64 | U2 |
| ATOM | 3664 | OD1 | ASP | 1169 | 12.013 | −5.510 | 13.021 | 1.00 | 27.64 | U2 |
| ATOM | 3665 | OD2 | ASP | 1169 | 12.278 | −7.468 | 12.103 | 1.00 | 27.64 | U2 |
| ATOM | 3666 | C | ASP | 1169 | 13.080 | −7.646 | 9.383 | 1.00 | 40.41 | U2 |
| ATOM | 3667 | O | ASP | 1169 | 12.095 | −7.373 | 8.701 | 1.00 | 40.41 | U2 |
| ATOM | 3668 | N | CYS | 1170 | 13.435 | −8.896 | 9.644 | 1.00 | 42.70 | U2 |
| ATOM | 3670 | CA | CYS | 1170 | 12.728 | −10.034 | 9.047 | 1.00 | 42.70 | U2 |
| ATOM | 3671 | CB | CYS | 1170 | 13.719 | −11.174 | 8.801 | 1.00 | 69.79 | U2 |
| ATOM | 3672 | SG | CYS | 1170 | 15.244 | −10.626 | 7.982 | 1.00 | 69.79 | U2 |
| ATOM | 3673 | C | CYS | 1170 | 11.484 | −10.574 | 9.779 | 1.00 | 42.70 | U2 |
| ATOM | 3674 | O | CYS | 1170 | 11.023 | −11.679 | 9.495 | 1.00 | 42.70 | U2 |
| ATOM | 3675 | N | GLY | 1171 | 10.927 | −9.780 | 10.687 | 1.00 | 40.83 | U2 |
| ATOM | 3677 | CA | GLY | 1171 | 9.753 | −10.206 | 11.429 | 1.00 | 40.83 | U2 |
| ATOM | 3678 | C | GLY | 1171 | 9.960 | −11.498 | 12.180 | 1.00 | 40.83 | U2 |
| ATOM | 3679 | O | GLY | 1171 | 11.083 | −11.957 | 12.285 | 1.00 | 40.83 | U2 |
| ATOM | 3680 | N | ILE | 1172 | 8.889 | −12.077 | 12.707 | 1.00 | 58.04 | U2 |
| ATOM | 3682 | CA | ILE | 1172 | 8.955 | −13.339 | 13.459 | 1.00 | 58.04 | U2 |
| ATOM | 3683 | CB | ILE | 1172 | 9.661 | −13.122 | 14.847 | 1.00 | 52.65 | U2 |
| ATOM | 3684 | CG2 | ILE | 1172 | 8.979 | −12.014 | 15.628 | 1.00 | 52.65 | U2 |
| ATOM | 3685 | CG1 | ILE | 1172 | 9.666 | −14.409 | 15.684 | 1.00 | 52.65 | U2 |
| ATOM | 3686 | CD1 | ILE | 1172 | 10.512 | −15.542 | 15.103 | 1.00 | 52.65 | U2 |
| ATOM | 3687 | C | ILE | 1172 | 7.519 | −13.867 | 13.667 | 1.00 | 58.04 | U2 |
| ATOM | 3688 | O | ILE | 1172 | 6.561 | −13.105 | 13.534 | 1.00 | 58.04 | U2 |
| ATOM | 3689 | N | GLU | 1173 | 7.380 | −15.157 | 13.973 | 1.00 | 73.12 | U2 |
| ATOM | 3691 | CA | GLU | 1173 | 6.083 | −15.801 | 14.217 | 1.00 | 73.12 | U2 |
| ATOM | 3692 | CB | GLU | 1173 | 5.302 | −15.065 | 15.318 | 1.00 | 77.49 | U2 |
| ATOM | 3693 | CG | GLU | 1173 | 3.903 | −15.605 | 15.620 | 1.00 | 77.49 | U2 |
| ATOM | 3694 | CD | GLU | 1173 | 2.856 | −14.490 | 15.703 | 1.00 | 77.49 | U2 |
| ATOM | 3695 | OE1 | GLU | 1173 | 2.192 | −14.226 | 14.674 | 1.00 | 77.49 | U2 |
| ATOM | 3696 | OE2 | GLU | 1173 | 2.701 | −13.869 | 16.784 | 1.00 | 77.49 | U2 |
| ATOM | 3697 | C | GLU | 1173 | 5.271 | −15.905 | 12.932 | 1.00 | 73.12 | U2 |
| ATOM | 3698 | O | GLU | 1173 | 5.567 | −16.832 | 12.150 | 1.00 | 73.12 | U2 |
| ATOM | 3699 | OT | GLU | 1173 | 4.381 | −15.058 | 12.695 | 1.00 | 77.49 | U2 |
| ATOM | 3700 | CB | LYS | 1186 | 13.671 | 26.957 | 35.046 | 1.00 | 59.61 | U2 |
| ATOM | 3701 | CG | LYS | 1186 | 14.580 | 28.142 | 34.659 | 1.00 | 59.61 | U2 |
| ATOM | 3702 | CD | LYS | 1186 | 15.820 | 28.287 | 35.536 | 1.00 | 59.61 | U2 |
| ATOM | 3703 | CE | LYS | 1186 | 16.593 | 26.985 | 35.645 | 1.00 | 59.61 | U2 |
| ATOM | 3704 | NZ | LYS | 1186 | 17.141 | 26.579 | 34.338 | 1.00 | 59.61 | U2 |
| ATOM | 3708 | C | LYS | 1186 | 11.836 | 25.594 | 34.017 | 1.00 | 42.49 | U2 |
| ATOM | 3709 | O | LYS | 1186 | 11.346 | 24.867 | 34.876 | 1.00 | 42.49 | U2 |
| ATOM | 3712 | N | LYS | 1186 | 11.338 | 27.800 | 35.170 | 1.00 | 42.49 | U2 |

TABLE 1-continued

Structure coordinates of CPP32

| ATOM | 3714 | CA | LYS | 1186 | 12.297 | 27.003 | 34.362 | 1.00 | 42.49 | U2 |
| ATOM | 3715 | N | ILE | 1187 | 11.929 | 25.256 | 32.730 | 1.00 | 33.95 | U2 |
| ATOM | 3717 | CA | ILE | 1187 | 11.588 | 23.920 | 32.200 | 1.00 | 33.95 | U2 |
| ATOM | 3718 | CB | ILE | 1187 | 10.263 | 23.890 | 31.409 | 1.00 | 37.31 | U2 |
| ATOM | 3719 | CG2 | ILE | 1187 | 9.078 | 23.925 | 32.346 | 1.00 | 37.31 | U2 |
| ATOM | 3720 | CG1 | ILE | 1187 | 10.210 | 25.021 | 30.390 | 1.00 | 37.31 | U2 |
| ATOM | 3721 | CD1 | ILE | 1187 | 8.968 | 24.970 | 29.520 | 1.00 | 37.31 | U2 |
| ATOM | 3722 | C | ILE | 1187 | 12.710 | 23.548 | 31.236 | 1.00 | 33.95 | U2 |
| ATOM | 3723 | O | ILE | 1187 | 13.432 | 24.426 | 30.747 | 1.00 | 33.95 | U2 |
| ATOM | 3724 | N | PRO | 1188 | 12.896 | 22.253 | 30.963 | 1.00 | 42.08 | U2 |
| ATOM | 3725 | CD | PRO | 1188 | 12.119 | 21.099 | 31.440 | 1.00 | 28.58 | U2 |
| ATOM | 3726 | CA | PRO | 1188 | 13.970 | 21.840 | 30.039 | 1.00 | 42.08 | U2 |
| ATOM | 3727 | CB | PRO | 1188 | 13.853 | 20.316 | 30.040 | 1.00 | 28.58 | U2 |
| ATOM | 3728 | CG | PRO | 1188 | 13.134 | 20.007 | 31.368 | 1.00 | 28.58 | U2 |
| ATOM | 3729 | C | PRO | 1188 | 13.759 | 22.408 | 28.616 | 1.00 | 42.08 | U2 |
| ATOM | 3730 | O | PRO | 1188 | 12.626 | 22.433 | 28.112 | 1.00 | 42.08 | U2 |
| ATOM | 3731 | N | VAL | 1189 | 14.838 | 22.840 | 27.961 | 1.00 | 41.66 | U2 |
| ATOM | 3733 | CA | VAL | 1189 | 14.719 | 23.391 | 26.614 | 1.00 | 41.66 | U2 |
| ATOM | 3734 | CB | VAL | 1189 | 16.012 | 24.015 | 26.087 | 1.00 | 20.98 | U2 |
| ATOM | 3735 | CG1 | VAL | 1189 | 16.356 | 25.263 | 26.868 | 1.00 | 20.98 | U2 |
| ATOM | 3736 | CG2 | VAL | 1189 | 17.128 | 23.020 | 26.144 | 1.00 | 20.98 | U2 |
| ATOM | 3737 | C | VAL | 1189 | 14.298 | 22.359 | 25.602 | 1.00 | 41.66 | U2 |
| ATOM | 3738 | O | VAL | 1189 | 13.643 | 22.713 | 24.625 | 1.00 | 41.66 | U2 |
| ATOM | 3739 | N | ASP | 1190 | 14.699 | 21.102 | 25.800 | 1.00 | 27.66 | U2 |
| ATOM | 3741 | CA | ASP | 1190 | 14.347 | 20.028 | 24.871 | 1.00 | 27.66 | U2 |
| ATOM | 3742 | CB | ASP | 1190 | 15.479 | 18.984 | 24.766 | 1.00 | 43.71 | U2 |
| ATOM | 3743 | CG | ASP | 1190 | 16.365 | 19.189 | 23.515 | 1.00 | 43.71 | U2 |
| ATOM | 3744 | OD1 | ASP | 1190 | 17.591 | 19.383 | 23.640 | 1.00 | 43.71 | U2 |
| ATOM | 3745 | OD2 | ASP | 1190 | 15.842 | 19.163 | 22.386 | 1.00 | 43.71 | U2 |
| ATOM | 3746 | C | ASP | 1190 | 13.023 | 19.371 | 25.241 | 1.00 | 27.66 | U2 |
| ATOM | 3747 | O | ASP | 1190 | 12.731 | 18.278 | 24.805 | 1.00 | 27.66 | U2 |
| ATOM | 3748 | N | ALA | 1191 | 12.165 | 20.098 | 25.937 | 1.00 | 34.17 | U2 |
| ATOM | 3750 | CA | ALA | 1191 | 10.886 | 19.557 | 26.386 | 1.00 | 34.17 | U2 |
| ATOM | 3751 | CB | ALA | 1191 | 10.573 | 20.104 | 27.785 | 1.00 | 33.71 | U2 |
| ATOM | 3752 | C | ALA | 1191 | 9.698 | 19.822 | 25.481 | 1.00 | 34.17 | U2 |
| ATOM | 3753 | O | ALA | 1191 | 9.717 | 20.742 | 24.686 | 1.00 | 34.17 | U2 |
| ATOM | 3754 | N | ASP | 1192 | 8.610 | 19.103 | 25.718 | 1.00 | 29.37 | U2 |
| ATOM | 3756 | CA | ASP | 1192 | 7.397 | 19.264 | 24.938 | 1.00 | 29.37 | U2 |
| ATOM | 3757 | CB | ASP | 1192 | 6.805 | 20.650 | 25.166 | 1.00 | 25.93 | U2 |
| ATOM | 3758 | CG | ASP | 1192 | 6.529 | 20.938 | 26.622 | 1.00 | 25.93 | U2 |
| ATOM | 3759 | OD1 | ASP | 1192 | 7.049 | 21.949 | 27.147 | 1.00 | 25.93 | U2 |
| ATOM | 3760 | OD2 | ASP | 1192 | 5.766 | 20.179 | 27.247 | 1.00 | 25.93 | U2 |
| ATOM | 3761 | C | ASP | 1192 | 7.689 | 19.053 | 23.452 | 1.00 | 29.37 | U2 |
| ATOM | 3762 | O | ASP | 1192 | 7.149 | 19.750 | 22.598 | 1.00 | 29.37 | U2 |
| ATOM | 3763 | N | PHE | 1193 | 8.581 | 18.111 | 23.174 | 1.00 | 22.62 | U2 |
| ATOM | 3765 | CA | PHE | 1193 | 8.982 | 17.750 | 21.826 | 1.00 | 22.62 | U2 |
| ATOM | 3766 | CB | PHE | 1193 | 10.506 | 17.717 | 21.718 | 1.00 | 30.74 | U2 |
| ATOM | 3767 | CG | PHE | 1193 | 11.107 | 18.914 | 21.032 | 1.00 | 30.74 | U2 |
| ATOM | 3768 | CD1 | PHE | 1193 | 11.355 | 18.894 | 19.661 | 1.00 | 30.74 | U2 |
| ATOM | 3769 | CD2 | PHE | 1193 | 11.469 | 20.042 | 21.759 | 1.00 | 30.74 | U2 |
| ATOM | 3770 | CE1 | PHE | 1193 | 11.957 | 19.976 | 19.039 | 1.00 | 30.74 | U2 |
| ATOM | 3771 | CE2 | PHE | 1193 | 12.068 | 21.124 | 21.146 | 1.00 | 30.74 | U2 |
| ATOM | 3772 | CZ | PHE | 1193 | 12.315 | 21.094 | 19.788 | 1.00 | 30.74 | U2 |
| ATOM | 3773 | C | PHE | 1193 | 8.498 | 16.333 | 21.600 | 1.00 | 22.62 | U2 |
| ATOM | 3774 | O | PHE | 1193 | 8.537 | 15.537 | 22.531 | 1.00 | 22.62 | U2 |
| ATOM | 3775 | N | LEU | 1194 | 8.050 | 16.008 | 20.388 | 1.00 | 22.72 | U2 |
| ATOM | 3777 | CA | LEU | 1194 | 7.628 | 14.643 | 20.071 | 1.00 | 22.72 | U2 |
| ATOM | 3778 | CB | LEU | 1194 | 6.121 | 14.522 | 20.011 | 1.00 | 33.15 | U2 |
| ATOM | 3779 | CG | LEU | 1194 | 5.703 | 13.060 | 19.916 | 1.00 | 33.15 | U2 |
| ATOM | 3780 | CD1 | LEU | 1194 | 4.488 | 12.828 | 20.777 | 1.00 | 33.15 | U2 |
| ATOM | 3781 | CD2 | LEU | 1194 | 5.415 | 12.670 | 18.498 | 1.00 | 33.15 | U2 |
| ATOM | 3782 | C | LEU | 1194 | 8.199 | 14.307 | 18.720 | 1.00 | 22.72 | U2 |
| ATOM | 3783 | O | LEU | 1194 | 8.232 | 15.167 | 17.851 | 1.00 | 22.72 | U2 |
| ATOM | 3784 | N | TYR | 1195 | 8.676 | 13.082 | 18.541 | 1.00 | 25.02 | U2 |
| ATOM | 3786 | CA | TYR | 1195 | 9.261 | 12.664 | 17.266 | 1.00 | 25.02 | U2 |
| ATOM | 3787 | CB | TYR | 1195 | 10.778 | 12.467 | 17.371 | 1.00 | 42.66 | U2 |
| ATOM | 3788 | CG | TYR | 1195 | 11.565 | 13.667 | 17.840 | 1.00 | 42.66 | U2 |
| ATOM | 3789 | CD1 | TYR | 1195 | 11.808 | 13.880 | 19.189 | 1.00 | 42.66 | U2 |
| ATOM | 3790 | CE1 | TYR | 1195 | 12.571 | 14.958 | 19.621 | 1.00 | 42.66 | U2 |
| ATOM | 3791 | CD2 | TYR | 1195 | 12.107 | 14.565 | 16.930 | 1.00 | 42.66 | U2 |
| ATOM | 3792 | CE2 | TYR | 1195 | 12.873 | 15.643 | 17.352 | 1.00 | 42.66 | U2 |
| ATOM | 3793 | CZ | TYR | 1195 | 13.096 | 15.829 | 18.697 | 1.00 | 42.66 | U2 |
| ATOM | 3794 | OH | TYR | 1195 | 13.831 | 16.896 | 19.119 | 1.00 | 42.66 | U2 |
| ATOM | 3796 | C | TYR | 1195 | 8.685 | 11.326 | 16.909 | 1.00 | 25.02 | U2 |
| ATOM | 3797 | O | TYR | 1195 | 9.131 | 10.326 | 17.455 | 1.00 | 25.02 | U2 |
| ATOM | 3798 | N | ALA | 1196 | 7.701 | 11.302 | 16.011 | 1.00 | 29.14 | U2 |
| ATOM | 3800 | CA | ALA | 1196 | 7.072 | 10.062 | 15.561 | 1.00 | 29.14 | U2 |

TABLE 1-continued

Structure coordinates of CPP32

| ATOM | 3801 | CB | ALA | 1196 | 5.656 | 10.335 | 15.130 | 1.00 | 4.42 | U2 |
|------|------|----|-----|------|-------|--------|--------|------|------|----|
| ATOM | 3802 | C | ALA | 1196 | 7.897 | 9.609 | 14.370 | 1.00 | 29.14 | U2 |
| ATOM | 3803 | O | ALA | 1196 | 7.886 | 10.276 | 13.337 | 1.00 | 29.14 | U2 |
| ATOM | 3804 | N | TYR | 1197 | 8.692 | 8.555 | 14.532 | 1.00 | 30.96 | U2 |
| ATOM | 3806 | CA | TYR | 1197 | 9.522 | 8.058 | 13.443 | 1.00 | 30.96 | U2 |
| ATOM | 3807 | CB | TYR | 1197 | 10.879 | 7.581 | 13.948 | 1.00 | 41.04 | U2 |
| ATOM | 3808 | CG | TYR | 1197 | 11.817 | 8.643 | 14.463 | 1.00 | 41.04 | U2 |
| ATOM | 3809 | CD1 | TYR | 1197 | 12.047 | 8.776 | 15.830 | 1.00 | 41.04 | U2 |
| ATOM | 3810 | CE1 | TYR | 1197 | 12.978 | 9.701 | 16.330 | 1.00 | 41.04 | U2 |
| ATOM | 3811 | CD2 | TYR | 1197 | 12.533 | 9.467 | 13.593 | 1.00 | 41.04 | U2 |
| ATOM | 3812 | CE2 | TYR | 1197 | 13.464 | 10.400 | 14.074 | 1.00 | 41.04 | U2 |
| ATOM | 3813 | CZ | TYR | 1197 | 13.684 | 10.511 | 15.456 | 1.00 | 41.04 | U2 |
| ATOM | 3814 | OH | TYR | 1197 | 14.598 | 11.418 | 15.978 | 1.00 | 41.04 | U2 |
| ATOM | 3816 | C | TYR | 1197 | 8.835 | 6.896 | 12.745 | 1.00 | 30.96 | U2 |
| ATOM | 3817 | O | TYR | 1197 | 8.105 | 6.131 | 13.373 | 1.00 | 30.96 | U2 |
| ATOM | 3818 | N | SER | 1198 | 9.109 | 6.722 | 11.458 | 1.00 | 30.52 | U2 |
| ATOM | 3820 | CA | SER | 1198 | 8.491 | 5.640 | 10.706 | 1.00 | 30.52 | U2 |
| ATOM | 3821 | CB | SER | 1198 | 8.621 | 5.903 | 9.219 | 1.00 | 58.42 | U2 |
| ATOM | 3822 | OG | SER | 1198 | 9.999 | 5.931 | 8.862 | 1.00 | 58.42 | U2 |
| ATOM | 3824 | C | SER | 1198 | 9.152 | 4.311 | 10.987 | 1.00 | 30.52 | U2 |
| ATOM | 3825 | O | SER | 1198 | 8.601 | 3.280 | 10.623 | 1.00 | 30.52 | U2 |
| ATOM | 3826 | N | THR | 1199 | 10.341 | 4.327 | 11.590 | 1.00 | 33.49 | U2 |
| ATOM | 3828 | CA | THR | 1199 | 11.068 | 3.075 | 11.875 | 1.00 | 33.49 | U2 |
| ATOM | 3829 | CB | THR | 1199 | 12.107 | 2.755 | 10.816 | 1.00 | 40.29 | U2 |
| ATOM | 3830 | OG1 | THR | 1199 | 11.939 | 3.625 | 9.696 | 1.00 | 40.29 | U2 |
| ATOM | 3832 | CG2 | THR | 1199 | 12.032 | 1.306 | 10.418 | 1.00 | 40.29 | U2 |
| ATOM | 3833 | C | THR | 1199 | 11.932 | 3.134 | 13.106 | 1.00 | 33.49 | U2 |
| ATOM | 3834 | O | THR | 1199 | 12.314 | 4.215 | 13.548 | 1.00 | 33.49 | U2 |
| ATOM | 3835 | N | ALA | 1200 | 12.355 | 1.947 | 13.533 | 1.00 | 30.57 | U2 |
| ATOM | 3837 | CA | ALA | 1200 | 13.241 | 1.768 | 14.668 | 1.00 | 30.57 | U2 |
| ATOM | 3838 | CB | ALA | 1200 | 13.397 | 0.296 | 14.986 | 1.00 | 23.52 | U2 |
| ATOM | 3839 | C | ALA | 1200 | 14.575 | 2.343 | 14.262 | 1.00 | 30.57 | U2 |
| ATOM | 3840 | O | ALA | 1200 | 14.896 | 2.424 | 13.075 | 1.00 | 30.57 | U2 |
| ATOM | 3841 | N | PRO | 1201 | 15.394 | 2.728 | 15.241 | 1.00 | 39.74 | U2 |
| ATOM | 3842 | CD | PRO | 1201 | 15.184 | 2.851 | 16.696 | 1.00 | 27.47 | U2 |
| ATOM | 3843 | CA | PRO | 1201 | 16.683 | 3.293 | 14.839 | 1.00 | 39.74 | U2 |
| ATOM | 3844 | CB | PRO | 1201 | 17.296 | 3.707 | 16.179 | 1.00 | 27.47 | U2 |
| ATOM | 3845 | CG | PRO | 1201 | 16.070 | 4.015 | 17.031 | 1.00 | 27.47 | U2 |
| ATOM | 3846 | C | PRO | 1201 | 17.531 | 2.281 | 14.091 | 1.00 | 39.74 | U2 |
| ATOM | 3847 | O | PRO | 1201 | 17.391 | 1.081 | 14.314 | 1.00 | 39.74 | U2 |
| ATOM | 3848 | N | GLY | 1202 | 18.306 | 2.757 | 13.121 | 1.00 | 36.50 | U2 |
| ATOM | 3850 | CA | GLY | 1202 | 19.187 | 1.884 | 12.363 | 1.00 | 36.50 | U2 |
| ATOM | 3851 | C | GLY | 1202 | 18.548 | 1.036 | 11.277 | 1.00 | 36.50 | U2 |
| ATOM | 3852 | O | GLY | 1202 | 19.243 | 0.256 | 10.592 | 1.00 | 36.50 | U2 |
| ATOM | 3853 | N | TYR | 1203 | 17.247 | 1.213 | 11.058 | 1.00 | 40.76 | U2 |
| ATOM | 3855 | CA | TYR | 1203 | 16.549 | 0.399 | 10.065 | 1.00 | 40.76 | U2 |
| ATOM | 3856 | CB | TYR | 1203 | 15.406 | −0.339 | 10.745 | 1.00 | 24.74 | U2 |
| ATOM | 3857 | CG | TYR | 1203 | 15.808 | −1.527 | 11.585 | 1.00 | 24.74 | U2 |
| ATOM | 3858 | CD1 | TYR | 1203 | 16.205 | −1.376 | 12.913 | 1.00 | 24.74 | U2 |
| ATOM | 3859 | CE1 | TYR | 1203 | 16.548 | −2.474 | 13.678 | 1.00 | 24.74 | U2 |
| ATOM | 3860 | CD2 | TYR | 1203 | 15.769 | −2.804 | 11.053 | 1.00 | 24.74 | U2 |
| ATOM | 3861 | CE2 | TYR | 1203 | 16.116 | −3.904 | 11.807 | 1.00 | 24.74 | U2 |
| ATOM | 3862 | CZ | TYR | 1203 | 16.505 | −3.742 | 13.117 | 1.00 | 24.74 | U2 |
| ATOM | 3863 | OH | TYR | 1203 | 16.844 | −4.866 | 13.849 | 1.00 | 24.74 | U2 |
| ATOM | 3865 | C | TYR | 1203 | 15.993 | 1.138 | 8.841 | 1.00 | 40.76 | U2 |
| ATOM | 3866 | O | TYR | 1203 | 15.966 | 2.377 | 8.793 | 1.00 | 40.76 | U2 |
| ATOM | 3867 | N | TYR | 1204 | 15.566 | 0.344 | 7.858 | 1.00 | 37.86 | U2 |
| ATOM | 3869 | CA | TYR | 1204 | 14.946 | 0.814 | 6.621 | 1.00 | 37.86 | U2 |
| ATOM | 3870 | CB | TYR | 1204 | 14.844 | −0.350 | 5.634 | 1.00 | 61.49 | U2 |
| ATOM | 3871 | CG | TYR | 1204 | 16.020 | −0.563 | 4.729 | 1.00 | 61.49 | U2 |
| ATOM | 3872 | CD1 | TYR | 1204 | 16.238 | −1.802 | 4.140 | 1.00 | 61.49 | U2 |
| ATOM | 3873 | CE1 | TYR | 1204 | 17.305 | −2.020 | 3.264 | 1.00 | 61.49 | U2 |
| ATOM | 3874 | CD2 | TYR | 1204 | 16.896 | 0.469 | 4.430 | 1.00 | 61.49 | U2 |
| ATOM | 3875 | CE2 | TYR | 1204 | 17.969 | 0.266 | 3.554 | 1.00 | 61.49 | U2 |
| ATOM | 3876 | CZ | TYR | 1204 | 18.169 | −0.985 | 2.975 | 1.00 | 61.49 | U2 |
| ATOM | 3877 | OH | TYR | 1204 | 19.237 | −1.202 | 2.123 | 1.00 | 61.49 | U2 |
| ATOM | 3879 | C | TYR | 1204 | 13.511 | 1.243 | 6.915 | 1.00 | 37.86 | U2 |
| ATOM | 3880 | O | TYR | 1204 | 12.851 | 0.665 | 7.775 | 1.00 | 37.86 | U2 |
| ATOM | 3881 | N | SER | 1205 | 13.001 | 2.168 | 6.122 | 1.00 | 28.55 | U2 |
| ATOM | 3883 | CA | SER | 1205 | 11.634 | 2.631 | 6.259 | 1.00 | 28.55 | U2 |
| ATOM | 3884 | CB | SER | 1205 | 11.633 | 4.137 | 6.488 | 1.00 | 50.82 | U2 |
| ATOM | 3885 | OG | SER | 1205 | 10.318 | 4.641 | 6.692 | 1.00 | 50.82 | U2 |
| ATOM | 3887 | C | SER | 1205 | 11.088 | 2.329 | 4.869 | 1.00 | 28.55 | U2 |
| ATOM | 3888 | O | SER | 1205 | 11.662 | 2.795 | 3.886 | 1.00 | 28.55 | U2 |
| ATOM | 3889 | N | TRP | 1206 | 10.015 | 1.542 | 4.770 | 1.00 | 42.77 | U2 |
| ATOM | 3891 | CA | TRP | 1206 | 9.447 | 1.141 | 3.478 | 1.00 | 42.77 | U2 |
| ATOM | 3892 | CB | TRP | 1206 | 8.864 | −0.256 | 3.578 | 1.00 | 37.37 | U2 |

TABLE 1-continued

Structure coordinates of CPP32

| | | | | | | | | | |
|---|---|---|---|---|---|---|---|---|---|
| ATOM | 3893 | CG | TRP | 1206 | 9.855 | −1.270 | 3.916 | 1.00 | 37.37 U2 |
| ATOM | 3894 | CD2 | TRP | 1206 | 10.834 | −1.835 | 3.043 | 1.00 | 37.37 U2 |
| ATOM | 3895 | CE2 | TRP | 1206 | 11.562 | −2.785 | 3.793 | 1.00 | 37.37 U2 |
| ATOM | 3896 | CE3 | TRP | 1206 | 11.173 | −1.634 | 1.700 | 1.00 | 37.37 U2 |
| ATOM | 3897 | CD1 | TRP | 1206 | 10.015 | −1.870 | 5.116 | 1.00 | 37.37 U2 |
| ATOM | 3898 | NE1 | TRP | 1206 | 11.036 | −2.787 | 5.058 | 1.00 | 37.37 U2 |
| ATOM | 3900 | CZ2 | TRP | 1206 | 12.613 | −3.537 | 3.246 | 1.00 | 37.37 U2 |
| ATOM | 3901 | CZ3 | TRP | 1206 | 12.210 | −2.371 | 1.156 | 1.00 | 37.37 U2 |
| ATOM | 3902 | CH2 | TRP | 1206 | 12.923 | −3.316 | 1.932 | 1.00 | 37.37 U2 |
| ATOM | 3903 | C | TRP | 1206 | 8.385 | 2.044 | 2.896 | 1.00 | 42.77 U2 |
| ATOM | 3904 | O | TRP | 1206 | 7.544 | 2.589 | 3.618 | 1.00 | 42.77 U2 |
| ATOM | 3905 | N | ARG | 1207 | 8.370 | 2.135 | 1.574 | 1.00 | 42.97 U2 |
| ATOM | 3907 | CA | ARG | 1207 | 7.390 | 2.963 | 0.885 | 1.00 | 42.97 U2 |
| ATOM | 3908 | CB | ARG | 1207 | 8.023 | 4.260 | 0.411 | 1.00 | 44.64 U2 |
| ATOM | 3909 | CG | ARG | 1207 | 7.057 | 5.216 | −0.243 | 1.00 | 44.64 U2 |
| ATOM | 3910 | CD | ARG | 1207 | 7.829 | 6.268 | −0.989 | 1.00 | 44.64 U2 |
| ATOM | 3911 | NE | ARG | 1207 | 8.571 | 5.642 | −2.079 | 1.00 | 44.64 U2 |
| ATOM | 3913 | CZ | ARG | 1207 | 9.833 | 5.911 | −2.378 | 1.00 | 44.64 U2 |
| ATOM | 3914 | NH1 | ARG | 1207 | 10.499 | 6.812 | −1.674 | 1.00 | 44.64 U2 |
| ATOM | 3917 | NH2 | ARG | 1207 | 10.444 | 5.237 | −3.343 | 1.00 | 44.64 U2 |
| ATOM | 3920 | C | ARG | 1207 | 6.883 | 2.169 | −0.308 | 1.00 | 42.97 U2 |
| ATOM | 3921 | O | ARG | 1207 | 7.587 | 1.294 | −0.826 | 1.00 | 42.97 U2 |
| ATOM | 3922 | N | ASN | 1208 | 5.622 | 2.395 | −0.657 | 1.00 | 45.21 U2 |
| ATOM | 3924 | CA | ASN | 1208 | 5.000 | 1.720 | −1.787 | 1.00 | 45.21 U2 |
| ATOM | 3925 | CB | ASN | 1208 | 3.634 | 1.154 | −1.388 | 1.00 | 49.00 U2 |
| ATOM | 3926 | CG | ASN | 1208 | 2.927 | 0.477 | −2.539 | 1.00 | 49.00 U2 |
| ATOM | 3927 | OD1 | ASN | 1208 | 2.441 | 1.130 | −3.454 | 1.00 | 49.00 U2 |
| ATOM | 3928 | ND2 | ASN | 1208 | 2.853 | −0.835 | −2.492 | 1.00 | 49.00 U2 |
| ATOM | 3931 | C | ASN | 1208 | 4.838 | 2.772 | −2.874 | 1.00 | 45.21 U2 |
| ATOM | 3932 | O | ASN | 1208 | 4.406 | 3.913 | −2.609 | 1.00 | 45.21 U2 |
| ATOM | 3933 | N | SER | 1209 | 5.162 | 2.376 | −4.099 | 1.00 | 54.63 U2 |
| ATOM | 3935 | CA | SER | 1209 | 5.097 | 3.266 | −5.254 | 1.00 | 54.63 U2 |
| ATOM | 3936 | CB | SER | 1209 | 5.663 | 2.547 | −6.463 | 1.00 | 52.69 U2 |
| ATOM | 3937 | OG | SER | 1209 | 6.775 | 1.760 | −6.076 | 1.00 | 52.69 U2 |
| ATOM | 3939 | C | SER | 1209 | 3.735 | 3.866 | −5.596 | 1.00 | 54.63 U2 |
| ATOM | 3940 | O | SER | 1209 | 3.664 | 5.004 | −6.058 | 1.00 | 54.63 U2 |
| ATOM | 3941 | N | LYS | 1210 | 2.658 | 3.112 | −5.410 | 1.00 | 49.10 U2 |
| ATOM | 3943 | CA | LYS | 1210 | 1.354 | 3.664 | −5.724 | 1.00 | 49.10 U2 |
| ATOM | 3944 | CB | LYS | 1210 | 0.624 | 2.816 | −6.760 | 1.00 | 96.79 U2 |
| ATOM | 3945 | CG | LYS | 1210 | 0.933 | 3.285 | −8.180 | 1.00 | 96.79 U2 |
| ATOM | 3946 | CD | LYS | 1210 | 0.593 | 4.776 | −8.344 | 1.00 | 96.79 U2 |
| ATOM | 3947 | CE | LYS | 1210 | 1.588 | 5.512 | −9.243 | 1.00 | 96.79 U2 |
| ATOM | 3948 | NZ | LYS | 1210 | 2.939 | 5.690 | −8.621 | 1.00 | 96.79 U2 |
| ATOM | 3952 | C | LYS | 1210 | 0.466 | 3.971 | −4.546 | 1.00 | 49.10 U2 |
| ATOM | 3953 | O | LYS | 1210 | −0.520 | 4.694 | −4.677 | 1.00 | 49.10 U2 |
| ATOM | 3954 | N | ASP | 1211 | 0.822 | 3.446 | −3.386 | 1.00 | 60.78 U2 |
| ATOM | 3956 | CA | ASP | 1211 | 0.036 | 3.702 | −2.190 | 1.00 | 60.78 U2 |
| ATOM | 3957 | CB | ASP | 1211 | −0.122 | 2.423 | −1.362 | 1.00 | 60.02 U2 |
| ATOM | 3958 | CG | ASP | 1211 | −0.867 | 1.333 | −2.105 | 1.00 | 60.02 U2 |
| ATOM | 3959 | OD1 | ASP | 1211 | −2.119 | 1.388 | −2.166 | 1.00 | 60.02 U2 |
| ATOM | 3960 | OD2 | ASP | 1211 | −0.194 | 0.417 | −2.622 | 1.00 | 60.02 U2 |
| ATOM | 3961 | C | ASP | 1211 | 0.674 | 4.793 | −1.332 | 1.00 | 60.78 U2 |
| ATOM | 3962 | O | ASP | 1211 | −0.029 | 5.629 | −0.743 | 1.00 | 60.78 U2 |
| ATOM | 3963 | N | GLY | 1212 | 2.003 | 4.832 | −1.332 | 1.00 | 38.30 U2 |
| ATOM | 3965 | CA | GLY | 1212 | 2.709 | 5.791 | −0.511 | 1.00 | 38.30 U2 |
| ATOM | 3966 | C | GLY | 1212 | 3.327 | 4.973 | 0.605 | 1.00 | 38.30 U2 |
| ATOM | 3967 | O | GLY | 1212 | 3.275 | 3.728 | 0.554 | 1.00 | 38.30 U2 |
| ATOM | 3968 | N | SER | 1213 | 3.887 | 5.640 | 1.618 | 1.00 | 34.91 U2 |
| ATOM | 3970 | CA | SER | 1213 | 4.547 | 4.940 | 2.732 | 1.00 | 34.91 U2 |
| ATOM | 3971 | CB | SER | 1213 | 5.486 | 5.880 | 3.493 | 1.00 | 43.97 U2 |
| ATOM | 3972 | OG | SER | 1213 | 4.790 | 7.001 | 4.022 | 1.00 | 43.97 U2 |
| ATOM | 3974 | C | SER | 1213 | 3.600 | 4.276 | 3.716 | 1.00 | 34.91 U2 |
| ATOM | 3975 | O | SER | 1213 | 2.521 | 4.801 | 4.002 | 1.00 | 34.91 U2 |
| ATOM | 3976 | N | TRP | 1214 | 4.028 | 3.139 | 4.259 | 1.00 | 34.17 U2 |
| ATOM | 3978 | CA | TRP | 1214 | 3.248 | 2.385 | 5.244 | 1.00 | 34.17 U2 |
| ATOM | 3979 | CB | TRP | 1214 | 4.086 | 1.220 | 5.765 | 1.00 | 33.18 U2 |
| ATOM | 3980 | CG | TRP | 1214 | 4.559 | 0.301 | 4.709 | 1.00 | 33.18 U2 |
| ATOM | 3981 | CD2 | TRP | 1214 | 5.388 | −0.854 | 4.886 | 1.00 | 33.18 U2 |
| ATOM | 3982 | CE2 | TRP | 1214 | 5.549 | −1.451 | 3.614 | 1.00 | 33.18 U2 |
| ATOM | 3983 | CE3 | TRP | 1214 | 6.004 | −1.450 | 5.996 | 1.00 | 33.18 U2 |
| ATOM | 3984 | CD1 | TRP | 1214 | 4.264 | 0.361 | 3.378 | 1.00 | 33.18 U2 |
| ATOM | 3985 | NE1 | TRP | 1214 | 4.851 | −0.690 | 2.716 | 1.00 | 33.18 U2 |
| ATOM | 3987 | CZ2 | TRP | 1214 | 6.303 | −2.619 | 3.420 | 1.00 | 33.18 U2 |
| ATOM | 3988 | CZ3 | TRP | 1214 | 6.756 | −2.623 | 5.802 | 1.00 | 33.18 U2 |
| ATOM | 3989 | CH2 | TRP | 1214 | 6.897 | −3.189 | 4.527 | 1.00 | 33.18 U2 |
| ATOM | 3990 | C | TRP | 1214 | 2.885 | 3.289 | 6.438 | 1.00 | 34.17 U2 |
| ATOM | 3991 | O | TRP | 1214 | 1.714 | 3.416 | 6.825 | 1.00 | 34.17 U2 |

TABLE 1-continued

Structure coordinates of CPP32

| | | | | | | | | | |
|---|---|---|---|---|---|---|---|---|---|
| ATOM | 3992 | N | PHE | 1215 | 3.903 | 3.962 | 6.972 | 1.00 | 31.63 U2 |
| ATOM | 3994 | CA | PHE | 1215 | 3.759 | 4.841 | 8.121 | 1.00 | 31.63 U2 |
| ATOM | 3995 | CB | PHE | 1215 | 5.119 | 5.379 | 8.532 | 1.00 | 31.77 U2 |
| ATOM | 3996 | CG | PHE | 1215 | 5.082 | 6.215 | 9.767 | 1.00 | 31.77 U2 |
| ATOM | 3997 | CD1 | PHE | 1215 | 4.600 | 5.688 | 10.960 | 1.00 | 31.77 U2 |
| ATOM | 3998 | CD2 | PHE | 1215 | 5.541 | 7.522 | 9.746 | 1.00 | 31.77 U2 |
| ATOM | 3999 | CE1 | PHE | 1215 | 4.581 | 6.450 | 12.112 | 1.00 | 31.77 U2 |
| ATOM | 4000 | CE2 | PHE | 1215 | 5.526 | 8.292 | 10.894 | 1.00 | 31.77 U2 |
| ATOM | 4001 | CZ | PHE | 1215 | 5.046 | 7.755 | 12.080 | 1.00 | 31.77 U2 |
| ATOM | 4002 | C | PHE | 1215 | 2.792 | 5.997 | 7.931 | 1.00 | 31.63 U2 |
| ATOM | 4003 | O | PHE | 1215 | 1.915 | 6.228 | 8.769 | 1.00 | 31.63 U2 |
| ATOM | 4004 | N | ILE | 1216 | 2.946 | 6.758 | 6.857 | 1.00 | 31.92 U2 |
| ATOM | 4006 | CA | ILE | 1216 | 2.027 | 7.865 | 6.671 | 1.00 | 31.92 U2 |
| ATOM | 4007 | CB | ILE | 1216 | 2.532 | 8.836 | 5.623 | 1.00 | 30.33 U2 |
| ATOM | 4008 | CG2 | ILE | 1216 | 1.588 | 10.040 | 5.561 | 1.00 | 30.33 U2 |
| ATOM | 4009 | CG1 | ILE | 1216 | 3.958 | 9.294 | 5.978 | 1.00 | 30.33 U2 |
| ATOM | 4010 | CD1 | ILE | 1216 | 4.034 | 10.297 | 7.168 | 1.00 | 30.33 U2 |
| ATOM | 4011 | C | ILE | 1216 | 0.628 | 7.364 | 6.321 | 1.00 | 31.92 U2 |
| ATOM | 4012 | O | ILE | 1216 | −0.362 | 7.986 | 6.703 | 1.00 | 31.92 U2 |
| ATOM | 4013 | N | GLN | 1217 | 0.548 | 6.228 | 5.626 | 1.00 | 29.17 U2 |
| ATOM | 4015 | CA | GLN | 1217 | −0.738 | 5.653 | 5.241 | 1.00 | 29.17 U2 |
| ATOM | 4016 | CB | GLN | 1217 | −0.552 | 4.342 | 4.486 | 1.00 | 45.23 U2 |
| ATOM | 4017 | CG | GLN | 1217 | −0.335 | 4.428 | 3.002 | 1.00 | 45.23 U2 |
| ATOM | 4018 | CD | GLN | 1217 | −0.152 | 3.044 | 2.394 | 1.00 | 45.23 U2 |
| ATOM | 4019 | OE1 | GLN | 1217 | 0.896 | 2.736 | 1.804 | 1.00 | 45.23 U2 |
| ATOM | 4020 | NE2 | GLN | 1217 | −1.157 | 2.185 | 2.570 | 1.00 | 45.23 U2 |
| ATOM | 4023 | C | GLN | 1217 | −1.468 | 5.333 | 6.513 | 1.00 | 29.17 U2 |
| ATOM | 4024 | O | GLN | 1217 | −2.639 | 5.674 | 6.659 | 1.00 | 29.17 U2 |
| ATOM | 4025 | N | SER | 1218 | −0.778 | 4.634 | 7.414 | 1.00 | 19.58 U2 |
| ATOM | 4027 | CA | SER | 1218 | −1.342 | 4.261 | 8.706 | 1.00 | 19.58 U2 |
| ATOM | 4028 | CB | SER | 1218 | −0.426 | 3.265 | 9.381 | 1.00 | 29.24 U2 |
| ATOM | 4029 | OG | SER | 1218 | −0.105 | 2.227 | 8.477 | 1.00 | 29.24 U2 |
| ATOM | 4031 | C | SER | 1218 | −1.601 | 5.463 | 9.630 | 1.00 | 19.58 U2 |
| ATOM | 4032 | O | SER | 1218 | −2.626 | 5.532 | 10.280 | 1.00 | 19.58 U2 |
| ATOM | 4033 | N | LEU | 1219 | −0.705 | 6.435 | 9.658 | 1.00 | 31.90 U2 |
| ATOM | 4035 | CA | LEU | 1219 | −0.903 | 7.604 | 10.500 | 1.00 | 31.90 U2 |
| ATOM | 4036 | CB | LEU | 1219 | 0.276 | 8.573 | 10.375 | 1.00 | 25.99 U2 |
| ATOM | 4037 | CG | LEU | 1219 | 0.273 | 9.811 | 11.263 | 1.00 | 25.99 U2 |
| ATOM | 4038 | CD1 | LEU | 1219 | 0.150 | 9.423 | 12.713 | 1.00 | 25.99 U2 |
| ATOM | 4039 | CD2 | LEU | 1219 | 1.544 | 10.590 | 11.038 | 1.00 | 25.99 U2 |
| ATOM | 4040 | C | LEU | 1219 | −2.199 | 8.319 | 10.158 | 1.00 | 31.90 U2 |
| ATOM | 4041 | O | LEU | 1219 | −3.047 | 8.487 | 11.017 | 1.00 | 31.90 U2 |
| ATOM | 4042 | N | CYS | 1220 | −2.377 | 8.716 | 8.905 | 1.00 | 35.94 U2 |
| ATOM | 4044 | CA | CYS | 1220 | −3.587 | 9.429 | 8.503 | 1.00 | 35.94 U2 |
| ATOM | 4045 | CB | CYS | 1220 | −3.524 | 9.792 | 7.029 | 1.00 | 38.52 U2 |
| ATOM | 4046 | SG | CYS | 1220 | −1.971 | 10.559 | 6.571 | 1.00 | 38.52 U2 |
| ATOM | 4047 | C | CYS | 1220 | −4.853 | 8.642 | 8.789 | 1.00 | 35.94 U2 |
| ATOM | 4048 | O | CYS | 1220 | −5.814 | 9.194 | 9.306 | 1.00 | 35.94 U2 |
| ATOM | 4049 | N | ALA | 1221 | −4.857 | 7.348 | 8.493 | 1.00 | 33.05 U2 |
| ATOM | 4051 | CA | ALA | 1221 | −6.051 | 6.545 | 8.743 | 1.00 | 33.05 U2 |
| ATOM | 4052 | CB | ALA | 1221 | −5.806 | 5.116 | 8.358 | 1.00 | 25.84 U2 |
| ATOM | 4053 | C | ALA | 1221 | −6.491 | 6.631 | 10.202 | 1.00 | 33.05 U2 |
| ATOM | 4054 | O | ALA | 1221 | −7.628 | 6.988 | 10.493 | 1.00 | 33.05 U2 |
| ATOM | 4055 | N | MET | 1222 | −5.570 | 6.360 | 11.122 | 1.00 | 35.97 U2 |
| ATOM | 4057 | CA | MET | 1222 | −5.870 | 6.405 | 12.557 | 1.00 | 35.97 U2 |
| ATOM | 4058 | CB | MET | 1222 | −4.637 | 6.042 | 13.395 | 1.00 | 37.47 U2 |
| ATOM | 4059 | CG | MET | 1222 | −4.239 | 4.592 | 13.318 | 1.00 | 37.47 U2 |
| ATOM | 4060 | SD | MET | 1222 | −5.711 | 3.647 | 13.692 | 1.00 | 37.47 U2 |
| ATOM | 4061 | CE | MET | 1222 | −5.401 | 2.138 | 12.768 | 1.00 | 37.47 U2 |
| ATOM | 4062 | C | MET | 1222 | −6.302 | 7.792 | 12.931 | 1.00 | 35.97 U2 |
| ATOM | 4063 | O | MET | 1222 | −7.350 | 7.976 | 13.533 | 1.00 | 35.97 U2 |
| ATOM | 4064 | N | LEU | 1223 | −5.514 | 8.776 | 12.539 | 1.00 | 36.03 U2 |
| ATOM | 4066 | CA | LEU | 1223 | −5.824 | 10.147 | 12.880 | 1.00 | 36.03 U2 |
| ATOM | 4067 | CB | LEU | 1223 | −4.897 | 11.122 | 12.153 | 1.00 | 29.70 U2 |
| ATOM | 4068 | CG | LEU | 1223 | −3.764 | 11.651 | 13.032 | 1.00 | 29.70 U2 |
| ATOM | 4069 | CD1 | LEU | 1223 | −2.770 | 12.428 | 12.213 | 1.00 | 29.70 U2 |
| ATOM | 4070 | CD2 | LEU | 1223 | −4.340 | 12.528 | 14.118 | 1.00 | 29.70 U2 |
| ATOM | 4071 | C | LEU | 1223 | −7.266 | 10.498 | 12.615 | 1.00 | 36.03 U2 |
| ATOM | 4072 | O | LEU | 1223 | −7.913 | 11.089 | 13.472 | 1.00 | 36.03 U2 |
| ATOM | 4073 | N | LYS | 1224 | −7.796 | 10.070 | 11.470 | 1.00 | 45.64 U2 |
| ATOM | 4075 | CA | LYS | 1224 | −9.184 | 10.399 | 11.128 | 1.00 | 45.64 U2 |
| ATOM | 4076 | CB | LYS | 1224 | −9.405 | 10.449 | 9.610 | 1.00 | 78.38 U2 |
| ATOM | 4077 | CG | LYS | 1224 | −9.146 | 9.155 | 8.867 | 1.00 | 78.38 U2 |
| ATOM | 4078 | CD | LYS | 1224 | −9.371 | 9.341 | 7.369 | 1.00 | 78.38 U2 |
| ATOM | 4079 | CE | LYS | 1224 | −8.655 | 10.586 | 6.815 | 1.00 | 78.38 U2 |
| ATOM | 4080 | NZ | LYS | 1224 | −7.164 | 10.525 | 6.861 | 1.00 | 78.38 U2 |
| ATOM | 4084 | C | LYS | 1224 | −10.192 | 9.487 | 11.771 | 1.00 | 45.64 U2 |

TABLE 1-continued

Structure coordinates of CPP32

| ATOM | 4085 | O | LYS | 1224 | −11.345 | 9.860 | 11.983 | 1.00 | 45.64 | U2 |
|---|---|---|---|---|---|---|---|---|---|---|
| ATOM | 4086 | N | GLN | 1225 | −9.745 | 8.295 | 12.115 | 1.00 | 39.24 | U2 |
| ATOM | 4088 | CA | GLN | 1225 | −10.620 | 7.325 | 12.744 | 1.00 | 39.24 | U2 |
| ATOM | 4089 | CB | GLN | 1225 | −10.138 | 5.914 | 12.418 | 1.00 | 64.85 | U2 |
| ATOM | 4090 | CG | GLN | 1225 | −11.153 | 4.830 | 12.720 | 1.00 | 64.85 | U2 |
| ATOM | 4091 | CD | GLN | 1225 | −10.763 | 3.513 | 12.095 | 1.00 | 64.85 | U2 |
| ATOM | 4092 | OE1 | GLN | 1225 | −10.222 | 3.476 | 10.984 | 1.00 | 64.85 | U2 |
| ATOM | 4093 | NE2 | GLN | 1225 | −11.024 | 2.419 | 12.808 | 1.00 | 64.85 | U2 |
| ATOM | 4096 | C | GLN | 1225 | −10.737 | 7.490 | 14.260 | 1.00 | 39.24 | U2 |
| ATOM | 4097 | O | GLN | 1225 | −11.775 | 7.146 | 14.824 | 1.00 | 39.24 | U2 |
| ATOM | 4098 | N | TYR | 1226 | −9.700 | 8.040 | 14.907 | 1.00 | 39.69 | U2 |
| ATOM | 4100 | CA | TYR | 1226 | −9.693 | 8.192 | 16.373 | 1.00 | 39.69 | U2 |
| ATOM | 4101 | CB | TYR | 1226 | −8.700 | 7.223 | 17.008 | 1.00 | 21.64 | U2 |
| ATOM | 4102 | CG | TYR | 1226 | −8.965 | 5.789 | 16.664 | 1.00 | 21.64 | U2 |
| ATOM | 4103 | CD1 | TYR | 1226 | −10.085 | 5.136 | 17.161 | 1.00 | 21.64 | U2 |
| ATOM | 4104 | CE1 | TYR | 1226 | −10.341 | 3.833 | 16.841 | 1.00 | 21.64 | U2 |
| ATOM | 4105 | CD2 | TYR | 1226 | −8.104 | 5.090 | 15.833 | 1.00 | 21.64 | U2 |
| ATOM | 4106 | CE2 | TYR | 1226 | −8.353 | 3.774 | 15.501 | 1.00 | 21.64 | U2 |
| ATOM | 4107 | CZ | TYR | 1226 | −9.476 | 3.154 | 16.007 | 1.00 | 21.64 | U2 |
| ATOM | 4108 | OH | TYR | 1226 | −9.746 | 1.851 | 15.649 | 1.00 | 21.64 | U2 |
| ATOM | 4110 | C | TYR | 1226 | −9.406 | 9.556 | 16.952 | 1.00 | 39.69 | U2 |
| ATOM | 4111 | O | TYR | 1226 | −9.462 | 9.723 | 18.164 | 1.00 | 39.69 | U2 |
| ATOM | 4112 | N | ALA | 1227 | −9.137 | 10.535 | 16.107 | 1.00 | 28.46 | U2 |
| ATOM | 4114 | CA | ALA | 1227 | −8.803 | 11.869 | 16.587 | 1.00 | 28.46 | U2 |
| ATOM | 4115 | CB | ALA | 1227 | −8.612 | 12.800 | 15.421 | 1.00 | 30.70 | U2 |
| ATOM | 4116 | C | ALA | 1227 | −9.778 | 12.471 | 17.582 | 1.00 | 28.46 | U2 |
| ATOM | 4117 | O | ALA | 1227 | −9.416 | 13.322 | 18.392 | 1.00 | 28.46 | U2 |
| ATOM | 4118 | N | ASP | 1228 | −11.025 | 12.044 | 17.510 | 1.00 | 52.19 | U2 |
| ATOM | 4120 | CA | ASP | 1228 | −12.028 | 12.568 | 18.417 | 1.00 | 52.19 | U2 |
| ATOM | 4121 | CB | ASP | 1228 | −13.284 | 13.021 | 17.645 | 1.00 | 71.70 | U2 |
| ATOM | 4122 | CG | ASP | 1228 | −13.766 | 11.991 | 16.617 | 1.00 | 71.70 | U2 |
| ATOM | 4123 | OD1 | ASP | 1228 | −14.092 | 10.847 | 16.997 | 1.00 | 71.70 | U2 |
| ATOM | 4124 | OD2 | ASP | 1228 | −13.839 | 12.342 | 15.418 | 1.00 | 71.70 | U2 |
| ATOM | 4125 | C | ASP | 1228 | −12.374 | 11.563 | 19.505 | 1.00 | 52.19 | U2 |
| ATOM | 4126 | O | ASP | 1228 | −13.459 | 11.608 | 20.080 | 1.00 | 52.19 | U2 |
| ATOM | 4127 | N | LYS | 1229 | −11.435 | 10.692 | 19.841 | 1.00 | 49.09 | U2 |
| ATOM | 4129 | CA | LYS | 1229 | −11.717 | 9.699 | 20.860 | 1.00 | 49.09 | U2 |
| ATOM | 4130 | CB | LYS | 1229 | −12.368 | 8.473 | 20.209 | 1.00 | 90.57 | U2 |
| ATOM | 4131 | CG | LYS | 1229 | −12.718 | 7.327 | 21.163 | 1.00 | 90.57 | U2 |
| ATOM | 4132 | CD | LYS | 1229 | −13.831 | 7.672 | 22.165 | 1.00 | 90.57 | U2 |
| ATOM | 4133 | CE | LYS | 1229 | −15.209 | 7.764 | 21.515 | 1.00 | 90.57 | U2 |
| ATOM | 4134 | NZ | LYS | 1229 | −15.394 | 8.992 | 20.687 | 1.00 | 90.57 | U2 |
| ATOM | 4138 | C | LYS | 1229 | −10.504 | 9.275 | 21.675 | 1.00 | 49.09 | U2 |
| ATOM | 4139 | O | LYS | 1229 | −10.638 | 8.929 | 22.850 | 1.00 | 49.09 | U2 |
| ATOM | 4140 | N | LEU | 1230 | −9.319 | 9.333 | 21.074 | 1.00 | 42.13 | U2 |
| ATOM | 4142 | CA | LEU | 1230 | −8.107 | 8.898 | 21.756 | 1.00 | 42.13 | U2 |
| ATOM | 4143 | CB | LEU | 1230 | −7.477 | 7.739 | 20.996 | 1.00 | 25.50 | U2 |
| ATOM | 4144 | CG | LEU | 1230 | −8.264 | 6.442 | 20.916 | 1.00 | 25.50 | U2 |
| ATOM | 4145 | CD1 | LEU | 1230 | −7.379 | 5.408 | 20.321 | 1.00 | 25.50 | U2 |
| ATOM | 4146 | CD2 | LEU | 1230 | −8.683 | 5.997 | 22.292 | 1.00 | 25.50 | U2 |
| ATOM | 4147 | C | LEU | 1230 | −7.050 | 9.954 | 21.972 | 1.00 | 42.13 | U2 |
| ATOM | 4148 | O | LEU | 1230 | −6.983 | 10.960 | 21.253 | 1.00 | 42.13 | U2 |
| ATOM | 4149 | N | GLU | 1231 | −6.184 | 9.681 | 22.942 | 1.00 | 29.52 | U2 |
| ATOM | 4151 | CA | GLU | 1231 | −5.085 | 10.577 | 23.272 | 1.00 | 29.52 | U2 |
| ATOM | 4152 | CB | GLU | 1231 | −4.564 | 10.250 | 24.685 | 1.00 | 28.38 | U2 |
| ATOM | 4153 | CG | GLU | 1231 | −3.591 | 11.265 | 25.262 | 1.00 | 28.38 | U2 |
| ATOM | 4154 | CD | GLU | 1231 | −2.173 | 11.006 | 24.844 | 1.00 | 28.38 | U2 |
| ATOM | 4155 | OE1 | GLU | 1231 | −1.835 | 9.827 | 24.587 | 1.00 | 28.38 | U2 |
| ATOM | 4156 | OE2 | GLU | 1231 | −1.384 | 11.981 | 24.774 | 1.00 | 28.38 | U2 |
| ATOM | 4157 | C | GLU | 1231 | −4.036 | 10.289 | 22.217 | 1.00 | 29.52 | U2 |
| ATOM | 4158 | O | GLU | 1231 | −3.930 | 9.143 | 21.751 | 1.00 | 29.52 | U2 |
| ATOM | 4159 | N | PHE | 1232 | −3.221 | 11.284 | 21.870 | 1.00 | 45.55 | U2 |
| ATOM | 4161 | CA | PHE | 1232 | −2.197 | 11.079 | 20.830 | 1.00 | 45.55 | U2 |
| ATOM | 4162 | CB | PHE | 1232 | −1.293 | 12.300 | 20.664 | 1.00 | 27.78 | U2 |
| ATOM | 4163 | CG | PHE | 1232 | −0.540 | 12.333 | 19.364 | 1.00 | 27.78 | U2 |
| ATOM | 4164 | CD1 | PHE | 1232 | −1.147 | 11.936 | 18.180 | 1.00 | 27.78 | U2 |
| ATOM | 4165 | CD2 | PHE | 1232 | 0.768 | 12.784 | 19.322 | 1.00 | 27.78 | U2 |
| ATOM | 4166 | CE1 | PHE | 1232 | −0.462 | 11.989 | 16.981 | 1.00 | 27.78 | U2 |
| ATOM | 4167 | CE2 | PHE | 1232 | 1.461 | 12.840 | 18.128 | 1.00 | 27.78 | U2 |
| ATOM | 4168 | CZ | PHE | 1232 | 0.845 | 12.443 | 16.956 | 1.00 | 27.78 | U2 |
| ATOM | 4169 | C | PHE | 1232 | −1.368 | 9.805 | 20.993 | 1.00 | 45.55 | U2 |
| ATOM | 4170 | O | PHE | 1232 | −1.490 | 8.905 | 20.165 | 1.00 | 45.55 | U2 |
| ATOM | 4171 | N | MET | 1233 | −0.618 | 9.649 | 22.086 | 1.00 | 22.19 | U2 |
| ATOM | 4173 | CA | MET | 1233 | 0.210 | 8.430 | 22.250 | 1.00 | 22.19 | U2 |
| ATOM | 4174 | CB | MET | 1233 | 0.799 | 8.337 | 23.653 | 1.00 | 48.02 | U2 |
| ATOM | 4175 | CG | MET | 1233 | 1.571 | 9.581 | 24.094 | 1.00 | 48.02 | U2 |
| ATOM | 4176 | SD | MET | 1233 | 2.975 | 9.827 | 23.042 | 1.00 | 48.02 | U2 |

TABLE 1-continued

Structure coordinates of CPP32

| ATOM | 4177 | CE  | MET | 1233 | 3.694  | 8.173  | 23.093 | 1.00 | 48.02 | U2 |
|------|------|-----|-----|------|--------|--------|--------|------|-------|-----|
| ATOM | 4178 | C   | MET | 1233 | −0.569 | 7.167  | 21.964 | 1.00 | 22.19 | U2 |
| ATOM | 4179 | O   | MET | 1233 | −0.012 | 6.161  | 21.481 | 1.00 | 22.19 | U2 |
| ATOM | 4180 | N   | HIS | 1234 | −1.861 | 7.209  | 22.267 | 1.00 | 25.79 | U2 |
| ATOM | 4182 | CA  | HIS | 1234 | −2.696 | 6.051  | 22.023 | 1.00 | 25.79 | U2 |
| ATOM | 4183 | CB  | HIS | 1234 | −3.957 | 6.112  | 22.864 | 1.00 | 30.14 | U2 |
| ATOM | 4184 | CG  | HIS | 1234 | −3.711 | 5.825  | 24.315 | 1.00 | 30.14 | U2 |
| ATOM | 4185 | CD2 | HIS | 1234 | −2.642 | 5.285  | 24.944 | 1.00 | 30.14 | U2 |
| ATOM | 4186 | ND1 | HIS | 1234 | −4.645 | 6.082  | 25.294 | 1.00 | 30.14 | U2 |
| ATOM | 4188 | CE1 | HIS | 1234 | −4.160 | 5.713  | 26.464 | 1.00 | 30.14 | U2 |
| ATOM | 4189 | NE2 | HIS | 1234 | −2.948 | 5.227  | 26.280 | 1.00 | 30.14 | U2 |
| ATOM | 4191 | C   | HIS | 1234 | −2.993 | 5.902  | 20.537 | 1.00 | 25.79 | U2 |
| ATOM | 4192 | O   | HIS | 1234 | −3.011 | 4.786  | 20.020 | 1.00 | 25.79 | U2 |
| ATOM | 4193 | N   | ILE | 1235 | −3.186 | 7.013  | 19.830 | 1.00 | 32.46 | U2 |
| ATOM | 4195 | CA  | ILE | 1235 | −3.391 | 6.919  | 18.392 | 1.00 | 32.46 | U2 |
| ATOM | 4196 | CB  | ILE | 1235 | −3.653 | 8.275  | 17.764 | 1.00 | 29.36 | U2 |
| ATOM | 4197 | CG2 | ILE | 1235 | −3.831 | 8.088  | 16.304 | 1.00 | 29.36 | U2 |
| ATOM | 4198 | CG1 | ILE | 1235 | −4.910 | 8.899  | 18.363 | 1.00 | 29.36 | U2 |
| ATOM | 4199 | CD1 | ILE | 1235 | −5.116 | 10.332 | 18.001 | 1.00 | 29.36 | U2 |
| ATOM | 4200 | C   | ILE | 1235 | −2.087 | 6.347  | 17.814 | 1.00 | 32.46 | U2 |
| ATOM | 4201 | O   | ILE | 1235 | −2.068 | 5.230  | 17.285 | 1.00 | 32.46 | U2 |
| ATOM | 4202 | N   | LEU | 1236 | −0.979 | 7.051  | 18.018 | 1.00 | 24.98 | U2 |
| ATOM | 4204 | CA  | LEU | 1236 | 0.312  | 6.588  | 17.517 | 1.00 | 24.98 | U2 |
| ATOM | 4205 | CB  | LEU | 1236 | 1.465  | 7.430  | 18.052 | 1.00 | 21.34 | U2 |
| ATOM | 4206 | CG  | LEU | 1236 | 1.511  | 8.888  | 17.567 | 1.00 | 21.34 | U2 |
| ATOM | 4207 | CD1 | LEU | 1236 | 2.673  | 9.654  | 18.203 | 1.00 | 21.34 | U2 |
| ATOM | 4208 | CD2 | LEU | 1236 | 1.641  | 8.920  | 16.073 | 1.00 | 21.34 | U2 |
| ATOM | 4209 | C   | LEU | 1236 | 0.554  | 5.123  | 17.821 | 1.00 | 24.98 | U2 |
| ATOM | 4210 | O   | LEU | 1236 | 1.059  | 4.409  | 16.969 | 1.00 | 24.98 | U2 |
| ATOM | 4211 | N   | THR | 1237 | 0.175  | 4.640  | 19.002 | 1.00 | 22.24 | U2 |
| ATOM | 4213 | CA  | THR | 1237 | 0.382  | 3.209  | 19.287 | 1.00 | 22.24 | U2 |
| ATOM | 4214 | CB  | THR | 1237 | 0.000  | 2.837  | 20.732 | 1.00 | 27.51 | U2 |
| ATOM | 4215 | OG1 | THR | 1237 | 0.947  | 3.411  | 21.637 | 1.00 | 27.51 | U2 |
| ATOM | 4217 | CG2 | THR | 1237 | 0.019  | 1.344  | 20.917 | 1.00 | 27.51 | U2 |
| ATOM | 4218 | C   | THR | 1237 | −0.398 | 2.334  | 18.290 | 1.00 | 22.24 | U2 |
| ATOM | 4219 | O   | THR | 1237 | 0.137  | 1.349  | 17.771 | 1.00 | 22.24 | U2 |
| ATOM | 4220 | N   | ARG | 1238 | −1.638 | 2.719  | 17.982 | 1.00 | 32.89 | U2 |
| ATOM | 4222 | CA  | ARG | 1238 | −2.458 | 1.969  | 17.025 | 1.00 | 32.89 | U2 |
| ATOM | 4223 | CB  | ARG | 1238 | −3.860 | 2.550  | 16.955 | 1.00 | 60.48 | U2 |
| ATOM | 4224 | CG  | ARG | 1238 | −4.724 | 2.087  | 18.120 | 1.00 | 60.48 | U2 |
| ATOM | 4225 | CD  | ARG | 1238 | −6.082 | 2.750  | 18.121 | 1.00 | 60.48 | U2 |
| ATOM | 4226 | NE  | ARG | 1238 | −6.895 | 2.380  | 19.282 | 1.00 | 60.48 | U2 |
| ATOM | 4228 | CZ  | ARG | 1238 | −7.565 | 1.240  | 19.399 | 1.00 | 60.48 | U2 |
| ATOM | 4229 | NH1 | ARG | 1238 | −7.522 | 0.332  | 18.431 | 1.00 | 60.48 | U2 |
| ATOM | 4232 | NH2 | ARG | 1238 | −8.306 | 1.028  | 20.474 | 1.00 | 60.48 | U2 |
| ATOM | 4235 | C   | ARG | 1238 | −1.793 | 1.945  | 15.652 | 1.00 | 32.89 | U2 |
| ATOM | 4236 | O   | ARG | 1238 | −1.815 | 0.918  | 14.964 | 1.00 | 32.89 | U2 |
| ATOM | 4237 | N   | VAL | 1239 | −1.151 | 3.063  | 15.290 | 1.00 | 32.53 | U2 |
| ATOM | 4239 | CA  | VAL | 1239 | −0.417 | 3.203  | 14.028 | 1.00 | 32.53 | U2 |
| ATOM | 4240 | CB  | VAL | 1239 | 0.189  | 4.577  | 13.923 | 1.00 | 17.78 | U2 |
| ATOM | 4241 | CG1 | VAL | 1239 | 1.193  | 4.623  | 12.836 | 1.00 | 17.78 | U2 |
| ATOM | 4242 | CG2 | VAL | 1239 | −0.892 | 5.581  | 13.686 | 1.00 | 17.78 | U2 |
| ATOM | 4243 | C   | VAL | 1239 | 0.703  | 2.174  | 14.052 | 1.00 | 32.53 | U2 |
| ATOM | 4244 | O   | VAL | 1239 | 0.927  | 1.459  | 13.062 | 1.00 | 32.53 | U2 |
| ATOM | 4245 | N   | ASN | 1240 | 1.369  | 2.066  | 15.205 | 1.00 | 25.06 | U2 |
| ATOM | 4247 | CA  | ASN | 1240 | 2.453  | 1.100  | 15.411 | 1.00 | 25.06 | U2 |
| ATOM | 4248 | CB  | ASN | 1240 | 2.929  | 1.117  | 16.870 | 1.00 | 30.02 | U2 |
| ATOM | 4249 | CG  | ASN | 1240 | 4.018  | 2.123  | 17.126 | 1.00 | 30.02 | U2 |
| ATOM | 4250 | OD1 | ASN | 1240 | 4.472  | 2.813  | 16.224 | 1.00 | 30.02 | U2 |
| ATOM | 4251 | ND2 | ASN | 1240 | 4.472  | 2.189  | 18.360 | 1.00 | 30.02 | U2 |
| ATOM | 4254 | C   | ASN | 1240 | 1.910  | −0.278 | 15.138 | 1.00 | 25.06 | U2 |
| ATOM | 4255 | O   | ASN | 1240 | 2.577  | −1.105 | 14.523 | 1.00 | 25.06 | U2 |
| ATOM | 4256 | N   | ARG | 1241 | 0.725  | −0.574 | 15.662 | 1.00 | 34.02 | U2 |
| ATOM | 4258 | CA  | ARG | 1241 | 0.180  | −1.897 | 15.412 | 1.00 | 34.02 | U2 |
| ATOM | 4259 | CB  | ARG | 1241 | −0.949 | −2.251 | 16.369 | 1.00 | 49.84 | U2 |
| ATOM | 4260 | CG  | ARG | 1241 | −1.165 | −3.767 | 16.444 | 1.00 | 49.84 | U2 |
| ATOM | 4261 | CD  | ARG | 1241 | −2.227 | −4.163 | 17.459 | 1.00 | 49.84 | U2 |
| ATOM | 4262 | NE  | ARG | 1241 | −3.534 | −3.579 | 17.153 | 1.00 | 49.84 | U2 |
| ATOM | 4264 | CZ  | ARG | 1241 | −4.163 | −2.682 | 17.914 | 1.00 | 49.84 | U2 |
| ATOM | 4265 | NH1 | ARG | 1241 | −3.610 | −2.243 | 19.047 | 1.00 | 49.84 | U2 |
| ATOM | 4268 | NH2 | ARG | 1241 | −5.363 | −2.238 | 17.552 | 1.00 | 49.84 | U2 |
| ATOM | 4271 | C   | ARG | 1241 | −0.299 | −2.046 | 13.974 | 1.00 | 34.02 | U2 |
| ATOM | 4272 | O   | ARG | 1241 | −0.324 | −3.160 | 13.450 | 1.00 | 34.02 | U2 |
| ATOM | 4273 | N   | LYS | 1242 | −0.676 | −0.948 | 13.317 | 1.00 | 30.61 | U2 |
| ATOM | 4275 | CA  | LYS | 1242 | −1.144 | −1.069 | 11.943 | 1.00 | 30.61 | U2 |
| ATOM | 4276 | CB  | LYS | 1242 | −1.741 | 0.230  | 11.416 | 1.00 | 46.42 | U2 |
| ATOM | 4277 | CG  | LYS | 1242 | −2.712 | −0.004 | 10.259 | 1.00 | 46.42 | U2 |

TABLE 1-continued

Structure coordinates of CPP32

| ATOM | 4278 | CD | LYS | 1242 | -3.326 | 1.294 | 9.732 | 1.00 | 46.42 | U2 |
|---|---|---|---|---|---|---|---|---|---|---|
| ATOM | 4279 | CE | LYS | 1242 | -4.131 | 1.085 | 8.446 | 1.00 | 46.42 | U2 |
| ATOM | 4280 | NZ | LYS | 1242 | -5.417 | 0.368 | 8.670 | 1.00 | 46.42 | U2 |
| ATOM | 4284 | C | LYS | 1242 | 0.009 | -1.509 | 11.074 | 1.00 | 30.61 | U2 |
| ATOM | 4285 | O | LYS | 1242 | 0.045 | -2.666 | 10.651 | 1.00 | 30.61 | U2 |
| ATOM | 4286 | N | VAL | 1243 | 1.019 | -0.645 | 10.944 | 1.00 | 30.31 | U2 |
| ATOM | 4288 | CA | VAL | 1243 | 2.182 | -0.954 | 10.097 | 1.00 | 30.31 | U2 |
| ATOM | 4289 | CB | VAL | 1243 | 3.129 | 0.270 | 9.886 | 1.00 | 23.76 | U2 |
| ATOM | 4290 | CG1 | VAL | 1243 | 2.544 | 1.521 | 10.502 | 1.00 | 23.76 | U2 |
| ATOM | 4291 | CG2 | VAL | 1243 | 4.515 | 0.003 | 10.385 | 1.00 | 23.76 | U2 |
| ATOM | 4292 | C | VAL | 1243 | 2.981 | -2.185 | 10.489 | 1.00 | 30.31 | U2 |
| ATOM | 4293 | O | VAL | 1243 | 3.742 | -2.722 | 9.684 | 1.00 | 30.31 | U2 |
| ATOM | 4294 | N | ALA | 1244 | 2.793 | -2.650 | 11.714 | 1.00 | 26.27 | U2 |
| ATOM | 4296 | CA | ALA | 1244 | 3.515 | -3.815 | 12.192 | 1.00 | 26.27 | U2 |
| ATOM | 4297 | CB | ALA | 1244 | 3.575 | -3.810 | 13.728 | 1.00 | 24.56 | U2 |
| ATOM | 4298 | C | ALA | 1244 | 2.857 | -5.092 | 11.708 | 1.00 | 26.27 | U2 |
| ATOM | 4299 | O | ALA | 1244 | 3.520 | -5.950 | 11.112 | 1.00 | 26.27 | U2 |
| ATOM | 4300 | N | THR | 1245 | 1.549 | -5.199 | 11.929 | 1.00 | 44.11 | U2 |
| ATOM | 4302 | CA | THR | 1245 | 0.826 | -6.402 | 11.564 | 1.00 | 44.11 | U2 |
| ATOM | 4303 | CB | THR | 1245 | -0.360 | -6.636 | 12.470 | 1.00 | 37.21 | U2 |
| ATOM | 4304 | OG1 | THR | 1245 | -1.199 | -5.479 | 12.449 | 1.00 | 37.21 | U2 |
| ATOM | 4306 | CG2 | THR | 1245 | 0.098 | -6.912 | 13.876 | 1.00 | 37.21 | U2 |
| ATOM | 4307 | C | THR | 1245 | 0.294 | -6.506 | 10.159 | 1.00 | 44.11 | U2 |
| ATOM | 4308 | O | THR | 1245 | 0.268 | -7.596 | 9.585 | 1.00 | 44.11 | U2 |
| ATOM | 4309 | N | GLU | 1246 | -0.174 | -5.406 | 9.597 | 1.00 | 41.09 | U2 |
| ATOM | 4311 | CA | GLU | 1246 | -0.734 | -5.516 | 8.265 | 1.00 | 41.09 | U2 |
| ATOM | 4312 | CB | GLU | 1246 | -2.181 | -4.997 | 8.264 | 1.00 | 42.44 | U2 |
| ATOM | 4313 | CG | GLU | 1246 | -2.368 | -3.576 | 8.698 | 1.00 | 42.44 | U2 |
| ATOM | 4314 | CD | GLU | 1246 | -3.829 | -3.187 | 8.722 | 1.00 | 42.44 | U2 |
| ATOM | 4315 | OE1 | GLU | 1246 | -4.635 | -3.945 | 9.307 | 1.00 | 42.44 | U2 |
| ATOM | 4316 | OE2 | GLU | 1246 | -4.163 | -2.118 | 8.158 | 1.00 | 42.44 | U2 |
| ATOM | 4317 | C | GLU | 1246 | 0.076 | -4.898 | 7.146 | 1.00 | 41.09 | U2 |
| ATOM | 4318 | O | GLU | 1246 | -0.458 | -4.171 | 6.320 | 1.00 | 41.09 | U2 |
| ATOM | 4319 | N | PHE | 1247 | 1.344 | -5.259 | 7.061 | 1.00 | 31.80 | U2 |
| ATOM | 4321 | CA | PHE | 1247 | 2.223 | -4.696 | 6.045 | 1.00 | 31.80 | U2 |
| ATOM | 4322 | CB | PHE | 1247 | 2.665 | -3.294 | 6.437 | 1.00 | 26.03 | U2 |
| ATOM | 4323 | CG | PHE | 1247 | 1.718 | -2.207 | 6.028 | 1.00 | 26.03 | U2 |
| ATOM | 4324 | CD1 | PHE | 1247 | 0.746 | -1.751 | 6.894 | 1.00 | 26.03 | U2 |
| ATOM | 4325 | CD2 | PHE | 1247 | 1.837 | -1.594 | 4.788 | 1.00 | 26.03 | U2 |
| ATOM | 4326 | CE1 | PHE | 1247 | -0.090 | -0.701 | 6.531 | 1.00 | 26.03 | U2 |
| ATOM | 4327 | CE2 | PHE | 1247 | 0.999 | -0.538 | 4.425 | 1.00 | 26.03 | U2 |
| ATOM | 4328 | CZ | PHE | 1247 | 0.041 | -0.097 | 5.294 | 1.00 | 26.03 | U2 |
| ATOM | 4329 | C | PHE | 1247 | 3.461 | -5.554 | 5.944 | 1.00 | 31.80 | U2 |
| ATOM | 4330 | O | PHE | 1247 | 4.034 | -5.935 | 6.958 | 1.00 | 31.80 | U2 |
| ATOM | 4331 | N | GLU | 1248 | 3.838 | -5.894 | 4.720 | 1.00 | 39.29 | U2 |
| ATOM | 4333 | CA | GLU | 1248 | 5.017 | -6.694 | 4.474 | 1.00 | 39.29 | U2 |
| ATOM | 4334 | CB | GLU | 1248 | 4.697 | -8.175 | 4.531 | 1.00 | 52.81 | U2 |
| ATOM | 4335 | CG | GLU | 1248 | 5.906 | -9.004 | 4.858 | 1.00 | 52.81 | U2 |
| ATOM | 4336 | CD | GLU | 1248 | 5.555 | -10.445 | 5.121 | 1.00 | 52.81 | U2 |
| ATOM | 4337 | OE1 | GLU | 1248 | 5.863 | -11.309 | 4.263 | 1.00 | 52.81 | U2 |
| ATOM | 4338 | OE2 | GLU | 1248 | 4.959 | -10.713 | 6.185 | 1.00 | 52.81 | U2 |
| ATOM | 4339 | C | GLU | 1248 | 5.468 | -6.294 | 3.085 | 1.00 | 39.29 | U2 |
| ATOM | 4340 | O | GLU | 1248 | 4.639 | -6.012 | 2.219 | 1.00 | 39.29 | U2 |
| ATOM | 4341 | N | SER | 1249 | 6.774 | -6.163 | 2.899 | 1.00 | 29.57 | U2 |
| ATOM | 4343 | CA | SER | 1249 | 7.296 | -5.747 | 1.618 | 1.00 | 29.57 | U2 |
| ATOM | 4344 | CB | SER | 1249 | 8.769 | -5.420 | 1.735 | 1.00 | 31.10 | U2 |
| ATOM | 4345 | OG | SER | 1249 | 9.478 | -6.629 | 1.965 | 1.00 | 31.10 | U2 |
| ATOM | 4347 | C | SER | 1249 | 7.161 | -6.904 | 0.681 | 1.00 | 29.57 | U2 |
| ATOM | 4348 | O | SER | 1249 | 7.138 | -8.049 | 1.112 | 1.00 | 29.57 | U2 |
| ATOM | 4349 | N | PHE | 1250 | 7.123 | -6.595 | -0.607 | 1.00 | 35.61 | U2 |
| ATOM | 4351 | CA | PHE | 1250 | 7.046 | -7.596 | -1.661 | 1.00 | 35.61 | U2 |
| ATOM | 4352 | CB | PHE | 1250 | 5.662 | -7.581 | -2.337 | 1.00 | 42.42 | U2 |
| ATOM | 4353 | CG | PHE | 1250 | 5.535 | -8.546 | -3.483 | 1.00 | 42.42 | U2 |
| ATOM | 4354 | CD1 | PHE | 1250 | 4.908 | -9.768 | -3.306 | 1.00 | 42.42 | U2 |
| ATOM | 4355 | CD2 | PHE | 1250 | 6.091 | -8.254 | -4.729 | 1.00 | 42.42 | U2 |
| ATOM | 4356 | CE1 | PHE | 1250 | 4.841 | -10.694 | -4.351 | 1.00 | 42.42 | U2 |
| ATOM | 4357 | CE2 | PHE | 1250 | 6.028 | -9.171 | -5.770 | 1.00 | 42.42 | U2 |
| ATOM | 4358 | CZ | PHE | 1250 | 5.403 | -10.394 | -5.580 | 1.00 | 42.42 | U2 |
| ATOM | 4359 | C | PHE | 1250 | 8.102 | -7.126 | -2.649 | 1.00 | 35.61 | U2 |
| ATOM | 4360 | O | PHE | 1250 | 8.167 | -5.932 | -2.965 | 1.00 | 35.61 | U2 |
| ATOM | 4361 | N | SER | 1251 | 8.973 | -8.025 | -3.086 | 1.00 | 37.58 | U2 |
| ATOM | 4363 | CA | SER | 1251 | 9.965 | -7.620 | -4.064 | 1.00 | 37.58 | U2 |
| ATOM | 4364 | CB | SER | 1251 | 11.132 | -6.890 | -3.400 | 1.00 | 52.14 | U2 |
| ATOM | 4365 | OG | SER | 1251 | 12.031 | -7.829 | -2.839 | 1.00 | 52.14 | U2 |
| ATOM | 4367 | C | SER | 1251 | 10.460 | -8.887 | -4.692 | 1.00 | 37.58 | U2 |
| ATOM | 4368 | O | SER | 1251 | 10.367 | -9.933 | -4.072 | 1.00 | 37.58 | U2 |
| ATOM | 4369 | N | PHE | 1252 | 10.968 | -8.801 | -5.917 | 1.00 | 60.08 | U2 |

TABLE 1-continued

Structure coordinates of CPP32

| ATOM | 4371 | CA | PHE | 1252 | 11.489 | −9.990 | −6.591 | 1.00 | 60.08 | U2 |
|------|------|-----|-----|------|--------|--------|--------|------|-------|-----|
| ATOM | 4372 | CB | PHE | 1252 | 11.430 | −9.851 | −8.129 | 1.00 | 41.98 | U2 |
| ATOM | 4373 | CG | PHE | 1252 | 10.094 | −9.355 | −8.651 | 1.00 | 41.98 | U2 |
| ATOM | 4374 | CD1 | PHE | 1252 | 10.008 | −8.161 | −9.357 | 1.00 | 41.98 | U2 |
| ATOM | 4375 | CD2 | PHE | 1252 | 8.917 | −10.045 | −8.374 | 1.00 | 41.98 | U2 |
| ATOM | 4376 | CE1 | PHE | 1252 | 8.775 | −7.662 | −9.770 | 1.00 | 41.98 | U2 |
| ATOM | 4377 | CE2 | PHE | 1252 | 7.671 | −9.540 | −8.789 | 1.00 | 41.98 | U2 |
| ATOM | 4378 | CZ | PHE | 1252 | 7.606 | −8.351 | −9.482 | 1.00 | 41.98 | U2 |
| ATOM | 4379 | C | PHE | 1252 | 12.918 | −10.164 | −6.096 | 1.00 | 60.08 | U2 |
| ATOM | 4380 | O | PHE | 1252 | 13.412 | −11.282 | −5.995 | 1.00 | 60.08 | U2 |
| ATOM | 4381 | N | ASP | 1253 | 13.569 | −9.047 | −5.767 | 1.00 | 50.43 | U2 |
| ATOM | 4383 | CA | ASP | 1253 | 14.937 | −9.059 | −5.235 | 1.00 | 50.43 | U2 |
| ATOM | 4384 | CB | ASP | 1253 | 15.514 | −7.635 | −5.220 | 1.00 | 60.03 | U2 |
| ATOM | 4385 | CG | ASP | 1253 | 17.001 | −7.594 | −4.872 | 1.00 | 60.03 | U2 |
| ATOM | 4386 | OD1 | ASP | 1253 | 17.522 | −8.580 | −4.284 | 1.00 | 60.03 | U2 |
| ATOM | 4387 | OD2 | ASP | 1253 | 17.644 | −6.561 | −5.195 | 1.00 | 60.03 | U2 |
| ATOM | 4388 | C | ASP | 1253 | 14.815 | −9.588 | −3.803 | 1.00 | 50.43 | U2 |
| ATOM | 4389 | O | ASP | 1253 | 14.595 | −8.820 | −2.867 | 1.00 | 50.43 | U2 |
| ATOM | 4390 | N | ALA | 1254 | 14.976 | −10.900 | −3.655 | 1.00 | 66.05 | U2 |
| ATOM | 4392 | CA | ALA | 1254 | 14.846 | −11.612 | −2.380 | 1.00 | 66.05 | U2 |
| ATOM | 4393 | CB | ALA | 1254 | 15.399 | −13.032 | −2.506 | 1.00 | 41.11 | U2 |
| ATOM | 4394 | C | ALA | 1254 | 15.394 | −10.967 | −1.125 | 1.00 | 66.05 | U2 |
| ATOM | 4395 | O | ALA | 1254 | 14.897 | −11.230 | −0.040 | 1.00 | 66.05 | U2 |
| ATOM | 4396 | N | THR | 1255 | 16.408 | −10.130 | −1.254 | 1.00 | 55.28 | U2 |
| ATOM | 4398 | CA | THR | 1255 | 16.988 | −9.502 | −0.083 | 1.00 | 55.28 | U2 |
| ATOM | 4399 | CB | THR | 1255 | 18.344 | −8.889 | −0.435 | 1.00 | 69.83 | U2 |
| ATOM | 4400 | OG1 | THR | 1255 | 19.088 | −9.824 | −1.234 | 1.00 | 69.83 | U2 |
| ATOM | 4402 | CG2 | THR | 1255 | 19.130 | −8.565 | 0.837 | 1.00 | 69.83 | U2 |
| ATOM | 4403 | C | THR | 1255 | 16.103 | −8.445 | 0.581 | 1.00 | 55.28 | U2 |
| ATOM | 4404 | O | THR | 1255 | 16.365 | −8.031 | 1.704 | 1.00 | 55.28 | U2 |
| ATOM | 4405 | N | PHE | 1256 | 15.057 | −8.006 | −0.101 | 1.00 | 45.06 | U2 |
| ATOM | 4407 | CA | PHE | 1256 | 14.182 | −6.985 | 0.459 | 1.00 | 45.06 | U2 |
| ATOM | 4408 | CB | PHE | 1256 | 14.300 | −5.706 | −0.365 | 1.00 | 78.77 | U2 |
| ATOM | 4409 | CG | PHE | 1256 | 15.696 | −5.181 | −0.469 | 1.00 | 78.77 | U2 |
| ATOM | 4410 | CD1 | PHE | 1256 | 16.140 | −4.597 | −1.643 | 1.00 | 78.77 | U2 |
| ATOM | 4411 | CD2 | PHE | 1256 | 16.571 | −5.272 | 0.609 | 1.00 | 78.77 | U2 |
| ATOM | 4412 | CE1 | PHE | 1256 | 17.437 | −4.110 | −1.747 | 1.00 | 78.77 | U2 |
| ATOM | 4413 | CE2 | PHE | 1256 | 17.870 | −4.789 | 0.518 | 1.00 | 78.77 | U2 |
| ATOM | 4414 | CZ | PHE | 1256 | 18.304 | −4.206 | −0.664 | 1.00 | 78.77 | U2 |
| ATOM | 4415 | C | PHE | 1256 | 12.719 | −7.419 | 0.505 | 1.00 | 45.06 | U2 |
| ATOM | 4416 | O | PHE | 1256 | 11.842 | −6.660 | 0.904 | 1.00 | 45.06 | U2 |
| ATOM | 4417 | N | HIS | 1257 | 12.454 | −8.639 | 0.077 | 1.00 | 36.23 | U2 |
| ATOM | 4419 | CA | HIS | 1257 | 11.103 | −9.162 | 0.039 | 1.00 | 36.23 | U2 |
| ATOM | 4420 | CB | HIS | 1257 | 10.991 | −10.203 | −1.076 | 1.00 | 19.94 | U2 |
| ATOM | 4421 | CG | HIS | 1257 | 9.891 | −11.186 | −0.877 | 1.00 | 19.94 | U2 |
| ATOM | 4422 | CD2 | HIS | 1257 | 9.917 | −12.487 | −0.512 | 1.00 | 19.94 | U2 |
| ATOM | 4423 | ND1 | HIS | 1257 | 8.560 | −10.851 | −1.019 | 1.00 | 19.94 | U2 |
| ATOM | 4425 | CE1 | HIS | 1257 | 7.813 | −11.909 | −0.747 | 1.00 | 19.94 | U2 |
| ATOM | 4426 | NE2 | HIS | 1257 | 8.613 | −12.914 | −0.436 | 1.00 | 19.94 | U2 |
| ATOM | 4428 | C | HIS | 1257 | 10.791 | −9.804 | 1.355 | 1.00 | 36.23 | U2 |
| ATOM | 4429 | O | HIS | 1257 | 11.583 | −10.589 | 1.861 | 1.00 | 36.23 | U2 |
| ATOM | 4430 | N | ALA | 1258 | 9.609 | −9.507 | 1.876 | 1.00 | 50.76 | U2 |
| ATOM | 4432 | CA | ALA | 1258 | 9.156 | −10.070 | 3.144 | 1.00 | 50.76 | U2 |
| ATOM | 4433 | CB | ALA | 1258 | 9.260 | −11.600 | 3.126 | 1.00 | 36.59 | U2 |
| ATOM | 4434 | C | ALA | 1258 | 9.890 | −9.480 | 4.357 | 1.00 | 50.76 | U2 |
| ATOM | 4435 | O | ALA | 1258 | 10.342 | −10.192 | 5.254 | 1.00 | 50.76 | U2 |
| ATOM | 4436 | N | LYS | 1259 | 10.033 | −8.166 | 4.359 | 1.00 | 56.22 | U2 |
| ATOM | 4438 | CA | LYS | 1259 | 10.672 | −7.512 | 5.472 | 1.00 | 56.22 | U2 |
| ATOM | 4439 | CB | LYS | 1259 | 11.808 | −6.589 | 5.012 | 1.00 | 43.96 | U2 |
| ATOM | 4440 | CG | LYS | 1259 | 12.992 | −7.371 | 4.455 | 1.00 | 43.96 | U2 |
| ATOM | 4441 | CD | LYS | 1259 | 13.198 | −8.649 | 5.263 | 1.00 | 43.96 | U2 |
| ATOM | 4442 | CE | LYS | 1259 | 14.040 | −9.685 | 4.525 | 1.00 | 43.96 | U2 |
| ATOM | 4443 | NZ | LYS | 1259 | 15.443 | −9.235 | 4.245 | 1.00 | 43.96 | U2 |
| ATOM | 4447 | C | LYS | 1259 | 9.573 | −6.760 | 6.191 | 1.00 | 56.22 | U2 |
| ATOM | 4448 | O | LYS | 1259 | 8.546 | −6.412 | 5.576 | 1.00 | 56.22 | U2 |
| ATOM | 4449 | N | LYS | 1260 | 9.773 | −6.572 | 7.498 | 1.00 | 45.40 | U2 |
| ATOM | 4451 | CA | LYS | 1260 | 8.829 | −5.896 | 8.368 | 1.00 | 45.40 | U2 |
| ATOM | 4452 | CB | LYS | 1260 | 8.620 | −6.754 | 9.600 | 1.00 | 30.50 | U2 |
| ATOM | 4453 | CG | LYS | 1260 | 8.220 | −8.175 | 9.288 | 1.00 | 30.50 | U2 |
| ATOM | 4454 | CD | LYS | 1260 | 6.826 | −8.215 | 8.723 | 1.00 | 30.50 | U2 |
| ATOM | 4455 | CE | LYS | 1260 | 5.809 | −7.733 | 9.734 | 1.00 | 30.50 | U2 |
| ATOM | 4456 | NZ | LYS | 1260 | 4.445 | −7.601 | 9.157 | 1.00 | 30.50 | U2 |
| ATOM | 4460 | C | LYS | 1260 | 9.307 | −4.488 | 8.773 | 1.00 | 45.40 | U2 |
| ATOM | 4461 | O | LYS | 1260 | 10.437 | −4.070 | 8.456 | 1.00 | 45.40 | U2 |
| ATOM | 4462 | N | GLN | 1261 | 8.436 | −3.757 | 9.462 | 1.00 | 35.78 | U2 |
| ATOM | 4464 | CA | GLN | 1261 | 8.756 | −2.423 | 9.905 | 1.00 | 35.78 | U2 |
| ATOM | 4465 | CB | GLN | 1261 | 8.416 | −1.418 | 8.818 | 1.00 | 37.45 | U2 |

TABLE 1-continued

Structure coordinates of CPP32

| ATOM | 4466 | CG | GLN | 1261 | 8.305 | 0.006 | 9.299 | 1.00 | 37.45 | U2 |
|---|---|---|---|---|---|---|---|---|---|---|
| ATOM | 4467 | CD | GLN | 1261 | 8.429 | 0.986 | 8.172 | 1.00 | 37.45 | U2 |
| ATOM | 4468 | OE1 | GLN | 1261 | 9.048 | 0.691 | 7.153 | 1.00 | 37.45 | U2 |
| ATOM | 4469 | NE2 | GLN | 1261 | 7.862 | 2.167 | 8.347 | 1.00 | 37.45 | U2 |
| ATOM | 4472 | C | GLN | 1261 | 7.955 | −2.093 | 11.134 | 1.00 | 35.78 | U2 |
| ATOM | 4473 | O | GLN | 1261 | 6.776 | −2.405 | 11.189 | 1.00 | 35.78 | U2 |
| ATOM | 4474 | N | ILE | 1262 | 8.607 | −1.476 | 12.118 | 1.00 | 37.23 | U2 |
| ATOM | 4476 | CA | ILE | 1262 | 7.957 | −1.053 | 13.362 | 1.00 | 37.23 | U2 |
| ATOM | 4477 | CB | ILE | 1262 | 8.434 | −1.895 | 14.614 | 1.00 | 34.57 | U2 |
| ATOM | 4478 | CG2 | ILE | 1262 | 9.964 | −1.916 | 14.709 | 1.00 | 34.57 | U2 |
| ATOM | 4479 | CG1 | ILE | 1262 | 7.903 | −1.280 | 15.911 | 1.00 | 34.57 | U2 |
| ATOM | 4480 | CD1 | ILE | 1262 | 6.416 | −1.331 | 16.059 | 1.00 | 34.57 | U2 |
| ATOM | 4481 | C | ILE | 1262 | 8.315 | 0.417 | 13.568 | 1.00 | 37.23 | U2 |
| ATOM | 4482 | O | ILE | 1262 | 9.495 | 0.797 | 13.525 | 1.00 | 37.23 | U2 |
| ATOM | 4483 | N | PRO | 1263 | 7.302 | 1.280 | 13.670 | 1.00 | 26.81 | U2 |
| ATOM | 4484 | CD | PRO | 1263 | 5.889 | 0.990 | 13.425 | 1.00 | 16.76 | U2 |
| ATOM | 4485 | CA | PRO | 1263 | 7.518 | 2.721 | 13.878 | 1.00 | 26.81 | U2 |
| ATOM | 4486 | CB | PRO | 1263 | 6.122 | 3.312 | 13.671 | 1.00 | 16.76 | U2 |
| ATOM | 4487 | CG | PRO | 1263 | 5.435 | 2.280 | 12.811 | 1.00 | 16.76 | U2 |
| ATOM | 4488 | C | PRO | 1263 | 8.052 | 2.970 | 15.304 | 1.00 | 26.81 | U2 |
| ATOM | 4489 | O | PRO | 1263 | 7.831 | 2.173 | 16.203 | 1.00 | 26.81 | U2 |
| ATOM | 4490 | N | CYS | 1264 | 8.669 | 4.120 | 15.523 | 1.00 | 23.02 | U2 |
| ATOM | 4492 | CA | CYS | 1264 | 9.284 | 4.414 | 16.807 | 1.00 | 23.02 | U2 |
| ATOM | 4493 | CB | CYS | 1264 | 10.796 | 4.379 | 16.625 | 1.00 | 30.05 | U2 |
| ATOM | 4494 | SG | CYS | 1264 | 11.756 | 4.925 | 18.016 | 1.00 | 30.05 | U2 |
| ATOM | 4495 | C | CYS | 1264 | 8.885 | 5.763 | 17.339 | 1.00 | 23.02 | U2 |
| ATOM | 4496 | O | CYS | 1264 | 9.372 | 6.770 | 16.854 | 1.00 | 23.02 | U2 |
| ATOM | 4497 | N | ILE | 1265 | 8.030 | 5.783 | 18.354 | 1.00 | 22.15 | U2 |
| ATOM | 4499 | CA | ILE | 1265 | 7.561 | 7.020 | 18.981 | 1.00 | 22.15 | U2 |
| ATOM | 4500 | CB | ILE | 1265 | 6.267 | 6.760 | 19.795 | 1.00 | 14.13 | U2 |
| ATOM | 4501 | CG2 | ILE | 1265 | 5.606 | 8.058 | 20.185 | 1.00 | 14.13 | U2 |
| ATOM | 4502 | CG1 | ILE | 1265 | 5.303 | 5.889 | 19.015 | 1.00 | 14.13 | U2 |
| ATOM | 4503 | CD1 | ILE | 1265 | 4.110 | 5.464 | 19.839 | 1.00 | 14.13 | U2 |
| ATOM | 4504 | C | ILE | 1265 | 8.595 | 7.480 | 20.024 | 1.00 | 22.15 | U2 |
| ATOM | 4505 | O | ILE | 1265 | 8.946 | 6.692 | 20.882 | 1.00 | 22.15 | U2 |
| ATOM | 4506 | N | VAL | 1266 | 9.056 | 8.729 | 19.976 | 1.00 | 21.06 | U2 |
| ATOM | 4508 | CA | VAL | 1266 | 10.008 | 9.252 | 20.963 | 1.00 | 21.06 | U2 |
| ATOM | 4509 | CB | VAL | 1266 | 11.348 | 9.661 | 20.336 | 1.00 | 20.34 | U2 |
| ATOM | 4510 | CG1 | VAL | 1266 | 12.232 | 10.274 | 21.363 | 1.00 | 20.34 | U2 |
| ATOM | 4511 | CG2 | VAL | 1266 | 12.058 | 8.460 | 19.735 | 1.00 | 20.34 | U2 |
| ATOM | 4512 | C | VAL | 1266 | 9.324 | 10.498 | 21.505 | 1.00 | 21.06 | U2 |
| ATOM | 4513 | O | VAL | 1266 | 9.256 | 11.515 | 20.810 | 1.00 | 21.06 | U2 |
| ATOM | 4514 | N | SER | 1267 | 8.811 | 10.409 | 22.735 | 1.00 | 22.92 | U2 |
| ATOM | 4516 | CA | SER | 1267 | 8.065 | 11.501 | 23.359 | 1.00 | 22.92 | U2 |
| ATOM | 4517 | CB | SER | 1267 | 6.713 | 10.980 | 23.841 | 1.00 | 11.29 | U2 |
| ATOM | 4518 | OG | SER | 1267 | 6.112 | 11.923 | 24.709 | 1.00 | 11.29 | U2 |
| ATOM | 4520 | C | SER | 1267 | 8.707 | 12.204 | 24.534 | 1.00 | 22.92 | U2 |
| ATOM | 4521 | O | SER | 1267 | 9.003 | 11.590 | 25.547 | 1.00 | 22.92 | U2 |
| ATOM | 4522 | N | MET | 1268 | 8.878 | 13.498 | 24.438 | 1.00 | 16.21 | U2 |
| ATOM | 4524 | CA | MET | 1268 | 9.437 | 14.246 | 25.542 | 1.00 | 16.21 | U2 |
| ATOM | 4525 | CB | MET | 1268 | 10.745 | 14.905 | 25.155 | 1.00 | 38.94 | U2 |
| ATOM | 4526 | CG | MET | 1268 | 11.806 | 13.871 | 24.995 | 1.00 | 38.94 | U2 |
| ATOM | 4527 | SD | MET | 1268 | 13.324 | 14.509 | 24.429 | 1.00 | 38.94 | U2 |
| ATOM | 4528 | CE | MET | 1268 | 13.437 | 13.632 | 22.912 | 1.00 | 38.94 | U2 |
| ATOM | 4529 | C | MET | 1268 | 8.381 | 15.252 | 25.866 | 1.00 | 16.21 | U2 |
| ATOM | 4530 | O | MET | 1268 | 8.650 | 16.412 | 26.146 | 1.00 | 16.21 | U2 |
| ATOM | 4531 | N | LEU | 1269 | 7.153 | 14.784 | 25.744 | 1.00 | 22.65 | U2 |
| ATOM | 4533 | CA | LEU | 1269 | 6.005 | 15.599 | 26.019 | 1.00 | 22.65 | U2 |
| ATOM | 4534 | CB | LEU | 1269 | 4.772 | 15.027 | 25.315 | 1.00 | 26.26 | U2 |
| ATOM | 4535 | CG | LEU | 1269 | 4.642 | 15.091 | 23.790 | 1.00 | 26.26 | U2 |
| ATOM | 4536 | CD1 | LEU | 1269 | 3.171 | 14.900 | 23.400 | 1.00 | 26.26 | U2 |
| ATOM | 4537 | CD2 | LEU | 1269 | 5.120 | 16.446 | 23.310 | 1.00 | 26.26 | U2 |
| ATOM | 4538 | C | LEU | 1269 | 5.807 | 15.550 | 27.520 | 1.00 | 22.65 | U2 |
| ATOM | 4539 | O | LEU | 1269 | 6.208 | 14.581 | 28.177 | 1.00 | 22.65 | U2 |
| ATOM | 4540 | N | THR | 1270 | 5.196 | 16.591 | 28.069 | 1.00 | 26.78 | U2 |
| ATOM | 4542 | CA | THR | 1270 | 4.956 | 16.623 | 29.486 | 1.00 | 26.78 | U2 |
| ATOM | 4543 | CB | THR | 1270 | 5.548 | 17.846 | 30.117 | 1.00 | 22.54 | U2 |
| ATOM | 4544 | OG1 | THR | 1270 | 4.840 | 18.980 | 29.639 | 1.00 | 22.54 | U2 |
| ATOM | 4546 | CG2 | THR | 1270 | 7.022 | 17.984 | 29.763 | 1.00 | 22.54 | U2 |
| ATOM | 4547 | C | THR | 1270 | 3.474 | 16.582 | 29.813 | 1.00 | 26.78 | U2 |
| ATOM | 4548 | O | THR | 1270 | 3.108 | 16.801 | 30.963 | 1.00 | 26.78 | U2 |
| ATOM | 4549 | N | LYS | 1271 | 2.614 | 16.374 | 28.812 | 1.00 | 24.75 | U2 |
| ATOM | 4551 | CA | LYS | 1271 | 1.171 | 16.261 | 29.044 | 1.00 | 24.75 | U2 |
| ATOM | 4552 | CB | LYS | 1271 | 0.476 | 17.615 | 29.096 | 1.00 | 26.34 | U2 |
| ATOM | 4553 | CG | LYS | 1271 | 1.109 | 18.657 | 29.970 | 1.00 | 26.34 | U2 |
| ATOM | 4554 | CD | LYS | 1271 | 0.292 | 19.924 | 29.919 | 1.00 | 26.34 | U2 |
| ATOM | 4555 | CE | LYS | 1271 | 1.033 | 21.074 | 30.531 | 1.00 | 26.34 | U2 |

TABLE 1-continued

Structure coordinates of CPP32

| ATOM | 4556 | NZ | LYS | 1271 | 0.311 | 22.324 | 30.195 | 1.00 | 26.34 | U2 |
|---|---|---|---|---|---|---|---|---|---|---|
| ATOM | 4560 | C | LYS | 1271 | 0.500 | 15.435 | 27.937 | 1.00 | 24.75 | U2 |
| ATOM | 4561 | O | LYS | 1271 | 1.100 | 15.139 | 26.893 | 1.00 | 24.75 | U2 |
| ATOM | 4562 | N | GLU | 1272 | −0.753 | 15.070 | 28.169 | 1.00 | 24.44 | U2 |
| ATOM | 4564 | CA | GLU | 1272 | −1.521 | 14.304 | 27.205 | 1.00 | 24.44 | U2 |
| ATOM | 4565 | CB | GLU | 1272 | −2.671 | 13.613 | 27.905 | 1.00 | 36.68 | U2 |
| ATOM | 4566 | CG | GLU | 1272 | −2.186 | 12.761 | 29.049 | 1.00 | 36.68 | U2 |
| ATOM | 4567 | CD | GLU | 1272 | −3.301 | 12.130 | 29.803 | 1.00 | 36.68 | U2 |
| ATOM | 4568 | OE1 | GLU | 1272 | −4.466 | 12.512 | 29.551 | 1.00 | 36.68 | U2 |
| ATOM | 4569 | OE2 | GLU | 1272 | −3.019 | 11.244 | 30.639 | 1.00 | 36.68 | U2 |
| ATOM | 4570 | C | GLU | 1272 | −2.013 | 15.281 | 26.146 | 1.00 | 24.44 | U2 |
| ATOM | 4571 | O | GLU | 1272 | −2.377 | 16.428 | 26.450 | 1.00 | 24.44 | U2 |
| ATOM | 4572 | N | LEU | 1273 | −2.021 | 14.821 | 24.903 | 1.00 | 32.07 | U2 |
| ATOM | 4574 | CA | LEU | 1273 | −2.380 | 15.653 | 23.774 | 1.00 | 32.07 | U2 |
| ATOM | 4575 | CB | LEU | 1273 | −1.217 | 15.613 | 22.791 | 1.00 | 34.42 | U2 |
| ATOM | 4576 | CG | LEU | 1273 | −1.197 | 16.462 | 21.539 | 1.00 | 34.42 | U2 |
| ATOM | 4577 | CD1 | LEU | 1273 | −1.646 | 17.857 | 21.864 | 1.00 | 34.42 | U2 |
| ATOM | 4578 | CD2 | LEU | 1273 | 0.213 | 16.469 | 20.995 | 1.00 | 34.42 | U2 |
| ATOM | 4579 | C | LEU | 1273 | −3.636 | 15.177 | 23.109 | 1.00 | 32.07 | U2 |
| ATOM | 4580 | O | LEU | 1273 | −3.682 | 14.063 | 22.593 | 1.00 | 32.07 | U2 |
| ATOM | 4581 | N | TYR | 1274 | −4.662 | 16.014 | 23.139 | 1.00 | 33.84 | U2 |
| ATOM | 4583 | CA | TYR | 1274 | −5.945 | 15.694 | 22.516 | 1.00 | 33.84 | U2 |
| ATOM | 4584 | CB | TYR | 1274 | −7.084 | 15.846 | 23.531 | 1.00 | 28.66 | U2 |
| ATOM | 4585 | CG | TYR | 1274 | −7.016 | 14.851 | 24.665 | 1.00 | 28.66 | U2 |
| ATOM | 4586 | CD1 | TYR | 1274 | −6.415 | 15.184 | 25.878 | 1.00 | 28.66 | U2 |
| ATOM | 4587 | CE1 | TYR | 1274 | −6.290 | 14.257 | 26.900 | 1.00 | 28.66 | U2 |
| ATOM | 4588 | CD2 | TYR | 1274 | −7.498 | 13.572 | 24.507 | 1.00 | 28.66 | U2 |
| ATOM | 4589 | CE2 | TYR | 1274 | −7.376 | 12.635 | 25.528 | 1.00 | 28.66 | U2 |
| ATOM | 4590 | CZ | TYR | 1274 | −6.769 | 12.984 | 26.716 | 1.00 | 28.66 | U2 |
| ATOM | 4591 | OH | TYR | 1274 | −6.624 | 12.041 | 27.701 | 1.00 | 28.66 | U2 |
| ATOM | 4593 | C | TYR | 1274 | −6.226 | 16.575 | 21.297 | 1.00 | 33.84 | U2 |
| ATOM | 4594 | O | TYR | 1274 | −6.206 | 17.804 | 21.378 | 1.00 | 33.84 | U2 |
| ATOM | 4595 | N | PHE | 1275 | −6.509 | 15.946 | 20.166 | 1.00 | 70.10 | U2 |
| ATOM | 4597 | CA | PHE | 1275 | −6.793 | 16.702 | 18.955 | 1.00 | 70.10 | U2 |
| ATOM | 4598 | CB | PHE | 1275 | −6.401 | 15.885 | 17.722 | 1.00 | 27.33 | U2 |
| ATOM | 4599 | CG | PHE | 1275 | −4.934 | 15.933 | 17.432 | 1.00 | 27.33 | U2 |
| ATOM | 4600 | CD1 | PHE | 1275 | −4.212 | 14.787 | 17.227 | 1.00 | 27.33 | U2 |
| ATOM | 4601 | CD2 | PHE | 1275 | −4.266 | 17.142 | 17.428 | 1.00 | 27.33 | U2 |
| ATOM | 4602 | CE1 | PHE | 1275 | −2.839 | 14.838 | 17.029 | 1.00 | 27.33 | U2 |
| ATOM | 4603 | CE2 | PHE | 1275 | −2.889 | 17.199 | 17.231 | 1.00 | 27.33 | U2 |
| ATOM | 4604 | CZ | PHE | 1275 | −2.179 | 16.044 | 17.033 | 1.00 | 27.33 | U2 |
| ATOM | 4605 | C | PHE | 1275 | −8.241 | 17.192 | 18.902 | 1.00 | 70.10 | U2 |
| ATOM | 4606 | O | PHE | 1275 | −8.980 | 16.904 | 17.964 | 1.00 | 70.10 | U2 |
| ATOM | 4607 | N | TYR | 1276 | −8.633 | 17.916 | 19.947 | 1.00 | 95.91 | U2 |
| ATOM | 4609 | CA | TYR | 1276 | −9.975 | 18.488 | 20.099 | 1.00 | 95.91 | U2 |
| ATOM | 4610 | CB | TYR | 1276 | −11.093 | 17.423 | 19.957 | 1.00 | 59.61 | U2 |
| ATOM | 4611 | CG | TYR | 1276 | −11.119 | 16.285 | 20.971 | 1.00 | 59.61 | U2 |
| ATOM | 4612 | CD1 | TYR | 1276 | −11.752 | 16.435 | 22.207 | 1.00 | 59.61 | U2 |
| ATOM | 4613 | CE1 | TYR | 1276 | −11.824 | 15.375 | 23.118 | 1.00 | 59.61 | U2 |
| ATOM | 4614 | CD2 | TYR | 1276 | −10.555 | 15.038 | 20.671 | 1.00 | 59.61 | U2 |
| ATOM | 4615 | CE2 | TYR | 1276 | −10.625 | 13.974 | 21.578 | 1.00 | 59.61 | U2 |
| ATOM | 4616 | CZ | TYR | 1276 | −11.260 | 14.155 | 22.796 | 1.00 | 59.61 | U2 |
| ATOM | 4617 | OH | TYR | 1276 | −11.333 | 13.114 | 23.694 | 1.00 | 59.61 | U2 |
| ATOM | 4619 | C | TYR | 1276 | −10.063 | 19.238 | 21.436 | 1.00 | 95.91 | U2 |
| ATOM | 4620 | O | TYR | 1276 | −9.030 | 19.522 | 22.051 | 1.00 | 95.91 | U2 |
| ATOM | 4621 | N | HIS | 1277 | −11.281 | 19.574 | 21.861 | 1.00 | 107.51 | U2 |
| ATOM | 4623 | CA | HIS | 1277 | −11.504 | 20.305 | 23.109 | 1.00 | 107.51 | U2 |
| ATOM | 4624 | CB | HIS | 1277 | −13.011 | 20.561 | 23.307 | 1.00 | 122.49 | U2 |
| ATOM | 4625 | CG | HIS | 1277 | −13.531 | 20.201 | 24.669 | 1.00 | 122.49 | U2 |
| ATOM | 4626 | CD2 | HIS | 1277 | −14.584 | 19.434 | 25.044 | 1.00 | 122.49 | U2 |
| ATOM | 4627 | ND1 | HIS | 1277 | −12.952 | 20.647 | 25.838 | 1.00 | 122.49 | U2 |
| ATOM | 4629 | CE1 | HIS | 1277 | −13.623 | 20.174 | 26.873 | 1.00 | 122.49 | U2 |
| ATOM | 4630 | NE2 | HIS | 1277 | −14.619 | 19.435 | 26.418 | 1.00 | 122.49 | U2 |
| ATOM | 4632 | C | HIS | 1277 | −10.891 | 19.624 | 24.334 | 1.00 | 107.51 | U2 |
| ATOM | 4633 | O | HIS | 1277 | −11.040 | 18.393 | 24.479 | 1.00 | 107.51 | U2 |
| ATOM | 4634 | OT | HIS | 1277 | −10.320 | 20.354 | 25.171 | 1.00 | 122.49 | U2 |
| ATOM | 4635 | CA | ACE | 989 | 23.971 | 17.297 | 46.584 | 1.00 | 44.53 | INH1 |
| ATOM | 4636 | C | ACE | 989 | 23.746 | 16.563 | 45.280 | 1.00 | 44.53 | INH1 |
| ATOM | 4637 | O | ACE | 989 | 23.831 | 15.337 | 45.234 | 1.00 | 44.53 | INH1 |
| ATOM | 4638 | N | ASP | 990 | 23.525 | 17.331 | 44.211 | 1.00 | 36.27 | INH1 |
| ATOM | 4640 | CA | ASP | 990 | 23.252 | 16.802 | 42.876 | 1.00 | 36.27 | INH1 |
| ATOM | 4641 | CB | ASP | 990 | 22.327 | 17.749 | 42.104 | 1.00 | 28.62 | INH1 |
| ATOM | 4642 | CG | ASP | 990 | 20.939 | 17.849 | 42.704 | 1.00 | 28.62 | INH1 |
| ATOM | 4643 | OD1 | ASP | 990 | 20.400 | 18.971 | 42.774 | 1.00 | 28.62 | INH1 |
| ATOM | 4644 | OD2 | ASP | 990 | 20.371 | 16.816 | 43.100 | 1.00 | 28.62 | INH1 |
| ATOM | 4645 | C | ASP | 990 | 24.486 | 16.546 | 42.027 | 1.00 | 36.27 | INH1 |
| ATOM | 4646 | O | ASP | 990 | 25.236 | 17.459 | 41.707 | 1.00 | 36.27 | INH1 |

TABLE 1-continued

Structure coordinates of CPP32

| ATOM | 4647 | N | VAL | 991 | 24.660 | 15.294 | 41.633 | 1.00 | 42.41 | INH1 |
|---|---|---|---|---|---|---|---|---|---|---|
| ATOM | 4649 | CA | VAL | 991 | 25.752 | 14.865 | 40.780 | 1.00 | 42.41 | INH1 |
| ATOM | 4650 | CB | VAL | 991 | 26.675 | 13.971 | 41.605 | 1.00 | 34.04 | INH1 |
| ATOM | 4651 | CG1 | VAL | 991 | 27.369 | 12.938 | 40.751 | 1.00 | 34.04 | INH1 |
| ATOM | 4652 | CG2 | VAL | 991 | 27.697 | 14.851 | 42.286 | 1.00 | 34.04 | INH1 |
| ATOM | 4653 | C | VAL | 991 | 25.227 | 14.176 | 39.479 | 1.00 | 42.41 | INH1 |
| ATOM | 4654 | O | VAL | 991 | 24.162 | 13.558 | 39.494 | 1.00 | 42.41 | INH1 |
| ATOM | 4655 | N | ALA | 992 | 25.926 | 14.359 | 38.350 | 1.00 | 32.32 | INH1 |
| ATOM | 4657 | CA | ALA | 992 | 25.519 | 13.760 | 37.056 | 1.00 | 32.32 | INH1 |
| ATOM | 4658 | CB | ALA | 992 | 26.095 | 14.542 | 35.889 | 1.00 | 7.78 | INH1 |
| ATOM | 4659 | C | ALA | 992 | 25.950 | 12.308 | 36.955 | 1.00 | 32.32 | INH1 |
| ATOM | 4660 | O | ALA | 992 | 26.938 | 11.931 | 37.578 | 1.00 | 32.32 | INH1 |
| ATOM | 4661 | N | ASK | 993 | 25.230 | 11.510 | 36.156 | 1.00 | 32.83 | INH1 |
| ATOM | 4663 | CA | ASK | 993 | 25.528 | 10.079 | 35.989 | 1.00 | 32.83 | INH1 |
| ATOM | 4664 | CB | ASK | 993 | 24.240 | 9.273 | 35.906 | 1.00 | 22.74 | INH1 |
| ATOM | 4665 | CG | ASK | 993 | 23.805 | 8.755 | 37.242 | 1.00 | 22.74 | INH1 |
| ATOM | 4666 | OD1 | ASK | 993 | 24.703 | 8.372 | 38.002 | 1.00 | 22.74 | INH1 |
| ATOM | 4667 | OD2 | ASK | 993 | 22.584 | 8.693 | 37.530 | 1.00 | 22.74 | INH1 |
| ATOM | 4668 | CM | ASK | 993 | 26.778 | 10.756 | 33.728 | 1.00 | 22.74 | INH1 |
| ATOM | 4669 | C | ASK | 993 | 26.429 | 9.754 | 34.798 | 1.00 | 32.83 | INH1 |
| ATOM | 4670 | O | ASK | 993 | 25.994 | 9.051 | 33.855 | 1.00 | 32.83 | INH1 |
| ATOM | 4671 | CA | ACE | 1989 | 6.515 | −1.429 | −5.711 | 1.00 | 63.02 | INH2 |
| ATOM | 4672 | C | ACE | 1989 | 7.059 | −0.964 | −4.381 | 1.00 | 63.02 | INH2 |
| ATOM | 4673 | O | ACE | 1989 | 7.106 | 0.238 | −4.106 | 1.00 | 63.02 | INH2 |
| ATOM | 4674 | N | ASP | 1990 | 7.462 | −1.918 | −3.546 | 1.00 | 59.05 | INH2 |
| ATOM | 4676 | CA | ASP | 1990 | 8.003 | −1.611 | −2.223 | 1.00 | 59.05 | INH2 |
| ATOM | 4677 | CB | ASP | 1990 | 7.736 | −2.765 | −1.252 | 1.00 | 48.41 | INH2 |
| ATOM | 4678 | CG | ASP | 1990 | 6.369 | −2.668 | −0.575 | 1.00 | 48.41 | INH2 |
| ATOM | 4679 | OD1 | ASP | 1990 | 5.977 | −3.642 | 0.096 | 1.00 | 48.41 | INH2 |
| ATOM | 4680 | OD2 | ASP | 1990 | 5.686 | −1.627 | −0.688 | 1.00 | 48.41 | INH2 |
| ATOM | 4681 | C | ASP | 1990 | 9.482 | −1.227 | −2.210 | 1.00 | 59.05 | INH2 |
| ATOM | 4682 | O | ASP | 1990 | 10.365 | −2.081 | −2.339 | 1.00 | 59.05 | INH2 |
| ATOM | 4683 | N | VAL | 1991 | 9.725 | 0.071 | −2.061 | 1.00 | 55.12 | INH2 |
| ATOM | 4685 | CA | VAL | 1991 | 11.063 | 0.647 | −2.016 | 1.00 | 55.12 | INH2 |
| ATOM | 4686 | CB | VAL | 1991 | 11.131 | 1.971 | −2.806 | 1.00 | 32.75 | INH2 |
| ATOM | 4687 | CG1 | VAL | 1991 | 12.264 | 1.933 | −3.776 | 1.00 | 32.75 | INH2 |
| ATOM | 4688 | CG2 | VAL | 1991 | 9.823 | 2.259 | −3.509 | 1.00 | 32.75 | INH2 |
| ATOM | 4689 | C | VAL | 1991 | 11.363 | 0.986 | −0.550 | 1.00 | 55.12 | INH2 |
| ATOM | 4690 | O | VAL | 1991 | 10.534 | 0.718 | 0.331 | 1.00 | 55.12 | INH2 |
| ATOM | 4691 | N | ALA | 1992 | 12.503 | 1.637 | −0.308 | 1.00 | 50.37 | INH2 |
| ATOM | 4693 | CA | ALA | 1992 | 12.929 | 2.031 | 1.032 | 1.00 | 50.37 | INH2 |
| ATOM | 4694 | CB | ALA | 1992 | 13.999 | 1.069 | 1.532 | 1.00 | 33.59 | INH2 |
| ATOM | 4695 | C | ALA | 1992 | 13.484 | 3.461 | 1.025 | 1.00 | 50.37 | INH2 |
| ATOM | 4696 | O | ALA | 1992 | 14.171 | 3.845 | 0.070 | 1.00 | 50.37 | INH2 |
| ATOM | 4697 | N | ASK | 1993 | 13.196 | 4.248 | 2.068 | 1.00 | 35.37 | INH2 |
| ATOM | 4699 | CA | ASK | 1993 | 13.700 | 5.620 | 2.151 | 1.00 | 35.37 | INH2 |
| ATOM | 4700 | CB | ASK | 1993 | 12.624 | 6.593 | 2.637 | 1.00 | 43.34 | INH2 |
| ATOM | 4701 | CG | ASK | 1993 | 11.455 | 6.687 | 1.696 | 1.00 | 43.34 | INH2 |
| ATOM | 4702 | OD1 | ASK | 1993 | 10.458 | 7.363 | 2.031 | 1.00 | 43.34 | INH2 |
| ATOM | 4703 | OD2 | ASK | 1993 | 11.532 | 6.081 | 0.617 | 1.00 | 43.34 | INH2 |
| ATOM | 4704 | CM | ASK | 1993 | 15.926 | 4.628 | 3.322 | 1.00 | 43.34 | INH2 |
| ATOM | 4705 | C | ASK | 1993 | 14.912 | 5.729 | 3.070 | 1.00 | 35.37 | INH2 |
| ATOM | 4706 | O | ASK | 1993 | 15.690 | 6.699 | 2.883 | 1.00 | 35.37 | INH2 |
| ATOM | 4707 | O1 | HOH | 2001 | 9.093 | 9.255 | 31.359 | 1.00 | 15.25 | WAT |
| ATOM | 4710 | O1 | HOH | 2002 | 1.245 | 12.683 | 25.242 | 1.00 | 14.90 | WAT |
| ATOM | 4713 | O1 | HOH | 2003 | −1.523 | 0.542 | 34.547 | 1.00 | 17.33 | WAT |
| ATOM | 4716 | O1 | HOH | 2004 | 3.714 | 11.494 | 25.793 | 1.00 | 19.28 | WAT |
| ATOM | 4719 | O1 | HOH | 2005 | 0.750 | −12.340 | 25.214 | 1.00 | 37.74 | WAT |
| ATOM | 4722 | O1 | HOH | 2006 | 18.988 | 7.761 | 30.479 | 1.00 | 15.60 | WAT |
| ATOM | 4725 | O1 | HOH | 2007 | 3.127 | 2.998 | 23.194 | 1.00 | 29.56 | WAT |
| ATOM | 4728 | O1 | HOH | 2008 | 17.668 | 10.994 | 36.740 | 1.00 | 17.54 | WAT |
| ATOM | 4731 | O1 | HOH | 2009 | 14.360 | 7.529 | 44.761 | 1.00 | 27.44 | WAT |
| ATOM | 4734 | O1 | HOH | 2010 | −0.925 | 12.182 | 32.051 | 1.00 | 26.95 | WAT |
| ATOM | 4737 | O1 | HOH | 2011 | 6.771 | 3.640 | 6.143 | 1.00 | 28.59 | WAT |
| ATOM | 4740 | O1 | HOH | 2012 | 10.937 | 7.900 | 30.205 | 1.00 | 25.81 | WAT |
| ATOM | 4743 | O1 | HOH | 2013 | 22.696 | 5.648 | 28.126 | 1.00 | 25.35 | WAT |
| ATOM | 4746 | O1 | HOH | 2014 | 9.496 | −11.955 | 32.067 | 1.00 | 23.75 | WAT |
| ATOM | 4749 | O1 | HOH | 2015 | 17.397 | −9.424 | 45.784 | 1.00 | 43.99 | WAT |
| ATOM | 4752 | O1 | HOH | 2016 | 16.427 | 8.696 | 21.831 | 1.00 | 29.83 | WAT |
| ATOM | 4755 | O1 | HOH | 2017 | 1.683 | 1.591 | 25.100 | 1.00 | 26.41 | WAT |
| ATOM | 4758 | O1 | HOH | 2018 | 30.003 | 9.182 | 34.551 | 1.00 | 34.73 | WAT |
| ATOM | 4761 | O1 | HOH | 2019 | −1.136 | 6.902 | 1.735 | 1.00 | 45.05 | WAT |
| ATOM | 4764 | O1 | HOH | 2020 | 21.234 | 5.263 | 40.715 | 1.00 | 31.79 | WAT |
| ATOM | 4767 | O1 | HOH | 2021 | −10.888 | −3.916 | 33.302 | 1.00 | 31.30 | WAT |
| ATOM | 4770 | O1 | HOH | 2022 | 8.643 | 6.166 | 45.894 | 1.00 | 48.58 | WAT |
| ATOM | 4773 | O1 | HOH | 2023 | 5.734 | −4.580 | 9.091 | 1.00 | 42.20 | WAT |
| ATOM | 4776 | O1 | HOH | 2024 | 6.514 | 25.022 | −3.627 | 1.00 | 56.00 | WAT |

TABLE 1-continued

Structure coordinates of CPP32

| ATOM | 4779 | O1 | HOH | 2025 | 14.413 | 19.191 | 35.962 | 1.00 | 32.83 | WAT |
|---|---|---|---|---|---|---|---|---|---|---|
| ATOM | 4782 | O1 | HOH | 2026 | 18.256 | 24.139 | 47.024 | 1.00 | 44.74 | WAT |
| ATOM | 4785 | O1 | HOH | 2027 | −2.344 | −4.052 | 29.292 | 1.00 | 37.92 | WAT |
| ATOM | 4788 | O1 | HOH | 2028 | 2.367 | −4.559 | 2.332 | 1.00 | 37.53 | WAT |
| ATOM | 4791 | O1 | HOH | 2029 | 8.631 | 23.502 | 25.519 | 1.00 | 26.11 | WAT |
| ATOM | 4794 | O1 | HOH | 2030 | −6.896 | 7.814 | 24.986 | 1.00 | 26.27 | WAT |
| ATOM | 4797 | O1 | HOH | 2031 | 21.355 | 8.917 | 51.967 | 1.00 | 56.52 | WAT |
| ATOM | 4800 | O1 | HOH | 2032 | 11.618 | −1.439 | 11.105 | 1.00 | 37.41 | WAT |
| ATOM | 4803 | O1 | HOH | 2033 | 16.094 | −5.394 | 20.285 | 1.00 | 45.38 | WAT |
| ATOM | 4806 | O1 | HOH | 2034 | 15.159 | 7.219 | 18.683 | 1.00 | 29.00 | WAT |
| ATOM | 4809 | O1 | HOH | 2035 | −7.178 | 9.095 | 27.657 | 1.00 | 49.39 | WAT |
| ATOM | 4812 | O1 | HOH | 2036 | 16.294 | 9.946 | 9.151 | 1.00 | 46.60 | WAT |
| ATOM | 4815 | O1 | HOH | 2037 | 16.489 | 14.814 | 45.040 | 1.00 | 33.22 | WAT |
| ATOM | 4818 | O1 | HOH | 2038 | 3.855 | 0.252 | 44.075 | 1.00 | 41.40 | WAT |
| ATOM | 4821 | O1 | HOH | 2039 | 12.554 | −3.066 | 13.029 | 1.00 | 23.34 | WAT |
| ATOM | 4824 | O1 | HOH | 2040 | −3.819 | −11.952 | 22.240 | 1.00 | 52.94 | WAT |
| ATOM | 4827 | O1 | HOH | 2041 | −0.017 | 14.103 | 38.931 | 1.00 | 52.17 | WAT |
| ATOM | 4830 | O1 | HOH | 2042 | 23.941 | 0.676 | 21.876 | 1.00 | 32.96 | WAT |
| ATOM | 4833 | O1 | HOH | 2043 | 21.093 | 19.120 | 32.285 | 1.00 | 28.77 | WAT |
| ATOM | 4836 | O1 | HOH | 2044 | 16.854 | 3.530 | 22.030 | 1.00 | 34.78 | WAT |
| ATOM | 4839 | O1 | HOH | 2045 | 30.672 | 10.217 | 45.014 | 1.00 | 55.19 | WAT |
| ATOM | 4842 | O1 | HOH | 2046 | −8.162 | 4.138 | 25.108 | 1.00 | 52.53 | WAT |
| ATOM | 4845 | O1 | HOH | 2047 | 20.814 | 24.323 | 27.436 | 1.00 | 35.09 | WAT |
| ATOM | 4848 | O1 | HOH | 2048 | 10.206 | 27.367 | 37.710 | 1.00 | 60.29 | WAT |
| ATOM | 4851 | O1 | HOH | 2049 | 11.983 | 7.581 | 10.092 | 1.00 | 37.07 | WAT |
| ATOM | 4854 | O1 | HOH | 2050 | −14.320 | 16.628 | 20.310 | 1.00 | 61.19 | WAT |
| ATOM | 4857 | O1 | HOH | 2051 | 20.455 | 28.059 | 33.565 | 1.00 | 43.72 | WAT |
| ATOM | 4860 | O1 | HOH | 2052 | −9.827 | 8.520 | 37.642 | 1.00 | 57.43 | WAT |
| ATOM | 4863 | O1 | HOH | 2053 | 35.771 | 5.652 | 30.692 | 1.00 | 56.13 | WAT |
| ATOM | 4866 | O1 | HOH | 2054 | 12.960 | 5.624 | −1.587 | 1.00 | 60.64 | WAT |
| ATOM | 4869 | O1 | HOH | 2055 | −12.411 | 0.890 | 20.690 | 1.00 | 55.35 | WAT |
| ATOM | 4872 | O1 | HOH | 2056 | 12.573 | 24.582 | 38.471 | 1.00 | 41.39 | WAT |
| ATOM | 4875 | O1 | HOH | 2057 | 16.573 | 10.135 | 11.832 | 1.00 | 41.21 | WAT |
| ATOM | 4878 | O1 | HOH | 2058 | 2.459 | −11.756 | 39.322 | 1.00 | 41.35 | WAT |
| ATOM | 4881 | O1 | HOH | 2059 | 14.088 | −14.176 | 46.749 | 1.00 | 63.90 | WAT |
| ATOM | 4884 | O1 | HOH | 2060 | 23.382 | 5.048 | 48.371 | 1.00 | 47.42 | WAT |
| ATOM | 4887 | O1 | HOH | 2061 | −0.738 | 24.179 | 23.931 | 1.00 | 35.57 | WAT |
| ATOM | 4890 | O1 | HOH | 2062 | 10.416 | −2.568 | 49.873 | 1.00 | 31.79 | WAT |
| ATOM | 4893 | O1 | HOH | 2063 | 0.291 | −6.062 | 17.764 | 1.00 | 37.65 | WAT |
| ATOM | 4896 | O1 | HOH | 2064 | 14.230 | −1.517 | 19.153 | 1.00 | 48.21 | WAT |
| ATOM | 4899 | O1 | HOH | 2065 | 7.245 | −19.194 | 35.900 | 1.00 | 30.13 | WAT |
| ATOM | 4902 | O1 | HOH | 2066 | −7.991 | −5.333 | 31.364 | 1.00 | 53.39 | WAT |
| ATOM | 4905 | O1 | HOH | 2067 | 19.505 | 1.545 | 24.335 | 1.00 | 55.96 | WAT |
| ATOM | 4908 | O1 | HOH | 2068 | 9.996 | −20.990 | 24.686 | 1.00 | 54.89 | WAT |
| ATOM | 4911 | O1 | HOH | 2069 | −2.440 | 30.688 | 28.850 | 1.00 | 59.31 | WAT |
| ATOM | 4914 | O1 | HOH | 2070 | 39.596 | −1.937 | 34.877 | 1.00 | 49.79 | WAT |
| ATOM | 4917 | O1 | HOH | 2071 | 13.505 | 28.391 | 2.119 | 1.00 | 53.83 | WAT |
| ATOM | 4920 | O1 | HOH | 2072 | 0.791 | −9.143 | 21.463 | 1.00 | 46.05 | WAT |
| ATOM | 4923 | O1 | HOH | 2073 | 18.641 | 6.960 | 2.224 | 1.00 | 60.02 | WAT |
| ATOM | 4926 | O1 | HOH | 2074 | −4.704 | 7.102 | 51.137 | 1.00 | 67.43 | WAT |
| ATOM | 4929 | O1 | HOH | 2075 | 2.300 | 23.486 | 29.239 | 1.00 | 40.52 | WAT |
| ATOM | 4932 | O1 | HOH | 2076 | −2.389 | −4.567 | 2.623 | 1.00 | 59.72 | WAT |
| ATOM | 4935 | O1 | HOH | 2077 | 16.027 | 21.007 | −5.994 | 1.00 | 53.41 | WAT |
| ATOM | 4938 | O1 | HOH | 2078 | 3.627 | 9.930 | −6.329 | 1.00 | 55.00 | WAT |
| ATOM | 4941 | O1 | HOH | 2079 | 33.066 | 18.795 | 33.898 | 1.00 | 50.31 | WAT |
| ATOM | 4944 | O1 | HOH | 2080 | 2.981 | 15.384 | 38.188 | 1.00 | 46.69 | WAT |
| ATOM | 4947 | O1 | HOH | 2081 | 19.369 | −14.249 | 37.553 | 1.00 | 50.63 | WAT |
| ATOM | 4950 | O1 | HOH | 2082 | 25.706 | −0.916 | 45.005 | 1.00 | 56.31 | WAT |
| ATOM | 4953 | O1 | HOH | 2083 | 17.124 | 19.627 | 19.728 | 1.00 | 48.83 | WAT |
| ATOM | 4956 | O1 | HOH | 2084 | 24.343 | 4.352 | 19.926 | 1.00 | 58.49 | WAT |
| ATOM | 4959 | O1 | HOH | 2085 | 18.765 | 24.138 | 42.288 | 1.00 | 38.69 | WAT |
| ATOM | 4962 | O1 | HOH | 2086 | 6.203 | 7.718 | 47.174 | 1.00 | 53.22 | WAT |
| ATOM | 4965 | O1 | HOH | 2087 | 13.000 | −2.890 | −2.514 | 1.00 | 53.20 | WAT |
| ATOM | 4968 | O1 | HOH | 2088 | 5.375 | 21.804 | 29.712 | 1.00 | 38.00 | WAT |
| ATOM | 4971 | O1 | HOH | 2089 | 28.055 | 7.570 | 22.918 | 1.00 | 50.65 | WAT |
| ATOM | 4974 | O1 | HOH | 2090 | 0.247 | 26.143 | 26.469 | 1.00 | 33.72 | WAT |
| ATOM | 4977 | O1 | HOH | 2091 | −4.241 | −0.280 | 15.489 | 1.00 | 47.46 | WAT |
| ATOM | 4980 | O1 | HOH | 2092 | 20.324 | 7.346 | 17.321 | 1.00 | 69.07 | WAT |
| ATOM | 4983 | O1 | HOH | 2093 | 22.218 | −9.679 | 16.770 | 1.00 | 42.14 | WAT |
| ATOM | 4986 | O1 | HOH | 2094 | 36.554 | 2.024 | 51.327 | 1.00 | 63.46 | WAT |
| ATOM | 4989 | O1 | HOH | 2095 | 23.400 | −6.879 | 16.865 | 1.00 | 62.12 | WAT |
| ATOM | 4992 | O1 | HOH | 2096 | −9.110 | −7.874 | 4.651 | 1.00 | 61.40 | WAT |
| ATOM | 4995 | O1 | HOH | 2097 | 31.417 | −14.626 | 41.958 | 1.00 | 58.76 | WAT |
| ATOM | 4998 | O1 | HOH | 2098 | 20.915 | 5.167 | 22.539 | 1.00 | 48.78 | WAT |
| ATOM | 5001 | O1 | HOH | 2099 | 28.948 | 11.361 | 43.114 | 1.00 | 46.44 | WAT |
| ATOM | 5004 | O1 | HOH | 2100 | −0.845 | −5.767 | 46.399 | 1.00 | 53.36 | WAT |
| ATOM | 5007 | O1 | HOH | 2101 | 14.876 | −19.583 | 17.048 | 1.00 | 57.94 | WAT |

TABLE 1-continued

Structure coordinates of CPP32

| ATOM | 5010 | O1 | HOH | 2102 | 0.499 | −9.839 | 24.783 | 1.00 | 35.46 | WAT |
|---|---|---|---|---|---|---|---|---|---|---|
| ATOM | 5013 | O1 | HOH | 2103 | 11.936 | 6.043 | 56.094 | 1.00 | 57.19 | WAT |
| ATOM | 5016 | O1 | HOH | 2104 | −5.548 | 23.539 | −0.734 | 1.00 | 57.95 | WAT |
| ATOM | 5019 | O1 | HOH | 2105 | 17.889 | −5.351 | 47.811 | 1.00 | 50.39 | WAT |
| ATOM | 5022 | O1 | HOH | 2106 | −4.432 | −7.782 | 37.602 | 1.00 | 43.62 | WAT |
| ATOM | 5025 | O1 | HOH | 2107 | 0.041 | 34.026 | 16.418 | 1.00 | 31.98 | WAT |
| ATOM | 5028 | O1 | HOH | 2108 | 25.196 | 22.424 | 26.908 | 1.00 | 41.14 | WAT |
| ATOM | 5031 | O1 | HOH | 2109 | −4.432 | 6.894 | 5.421 | 1.00 | 72.94 | WAT |
| ATOM | 5034 | O1 | HOH | 2110 | 17.368 | 19.048 | 43.177 | 1.00 | 45.14 | WAT |
| ATOM | 5037 | O1 | HOH | 2111 | 32.495 | −5.813 | 39.718 | 1.00 | 39.64 | WAT |
| ATOM | 5040 | O1 | HOH | 2112 | 5.842 | 22.547 | 42.817 | 1.00 | 57.24 | WAT |
| ATOM | 5043 | O1 | HOH | 2113 | −14.379 | −10.119 | 33.949 | 1.00 | 55.63 | WAT |
| ATOM | 5046 | O1 | HOH | 2114 | −6.629 | 19.199 | 32.883 | 1.00 | 50.63 | WAT |
| ATOM | 5049 | O1 | HOH | 2115 | 2.357 | 18.250 | 37.438 | 1.00 | 60.86 | WAT |
| ATOM | 5052 | O1 | HOH | 2116 | 7.751 | −18.101 | 10.565 | 1.00 | 54.17 | WAT |
| ATOM | 5055 | O1 | HOH | 2117 | 25.968 | −12.067 | 37.827 | 1.00 | 55.13 | WAT |
| ATOM | 5058 | O1 | HOH | 2118 | 18.924 | 9.331 | 19.006 | 1.00 | 46.38 | WAT |
| ATOM | 5061 | O1 | HOH | 2119 | 8.363 | 35.077 | 19.355 | 1.00 | 55.58 | WAT |
| ATOM | 5064 | O1 | HOH | 2120 | 24.313 | 8.579 | 1.487 | 1.00 | 68.43 | WAT |
| ATOM | 5067 | O1 | HOH | 2121 | 29.773 | 20.226 | 29.332 | 1.00 | 57.70 | WAT |
| ATOM | 5070 | O1 | HOH | 2122 | −5.290 | 5.985 | 29.995 | 1.00 | 61.29 | WAT |
| ATOM | 5073 | O1 | HOH | 2123 | −0.492 | 22.703 | 2.514 | 1.00 | 65.11 | WAT |
| ATOM | 5076 | O1 | HOH | 2124 | −4.311 | 6.509 | 43.597 | 1.00 | 49.65 | WAT |
| ATOM | 5079 | O1 | HOH | 2125 | −0.397 | −11.679 | 35.620 | 1.00 | 51.15 | WAT |
| ATOM | 5082 | O1 | HOH | 2126 | 0.485 | −17.537 | 40.207 | 1.00 | 63.05 | WAT |
| ATOM | 5085 | O1 | HOH | 2127 | −8.353 | 31.954 | 14.454 | 1.00 | 46.68 | WAT |
| ATOM | 5088 | O1 | HOH | 2128 | 15.395 | 11.233 | 18.489 | 1.00 | 46.20 | WAT |
| ATOM | 5091 | O1 | HOH | 2129 | −4.412 | −3.686 | 12.851 | 1.00 | 56.16 | WAT |
| ATOM | 5094 | O1 | HOH | 2130 | −4.354 | 11.093 | −1.852 | 1.00 | 47.92 | WAT |
| ATOM | 5097 | O1 | HOH | 2131 | 13.031 | 9.032 | 47.538 | 1.00 | 49.56 | WAT |
| ATOM | 5100 | O1 | HOH | 2132 | 10.494 | 0.328 | 53.261 | 1.00 | 59.14 | WAT |
| ATOM | 5103 | O1 | HOH | 2133 | 23.368 | 28.332 | 3.403 | 1.00 | 60.23 | WAT |
| ATOM | 5106 | O1 | HOH | 2134 | −7.220 | −3.276 | 39.297 | 1.00 | 66.06 | WAT |
| ATOM | 5109 | O1 | HOH | 2135 | 3.026 | −7.453 | 18.553 | 1.00 | 63.71 | WAT |
| ATOM | 5112 | O1 | HOH | 2136 | −7.586 | −2.763 | 30.225 | 1.00 | 47.35 | WAT |
| ATOM | 5115 | O1 | HOH | 2137 | 32.430 | 16.948 | 32.021 | 1.00 | 72.28 | WAT |
| ATOM | 5118 | O1 | HOH | 2138 | 21.732 | 19.591 | 47.314 | 1.00 | 66.33 | WAT |
| ATOM | 5121 | O1 | HOH | 2139 | 30.167 | 17.274 | 41.305 | 1.00 | 51.63 | WAT |
| ATOM | 5124 | O1 | HOH | 2140 | 6.665 | −4.504 | −4.865 | 1.00 | 50.05 | WAT |
| ATOM | 5127 | O1 | HOH | 2141 | −15.963 | 12.359 | −0.588 | 1.00 | 69.01 | WAT |
| ATOM | 5130 | O1 | HOH | 2142 | −3.200 | 20.138 | 34.420 | 1.00 | 52.22 | WAT |
| ATOM | 5133 | O1 | HOH | 2143 | −11.566 | −7.694 | 38.654 | 1.00 | 52.57 | WAT |
| ATOM | 5136 | O1 | HOH | 2144 | 27.100 | 14.832 | 24.345 | 1.00 | 40.47 | WAT |
| ATOM | 5139 | O1 | HOH | 2145 | 29.004 | 11.955 | 46.362 | 1.00 | 42.87 | WAT |
| ATOM | 5142 | O1 | HOH | 2146 | 17.972 | 10.618 | 15.635 | 1.00 | 40.34 | WAT |
| ATOM | 5145 | O1 | HOH | 2147 | −12.684 | 21.729 | 0.592 | 1.00 | 65.46 | WAT |
| ATOM | 5148 | O1 | HOH | 2148 | 26.140 | −8.357 | 1.230 | 1.00 | 61.27 | WAT |
| ATOM | 5151 | O1 | HOH | 2149 | 24.491 | 71.445 | 2.037 | 1.00 | 58.77 | WAT |
| ATOM | 5154 | O1 | HOH | 2150 | 13.007 | −18.434 | 26.291 | 1.00 | 55.30 | WAT |
| ATOM | 5157 | O1 | HOH | 2151 | 1.079 | −1.818 | −10.480 | 1.00 | 65.83 | WAT |
| ATOM | 5160 | O1 | HOH | 2152 | −10.058 | 1.102 | 0.082 | 1.00 | 55.50 | WAT |
| ATOM | 5163 | O1 | HOH | 2153 | 17.987 | 6.867 | 56.232 | 1.00 | 62.08 | WAT |
| ATOM | 5166 | O1 | HOH | 2154 | 13.423 | 5.135 | −4.529 | 1.00 | 57.52 | WAT |
| ATOM | 5169 | O1 | HOH | 2155 | 25.437 | −4.801 | 20.232 | 1.00 | 61.42 | WAT |
| ATOM | 5172 | O1 | HOH | 2156 | 8.930 | 15.513 | 53.195 | 1.00 | 59.40 | WAT |
| ATOM | 5175 | O1 | HOH | 2157 | 0.486 | 8.114 | 46.697 | 1.00 | 59.80 | WAT |
| ATOM | 5178 | O1 | HOH | 2158 | 34.663 | −11.044 | 38.077 | 1.00 | 54.32 | WAT |
| ATOM | 5181 | O1 | HOH | 2159 | −13.642 | −5.199 | 38.732 | 1.00 | 62.99 | WAT |
| ATOM | 5184 | O1 | HOH | 2160 | 25.678 | 23.999 | 1.135 | 1.00 | 55.84 | WAT |
| ATOM | 5187 | O1 | HOH | 2161 | 29.704 | 11.916 | 38.116 | 1.00 | 43.40 | WAT |
| ATOM | 5190 | O1 | HOH | 2162 | 33.520 | 21.202 | 35.278 | 1.00 | 56.88 | WAT |
| ATOM | 5193 | O1 | HOH | 2163 | 10.639 | 3.431 | 63.505 | 1.00 | 73.95 | WAT |
| ATOM | 5196 | O1 | HOH | 2164 | 17.587 | 16.340 | 22.145 | 1.00 | 44.24 | WAT |
| ATOM | 5199 | O1 | HOH | 2165 | 1.299 | −10.868 | 17.728 | 1.00 | 62.48 | WAT |
| ATOM | 5202 | O1 | HOH | 2166 | 35.609 | 25.832 | −11.624 | 1.00 | 61.56 | WAT |
| ATOM | 5205 | O1 | HOH | 2167 | 24.028 | 7.999 | 10.833 | 1.00 | 57.16 | WAT |
| ATOM | 5208 | O1 | HOH | 2168 | 27.720 | −6.537 | 50.507 | 1.00 | 55.60 | WAT |
| ATOM | 5211 | O1 | HOH | 2169 | −10.296 | 21.811 | 18.518 | 1.00 | 46.62 | WAT |
| ATOM | 5214 | O1 | HOH | 2170 | −3.999 | 14.628 | −4.751 | 1.00 | 46.47 | WAT |
| ATOM | 5217 | O1 | HOH | 2171 | −0.442 | −14.786 | 21.272 | 1.00 | 65.53 | WAT |
| ATOM | 5220 | O1 | HOH | 2172 | 6.948 | −26.529 | 25.105 | 1.00 | 59.64 | WAT |
| ATOM | 5223 | O1 | HOH | 2173 | 1.089 | −13.530 | 11.244 | 1.00 | 64.90 | WAT |
| ATOM | 5226 | O1 | HOH | 2174 | −5.597 | −2.612 | 1.137 | 1.00 | 49.95 | WAT |
| ATOM | 5229 | O1 | HOH | 2175 | 19.244 | −27.907 | 24.668 | 1.00 | 65.08 | WAT |
| ATOM | 5232 | O1 | HOH | 2176 | 21.954 | −12.068 | 20.304 | 1.00 | 49.26 | WAT |
| ATOM | 5235 | O1 | HOH | 2177 | −3.361 | 20.103 | −4.709 | 1.00 | 61.65 | WAT |
| ATOM | 5238 | O1 | HOH | 2178 | −8.511 | 3.584 | 8.915 | 1.00 | 55.03 | WAT |

TABLE 1-continued

Structure coordinates of CPP32

| ATOM | 5241 | O1 | HOH | 2179 | 13.371 | 23.215 | 42.531 | 1.00 | 40.23 | WAT |
|------|------|----|-----|------|--------|--------|--------|------|-------|-----|
| ATOM | 5244 | O1 | HOH | 2180 | -13.909 | 14.833 | 25.488 | 1.00 | 56.67 | WAT |
| ATOM | 5247 | O1 | HOH | 2181 | -11.013 | 4.971 | 25.521 | 1.00 | 52.81 | WAT |
| ATOM | 5250 | O1 | HOH | 2182 | 16.702 | -1.049 | 17.348 | 1.00 | 57.39 | WAT |
| ATOM | 5253 | O1 | HOH | 2183 | 11.947 | -20.385 | 32.853 | 1.00 | 65.58 | WAT |
| ATOM | 5256 | O1 | HOH | 2184 | 18.250 | -17.609 | 34.233 | 1.00 | 51.12 | WAT |
| ATOM | 5259 | O1 | HOH | 2185 | 13.476 | -12.722 | 44.289 | 1.00 | 28.08 | WAT |
| ATOM | 5262 | O1 | HOH | 2186 | 29.328 | 8.920 | 31.941 | 1.00 | 57.71 | WAT |
| ATOM | 5265 | O1 | HOH | 2187 | -12.699 | 21.038 | 9.839 | 1.00 | 56.16 | WAT |
| ATOM | 5268 | O1 | HOH | 2188 | 16.836 | 4.722 | -2.612 | 1.00 | 57.46 | WAT |
| ATOM | 5271 | O1 | HOH | 2189 | 3.891 | 14.494 | 42.203 | 1.00 | 59.64 | WAT |
| ATOM | 5274 | O1 | HOH | 2190 | 17.491 | 18.443 | 28.332 | 1.00 | 28.80 | WAT |
| ATOM | 5277 | O1 | HOH | 2191 | 21.787 | -3.744 | 4.522 | 1.00 | 40.35 | WAT |
| ATOM | 5280 | O1 | HOH | 2192 | 17.122 | 34.543 | 23.294 | 1.00 | 53.51 | WAT |
| ATOM | 5283 | O1 | HOH | 2193 | 12.497 | 24.289 | 45.960 | 1.00 | 57.43 | WAT |
| ATOM | 5286 | O1 | HOH | 2194 | 26.256 | 18.486 | 51.290 | 1.00 | 62.25 | WAT |
| ATOM | 5289 | O1 | HOH | 2195 | -7.617 | 6.435 | 1.919 | 1.00 | 59.72 | WAT |
| ATOM | 5292 | O1 | HOH | 2196 | -7.957 | 19.516 | -3.285 | 1.00 | 45.35 | WAT |
| ATOM | 5295 | O1 | HOH | 2197 | 34.447 | 19.190 | 37.112 | 1.00 | 55.05 | WAT |
| ATOM | 5298 | O1 | HOH | 2198 | -12.890 | 9.893 | 14.142 | 1.00 | 70.25 | WAT |
| ATOM | 5301 | O1 | HOH | 2199 | -5.825 | -5.408 | 40.419 | 1.00 | 59.19 | WAT |
| ATOM | 5304 | O1 | HOH | 2200 | -17.148 | 18.653 | 27.505 | 1.00 | 41.56 | WAT |
| ATOM | 5307 | O1 | HOH | 2201 | 10.808 | -5.154 | 48.926 | 1.00 | 43.68 | WAT |
| ATOM | 5310 | O1 | HOH | 2202 | 23.987 | -8.458 | 45.651 | 1.00 | 49.09 | WAT |
| ATOM | 5313 | O1 | HOH | 2203 | 24.730 | 27.439 | 30.487 | 1.00 | 57.86 | WAT |
| ATOM | 5316 | O1 | HOH | 2204 | 13.525 | 37.087 | 40.416 | 1.00 | 66.57 | WAT |
| ATOM | 5319 | O1 | HOH | 2205 | 22.610 | 5.556 | 10.251 | 1.00 | 53.18 | WAT |
| ATOM | 5322 | O1 | HOH | 2206 | 10.716 | 21.479 | 43.962 | 1.00 | 41.03 | WAT |
| ATOM | 5325 | O1 | HOH | 2207 | 9.223 | 40.069 | 7.223 | 1.00 | 57.62 | WAT |
| ATOM | 5328 | O1 | HOH | 2208 | 10.367 | 28.487 | -7.871 | 1.00 | 68.03 | WAT |
| END | | | | | | | | | | |

---

What is claimed is:

1. A co-complex crystal having the monoclinic space group symmetry $P2_1$, consisting of CPP32 and a derivatized tetrapeptide Ac-Asp-Val-Ala-Asp-fluoromethyl ketone (SEQ ID NO:3).

2. The crystal of claim 1, wherein said crystal comprises a unit cell having the dimensions of a=50.9 Å±5 Å, b=69.1 Å±5 Å, c=93.8 Å±5 Å, α=90°, β=101.2°±5°, and γ=90°.

* * * * *